US008217042B2

(12) United States Patent
Claus et al.

(10) Patent No.: US 8,217,042 B2
(45) Date of Patent: *Jul. 10, 2012

(54) PYRIDOPYRAZINES AND THEIR USE AS MODULATORS OF KINASES

(75) Inventors: Eckhard Claus, Frankfurt (DE); Irene Seipelt, Offenbach (DE); Eckhard Guenther, Maintal (DE); Emmanuel Polymeropoulos, Frankfurt (DE); Michael Czech, Frankfurt (DE); Tilmann Schuster, Frankfurt (DE)

(73) Assignee: Zentaris GmbH, Frankfurt (DE)

(*) Notice: Subject to any disclaimer, the term of this patent is extended or adjusted under 35 U.S.C. 154(b) by 683 days.

This patent is subject to a terminal disclaimer.

(21) Appl. No.: 11/558,503

(22) Filed: Nov. 10, 2006

(65) Prior Publication Data

US 2007/0149484 A1 Jun. 28, 2007

Related U.S. Application Data

(60) Provisional application No. 60/849,761, filed on Oct. 6, 2006, provisional application No. 60/735,698, filed on Nov. 11, 2005.

(51) Int. Cl.
*A61K 31/4965* (2006.01)

(52) U.S. Cl. ........................................ 514/249; 544/350

(58) Field of Classification Search .................... 544/350
See application file for complete search history.

(56) References Cited

U.S. PATENT DOCUMENTS

| | | | |
|---|---|---|---|
| 3,180,868 A | 4/1965 | Osdene et al. | |
| 3,209,004 A | 9/1965 | Santilli et al. | |
| 4,082,845 A | 4/1978 | Saari et al. | |
| 5,480,883 A | 1/1996 | Spada et al. | |
| 2004/0092521 A1 | 5/2004 | Altenbach et al. | |
| 2004/0102360 A1 | 5/2004 | Barnett et al. | |
| 2004/0266777 A1 | 12/2004 | Claus et al. | |
| 2005/0032803 A1 | 2/2005 | Claus et al. | |
| 2005/0165028 A1 | 7/2005 | Norman et al. | |
| 2005/0256118 A1 | 11/2005 | Altenbach et al. | |
| 2005/0256309 A1 | 11/2005 | Altenbach et al. | |
| 2005/0272728 A1 | 12/2005 | Altenbach et al. | |
| 2005/0272736 A1 | 12/2005 | Altenbach et al. | |

FOREIGN PATENT DOCUMENTS

| | | |
|---|---|---|
| EP | 0 735 025 B1 | 7/1998 |
| EP | 1 661 889 A1 | 5/2006 |
| GB | 1184848 | 3/1970 |
| JP | 50-53394 | 5/1975 |
| JP | 2006-137723 | 6/2006 |
| WO | WO 95/15758 | 6/1995 |
| WO | WO 99/17759 | 4/1999 |
| WO | WO 99/32111 | 7/1999 |
| WO | WO 99/43681 | 9/1999 |
| WO | WO 00/12497 | 3/2000 |
| WO | WO 00/35435 A1 | 6/2000 |
| WO | WO 00/37141 A1 | 6/2000 |
| WO | WO 01/81346 A2 | 11/2001 |
| WO | WO 02/06213 A2 | 1/2002 |
| WO | WO 02/055079 A2 | 7/2002 |
| WO | WO 02/090355 A1 | 11/2002 |
| WO | WO 03/024448 A2 | 3/2003 |
| WO | WO 03/064421 A1 | 8/2003 |
| WO | WO 03/064431 A2 | 8/2003 |
| WO | WO 03/068223 A1 | 8/2003 |
| WO | WO 03/084473 A2 | 10/2003 |
| WO | WO 03/086394 A1 | 10/2003 |
| WO | WO 03/086403 A1 | 10/2003 |
| WO | WO 2004/005472 A2 | 1/2004 |
| WO | WO 2004/017950 A2 | 3/2004 |
| WO | WO 2004/030635 A2 | 4/2004 |
| WO | WO 2004/055003 A1 | 7/2004 |
| WO | WO 2004/104002 A1 | 12/2004 |
| WO | WO 2004/104003 A1 | 12/2004 |
| WO | WO 2004/108702 A1 | 12/2004 |
| WO | WO 2005/007099 A2 | 1/2005 |
| WO | WO 2005/021513 A1 | 3/2005 |
| WO | WO 2005/023771 A1 | 3/2005 |
| WO | WO 2005/023807 A2 | 3/2005 |
| WO | WO 2005/056547 A2 | 6/2005 |
| WO | WO 2005/061519 A1 | 7/2005 |
| WO | WO 2005/103029 A1 | 11/2005 |
| WO | WO 2005/123698 A1 | 12/2005 |
| WO | WO 2005/123733 A1 | 12/2005 |
| WO | WO 2006/002047 A2 | 1/2006 |
| WO | WO 2006/012396 A1 | 2/2006 |
| WO | WO 2006/014580 A1 | 2/2006 |

(Continued)

OTHER PUBLICATIONS

West, Anthony R., Solid State Chemistry and its Applications, Wiley, New York, 1988, pp. 358 and 365.* U.S. Appl. No. 11/558,493, filed Nov. 10, 2006, Seipelt, et al.
Dario R. Alessi, et al. "Mechanism of Activation of Protein Kinase B by Insulin and IGF-1", The EMBO Journal, vol. 15, No. 23, 1996, pp. 6541-6551.
Khaled All, et al. "Essential Role for the p110β Phosphoinositide 3-Kinase in the Allergic Response", Letters to Nature, vol. 43, Oct. 21, 2004, pp. 1007-1011.
C.M. Atkinson, et al. "Cinnolines and Other Heterocyclic Types in Relation to the Chemotherapy of Trypanosomiasis. Part XI. Some Reactions of Simple Quinoxaline Derivatives", 1955.
Brydon L. Bennett, et al. "SP600125, An Anthrapyrazolone Inhibitor of JUN N-Terminal Kinase", PNAS, vol. 98, No. 24, Nov. 20, 2001, pp. 13681-13686.
Andrey Bondev, et al. "Differential Regulation of Lipid and Protein Kinase Activities of Phosphoinositide 3-Kinaseγ in Vitro", Biological Chemistry, vol. 380, Nov. 1999, pp. 1337-1340.
Tzvetanka Bondeva, et al. "Bifurcation of Lipid and Protein Kinase Signals of PI3Kγ to the Protein Kinases PKB and MAPK", Science, vol. 282, Oct. 9, 1998, pp. 293-296.

(Continued)

*Primary Examiner* — James O Wilson
*Assistant Examiner* — Brian McDowell
(74) *Attorney, Agent, or Firm* — Oblon, Spivak, McClelland, Maier & Neustadt, L.L.P.

(57) ABSTRACT

The invention relates to pyrido[2,3-b]pyrazines of the general formulae (I) and (II), and to their preparation and use as medicaments, especially for the treatment of malignant disorders and other disorders based on pathological cell proliferations.

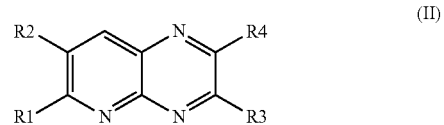

8 Claims, No Drawings

FOREIGN PATENT DOCUMENTS

| | | |
|---|---|---|
| WO | WO 2006/017326 A1 | 2/2006 |
| WO | WO 2006/017468 A2 | 2/2006 |
| WO | WO 2006/020561 A2 | 2/2006 |
| WO | WO 2006/021448 A1 | 3/2006 |
| WO | WO 2006/024666 A1 | 3/2006 |
| WO | WO 2006/059103 A2 | 6/2006 |
| WO | WO 2006/074147 A2 | 7/2006 |
| WO | WO 2006/081178 A2 | 8/2006 |
| WO | WO 2006/081179 A1 | 8/2006 |
| WO | WO 2006/081182 A2 | 8/2006 |
| WO | WO 2006/081264 A1 | 8/2006 |
| WO | WO 2006/091395 A2 | 8/2006 |
| WO | WO 2006/128129 A2 | 11/2006 |
| WO | WO 2006/128172 A2 | 11/2006 |
| WO | WO 2007/023186 A1 | 3/2007 |
| WO | WO 2007/044729 A2 | 4/2007 |
| WO | WO 2007/054556 A1 | 5/2007 |

OTHER PUBLICATIONS

Robert H. Bradbury, et al. "New Non-Peptide Endothelin-A Receptor Antagonists: Synthesis, Biological Properties, and Structure-Activity Relationships of 5-(Dimethylamino)-N-Pyridyl-, N-Pyrimidinyl-, N-Pyridazinyl-, and N-Pyrazinyl-1-Naphthalenesulfonamides", Journal of Medicinal Chemistry, vol. 40, No. 6, 1997, pp. 996-1004.

Richard J. Brown, et al. "Synthesis and Properties of Axially-Chiral N-(2,6-Disubstituted) Phenyl Triazolones", Tetrahedron, vol. 60, 2004, pp. 4361-4375.

Ian G. Campbell, et al. "Mutation of the PIK3CA Gene in Ovarian and Breast Cancer", Cancer Research, vol. 64, Nov. 1, 2004, pp. 7678-7681.

Adindo L. Castelhano, et al. "Glucokinase-Activating Ureas", Bioorganic & Medicinal Shemistry Letters, vol. 15, 2005, pp. 1501-1504.

Daniela Catarzi, et al. "Tricyclic Heteroaromatic Systems. Synthesis and $A_1$ and $A_{2a}$ Adenosine Binding Activities of Some 1-Aryl-1,4-Dihydro-3-Methyl[1]Benzopyrano[2,3-c]Pyrazol-4-Ones,1-Aryl-4,9-Dihydro-3-Methyl-1*H*-Pyrazolo[3,4-b]Quinolin-4-Ones, and 1-Aryl-1*H*-Imidazo[4,5-b]Quinoxalines", Journal of Medicinal Chemistry, vol. 38, 1995, pp. 1330-1336.

Hwai Wen Chang, et al. "Transformation of Chicken Cells by the Gene Encoding the Catalytic Subunit of PI 3-Kinase", Science, vol. 276, Jun. 20, 1997, pp. 1848-1850.

F. Chang, et al. "Involvement of PI3K/Akt Pathway in Cell Cycle Progression, Apoptosis, and Neoplastic Transformation: A Target for Cancer Chemotherapy", Leukemia, vol. 17, 2003, pp. 590-603.

F. Chang, et al. "Signal Transduction Mediated by the RAS/RAF/MEK/ERK Pathway From Cytokine Receptors to Transcription Factors: Potential Targeting for Therapeutic Intervention", Leukemia, vol. 17, 2003, pp. 1263-1293.

Jiong J. Chen, et al. "Pyrido[2,3-b] Pyrazines From Pyrazine C-Nucleosides: An Unusual Intramolecular Rearrangement", Journal of the American Chemical Society, vol. 118, 1996, pp. 8953-8954.

Jing Chen, et al. "RAF-1 Promotes Cell Survival by Antagonizing Apoptosis Signal-Regulating Kinase 1 Through a MEK-ERK Independent Mechanism", PNAS, vol. 98, No. 14, Jul. 3, 2001, pp. 7783-7788.

Jie-Fei Cheng, et al. "Discovery and Structure-Activity Relationship of Coumarin Derivatives As TNF-α Inhibitors" Bioorganic & Medicinal Chemistry Letters, vol. 14, 2004, pp. 2411-2415.

Gary G. Chiang, et al. "Determination of the Catalytic Activities of Mtor and Other Members of the Phosphoinositide-3-Kinase-Related Kinase Family", Methods in Molecular Biology, vol. 281, pp. 125-141.

Michael A. Crackower, et al. "Regulation of Myocadial Contractility and Cell Size by Distinct PI3K-PTEN Signaling Pathways", Cell, vol. 110, Sep. 20, 2002, pp. 737-749.

Natalie A. Dales, et al. "Design and Synthesis of Unsymmetrical Peptidyl Urea Inhibitors of Aspartic Peptidases", Letters vol. 3, No. 15, 2001, pp. 2313-2316.

Gerd Dannhardt, et al. "A Novel Series of 2-Carboxytetrahydroquinolines Provides New Insights Into the Eastern Region of Glycine Site NMDA Antagonists", Arch. Pharm. Pharm. Med. Chem., vol. 333, 2000, pp. 267-274.

Mircea Darabantu, et al. "Synthesis of New Polyaza Heterocycles. Part 42: Diazines", Tetrahedraon, vol. 61, 2005, pp. 2897-2905.

Stephen P. Davies, et al. "Specificity and Mechanism of Action of Some Commonly Used Protein Kinase Inhibitors", Biochem. J., vol. 351, 2000, pp. 95-105.

Helen Davies, et al. "Mutations of the Braf Gene in Human Cancer", Letters to Nature, Jun. 9, 2002, pp. 1-6.

Ritu Dhand, et al. "PI 3-Kinase Is a Dual Specificity Enzyme: Autoregulation by an Intrinsic Protein-Serine Kinase Activity", The EMBO Journal, vol. 13, No. 3, 1994, pp. 522-533.

M.S.A. El-Gaby, et al. "Some Nucleophilic Reactions With 6-Benzoyl-2,3-Dichloroquinoxaline: Synthesis of Tetrazolo[1,5-a]Quinoxaline, 2-Methylidene-1, 3-Dithiolo[4,5-b] Quinoxalines, Quinoxalino[2,3-b] Quinoxlines and Pyrazolo[1',5':1,2] Imidazolo[4,5-b]-Quinoxalines", Indian Journal of Chemistry, vol. 40B, Mar. 2001, pp. 195-200.

Robert D. Elliott, et al. "The Isomeric Pyridopyrazines From the Reaction of Some Tetraaminopyridines With Pyruvaldehyde and Benzil", The Journal of Organic Chemistry, vol. 33, No. 6, 1968, pp. 2393-2397.

Ola A. El-Sayed, et al. "Synthesis of Some Novel Quinoline-3-Carboxylic Acids and Pyrimidoquinoline Derivatives as Potential Antimicrobial Agents", Arch. Pharm. Pharm. Med. Chem., vol. 9, 2002, pp. 403-410.

Emma Ford, et al. "Regioselective Substitution of 2,3-Dichloro-6-Amino-Quinoxaline", Tetrahedron Letters, vol. 41, 2000, pp. 3197-3198.

H. Friess, et al. "Pancreatic Cancer: The Potential Clinical Relevance of Alterations in Growth Factors and Their Receptors", Journal of Molecular Medicine, vol. 74, 1996, pp. 35-42.

Rudolph Gotz, et al. "Essential Role of Bag-1 in Differentiation and Survival of Hematopoietic and Neuronal Cells", Nat. Neuroscience, vol. 8, No. 9, Sep. 2005, pp. 1169-1178.

Ariamala Gopalsamy, et al. "Pyrazolo[1,5-a] Pyrimidin-7-YL Phenyl Amides as Novel Anti-Proliferative Agents: Parallel Synthesis for Lead Optimization of Amide Region", Bioorganic & Medicinal Chemistry Letters, vol. 15, 2005, pp. 1591-1594.

S. Goswami, et al. "Simple and Effiecient Synthesis of 2,7-Difunctionalized-1,8-Naphthyridines", Molecules, vol. 10, 2005, pp. 929-936.

Rebecca J. Gum, et al. "Acquisition of Sensitivity of Stress-Activated Protein Kinases to the p38 Inhibitor, SB 203580, by Alteration of One or More Amino Acids Within the ATP Binding Pocket", The Journal of Biological Chemistry, vol. 273, No. 25, Jun. 19, 1998, pp. 15605-15610.

Wei He, et al. "Potent Quinoxaline-Based Inhibitors of PDGF Receptor Tyrosine Kinase Activity. Part 2: The Synthesis and Biological Activities of RPR127963 an Orally Bioavailable Inhibitor", Bioorganic and Medicinal Chemistry Letters, vol. 13, 2003, pp. 3097-3100.

Xungui He, et al. "Synthesis and Biological Evaluation of Bis and Monocarbonate Prodrugs of 10-Hydroxycamptothecins", Bioorganic and Medicinal Chemistry, vol. 12, 2004, pp. 4003-4008.

Gottfried Heinisch, et al. "Synthesis of N-Aryl-N'-Heteroaryl-Substituted Urea and Thiourea Derivatives and Evaluation of Their Anticonvulsant Activity", Arch. Pharm. Pharm. Med. Chem., vol. 330, 1997, pp. 207-210.

Corey R. Hopkins, et al. "An Improved Method for the Synthesis of 6-Substituted-5H-Pyrrolo[2,3-b] Pyrazines Via Palladium-Catalyzed Heteroannulation Using Microwave Heating", Tetrahedron Letters, vol. 45, 2004, pp. 8631-8633.

Rika Hoshino, et al. "Constitutive Activation of the 41-/43-kDa Mitogen-Activated Protein Kinase Signaling Pathway in Human Tumors", Oncogene, vol. 18, 1999, pp. 813-822.

Eugen Muller, et al. "Methoden Der Organischen Chemie (Houben-Weyl)", 1981, pp. 1-11.

S. Gobec, et al. "Houben-Weyl Methods of Molecular Transformation", Science of Synthesis, vol. 16, 1981, pp. 1-25.

M. Bohle, et al. "Hetarenes IV. Six Member and Larger Heteroringswith Maximum Unsaturation", Methods of Organic Chemistry(Houben-Weyl), vol. E9, Dec. 18, 1997, pp. 1-8.

"Methoden Der Organischen Chemie (Houben-Weyl)", Dec. 3, 1992, pp. 1-4.

John W. Huffman, et al. "Enantioselective Synthesis of 1-Methoxy- and 1-Deoxy-2-Methy$\Delta^8$- Tetrahydrocannabinols: New Selective Ligands for the $CB_2$ Receptor", Bioorganic & Medicinal Chemistry, vol. 14, 2006, pp. 247-262.

Gregory Hughes, et al. "Ethynyl Π-Extended 2,5-Diphenyl-1,3,4-Oxadiazoles and 2-Phenyl 5-(2-Thienyl)-1,3,4-Oxadiazoles: Synthesis, X-Ray Crystal Structures and Optical Properties", Org. Biomol. Chem., vol. 2, 2004, pp. 3363-3367.

Alessio Innocenti, et al. "Carbonic Anhydrase Inhibitors: The First On-Resin Screening of a 4-Sulfamoylphenylthiourea Library", Journal of Medicinal Chemistry, vol. 47, 2004, pp. 5224-5229.

Roy Katso, et al. "Cellular Function of Phosphoinositide 3-Kinases: Implications for Development, Immunity, Homeostasis, and Cancer", Annu. Rev. Cell Dev. Biol., vol. 17, 2001, pp. 615-675.

Samir N. Khleif, et al. "A Phase I Vaccine Trial With Peptides Reflecting RAS Oncogene Mutations of Solid Tumors", Journal of Immunotherapy, vol. 22, No. 2, 1999, pp. 155-165.

C.L. Leese, et al. "Polyazanaphthalenes. Part I. Some Derivatives of 1:4:5-Triazanaphthalene and Quinoxaline", Japanese Chem. Society, 1955, pp. 303-309.

Douglas A. Levin, et al. "Frequent Mutation of the PIK3CA Gene in Ovarian and Breast Cancer", Clinical Cancer Research, vol. 11, No. 8, Apr. 15, 2005, pp. 2875-2878.

Timothy S. Lewis, et al. "Signal Transduction Through Map Kinase Cascades", 1998.

Jing Li, et al. "PTEN, a Putative Protein Tyrosine Phosphatase Gene Mutated in Human Brain, Breast, and Prostate Cancer", Science, vol. 275, Mar. 28, 1997.

Tony Liu, et al. "Mechanistic Studies of $LA^{3+/\ -and\ ZN2+}$-Catalyzed Methanolysis of Aryl Phosphate and Phosphorothioate Triesters. Development of Artificial Phosphotriesterase Systems", OBC, vol. 3, 2005, pp. 1525-1533.

Yiling Lu, et al. "Targeting PI3K-AKT Pathway for Cancer Therapy", Rev. Exp. Clin. Hematol. vol. 7.2, Jun. 2003, pp. 205-228.

Ying Lu, et al. "Design, Synthesis, and Evaluation of 2-Alkoxydihyrocinnamates As PPAR Agonists", Bioorganic & Medicinal Chemistry Letters, vol. 16, 2006, pp. 915-919.

Yen-Ying Ma, et al. PIK3CA as an Oncogene in Cervical Cancer, Oncogene, vol. 19, 2000, pp. 2739-2744.

Lisheng Mao, et al. "Facile Synthesis of 2,3-Distributed Quinoxalines by Suzuki-Miyaura Coupling", Synthesis, No. 15, 2004, pp. 2535-2539.

Chris Marshall, "How Do Small GTPASE Signal Transduction Pathways Regulate Cell Cycle Entry", Current Opinion in Cell Biology, vol. 11, 1999, pp. 732-736.

Kenji Matsuno, et al. "Potent and Selective Inhibitors of PDGF Receptor Phosphorylation. 2. Synthesis, Structure Activity Relationship, Improvement of Aqueous Solubility, and Biological Effects of 4-[4-(N-Substituted (Thio) Carbamoyl)-1-Piperazinyl]-6,7-Dimethoxyquinazoline Derivatives", Journal of Medicinal Chemistry, vol. 45, No. 20, 2002, pp. 4513-4523.

F. McPhillips, et al. "Association of C-RAF Expression With Survival and its Targeting With Antisense Oligonucleotides in Ovarian Cancer", British Journal of Cancer, vol. 85, No. 11, 2001, pp. 1753-1758.

W. Mederski, et al. "A General Synthesis of 1-Aryl Carbamoyl-2-Alkyl-4-Aryl Substituted Semicarbazides As Nonbasic Factor Xa Inhibitors", Bioorganic and Medicinal Chemistry Letters, vol. 13, 2003, pp. 3715-3718.

John Mendelsohn, et al. "The EGF Receptor Family as Targets for Cancer Therapy", Oncogene, vol. 19, 2000, pp. 6550-6565.

Jaromir Mindl, et al. "Kinetics and Mechanism of Hyrolysis of Aryl N-Methoxycarbamates and Their Derivatives", Collection Czechoslovak Chem. Commun. vol. 48, 1983, pp. 900-905.

Juan F. Miravet, et al. "Reactive Organogels: Self-Assembled Support for Functional Materials", Organic Letters, vol. 7, No. 22, 2005, pp. 4791-4794.

Gary A. Molander, et al. "Suzuki-Miyaura Cross-Coupling Reactions of Potassium Alkenyltrifluoroncarborates", Journal of Organic Chemistry, vol. 67, No. 24, 2002, pp. 8424-8429.

Sarah M. Moore, et al. "The Presence of a Constitutively Active Phosphoinositide 3-Kinase in Small Cell Lung Cancer Cells Mediates Anchorage-Independent Proliferation Via a Protein Kinase B and $p70^{s6k}$-Dependent Pathway[1]", Cancer Research, vol. 58, Nov. 15, 1998, pp. 5239-5247.

Michael R. Myers, et al. "Potent Quinoxaline-Based Inhibitors of PDGF Receptor Tyrosine Kinase Activity. Part 1: SAR Exploration and Effective Bioisosteric Replacement of a Phenyl Substituent", Bioorganic and Medicinal Chemistry Letters, vol. 13, 2003, pp. 3091-3095.

A. Nagel, et al. "Nuclear and Magnetic Resonance Data of Pyrido [2,3-b] Pyrazines and Their αAdducts With Amide Ion and Water", Journal of Heterocyclic Chemistry, vol. 16, 1979, pp. 301-304.

Charles O. Okafor, et al. "Synthesis of Analogues of the 2,3,6,-Triazaphenothiazine Ring System", Journal of Heterocyclic Chemistry, vol. 20, 1983, pp. 199-203.

Klaus Okkenhaug, et al. "PI3K in Lymphocyte Development, Differentiation and Activation", Immunology, vol. 3, Apr. 2003, pp. 317-330.

T.S. Osdene, et al. The Synthesis of Compounds With Potential Anti-Folic Acid Activity. Part IV. 3: 6-Diaminopyrido(2:3) Pyrazines., J. Chem. Soc., 1955, pp. 2032-2035.

Emma R. Parmee, et al. "4-Amino Cyclohexylglycine Analogues as Potent Dipeptidyl Peptidase IV Inhibitors", Bioorganic and Medicinal Chemistry Letters, vol. 14, 2004, pp. 43-46.

Enrico Patrucco, et al. "PI3Kγ Modulates the Cardiac Response to Chronic Pressure Overload by Distinct Kinase-Dependent and -Independent Effects", Cell, vol. 118, Aug. 6, 2004, pp. 375-387.

Graham S. Poindexter, et al. "Dihydropyridine Neuropeptide Y $Y_1$ Receptor Antagonists 2: Bioisoteric Urea Replacements", Bioorganic and Medicinal Chemistry, vol. 12, 2004, pp. 507-521.

Ulf R. Rapp, et al. "BCL-2 Proteins: Master Switches at the Intersection of Death Signaling and the Survival Control by RAF Kinases", Biochimica et Biophysica Acta, vol. 1644, 2004, pp. 149-158.

Jean-Marie Receveur, et al. "4-Acylamino- and 4-Ureidobenzamides as Melanin-Concentrating Hormone (MCH) Receptor 1 Antagonists", Bioorganic and Medicinal Chemistry Letters, vol. 14, 2004, pp. 5075-5080.

Adam R. Renslo, et al. "Self Complimentary Cavitands", Journal of the American Chemical Society, vol. 121, 1999, pp. 7459-7460.

Pablo Rodriguez-Vicana, et al. "Phosphatidylinositol-3-OH Kinase as a Direct Target of RAS", Nature, vol. 70, Aug. 18, 1994, pp. 527-532.

M. Sako, "Product Class 20: Pyridopyrazines", Science of Synthesis, vol. 16, No. 20, 2004, pp. 1269-1290.

Yardena Samuels, et al. "High Frequency of Mutations of the PIK3CA Gene in Human Cancers", Science, vol. 304, Apr. 23, 2004.

Satoshi Sasaki, et al. "Discovery of a Thieno[2,3-d] Pyraimidine-2,4-Dione Bearing a p-Methoxyureidophenyl Moiety at the 6-Position: A Highly Potent and Orally Bioavailable Non-peptide Antagonist for the Human Luteinizing Hormone-Releasing Hormone Receptor", Journal of Medicinal Chemistry, vol. 46, 2003, pp. 113-124.

Judith S. Sebolt-Leopold et al. "Targeting the Mitogen-Activated Protein Kinase Cascade to Treat Cancer", Nature Reviews, vol. 4, Dec. 2004, pp. 937-947.

Laleh Shayesteh, et al. "PIK3CA Is Implicated as an Oncogene in Ovarian Cancer", Nature Genetics, vol. 21, Jan. 1999, pp. 99-102.

Joachim K. Seydel, et al. "Synthesis and Quantitative Structure-Activity Relationships of Anticonvulsant 2,3,6-Triaminopyridines", Journal of Medicinal Chemistry, vol. 37, 1994, pp. 3016-3022.

Takeshi Shiota, et al. "Regioselective Reactions of Organozinc Reagents With 2,4- Dichloroquinoline and 5,7-Dichloropyrazolo[1,5-a] Pyrimidine", Journal of Organic Chemistry, vol. 64, 1999, pp. 453-457.

V. Sirivatanauksorn, et al. "Molecular Pattern of Ductal Pancreatic Cancer", Langenbeck'S Arch Surg., vol. 383, 1998, pp. 105-115.

Peter A. Steck, et al. "Identification of a Candidate Tumour Suppressor Gene, MMAC1, at Chromosome 10q23.3 That is Mutated in Multiple Advanced Cancers", Nature Genetics, vol. 15, Apr. 1997, pp. 356-362.

Pierre Sujobert, et al. "Essential Role for the p110δISOFORM in Phosphoinositide 3-Kinase Activation and Cell Proliferation in Acute Myeloid Leukemia", Blood, vol. 106, No. 3, Aug. 2005, pp. 1063-1066.

Jason W. Szewczyk, et al. "SAR Studies: Designing Potent and Selective LXR Agonists", Bioorganic and Medicinal Chemistry Letters, vol. 16, 2006, pp. 3055-3060.

Teruo Tanaka, et al. "Syntheses of Pyrido[2,3-]pyrazine Derivatives", Yakugaku Zasshi, vol. 95, No. 9, 1975, pp. 1092-1097 (with partial English Translation).

Rajendra P. Tangallapally, et al. Synthesis and Evaluation of Nitrofuranylamides As Novel Antituberculosis Agents, Journal of Medicinal Chemistry, vol. 47, 2004, pp. 5276-5283.

Edward C. Taylor, et al. Pterdines. 52. A Convienient Synthesis of 6-Formylpterin, Synthetic Communications, vol. 16, No. 17, 1987, pp. 1865-1868.

Carroll Temple, et al. "Synthesis of Potential Antimalarial Agents. II. 6,8-Disubstituted Pyrido[2,3-b] Pyrazines", Journal of Medicinal Chemistry, vol. 11, Nov. 1968, pp. 1216-1218.

Carroll Temple, et al. "Potential Antimitotic Agents. Synthesis of Some Ethyl Benzopyrazin-7-Ylcarbamates, Ethyl Pyrido 3,4b]-pyrazine-7-Ylcarbamates, and Ethyl Pyrido[3,4-e]-AS-Triazin-7-Ylcarbamates", Journal of Medicinal Chemistry, vol. 33, 1990, pp. 3044-3050.

Carroll Temple, et al. "Antimitotic Agents. Chiral Isomers of Ethyl [5-Amino-1,2-Dihydro-3-(4-Hydroxyhpenyl)-2-Methylpyrido[3,4-b] Pyrazin-7-Yl]Carbamate", Journal of Medicinal Chemistry, vol. 35, 1992, pp. 988-993.

Andrew M. Thompson, et al. "3-(3,5-Dimethoxyphenyl)-1,6-Naphthyridine-2,7-Diamines and Related 2-Urea Derivatives Are Potent and Selective Inhibitors of the FGF Receptor-1 Tyrosine Kinase", Journal of Medicinal Chemistry, vol. 43, 2000, pp. 4200-4211.

Jakob Troppmair, et al. "RAF and the Road to Cell Survival: A Tale of Bad Spells, Ring Bearers and Detours", Biochemical Pharmacology, vol. 66, 2003, pp. 1341-1345.

Bart Vanhaesebroeck, et al. "Autophosphorylation of p110δPhosphoinositide 3-Kinase: A New Paradigm for the Regulation of Lipid Kinases in Vitro and in Vivo", The EMBO Journal, vol. 18, No. 5, 1999, pp. 1292-1302.

Bart Vanhaesebroeck, et al. "Synthesis and Function of 3-Phosphorylated Inositol Lipids", Annuual Reviews Biochem., vol. 70, 2001, pp. 535-602.

Quingmin Wang et al, "A Convenient Synthesis of Novel N'-Tert-Butyl-N'-Substituted Benzoyl-N(Substituted Phenyl) Aminocarbonylhydrazines and Their Derivatives", Synthetic Communications, vol. 34, No. 2, 2004, pp. 255-264.

Caroline R. Weinstein-Oppenheimer, et al. "The RAF Signal Transduction Cascade as a Target for Chemotherapeutic Intervention in Growth Factor-Responsive Tumors", Pharmacology & Therapeutics, vol. 88, 2000, pp. 229-279.

Reinhard Wetzker, et al. "Phosphoinositide 3-Kinases as Targets for Therapeutic Intervention", Current Pharmaceutical Design, vol. 10, 2004, pp. 1915-1922.

Ho Bum Woo, et al. "Synthesis of Novel Curcumin Mimics With Asymmetrical Units and Their Anti-Angiogenic Activity", Bioorganic and Medicinal Chemistry Letters, vol. 15, 2005, pp. 3782-3786.

Matthias P. Wymann, et al. "Structure and Function of Phosphoinositide 3-Kinases",Biochimica et Biophysica Acta, vol. 1436, 1998, pp. 127-150.

Guichun Yang, et al "Synthesis of Methyl N-Aryl Oxamate Using Soluble Polymer Support", Synthetic Communications, vol. 36, 2000, pp. 611-619.

Jingjun Yin, et al. "PD-Catalyzed N-Arylation of Heteroarylamines", Organic Letters, vol. 4, No. 20, 2002, pp. 3481-3484.

Bu-Bing Zeng, et al. "Nitroxyl (HNO) Release From New Functionalized N-Hydroxyurea-Derived Acyl Nitroso-9,10-Dimethylanthracene Cycloadducts", Bioorganic & Medicinal Chemistry Letters, vol. 14, 2004, pp. 5565-5568.

* cited by examiner

PYRIDOPYRAZINES AND THEIR USE AS MODULATORS OF KINASES

REFERENCE TO PRIOR APPLICATIONS

This application claims priority to U.S. provisional applications 60/735,698 filed Nov. 11, 2005, and 60/849,761 filed Oct. 6, 2006, both incorporated herein by reference.

DESCRIPTION

1. Technical Field

The invention relates to kinase modulators of the pyrido[2,3-b]pyrazine type and to the preparation and use thereof as medicaments for the modulation of misdirected cellular signal transduction processes, in particular for influencing the function of tyrosine kinases, serine/threonine kinases and lipid kinases and for the treatment of malignant or benign oncoses and other disorders based on pathological cell proliferation, for example restenosis, psoriasis, arteriosclerosis and cirrhosis of the liver.

2. State of the Art

The activation of protein kinases is a central event in cellular signal transduction processes. Aberrant kinase activation is observed in various pathological states. Targeted inhibition of kinases is therefore a fundamental therapeutic aim.

The phosphorylation of proteins is generally initiated by extracellular signals and represents a universal mechanism for controlling various cellular events, for example metabolic processes, cell growth, cell migration, cell differentiation, membrane transport and apoptosis. The kinase protein family is responsible for protein phosphorylation. These enzymes catalyse transfer of phosphate to specific substrate proteins. Based on the substrate specificity, the kinases are divided into three main classes, the tyrosine kinases, the serine/threonine kinases and the lipid kinases. Both the receptor tyrosine kinases and the cytoplasmic tyrosine, serine/threonine and lipid kinases are important proteins in cellular signal transduction. Overexpression or degradation of these proteins plays an important part in disorders based on pathological cell proliferations. These include metabolic disorders, disorders of the connective tissue and of the blood vessels, and malignant and benign oncoses. In tumour initiation and development they frequently occur as oncogens, i.e. as aberrant, constitutively active kinase proteins. The consequences of this excessive kinase activation are, for example, uncontrolled cell growth and reduced cell death. Stimulation of tumour-induced growth factors may also be the cause of overstimulation of kinases. The development of kinase modulators is therefore of particular interest for all pathogenic processes influenced by kinases.

The ras-Raf-Mek-Erk and PI3K-Akt signal transduction cascades play a central role in cell growth, cell proliferation, apoptosis, adhesion, migration and glucose metabolism. Thus, the fundamental involvement in the pathogenesis of disorders such as cancer, neurodegeneration and inflammatory disorders has been demonstrated both for the ras-Raf-Mek-Erk and for the PI3K-Akt signal pathway. Therefore, the individual components of these signal cascades constitute important therapeutic points of attack for the intervention in the various disease processes (Weinstein-Oppenheimer C. R. et al 2000, Chang F. et al 2003, Katso R. et al 2001 and Lu Y. et al 2003).

The molecular and biochemical properties of the two signal pathways will first be described separately below.

A multitude of growth factors, cytokines and oncogens transduce their growth-promoting signals via the activation of G-protein-coupled ras, which leads to the activation of the serine-threonine kinase Raf and to the activation of the mitogen-activated protein kinase kinase 1 and 2 (MAPKK1/2 or Mek1/2), and results in the phosphorylation and activation of MAPK 1 and 2—also known as extracellular signal-regulated kinase (Erk1 and 2). Compared to other single pathways, the ras-Raf-Mek-Erk signal pathway combines a large number of proto-oncogens, including ligands, tyrosine kinase receptors, G proteins, kinases and nuclear transcription factors. Tyrosine-kinases, for example EGFR (Mendelsohn J. et al., 2000) mediate, in the course of the tumour process, caused by overexpression and mutation, frequently constitutively active signals to the downstream ras-Raf-Mek-Erk signal pathway. Ras mutations have mutated in 30% of all human tumours (Khleif S. N. et al., 1999, Marshall C., 1999), the highest incidence at 90% being in pancreas carcinomas (Friess H. et al., 1996, Sirivatanauksorn V. et al., 1998). For c-Raf, deregulated expression and/or activation have been described in various tumours (Hoshino R. et al., 1999, McPhillips F. et al., 2001). B-Raf point mutants have been detected in 66% of all human malignant melanomas, 14% of ovarian carcinomas and 12% of colon carcinomas (Davies H. et al., 2002). It is therefore not surprising that Erk1/2 is involved at primary stage in many cellular processes, such as cell growth, cell proliferation and cell differentiation (Lewis T. S. et al., 1998, Chang F. et al., 2003).

In addition, the members of Raf kinases also have Mek-Erk-independent, anti-apoptotic functions whose molecular steps have not yet been described fully. Possible interaction partners described for the Mek-Erk-independent Raf activity have been Ask1, Bcl-2, Akt and Bag1 (Chen J et al., 2001, Troppmaier J. et al., 2003, Rapp U. R. et al., 2004, Gotz R. et al., 2005). It is now assumed that both Mek-Erk-dependent and Mek-Erk-independent signal transduction mechanisms control the activation of the up-stream ras and Raf stimuli.

The isoenzymes of the phosphatidylinositol 3-kinases (PI3Ks) function primarily as lipid kinases and catalyse the D3 phosphorylation of the second messenger lipids PtdIns (phosphatidylinositol) to PtdIns(3)P, PtdIns(3,4)$P_2$, PtdIns(3,4,5)$P_3$ phosphatidylinositol phosphates. The PI3Ks of class I are composed in structural terms of the catalytic subunit (p110alpha, beta, gamma, delta) and of the regulatory subunit (p85alpha, beta or p101gamma). In addition, the class II (PI3K-C2alpha, PI3K-C2beta) and class III (Vps34p) enzymes belong to the family of the PI3 kinases (Wymann M. P. et al., 1998, VanHaesebroeck B. et al., 2001). The PIP rise induced by the PI3Ks firstly activates the proliferative ras-Raf-Mek-Erk signal pathway via the coupling of ras (Rodriguez-Viciana P. et al., 1994) and secondly stimulates the anti-apoptotic signal pathway by recruiting Akt to the cell membrane and consequently overactivating this kinase (Alessi D. R. et al., 1996, Chang H. W. et al., 1997, Moore S. M. et al., 1998). Thus, the activation of the PI3Ks fulfills at least 2 crucial mechanisms of tumour development, specifically the activation of cell growth and cell differentiation, and the inhibition of apoptosis. In addition, the PI3Ks also have protein-phosphorylating properties (Dhand et al., 1994, Bondeva T. et al., 1998, Bondev A. et al., 1999, VanHaesebroeck B. et al., 1999), which, for example, can induce serine autophosphorylation which intrinsically regulates the PI3Ks. It is also known that PI3Ks have kinase-independent, regulating effector properties, for example in the control of heart contraction (Crackower M. A. et al., 2002, Patrucco et al., 2004). It has also been demonstrated that PI3Kdelta and PI3Kgamma are expressed specifically on haematopoietic cells and are thus potential points of attack for isoenzyme-specific PI3Kdelta and PI3Kgamma inhibitors in the treatment of inflammatory disorders such as rheumatism, asthmas and allergies and in the treatment of B and T cell lymphomas (Okkenhaug K., 2003, Ail K. et al., 2004, Sujobert P. et al., 2005). PI3Kalpha, which has recently been identified as a protooncogen (Shayesteh L. et al., 1999, Ma Y. Y. et al., 2000, Samuels Y. et al., 2004, Campbell I. G. et al., 2004, Levine D. A., 2005) is an important target in the therapy of tumour disorders. The significance of the PI3K species as a target for active ingredient development is therefore extremely wide (Chang F. & Lee J. T. et al, 2003).

Of equally great interest are the PI3K-related kinases (PIKKs), which include the serine/threonine kinases mTOR, ATM, ATR, h-SMG-1 and DNA-PK (Chiang G. G. et al 2004). Their catalytic domains have a high sequence homology to the catalytic domains of the PI3Ks.

Moreover, the loss of the tumour suppressor protein PTEN (Li J. et al., 1997, Steck P. A. et al., 1997)—whose function is the reversal of the phosphorylation initiated by PI3K—contributes to overactivation of Akt and its downstream cascade components and hence underlines the causal significance of PI3K as a target molecule for tumour therapy.

Various inhibitors of individual components of the ras-Raf-Mek-Erk and PI3K-Akt signal pathways have already been published and patented.

The current state of development in the field of the kinase-inhibitors, particularly of the ras-Raf-Mek-Erk and of the PI3K-Akt pathway, is detailed in the reviews by J. S. Sebolt-Leopold et al., 2004, and R. Wetzker et al., 2004. Said publications contain a comprehensive list of the published patents which describe the synthesis and use of low molecular weight ras-Raf-Mek-Erk and PI3K inhibitors.

The kinase inhibitor Bay 43-9006 (WO 99/32111, WO 03/068223) already in clinical trials exhibits a relatively unspecific inhibition pattern of serine/threonine kinases and of tyrosine kinases such as Raf, VEGFR2/3, Flt-3, PDGFR, c-Kit and further kinases. Great significance is attributed to this inhibitor in advanced tumour disorders induced by angiogenesis (for example in the case of kidney cell carcinoma) but also in the case of melanomas with high B-Raf mutation rate. The clinical action of Bay 43-9006 is currently also being determined in patients having refractory solid tumours in combination, for example, with docetaxel. To date, mild side effects and promising anti-tumour effects have been described. Inhibition of the kinases in the PI3K-Akt signal pathway has neither been described nor disclosed for Bay 43-9006.

The Mek1/2 inhibitor PD0325901 (WO 02/06213) is currently in phase I clinical trials. The precursor substance CI-1040 (WO 00/35435, WO 00/37141) was noticeable by its high Mek specificity and target affinity. However, this compound was found to be metabolically unstable in phase I/II studies. Clinical data for the current successor substance PD0325901 are still to come. However, neither interaction with Erk1 or Erk2 nor a function inhibiting the PI3K-Akt signal pathway or their simultaneous modulation has been published or disclosed for this Mek inhibitor.

The PI3K inhibitors published to date are still in preclinical trials. ICOS disclosed a PI3K inhibitor IC87114 with high PI3Kdelta isoenzyme specificity (WO 01/81346). For PI103 (WO 04/017950), Yamanouchi/Piramed describe a selectivity versus the PI3Kalpha isoform. Moreover, a highly noted field of research exists in the early development of PI3K inhibitors (see review of R. Wetzker et al., 2004).

Inhibitors of the SAPK signal pathway, either of Jnk or of p38, are described in the literature (Gum R. J., 1998, Bennett B. L. et al 2001, Davies S. P. et al 2000). However, no function of inhibiting the PI3Ks nor any specific inhibition of Erk1 or Erk2 or else any specific inhibition of SAPKs, Erk1, Erk2, or PI3Ks has been disclosed for these SAPK inhibitors.

6- or 7-substituted pyrido[2,3-b]pyrazine derivatives find wide use in pharmaceutical chemistry as pharmacologically active compounds and as synthetic units.

For example, the patents WO 04/104002 and WO 04/104003 describe pyrido[2,3-b]pyrazines which may be 6- or 7-substituted by urea, thiourea, amidine or guanidine groups. These compounds have properties as inhibitors or modulators of kinases, especially of tyrosine and serine/threonine kinases, and a use as a medicament is reported. In contrast, a use of these compounds as modulators of lipid kinases, alone or in combination with tyrosine and serine/threonine kinases, has not been described.

Moreover, the patent WO 99/17759 describes pyrido[2,3-b]pyrazines which bear, in the 6-position, inter alia, alkyl-, aryl- and heteroaryl-substituted carbamates. These compounds are intended for use to modulate the function of serine-threonine protein kinases.

The patent WO 05/007099 (Kawakami et al.) describes, inter alia, urea-substituted pyrido[2,3-b]pyrazines as inhibitors of the serine/threonine kinase PKB. However, this patent does not further define the R radical, which should describe the range of substitution on the urea, and the range of substitution on the urea is thus not clearly disclosed. For these compounds, use in the treatment of cancer disorders is reported. However, no specific examples of urea-substituted pyridopyrazines having these biological properties are given. In addition, the pyridopyrazines described here differ structurally significantly from the inventive pyrido[2,3-b]pyrazines described in this invention.

Further examples of 6- and 7-urea-substituted pyrido[2,3-b]pyrazines are reported in the patent WO 05/056547 (Bemis et al.). However, the compounds in this patent have additional carbonyl, sulphoxy, sulphone or imine substitution in the 2- or 3-position, which means that the compounds differ structurally significantly from the inventive pyrido[2,3-b]pyrazines described in this invention. The pyridopyrazines reported in WO 05/056547 are described as inhibitors of protein kinases, especially of GSK-3, Syk and JAK-3. For these compounds, the uses reported include use in the treatment of proliferative disorders. Use of these compounds as modulators of lipid kinases, alone or in combination with serine/threonine kinases, is not described.

The patent WO 04/005472 by White et al. describes, inter alia, 6-carbamate-substituted pyrido[2,3-b]pyrazines which, as antibacterial substances, inhibit the growth of bacteria. Antitumour action is not described.

Certain diphenylquinoxalines and -pyrido[2,3-b]pyrazines with specific alkylpyrrolidine, alkylpiperidine or alkylsulphonamide radicals on a phenyl ring, which may additionally also bear urea or carbamate substitutions in the 6- or 7-position, are described in the patents WO 03/084473 (Barnett et al.), WO 03/086394 (Bilodeau et al.) and WO 03/086403 (Lindsley et al.) as inhibitors of the activity of the serine/threonine kinase Akt. For these compounds, use in the treatment of cancer disorders is reported. For the pyrido[2,3-b]pyrazine example compounds described there, no defined indication of biological action is specified. Moreover, there is a significant structural difference from the inventive pyrido[2,3-b]pyrazines described in this invention.

Moreover, the patent WO 03/024448 by Delorme et al. describes amide- and acrylamide-substituted pyrido[2,3-b]pyrazines which also contain carbamates as additional substitutents and can be used as histone deacetylase inhibitors for the treatment of cell proliferation disorders.

A further publication (C. Temple, Jr.; *J. Med. Chem.* 1990, 3044-3050) uses an example to describe the synthesis of a 6-ethyl carbamate-substituted pyrido[2,3-b]pyrazine derivative. Antitumour action is neither disclosed nor rendered obvious.

The synthesis of further derivatives of the 6-ethyl carbamate-substituted pyrido[2,3-b]pyrazine is described in a publication by R. D. Elliott (*J. Org. Chem.* 1968, 2393-2397). Biological action of these compounds is neither described nor rendered obvious.

The publication by C. Temple, Jr. *J. Med. Chem.* 1968, 1216-1218 describes the synthesis and examination of 6-ethyl carbamate-substituted pyrido[2,3-b]pyrazines as potential active antimalarial ingredients. Antitumour action is neither disclosed nor rendered obvious.

STATEMENT OF THE INVENTION

The invention is therefore directed to the provision of novel compounds which are suitable as modulators of receptor tyrosine kinases, of cytoplasmic tyrosine kinases, serine/threonine kinases and lipid kinases. Since not all kinases which are present in series in misregulated signal transduction cascades—for example in the case of Raf-Mek-Erk or PI3K-Akt-, need be present as oncogenic kinases or as constitutively active enzymes, this invention also considers the inactive kinases as therapeutic target proteins, i.e. the novel compounds can bind both to active and to inactive kinases and hence influence signal transduction.

The invention is also directed to the provision of novel compounds which, as modulators of receptor tyrosine kinases, cytoplasmic tyrosine kinases, serine/threonine kinases and lipid kinases, have the property of influencing either an individual kinase or two or more kinases, especially Erk1/2 and PI3K, from one signal transduction cascade or different signal transduction cascades, especially ras-Raf-Mek-Erk and PI3K-Akt. A dual mechanism, i.e. the simultaneous inhibition of two or more signal transduction cascades compared to the therapeutic attack on only one signal transduction pathway, should, by virtue of the additive effect, lead to an increase in the effect in the treatment of all pathogenic processes which are influenced by kinases.

It has now been found that, surprisingly, novel compounds from the group of the pyrido[2,3-b]pyrazines which are 6- or 7-substituted, for example by urea or thiourea moieties, are suitable for producing medicaments for modulating misdirected cellular signal transduction processes, especially for influencing the function of receptor tyrosine kinases, cytoplasmic tyrosine kinases, serine/threonine kinases and lipid kinases, and for treating malignant or benign tumour disorders, for example of the breast, prostate, lung, skin, ovaries, and other disorders based on pathological cell proliferations.

A first aspect of the present application describes novel compounds from the group of the pyrido[2,3-b]pyrazines of the general formula (I)

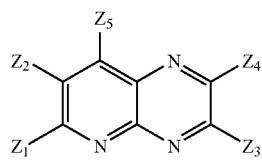

(I)

in which:
(A) one of the Z3, Z4 radicals is, or both Z3, Z4 radicals are, independently "substituted aryl", where "substituted aryl" is substituted by at least one substituent selected identically or differently from the group consisting of:
  (a) "alkyl, cycloalkyl, heterocyclyl, aryl, heteroaryl, —NH—X1, —N(alkyl)₂, —NHC(O)-alkyl, —NHC(O)-cycloalkyl, —NHC(O)-heterocyclyl, —NHC(O)-aryl, —NHC(O)-heteroaryl, —NHC(O)-arylalkyl, —NHC(O)-heteroarylalkyl, —NHS(O₂)-alkyl, —NHS(O₂)-cycloalkyl, —NHS(O₂)-heterocyclyl, —NHS(O₂)-aryl, —NHS(O₂)-heteroaryl, —NHS(O₂)-arylalkyl, —NHS(O₂)-heteroarylalkyl, —S-alkyl, —S-aryl, —S-heteroaryl, —O—X2, —OC(O)-alkyl, —OC(O)-cycloalkyl, —OC(O)-heterocyclyl, —OC(O)-aryl, —OC(O)-heteroaryl, —OC(O)-arylalkyl, —OC(O)-heteroarylalkyl, —OS(O₂)-alkyl, —OS(O₂)-cycloalkyl, —OS(O₂)-heterocyclyl, —OS(O₂)-aryl, —OS(O₂)-heteroaryl, —OS(O₂)-arylalkyl, —OS(O₂)-heteroarylalkyl, —C(O)-alkyl, —C(O)-aryl, —C(O)-heteroaryl, —C(O)O—X3, —C(O)NH—X4, —C(O)N(alkyl)₂, —C(O)N(cycloalkyl)₂, —C(O)N(aryl)₂, —C(O)N(heteroaryl)₂, —S(O)-alkyl, —S(O)-aryl, —S(O₂)-alkyl, —S(O₂)-aryl, —S(O₂)NH-alkyl, —S(O₂)NH-aryl, —S(O₂)NH-heteroaryl, —S(O₂)NH-arylalkyl, S(O₂)O-alkyl, —S(O₂)O-aryl, —S(O₂)O-arylalkyl";
  where X1, X2, X3, X4 are each independently selected from the group consisting of: "alkyl, cycloalkyl, cycloalkylalkyl, heterocyclyl, heterocyclylalkyl, aryl, arylalkyl, heteroaryl, heteroarylalkyl";
  with the proviso that the above substituents of substituent group (a) are each independently substituted further by at least one substituent selected identically or differently from the group consisting of:
    (i) "(C₉-C₃₀)alkyl, cycloalkyl, cycloalkylalkyl, heterocyclyl, heterocyclylalkyl, aryl, arylalkyl, heteroaryl, heteroarylalkyl, N₃, —NH-cycloalkyl, —NH-cycloalkylalkyl, —NH-heteroaryl, —NH-heteroarylalkyl, —NH-arylalkyl, —NH-heterocyclyl, —NH-heterocyclylalkyl, —NX5X6, —S-cycloalkyl, —S-cycloalkylalkyl, —S-aryl, —S-arylalkyl, —S-heteroaryl, —S-heteroarylalkyl, —S-heterocyclyl, —S-heterocyclylalkyl, —O-cycloalkyl, —O-cycloalkylalkyl, —O-arylalkyl, —O-heteroaryl, —O-heteroarylalkyl, —O-heterocyclyl, —O-heterocyclylalkyl, —O(—X7-O)ₚ—X8 (p=1, 2, 3, 4, 5), —OP(O)(OX9)(OX10), —C(O)O—X11, —C(O)NH₂, —C(O)NH—X12, —C(O)NX13X14, —S(O₂)—X15, —P(O)(OH)₂, —P(O)(OX16)(OX17), —Si(X18)(X19)(X20), —O—Si(X21)(X22)(X23), —O—C(O)—O—X24, —O—C(O)—NH—X25, —O—C(O)—NX26X27, —NH—C(O)—O—X28, —NH—C(O)—NH—X29, —NH—C(O)—NX30X31, —NX32-C(O)—O—X33, —NX34-C(O)—NH—X35, —NX36-C(O)—NX37X38, —O—S(O₂)—X39, —NH—C(O)—X40, —NX41-C(O)—X42, —C(O)—X43, —OC(O)—X44, —S(O)—X45, —S(O₂)—NHX46, —S(O₂)—NX47X48, —S(O₂)—OX49, —O(—X50-O)ₚ—H (p=1, 2, 3, 4, 5)";
    with the further proviso that "—N(alkyl)₂" is further substituted by at least one substituent selected from the following substituent group (b);
    where X5, X6, X7, X8, X9, X10, X11, X12, X13, X14, X15, X16, X17, X18, X19, X20, X21, X22, X23, X24, X25, X26, X27, X28, X29, X30, X31, X32, X33, X34, X35, X36, X37, X38, X39, X40, X41, X42, X43, X44, X45, X46, X47, X48, X49, X50 are each independently selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and where, alternatively, X13, X14 and/or X26, X27 and/or X30, X31 and/or X37, X38 and/or X47, X48 together may also form "heterocyclyl";

and with the further proviso that when one of the Z3 or Z4 radicals is "substituted aryl" substituted by "heterocyclylalkyl", the other Z3 or Z4 radical in each case is not "substituted or unsubstituted aryl";

where, optionally, additionally one of the Z3, Z4 radicals or additionally both Z3, Z4 radicals may each independently be further substituted by at least one substituent selected identically or differently from the group consisting of:

(b) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHX51, —NX52X53, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)—X54, —C(O)O—X55, —C(O)NH—X56, —C(O)NX57X58, —O—X59, —O(—X60-O)$_r$—H (r=1, 2, 3, 4, 5), —O(—X61-O)$_r$—X62 (r=1, 2, 3, 4, 5), —OC(O)—X63, —OC(O)—O—X64, —OC(O)—NHX65, —O—C(O)—NX66X67, —OP(O)(OX68)(OX69), —OSi(X70)(X71)(X72), —OS(O$_2$)—X73, —NHC(O)—X74, —NX75C(O)—X76, —NH—C(O)—O—X77, —NH—C(O)—NH—X78, —NH—C(O)—NX79X80, —NX81-C(O)—O—X82, —NX83-C(O)—NH—X84, —NX85-C(O)—NX86X87, —NHS(O$_2$)—X88, —NX89S(O$_2$)—X90, —S—X91, —S(O)—X92, —S(O$_2$)—X93, —S(O$_2$)NH—X94, —S(O$_2$)NX95X96, —S(O$_2$)O—X97, —P(O)(OX98)(OX99), —Si(X100)(X101)(X102)";

where X51, X52, X53, X54, X55, X56, X57, X58, X59, X60, X61, X62, X63, X64, X65, X66, X67, X68, X69, X70, X71, X72, X73, X74, X75, X76, X77, X78, X79, X80, X81, X82, X83, X84, X85, X86, X87, X88, X89, X90, X91, X92, X93, X94, X95, X96, X97, X98, X99, X100, X101, X102 are each independently selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and where, alternatively, X57, X58 and/or X66, X67 and/or X79, X80 and/or X86, X87 and/or X95, X96 together may also form "heterocyclyl";

where, optionally, the above substituents of substituent group (b) may each independently in turn be substituted by at least one substituent selected identically or differently from the group consisting of:

(ii) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHX103, —NX104X105, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)—X106, —C(O)O—X107, —C(O)NH—X108, —C(O)NX109X110, —O—X111, —O(—X112-O)$_s$—H (s=1, 2, 3, 4, 5), —O(—X113-O)$_s$—X114 (s=1, 2, 3, 4, 5), —OC(O)—X115, —OC(O)—O—X116, —OC(O)—NHX117, —O—C(O)—NX118X119, —OP(O)(OX120)(OX121), —OSi(X122)(X123)(X124), —OS(O$_2$)—X125, —NHC(O)—X126, —NX127C(O)—X128, —NH—C(O)—O—X129, —NH—C(O)—NH—X130, —NH—C(O)—NX131X132, —NX133-C(O)—O—X134, —NX135-C(O)—NH—X136, —NX137-C(O)—NX138X139, —NHS(O$_2$)—X140, —NX141S(O$_2$)—X142, —S—X143, —S(O)—X144, —S(O$_2$)—X145, —S(O$_2$)NH—X146, —S(O$_2$)NX147X148, —S(O$_2$)O—X149, —P(O)(OX150)(OX151), —Si(X152)(X153)(X154)";

where X103, X104, X105, X106, X107, X108, X109, X110, X111, X112, X113, X114, X115, X116, X117, X118, X119, X120, X121, X122, X123, X124, X125, X126, X127, X128, X129, X130, X131, X132, X133, X134, X135, X136, X137, X138, X139, X140, X141, X142, X143, X144, X145, X146, X147, X148, X149, X150, X151, X152, X153, X154 are each independently selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and where, alternatively, X109, X110 and/or X118, X119 and/or X131, X132 and/or X138, X139 and/or X147, X148 together may also form "heterocyclyl";

where, optionally, the above substituents of substituent group (i) and/or substituent group (ii) may each independently in turn be substituted by at least one substituent selected identically or differently from the group consisting of:

(iii) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHX155, —NX156X157, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)—X158, —C(O)O—X159, —C(O)NH—X160, —C(O)NX161X162, —O—X163, —O(—X164-O)$_t$—H (t=1, 2, 3, 4, 5), —O(—X165-O)$_t$—X166 (t=1, 2, 3, 4, 5), —OC(O)—X167, —OC(O)—O—X168, —OC(O)—NHX169, —O—C(O)—NX170X171, —OP(O)(OX172)(OX173), —OSi(X174)(X175)(X176), —OS(O$_2$)—X177, —NHC(O)—X178, —NX179C(O)—X180, —NH—C(O)—O—X181, —NH—C(O)—NH—X182, —NH—C(O)—NX183X184, —NX185-C(O)—O—X186, —NX187-C(O)—NH—X188, —NX189-C(O)—NX190X191, —NHS(O$_2$)—X192, —NX193S(O$_2$)—X194, —S—X195, —S(O)—X196, —S(O$_2$)—X197, —S(O$_2$)NH—X198, —S(O$_2$)NX199X200, —S(O$_2$)O—X201, —P(O)(OX202)(OX203), —Si(X204)(X205)(X206)";

where X155, X156, X157, X158, X159, X160, X161, X162, X163, X164, X165, X166, X167, X168, X169, X170, X171, X172, X173, X174, X175, X176, X177, X178, X179, X180, X181, X182, X183, X184, X185, X186, X187, X188, X189, X190, X191, X192, X193, X194, X195, X196, X197, X198, X199, X200, X201, X202, X203, X204, X205, X206 are each independently selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and where, alternatively, X161, X162 and/or X170, X171 and/or X183, X184 and/or X190, X191 and/or X199, X200 together may also form "heterocyclyl";

or one of the Z3, Z4 radicals is, or both Z3, Z4 radicals are, independently "substituted aryl", where "substituted aryl" is substituted by at least one substituent selected identically or differently from the group consisting of:

(c) "$(C_9-C_{30})$alkyl, —NX207X208, —NH—$(C_9-C_{30})$alkyl, —NHC(O)-cycloalkylalkyl, —NHC(O)-heterocyclylalkyl, —NHC(O)—$(C_9-C_{30})$alkyl, —NX209C(O)—X210, —NX211C(O)—$(C_9-C_{30})$alkyl, —NHC(O)—OX212, —NX213C(O)—OX214, —NHC(O)—NHX215, —NHC(O)—NX216X217, —NX218C(O)—NHX219, —NX220C(O)—NX221X222, —NHS(O$_2$)-cycloalkylalkyl, —NHS(O$_2$)-heterocyclylalkyl, —NX223S(O$_2$)—X224, —O—$(C_9-C_{30})$alkyl, —S-cycloalkyl, —S-heterocyclyl, —S-arylalkyl, —S-heteroarylalkyl, —S-cycloalkylalkyl, —S-heterocyclylalkyl, —S—$(C_9-C_{30})$alkyl, —OC(O)-cycloalkylalkyl, —OC(O)-heterocyclylalkyl, —OC(O)—$(C_9-C_{30})$alkyl, —OS(O$_2$)-cycloalkylalkyl, —OS(O$_2$)-heterocyclylalkyl, —OS(O$_2$)—$(C_9-C_{30})$alkyl, —OC(O)—OX225, —OC(O)—NHX226, —OC(O)—NX227X228, —OP(O)(OX229)(OX230), —C(O)-cycloalkyl, —C(O)-heterocyclyl, —C(O)-arylalkyl, —C(O)-heteroarylalkyl, —C(O)-cycloalkylalkyl, —C(O)-heterocyclylalkyl, —C(O)—$(C_9-C_{30})$alkyl, —C(O)O—$(C_9-C_{30})$alkyl, —C(O)NH—$(C_9-C_{30})$alkyl, —C(O)NX231X232, —C(O)NH—OX233, —C(O)NX234-OX235, —C(O)NH—NX236X237, —C(O)NX238-NX239X240, —S(O)-cycloalkyl, —S(O)-heterocyclyl, —S(O)-heteroaryl, —S(O)-arylalkyl, —S(O)-heteroarylalkyl, —S(O)-cycloalkylalkyl, —S(O)-heterocyclylalkyl, —S(O)—$(C_9-C_{30})$alkyl, —S(O$_2$)-cycloalkyl, —S(O$_2$)-heterocyclyl, —S(O$_2$)-heteroaryl, —S(O$_2$)-arylalkyl, —S(O$_2$)-heteroarylalkyl, —S(O$_2$)-cycloalkylalkyl, —S(O$_2$)-heterocyclylalkyl, —S(O$_2$)—$(C_9-C_{30})$alkyl, —S(O$_2$)NH-cycloalkyl, —S(O$_2$)NH-heterocyclyl, —S(O$_2$)NH-heteroarylalkyl, —S(O$_2$)NH-cycloalkylalkyl, —S(O$_2$)NH-heterocyclylalkyl, —S(O$_2$)NH—$(C_9-C_{30})$alkyl, —S(O$_2$)O-cycloalkyl, —S(O$_2$)O-heterocyclyl, —S(O$_2$)O-heteroaryl, —S(O$_2$)O-heteroarylalkyl, —S(O$_2$)O-cycloalkylalkyl, —S(O$_2$)O-heterocyclylalkyl, —S(O$_2$)O—$(C_9-C_{30})$alkyl, —P(O)(OH)$_2$, —P(O)(OX241)(OX242), —Si(X243)(X244)(X245), —O—Si(X246)(X247)(X248)";

where X207, X208, X209, X210, X211, X212, X213, X214, X215, X216, X217, X218, X219, X220, X221, X222, X223, X224, X225, X226, X227, X228, X229, X230, X231, X232, X233, X234, X235, X236, X237, X238, X239, X240, X241, X242, X243, X244, X245, X246, X247, X248 are each independently selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and where, alternatively, X216, X217 and/or X221, X222 and/or X227, X228 and/or X231, X232 and/or X236, X237 and/or X239, X240, in each case together, may also form "heterocyclyl";

with the proviso that the substituents "—N(alkyl)$_2$", "—C(O)N(alkyl)$_2$", "—C(O)N(cycloalkyl)$_2$", "—C(O)N(aryl)$_2$", "—C(O)N(heteroaryl)$_2$" are substituted further by at least one substituent selected from the following substituent group (i);

with the further proviso that when one of the Z3 or Z4 radicals is "substituted aryl" substituted by "heterocyclylalkyl", the other Z3 or Z4 radical in each case is not "unsubstituted or substituted aryl";

where, optionally, the above substituents of substituent group (c) may each independently in turn be substituted by at least one substituent selected identically or differently from the group consisting of:

(i) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHX249, —NX250X251, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—X252, —C(O)O—X253, —C(O)NH—X254, —C(O)NX255X256, —O—X257, —O(—X258-O)$_u$—H (u=1, 2, 3, 4, 5), —O(—X259-O)$_u$—X260 (u=1, 2, 3, 4, 5), —OC(O)—X261, —OC(O)—O—X262, —OC(O)—NHX263, —O—C(O)—NX264X265, —OP(O)(OX266)(OX267), —OSi(X268)(X269)(X270), —OS(O$_2$)—X271, —NHC(O)—X272, —NX273C(O)—X274, —NH—C(O)—O—X275, —NH—C(O)—NH—X276, —NH—C(O)—NX277X278, —NX279-C(O)—O—X280, —NX281-C(O)—NH—X282, —NX283-C(O)—NX284X285, —NHS(O$_2$)—X286, —NX287S(O$_2$)—X288, —S—X289, —S(O)—X290, —S(O$_2$)—X291, —S(O$_2$)NH—X292, —S(O$_2$)NX293X294, —S(O$_2$)O—X295, —P(O)(OX296)(OX297), —Si(X298)(X299)(X300)";

where X249, X250, X251, X252, X253, X254, X255, X256, X257, X258, X259, X260, X261, X262, X263, X264, X265, X266, X267, X268, X269, X270, X271, X272, X273, X274, X275, X276, X277, X278, X279, X280, X281, X282, X283, X284, X285, X286, X287, X288, X289, X290, X291, X292, X293, X294, X295, X296, X297, X298, X299, X300 are each independently selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and where, alternatively, X255, X256 and/or X264, X265 and/or X277, X278 and/or X284, X285 and/or X293, X294, in each case together, may also form "heterocyclyl";

where, optionally, additionally one of the Z3, Z4 radicals or additionally both Z3, Z4 radicals may each independently be further substituted by at least one substituent selected identically or differently from the group consisting of:

(d) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHX301, —NX302X303, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—X304, —C(O)O—X305, —C(O)NH—X306, —C(O)NX307X308, —O—X309, —O(—X310-O)$_{uu}$—H (uu=1, 2, 3, 4, 5), —O(—X311-O)$_{uu}$—X312 (uu=1, 2, 3, 4, 5), —OC(O)—X313, —OC(O)—O—X314, —OC(O)—NHX315, —O—C(O)—NX316X317, —OP(O)(OX318)(OX319), —OSi(X320)(X321)(X322), —OS(O$_2$)—X323, —NHC(O)—X324, —NX325C(O)—X326, —NH—C(O)—O—X327, —NH—C(O)—NH—X328, —NH—C(O)—NX329X330, —NX331-C(O)—O—X332, —NX333-C(O)—NH—X334, —NX335-C(O)—NX336X337, —NHS(O$_2$)—X338, —NX339S(O$_2$)—X340, —S—X341, —S(O)—X342, —S(O$_2$)—X343, —S(O$_2$)NH—X344, —S(O$_2$)NX345X346, —S(O$_2$)O—X347, —P(O)(OX348)(OX349), —Si(X350)(X351)(X352)";

where X301, X302, X303, X304, X305, X306, X307, X308, X309, X310, X311, X312, X313, X314, X315, X316, X317, X318, X319, X320, X321, X322, X323, X324, X325, X326, X327, X328, X329, X330, X331, X332, X333, X334, X335, X336, X337, X338, X339, X340, X341, X342, X343, X344, X345, X346, X347, X348, X349, X350, X351, X352 are each independently selected from the group consisting of: "alkyl, ($C_9$-$C_{30}$) alkyl, cycloalkyl, cycloalkylalkyl, heterocyclyl, heterocyclylalkyl, aryl, arylalkyl, heteroaryl, heteroarylalkyl" and where, alternatively, X307, X308 and/or X316, X317 and/or X329, X330 and/or X336, X337 and/or X345, X346, in each case together, may also form "heterocyclyl";

where, optionally, the above substituents of substituent group (d) may each independently in turn be substituted by at least one substituent selected identically or differently from the group consisting of:

(ii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHX353, —NX354X355, —$NO_2$, —OH, —$OCF_3$, —SH, —O—$SO_3H$, —OP(O)$(OH)_2$, —CHO, —COOH, —C(O)$NH_2$, —$SO_3H$, —P(O)$(OH)_2$, —C(O)—X356, —C(O)O—X357, —C(O)NH—X358, —C(O)NX359X360, —O—X361, —O(—X362-O)$_v$—H (v=1, 2, 3, 4, 5), —O(—X363-O)$_v$—X364 (v=1, 2, 3, 4, 5), —OC(O)—X365, —OC(O)—O—X366, —OC(O)—NHX367, —O—C(O)—NX368X369, —OP(O)(OX370)(OX371), —OSi(X372)(X373)(X374), —OS($O_2$)—X375, —NHC(O)—X376, —NX377C(O)—X378, —NH—C(O)—O—X379, —NH—C(O)—NH—X380, —NH—C(O)—NX381X382, —NX383-C(O)—O—X384, —NX385-C(O)—NH—X386, —NX387-C(O)—NX388X389, —NHS($O_2$)—X390, —NX391S($O_2$)—X392, —S—X393, —S(O)—X394, —S($O_2$)—X395, —S($O_2$)NH—X396, —S($O_2$)NX397X398, —S($O_2$)O—X399, —P(O)(OX400)(OX401), —Si(X402)(X403)(X404)";

where X353, X354, X355, X356, X357, X358, X359, X360, X361, X362, X363, X364, X365, X366, X367, X368, X369, X370, X371, X372, X373, X374, X375, X376, X377, X378, X379, X380, X381, X382, X383, X384, X385, X386, X387, X388, X389, X390, X391, X392, X393, X394, X395, X396, X397, X398, X399, X400, X401, X402, X403, X404 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, X359, X360 and/or X368, X369 and/or X381, X382 and/or X388, X389 and/or X397, X398, in each case together, may also form "heterocyclyl";

where, optionally, the above substituents of substituent group (i) and/or substituent group (ii) may each independently in turn be substituted by at least one substituent selected identically or differently from the group consisting of:

(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHX405, —NX406X407, —$NO_2$, —OH, —$OCF_3$, —SH, —O—$SO_3H$, —OP(O)$(OH)_2$, —CHO, —COOH, —C(O)$NH_2$, —$SO_3H$, —P(O)$(OH)_2$, —C(O)—X408, —C(O)O—X409, —C(O)NH—X410, —C(O)NX411X412, —O—X413, —O(—X414-O)$_w$—H (w=1, 2, 3, 4, 5), —O(—X415-O)$_w$—X416 (w=1, 2, 3, 4, 5), —OC(O)—X417, —OC(O)—O—X418, —OC(O)—NHX419, —O—C(O)—NX420X421, —OP(O)(OX422)(OX423), —OSi(X424)(X425)(X426), —OS($O_2$)—X427, —NHC(O)—X428, —NX429C(O)—X430, —NH—C(O)—O—X431, —NH—C(O)—NH—X432, —NH—C(O)—NX433X434, —NX435-C(O)—O—X436, —NX437-C(O)—NH—X438, —NX439-C(O)—NX440X441, —NHS($O_2$)—X442, —NX443S($O_2$)—X444, —S—X445, —S(O)—X446, —S($O_2$)—X447, —S($O_2$)NH—X448, —S($O_2$)NX449X450, —S($O_2$)O—X451, —P(O)(OX452)(OX453), —Si(X454)(X455)(X456)";

where X405, X406, X407, X408, X409, X410, X411, X412, X413, X414, X415, X416, X417, X418, X419, X420, X421, X422, X423, X424, X425, X426, X427, X428, X429, X430, X431, X432, X433, X434, X435, X436, X437, X438, X439, X440, X441, X442, X443, X444, X445, X446, X447, X448, X449, X450, X451, X452, X453, X454, X455, X456 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, X411, X412 and/or X420, X421 and/or X433, X434 and/or X440, X441 and/or X449, X450, in each case together, may also form "heterocyclyl";

and one of the Z3, Z4 radicals or neither of the Z3, Z4 radicals is independently selected from the group consisting of:

(e) hydrogen;

(f) halogen, F, Cl, Br, I;

(g) unsubstituted or substituted alkyl or ($C_9$-$C_{30}$)alkyl, where, optionally, the alkyl or ($C_9$-$C_{30}$)alkyl radical may be substituted by at least one substituent selected identically or differently from the group consisting of:

(i) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHX457, —NX458X459, —$NO_2$, —OH, —$OCF_3$, —SH, —O—$SO_3H$, —OP(O)$(OH)_2$, —CHO, —COOH, —C(O)$NH_2$, —$SO_3H$, —P(O)$(OH)_2$, —C(O)—X460, —C(O)O—X461, —C(O)NH—X462, —C(O)NX463X464, —O—X465, —O(—X466-O)$_x$—H (x=1, 2, 3, 4, 5), —O(—X467-O)$_x$—X468 (x=1, 2, 3, 4, 5), —OC(O)—X469, —OC(O)—O—X470, —OC(O)—NHX471, —O—C(O)—NX472X473, —OP(O)(OX474)(OX475), —OSi(X476)(X477)(X478), —OS($O_2$)—X479, —NHC(O)—X480, —NX481C(O)—X482, —NH—C(O)—O—X483, —NH—C(O)—NH—X484, —NH—C(O)—NX485X486, —NX487-C(O)—O—X488, —NX489-C(O)—NH—X490, —NX491-C(O)—NX492X493, —NHS($O_2$)—X494, —NX495S($O_2$)—X496, —S—X497, —S(O)—X498, —S($O_2$)—X499, —S($O_2$)NH—X500, —S($O_2$)NX501X502, —S($O_2$)O—X503, —P(O)(OX504)(OX505), —Si(X506)(X507)(X508)";

where X457, X458, X459, X460, X461, X462, X463, X464, X465, X466, X467, X468, X469, X470, X471, X472, X473, X474, X475, X476, X477, X478, X479, X480, X481, X482, X483, X484, X485, X486, X487, X488, X489, X490, X491, X492, X493, X494, X495, X496, X497, X498, X499, X500, X501, X502, X503, X504, X505, X506, X507, X508 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, X463, X464 and/or X472, X473 and/or X485, X486 and/or X492, X493 and/or X501, X502, in each case together, may also form "heterocyclyl";

where, optionally, the above substituents of substituent group (i) may in turn each independently be substituted by at least one substituent selected identically or differently from the group consisting of:

(ii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHX509, —NX510X511, —$NO_2$, —OH, —$OCF_3$, —SH, —O—$SO_3H$, —OP(O)(OH)$_2$, —CHO, —COOH, —C(O)$NH_2$, —$SO_3H$, —P(O)(OH)$_2$, —C(O)—X512, —C(O)O—X513, —C(O)NH—X514, —C(O)NX515X516, —O—X517, —O(—X518-O)$_y$—H (y=1, 2, 3, 4, 5), —O(—X519-O)$_y$—X520 (y=1, 2, 3, 4, 5), —OC(O)—X521, —OC(O)—O—X522, —OC(O)—NHX523, —O—C(O)—NX524X525, —OP(O)(OX526)(OX527), —OSi(X528)(X529)(X530), —OS($O_2$)—X531, —NHC(O)—X532, —NX533C(O)—X534, —NH—C(O)—O—X535, —NH—C(O)—NH—X536, —NH—C(O)—NX537X538, —NX539-C(O)—O—X540, —NX541-C(O)—NH—X542, —NX543-C(O)—NX544X545, —NHS($O_2$)—X546, —NX547S($O_2$)—X548, —S—X549, —S(O)—X550, —S($O_2$)—X551, —S($O_2$)NH—X552, —S($O_2$)NX553X554, —S($O_2$)O—X555, —P(O)(OX556)(OX557), —Si(X558)(X559)(X560)";

where X509, X510, X511, X512, X513, X514, X515, X516, X517, X518, X519, X520, X521, X522, X523, X524, X525, X526, X527, X528, X529, X530, X531, X532, X533, X534, X535, X536, X537, X538, X539, X540, X541, X542, X543, X544, X545, X546, X547, X548, X549, X550, X551, X552, X553, X554, X555, X556, X557, X558, X559, X560 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, X515, X516 and/or X524, X525 and/or X537, X538 and/or X544, X545 and/or X553, X554, in each case together, may also form "heterocyclyl";

where, optionally, the above substituents of substituent group (ii) may in turn each independently be substituted by at least one substituent selected identically or differently from the group consisting of:

(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHX561, —NX562X563, —$NO_2$, —OH, —$OCF_3$, —SH, —O—$SO_3H$, —OP(O)(OH)$_2$, —CHO, —COOH, —C(O)$NH_2$, —$SO_3H$, —P(O)(OH)$_2$, —C(O)—X564, —C(O)O—X565, —C(O)NH—X566, —C(O)NX567X568, —O—X569, —O(—X570-O)$_z$—H (z=1, 2, 3, 4, 5), —O(—X571-O)$_z$—X572 (z=1, 2, 3, 4, 5), —OC(O)—X573, —OC(O)—O—X574, —OC(O)—NHX575, —O—C(O)—NX576X577, —OP(O)(OX578)(OX579), —OSi(X580)(X581)(X582), —OS($O_2$)—X583, —NHC(O)—X584, —NX585C(O)—X586, —NH—C(O)—O—X587, —NH—C(O)—NH—X588, —NH—C(O)—NX589X590, —NX591-C(O)—O—X592, —NX593-C(O)—NH—X594, —NX595-C(O)—NX596X597, —NHS($O_2$)—X598, —NX599S($O_2$)—X600, —S—X601, —S(O)—X602, —S($O_2$)—X603, —S($O_2$)NH—X604, —S($O_2$)NX605X606, —S($O_2$)O—X607, —P(O)(OX608)(OX609), —Si(X610)(X611)(X612)";

where X561, X562, X563, X564, X565, X566, X567, X568, X569, X570, X571, X572, X573, X574, X575, X576, X577, X578, X579, X580, X581, X582, X583, X584, X585, X586, X587, X588, X589, X590, X591, X592, X593, X594, X595, X596, X597, X598, X599, X600, X601, X602, X603, X604, X605, X606, X607, X608, X609, X610, X611, X612 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, X567, X568 and/or X576, X577 and/or X589, X590 and/or X596, X597 and/or X605, X606, in each case together, may also form "heterocyclyl";

(h) unsubstituted or substituted aryl where, optionally, the aryl radical may be substituted by at least one substituent selected identically or differently from the group consisting of:

(i) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHX613, —NX614X615, —$NO_2$, —OH, —$OCF_3$, —SH, —O—$SO_3H$, —OP(O)(OH)$_2$, —CHO, —COOH, —C(O)$NH_2$, —$SO_3H$, —P(O)(OH)$_2$, —C(O)—X616, —C(O)O—X617, —C(O)NH—X618, —C(O)NX619X620, —O—X621, —O(—X622-O)$_a$—H (a=1, 2, 3, 4, 5), —O(—X623-O)$_a$—X624 (a=1, 2, 3, 4, 5), —OC(O)—X625, —OC(O)—O—X626, —OC(O)—NHX627, —O—C(O)—NX628X629, —OP(O)(OX630)(OX631), —OSi(X632)(X633)(X634), —OS($O_2$)—X635, —NHC(O)—X636, —NX637C(O)—X638, —NH—C(O)—O—X639, —NH—C(O)—NH—X640, —NH—C(O)—NX641X642, —NX643-C(O)—O—X644, —NX645-C(O)—NH—X646, —NX647-C(O)—NX648X649, —NHS($O_2$)—X650, —NX651S($O_2$)—X652, —S—X653, —S(O)—X654, —S($O_2$)—X655, —S($O_2$)NH—X656, —S($O_2$)NX657X658, —S($O_2$)O—X659, —P(O)(OX660)(OX661), —Si(X662)(X663)(X664)";

where X613, X614, X615, X616, X617, X618, X619, X620, X621, X622, X623, X624, X625, X626, X627, X628, X629, X630, X631, X632, X633, X634, X635, X636, X637, X638, X639, X640, X641, X642, X643, X644, X645, X646, X647, X648, X649, X650, X651, X652, X653, X654, X655, X656, X657, X658, X659, X660, X661, X662, X663, X664 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, X619, X620 and/or X628, X629 and/or X641, X642 and/or X648, X649 and/or X657, X658, in each case together, may also form "heterocyclyl";

where, optionally, the above substituents of substituent group (i) may in turn each independently be substituted by at least one substituent selected identically or differently from the group consisting of:
(ii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHX665, —NX666X667, —$NO_2$, —OH, —$OCF_3$, —SH, —O—$SO_3$H, —OP(O)(OH)$_2$, —CHO, —COOH, —C(O)$NH_2$, —$SO_3$H, —P(O)(OH)$_2$, —C(O)—X668, —C(O)O—X669, —C(O)NH—X670, —C(O)NX671X672, —O—X673, —O(—X674-O)$_b$—H (b=1, 2, 3, 4, 5), —O(—X675-O)$_b$—X676 (b=1, 2, 3, 4, 5), —OC(O)—X677, —OC(O)—O—X678, —OC(O)—NHX679, —O—C(O)—NX680X681, —OP(O)(OX682)(OX683), —OSi(X684)(X685)(X686), —OS($O_2$)—X687, —NHC(O)—X688, —NX689C(O)—X690, —NH—C(O)—O—X691, —NH—C(O)—NH—X692, —NH—C(O)—NX693X694, —NX695-C(O)—O—X696, —NX697-C(O)—NH—X698, —NX699-C(O)—NX700X701, —NHS($O_2$)—X702, —NX703S($O_2$)—X704, —S—X705, —S(O)—X706, —S($O_2$)—X707, —S($O_2$)NH—X708, —S($O_2$)NX709X710, —S($O_2$)O—X711, —P(O)(OX712)(OX713), —Si(X714)(X715)(X716)";
where X665, X666, X667, X668, X669, X670, X671, X672, X673, X674, X675, X676, X677, X678, X679, X680, X681, X682, X683, X684, X685, X686, X687, X688, X689, X690, X691, X692, X693, X694, X695, X696, X697, X698, X699, X700, X701, X702, X703, X704, X705, X706, X707, X708, X709, X710, X711, X712, X713, X714, X715, X716 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, X671, X672 and/or X680, X681 and/or X693, X694 and/or X700, X701 and/or X709, X710, in each case together, may also form "heterocyclyl";
where, optionally, the above substituents of substituent group (ii) may in turn each independently be substituted by at least one substituent selected identically or differently from the group consisting of:
(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHX717, —NX718X719, —$NO_2$, —OH, —$OCF_3$, —SH, —O—$SO_3$H, —OP(O)(OH)$_2$, —CHO, —COOH, —C(O)$NH_2$, —$SO_3$H, —P(O)(OH)$_2$, —C(O)—X720, —C(O)O—X721, —C(O)NH—X722, —C(O)NX723X724, —O—X725, —O(—X726-O)$_c$—H (c=1, 2, 3, 4, 5), —O(—X727-O)$_c$—X728 (c=1, 2, 3, 4, 5), —OC(O)—X729, —OC(O)—O—X730, —OC(O)—NHX731, —O—C(O)—NX732X733, —OP(O)(OX734)(OX735), —OSi(X736)(X737)(X738), —OS($O_2$)—X739, —NHC(O)—X740, —NX741C(O)—X742, —NH—C(O)—O—X743, —NH—C(O)—NH—X744, —NH—C(O)—NX745X746, —NX747-C(O)—O—X748, —NX749-C(O)—NH—X750, —NX751-C(O)—NX752X753, —NHS($O_2$)—X754, —NX755S($O_2$)—X756, —S—X757, —S(O)—X758, —S($O_2$)—X759, —S($O_2$)NH—X760, —S($O_2$)NX761X762, —S($O_2$)O—X763, —P(O)(OX764)(OX765), —Si(X766)(X767)(X768)";
where X717, X718, X719, X720, X721, X722, X723, X724, X725, X726, X727, X728, X729, X730, X731, X732, X733, X734, X735, X736, X737, X738, X739, X740, X741, X742, X743, X744, X745, X746, X747, X748, X749, X750, X751, X752, X753, X754, X755, X756, X757, X758, X759, X760, X761, X762, X763, X764, X765, X766, X767, X768 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, X723, X724 and/or X732, X733 and/or X745, X746 and/or X752, X753 and/or X761, X762, in each case together, may also form "heterocyclyl";
(j) unsubstituted or substituted heteroaryl where, optionally, the heteroaryl radical may be substituted by at least one substituent selected identically or differently from the group consisting of:
(i) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHX769, —NX770X771, —$NO_2$, —OH, —$OCF_3$, —SH, —O—$SO_3$H, —OP(O)(OH)$_2$, —CHO, —COOH, —C(O)$NH_2$, —$SO_3$H, —P(O)(OH)$_2$, —C(O)—X772, —C(O)O—X773, —C(O)NH—X774, —C(O)NX775X776, —O—X777, —O(—X778-O)$_d$—H (d=1, 2, 3, 4, 5), —O(—X779-O)$_d$—X780 (d=1, 2, 3, 4, 5), —OC(O)—X781, —OC(O)—O—X782, —OC(O)—NHX783, —O—C(O)—NX784X785, —OP(O)(OX786)(OX787), —OSi(X788)(X789)(X790), —OS($O_2$)—X791, —NHC(O)—X792, —NX793C(O)—X794, —NH—C(O)—O—X795, —NH—C(O)—NH—X796, —NH—C(O)—NX797X798, —NX799-C(O)—O—X800, —NX801-C(O)—NH—X802, —NX803-C(O)—NX804X805, —NHS($O_2$)—X806, —NX807S($O_2$)—X808, —S—X809, —S(O)—X810, —S($O_2$)—X811, —S($O_2$)NH—X812, —S($O_2$)NX813X814, —S($O_2$)O—X815, —P(O)(OX816)(OX817), —Si(X818)(X819)(X820)";
where X769, X770, X771, X772, X773, X774, X775, X776, X777, X778, X779, X780, X781, X782, X783, X784, X785, X786, X787, X788, X789, X790, X791, X792, X793, X794, X795, X796, X797, X798, X799, X800, X801, X802, X803, X804, X805, X806, X807, X808, X809, X810, X811, X812, X813, X814, X815, X816, X817, X818, X819, X820 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, X775, X776 and/or X784, X785 and/or X797, X798 and/or X804, X805 and/or X813, X814, in each case together, may also form "heterocyclyl";
where, optionally, the above substituents of substituent group (i) may in turn each independently be substituted by at least one substituent selected identically or differently from the group consisting of:
(ii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, N₃, NH₂, —NHX821, —NX822X823, —NO₂, —OH, —OCF₃, —SH, —O—SO₃H, —OP(O)(OH)₂, —CHO, —COOH, —C(O)NH₂, —SO₃H, —P(O)(OH)₂, —C(O)—X824, —C(O)O—X825, —C(O)NH—X826, —C(O)NX827X828, —O—X829, —O(—X830-O)$_e$—H (e=1, 2, 3, 4, 5), —O(—X831-O)$_e$—X832 (e=1, 2, 3, 4, 5), —OC(O)—X833, —OC(O)—O—X834, —OC(O)—NHX835, —O—C(O)—NX836X837, —OP(O)(OX838)(OX839), —OSi(X840)(X841)(X842), —OS(O₂)—X843, —NHC(O)—X844, —NX845C(O)—X846, —NH—C(O)—O—X847, —NH—C(O)—NH—X848, —NH—C(O)—NX849X850, —NX851-C(O)—O—X852, —NX853-C(O)—NH—X854, —NX855-C(O)—NX856X857, —NHS(O₂)—X858, —NX859S(O₂)—X860, —S—X861, —S(O)—X862, —S(O₂)—X863, —S(O₂)NH—X864, —S(O₂)NX865X866, —S(O₂)O—X867, —P(O)(OX868)(OX869), —Si(X870)(X871)(X872)";

where X821, X822, X823, X824, X825, X826, X827, X828, X829, X830, X831, X832, X833, X834, X835, X836, X837, X838, X839, X840, X841, X842, X843, X844, X845, X846, X847, X848, X849, X850, X851, X852, X853, X854, X855, X856, X857, X858, X859, X860, X861, X862, X863, X864, X865, X866, X867, X868, X869, X870, X871, X872 are each independently selected from the group consisting of: "alkyl, (C₉-C₃₀)alkyl, cycloalkyl, cycloalkylalkyl, heterocyclyl, heterocyclylalkyl, aryl, arylalkyl, heteroaryl, heteroarylalkyl" and where, alternatively, X827, X828 and/or X836, X837 and/or X849, X850 and/or X856, X857 and/or X865, X866, in each case together, may also form "heterocyclyl";

where, optionally, the above substituents of substituent group (ii) may in turn each independently be substituted by at least one substituent selected identically or differently from the group consisting of:

(iii) "alkyl, (C₉-C₃₀)alkyl, cycloalkyl, cycloalkylalkyl, heterocyclyl, heterocyclylalkyl, aryl, arylalkyl, heteroaryl, heteroarylalkyl, F, Cl, Br, I, CN, CF₃, N₃, NH₂, —NHX873, —NX874X875, —NO₂, —OH, —OCF₃, —SH, —O—SO₃H, —OP(O)(OH)₂, —CHO, —COOH, —C(O)NH₂, —SO₃H, —P(O)(OH)₂, —C(O)—X876, —C(O)O—X877, —C(O)NH—X878, —C(O)NX879X880, —O—X881, —O(—X882-O)$_f$—H (f=1, 2, 3, 4, 5), —O(—X883-O)$_f$—X884 (f=1, 2, 3, 4, 5), —OC(O)—X885, —OC(O)—O—X886, —OC(O)—NHX887, —O—C(O)—NX888X889, —OP(O)(OX890)(OX891), —OSi(X892)(X893)(X894), —OS(O₂)—X895, —NHC(O)—X896, —NX897C(O)—X898, —NH—C(O)—O—X899, —NH—C(O)—NH—X900, —NH—C(O)—NX901X902, —NX903-C(O)—O—X904, —NX905-C(O)—NH—X906, —NX907-C(O)—NX908X909, —NHS(O₂)—X910, —NX911S(O₂)—X912, —S—X913, —S(O)—X914, —S(O₂)—X915, —S(O₂)NH—X916, —S(O₂)NX917X918, —S(O₂)O—X919, —P(O)(OX920)(OX921), —Si(X922)(X923)(X924)";

where X873, X874, X875, X876, X877, X878, X879, X880, X881, X882, X883, X884, X885, X886, X887, X888, X889, X890, X891, X892, X893, X894, X895, X896, X897, X898, X899, X900, X901, X902, X903, X904, X905, X906, X907, X908, X909, X910, X911, X912, X913, X914, X915, X916, X917, X918, X919, X920, X921, X922, X923, X924 are each independently selected from the group consisting of: "alkyl, (C₉-C₃₀)alkyl, cycloalkyl, cycloalkylalkyl, heterocyclyl, heterocyclylalkyl, aryl, arylalkyl, heteroaryl, heteroarylalkyl" and where, alternatively, X879, X880 and/or X888, X889 and/or X901, X902 and/or X908, X909 and/or X917, X918, in each case together, may also form "heterocyclyl";

(k) OZ6 where Z6 is independently selected from the group consisting of:

(i) "hydrogen, alkyl, (C₉-C₃₀)alkyl, cycloalkyl, cycloalkylalkyl, heterocyclyl, heterocyclylalkyl, aryl, arylalkyl, heteroaryl, heteroarylalkyl";

where, optionally, the above substituents of substituent group (i) may in turn each independently be substituted by at least one substituent selected identically or differently from the group consisting of:

(ii) "alkyl, (C₉-C₃₀)alkyl, cycloalkyl, cycloalkylalkyl, heterocyclyl, heterocyclylalkyl, aryl, arylalkyl, heteroaryl, heteroarylalkyl, F, Cl, Br, I, CN, CF₃, N₃, NH₂, —NHX925, —NX926X927, —NO₂, —OH, —OCF₃, —SH, —O—SO₃H, —OP(O)(OH)₂, —CHO, —COOH, —C(O)NH₂, —SO₃H, —P(O)(OH)₂, —C(O)—X928, —C(O)O—X929, —C(O)NH—X930, —C(O)NX931X932, —O—X933, —O(—X934-O)$_g$—H (g=1, 2, 3, 4, 5), —O(—X935-O)$_g$—X936 (g=1, 2, 3, 4, 5), —OC(O)—X937, —OC(O)—O—X938, —OC(O)—NHX939, —O—C(O)—NX940X941, —OP(O)(OX942)(OX943), —OSi(X944)(X945)(X946), —OS(O₂)—X947, —NHC(O)—X948, —NX949C(O)—X950, —NH—C(O)—O—X951, —NH—C(O)—NH—X952, —NH—C(O)—NX953X954, —NX955-C(O)—O—X956, —NX957-C(O)—NH—X958, —NX959-C(O)—NX960X961, —NHS(O₂)—X962, —NX963S(O₂)—X964, —S—X965, —S(O)—X966, —S(O₂)—X967, —S(O₂)NH—X968, —S(O₂)NX969X970, —S(O₂)O—X971, —P(O)(OX972)(OX973), —Si(X974)(X975)(X976)";

where X925, X926, X927, X928, X929, X930, X931, X932, X933, X934, X935, X936, X937, X938, X939, X940, X941, X942, X943, X944, X945, X946, X947, X948, X949, X950, X951, X952, X953, X954, X955, X956, X957, X958, X959, X960, X961, X962, X963, X964, X965, X966, X967, X968, X969, X970, X971, X972, X973, X974, X975, X976 are each independently selected from the group consisting of: "alkyl, (C₉-C₃₀)alkyl, cycloalkyl, cycloalkylalkyl, heterocyclyl, heterocyclylalkyl, aryl, arylalkyl, heteroaryl, heteroarylalkyl" and where, alternatively, X931, X932 and/or X940, X941 and/or X953, X954 and/or X960, X961 and/or X969, X970, in each case together, may also form "heterocyclyl";

where, optionally, the above substituents of substituent group (ii) may in turn each independently be substituted by at least one substituent selected identically or differently from the group consisting of:

(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHX977, —NX978X979, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)—X980, —C(O)O—X981, —C(O)NH—X982, —C(O)NX983X984, —O—X985, —O(—X986-O)$_h$—H (h=1, 2, 3, 4, 5), —O(—X987-O)$_h$—X988 (h=1, 2, 3, 4, 5), —OC(O)—X989, —OC(O)—O—X990, —OC(O)—NHX991, —O—C(O)—NX992X993, —OP(O)(OX994)(OX995), —OSi(X996)(X997)(X998), —OS(O$_2$)—X999, —NHC(O)—X1000, —NX1001C(O)—X1002, —NH—C(O)—O—X1003, —NH—C(O)—NH—X1004, —NH—C(O)—NX1005X1006, —NX1007-C(O)—O—X1008, —NX1009-C(O)—NH—X1010, —NX1011-C(O)—NX1012X1013, —NHS(O$_2$)—X1014, —NX1015S(O$_2$)—X1016, —S—X1017, —S(O)—X1018, —S(O$_2$)—X1019, —S(O$_2$)NH—X1020, —S(O$_2$)NX1021X1022, —S(O$_2$)O—X1023, —P(O)(OX1024)(OX1025), —Si(X1026)(X1027)(X1028)";

where X977, X978, X979, X980, X981, X982, X983, X984, X985, X986, X987, X988, X989, X990, X991, X992, X993, X994, X995, X996, X997, X998, X999, X1000, X1001, X1002, X1003, X1004, X1005, X1006, X1007, X1008, X1009, X1010, X1011, X1012, X1013, X1014, X1015, X1016, X1017, X1018, X1019, X1020, X1021, X1022, X1023, X1024, X1025, X1026, X1027, X1028 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, X983, X984 and/or X992, X993 and/or X1005, X1006 and/or X1012, X1013 and/or X1021, X1022, in each case together, may also form "heterocyclyl";

(l) SZ7 where Z7 is independently selected from the group consisting of:
(i) "hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl";
where, optionally, the above substituents of substituent group (i) may in turn each independently be substituted by at least one substituent selected identically or differently from the group consisting of:
(ii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$,—NHX1029, —NX1030X1031, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)—X1032, —C(O)O—X1033, —C(O)NH—X1034, —C(O)NX1035X1036, —O—X1037, —O(—X1038-O)$_i$—H (i=1, 2, 3, 4, 5), —O(—X1039-O)$_i$—X1040 (i=1, 2, 3, 4, 5), —OC(O)—X1041, —OC(O)—O—X1042, —OC(O)—NHX1043, —O—C(O)—NX1044X1045, —OP(O)(OX1046)(OX1047), —OSi(X1048)(X1049)(X1050), —OS(O$_2$)—X1051, —NHC(O)—X1052, —NX1053C(O)—X1054, —NH—C(O)—O—X1055, —NH—C(O)—NH—X1056, —NH—C(O)—NX1057X1058, —NX1059-C(O)—O—X1060, —NX1061-C(O)—NH—X1062, —NX1063-C(O)—NX1064X1065, —NHS(O$_2$)—X1066, —NX1067S(O$_2$)—X1068, —S—X1069, —S(O)—X1070, —S(O$_2$)—X1071, —S(O$_2$)NH—X1072, —S(O$_2$)NX1073X1074, —S(O$_2$)O—X1075, —P(O)(OX1076)(OX1077), —Si(X1078)(X1079)(X1080)";

where X1029, X1030, X1031, X1032, X1033, X1034, X1035, X1036, X1037, X1038, X1039, X1040, X1041, X1042, X1043, X1044, X1045, X1046, X1047, X1048, X1049, X1050, X1051, X1052, X1053, X1054, X1055, X1056, X1057, X1058, X1059, X1060, X1061, X1062, X1063, X1064, X1065, X1066, X1067, X1068, X1069, X1070, X1071, X1072, X1073, X1074, X1075, X1076, X1077, X1078, X1079, X1080 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, X1035, X1036 and/or X1044, X1045 and/or X1057, X1058 and/or X1064, X1065 and/or X1073, X1074, in each case together, may also form "heterocyclyl";

where, optionally, the above substituents of substituent group (ii) may in turn each independently be substituted by at least one substituent selected identically or differently from the group consisting of:
(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHX1081, —NX1082X1083, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)—X1084, —C(O)O—X1085, —C(O)NH—X1086, —C(O)NX1087X1088, —O—X1089, —O(—X1090-O)$_j$—H (j=1, 2, 3, 4, 5), —O(—X1091-O)$_j$—X1092 (j=1, 2, 3, 4, 5), —OC(O)—X1093, —OC(O)—O—X1094, —OC(O)—NHX1095, —O—C(O)—NX1096X1097, —OP(O)(OX1098)(OX1099), —OSi(X1100)(X1101)(X1102), —OS(O$_2$)—X1103, —NHC(O)—X1104, —NX1105C(O)—X1106, —NH—C(O)—O—X1107, —NH—C(O)—NH—X1108, —NH—C(O)—NX1109X1110, —NX1111-C(O)—O—X1112, —NX1113-C(O)—NH—X1114, —NX1115-C(O)—NX1116X1117, —NHS(O$_2$)—X1118, —NX1119S(O$_2$)—X1120, —S—X1121, —S(O)—X1122, —S(O$_2$)—X1123, —S(O$_2$)NH—X1124, —S(O$_2$)NX1125X1126, —S(O$_2$)O—X1127, —P(O)(OX1128)(OX1129), —Si(X1130)(X1131)(X1132)";

where X1081, X1082, X1083, X1084, X1085, X1086, X1087, X1088, X1089, X1090, X1091, X1092, X1093, X1094, X1095, X1096, X1097, X1098, X1099, X1100, X1101, X1102, X1103, X1104, X1105, X1106, X1107, X1108, X1109, X1110, X1111, X1112, X1113, X1114, X1115, X1116, X1117, X1118, X1119, X1120, X1121, X1122, X1123, X1124, X1125, X1126, X1127, X1128, X1129, X1130, X1131, X1132 are each independently selected from the group consisting of: "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl" and where, alternatively, X1087, X1088 and/or X1096, X1097 and/or X1109, X1110 and/or X1116, X1117 and/or X1125, X1126, in each case together, may also form "heterocyclyl";

(m) NZ8Z9 where Z8, Z9 are each independently selected from the group consisting of:

(i) "hydrogen, alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl, —C(O)—X1133, —C(O)O—X1134, —C(O)—NX1135X1136, —S(O$_2$)—X1137, —S(O$_2$)O—X1138";

where X1133, X1134, X1135, X1136, X1137, X1138 are each independently selected from the group consisting of: hydrogen, alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl" and where, alternatively, X1135, X1136 together may also form "heterocyclyl";

where, optionally, the above substituents of substituent group (i) may in turn each independently be substituted by at least one substituent selected identically or differently from the group consisting of:

(ii) "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHX1139, —NX1140X1141, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—X1142, —C(O)O—X1143, —C(O)NH—X1144, —C(O)NX1145X1146, —O—X1147, —O(—X1148-O)$_k$—H (k=1, 2, 3, 4, 5), —O(—X1149-O)$_k$—X1150 (k=1, 2, 3, 4, 5), —OC(O)—X1151, —OC(O)—O—X1152, —OC(O)—NHX1153, —O—C(O)—NX1154X1155, —OP(O)(OX1156)(OX1157), —OSi(X1158)(X1159)(X1160), —OS(O$_2$)—X1161, —NHC(O)—X1162, —NX1163C(O)—X1164, —NH—C(O)—O—X1165, —NH—C(O)—NH—X1166, —NH—C(O)—NX1167X1168, —NX1169-C(O)—O—X1170, —NX1171-C(O)—NH—X1172, —NX1173-C(O)—NX1174X1175, —NHS(O$_2$)—X1176, —NX1177S(O$_2$)—X1178, —S—X1179, —S(O)—X1180, —S(O$_2$)—X1181, —S(O$_2$)NH—X1182, —S(O$_2$)NX1183X1184, —S(O$_2$)O—X1185, —P(O)(OX1186)(OX1187), —Si(X1188)(X1189)(X1190)";

where X1139, X1140, X1141, X1142, X1143, X1144, X1145, X1146, X1147, X1148, X1149, X1150, X1151, X1152, X1153, X1154, X1155, X1156, X1157, X1158, X1159, X1160, X1161, X1162, X1163, X1164, X1165, X1166, X1167, X1168, X1169, X1170, X1171, X1172, X1173, X1174, X1175, X1176, X1177, X1178, X1179, X1180, X1181, X1182, X1183, X1184, X1185, X1186, X1187, X1188, X1189, X1190 are each independently selected from the group consisting of: "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl" and where, alternatively, X1145, X1146 and/or X1154, X1155 and/or X1167, X1168 and/or X1174, X1175 and/or X1183, X1184, in each case together, may also form "heterocyclyl";

where, optionally, the above substituents of substituent group (ii) may in turn each independently be substituted by at least one substituent selected identically or differently from the group consisting of:

(iii) "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHX1191, —NX1192X1193, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—X1194, —C(O)O—X1195, —C(O)NH—X1196, —C(O)NX1197X1198, —O—X1199, —O(—X1200-O)$_l$—H (l=1, 2, 3, 4, 5), —O(—X1201-O)$_l$—X1202 (l=1, 2, 3, 4, 5), —OC(O)—X1203, —OC(O)—O—X1204, —OC(O)—NHX1205, —O—C(O)—NX1206X1207, —OP(O)(OX1208)(OX1209), —OSi(X1210)(X1211)(X1212), —OS(O$_2$)—X1213, —NHC(O)—X1214, —NX1215C(O)—X1216, —NH—C(O)—O—X1217, —NH—C(O)—NH—X1218, —NH—C(O)—NX1219X1220, —NX1221-C(O)—O—X1222, —NX1223-C(O)—NH—X1224, —NX1225-C(O)—NX1226X1227, —NHS(O$_2$)—X1228, —NX1229S(O$_2$)—X1230, —S—X1231, —S(O)—X1232, —S(O$_2$)—X1233, —S(O$_2$)NH—X1234, —S(O$_2$)NX1235X1236, —S(O$_2$)O—X1237, —P(O)(OX1238)(OX1239), —Si(X1240)(X1241)(X1242)";

where X1191, X1192, X1193, X1194, X1195, X1196, X1197, X1198, X1199, X1200, X1201, X1202, X1203, X1204, X1205, X1206, X1207, X1208, X1209, X1210, X1211, X1212, X1213, X1214, X1215, X1216, X1217, X1218, X1219, X1220, X1221, X1222, X1223, X1224, X1225, X1226, X1227, X1228, X1229, X1230, X1231, X1232, X1233, X1234, X1235, X1236, X1237, X1238, X1239, X1240, X1241, X1242 are each independently selected from the group consisting of: "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl" and where, alternatively, —X1197, X1198 and/or X1206, X1207 and/or X1219, X1220 and/or X1226, X1227 and/or X1235, X1236, in each case together, may also form "heterocyclyl"; or (B) one of the Z3, Z4 radicals is, or both Z3, Z4 radicals are, independently "substituted heteroaryl", where "substituted heteroaryl" is substituted by at least one substituent selected from the group consisting of:

(a) "alkyl, cycloalkyl, heterocyclyl, aryl, heteroaryl, —NH—V1, —N(alkyl)$_2$, —NHC(O)-alkyl, —NHC(O)-cycloalkyl, —NHC(O)-heterocyclyl, —NHC(O)-aryl, —NHC(O)-heteroaryl, —NHC(O)-arylalkyl, —NHC(O)-heteroarylalkyl, —NHS(O$_2$)-alkyl, —NHS(O$_2$)-cycloalkyl, —NHS(O$_2$)-heterocyclyl, —NHS(O$_2$)-aryl, —NHS(O$_2$)-heteroaryl, —NHS(O$_2$)-arylalkyl, —NHS(O$_2$)-heteroarylalkyl, —S-alkyl, —S-aryl, —S-heteroaryl, —O-alkyl, —O-cycloalkyl, —O-cycloalkylalkyl, —O-aryl, —O-arylalkyl, —O-heteroaryl, —O-heteroarylalkyl, —O-heterocyclylalkyl, —OC(O)-alkyl, —OC(O)-cycloalkyl, —OC(O)-heterocyclyl, —OC(O)-aryl, —OC(O)-heteroaryl, —OC(O)-arylalkyl, —OC(O)-heteroarylalkyl, —OS(O$_2$)-alkyl, —OS(O$_2$)-cycloalkyl, —OS(O$_2$)-heterocyclyl, —OS(O$_2$)-aryl, —OS(O$_2$)-heteroaryl, —OS(O$_2$)-arylalkyl, —OS(O$_2$)-heteroarylalkyl, —C(O)-alkyl, —C(O)-aryl, —C(O)-heteroaryl, —C(O)O—V2, —C(O)NH—V3, —C(O)N(alkyl)$_2$, —C(O)N(cycloalkyl)$_2$, —C(O)N(aryl)$_2$, —C(O)N(heteroaryl)$_2$, —S(O$_2$)NH-alkyl, —S(O$_2$)NH-aryl, —S(O$_2$)NH-heteroaryl, —S(O$_2$)NH-arylalkyl, —S(O$_2$)O-alkyl, —S(O$_2$)O-aryl, —S(O$_2$)O-arylalkyl";

where V1, V2, V3 are each independently selected from the group consisting of: "alkyl, cycloalkyl, cycloalkylalkyl, heterocyclyl, heterocyclylalkyl, aryl, arylalkyl, heteroaryl, heteroarylalkyl";

with the proviso that the above substituents of substituent group (a) are each independently substituted further by at least one substituent selected identically or differently from the group consisting of:

(i) "(C$_9$-C$_{30}$)alkyl, cycloalkyl, cycloalkylalkyl, heterocyclyl, heterocyclylalkyl, aryl, arylalkyl, heteroaryl, heteroarylalkyl, N$_3$, —NH-cycloalkyl, —NH-cycloalkylalkyl, —NH-heteroaryl, —NH-heteroarylalkyl, —NH-arylalkyl, —NH-heterocyclyl, —NH-heterocyclylalkyl, —NV4V5, —S-cycloalkyl, —S-cycloalkylalkyl, —S-aryl, —S-arylalkyl, —S-heteroaryl, —S-heteroarylalkyl, —S-heterocyclyl, —S-heterocyclylalkyl, —O-cycloalkyl, —O-cycloalkylalkyl, —O-arylalkyl, —O-heteroaryl, —O-heteroarylalkyl, —O-heterocyclyl, —O-heterocyclylalkyl, —O(—V6-O)$_p$—H (p=1, 2, 3, 4, 5), —O(—V7-O)$_p$—V8 (p=1, 2, 3, 4, 5), —OP(O)(OV9)(OV10), —C(O)O—V11, —C(O)NH$_2$, —C(O)NH—V12, —C(O)NV13V14, —S(O$_2$)—V15, —P(O)(OH)$_2$, —P(O)(OV16)(OV17), —Si(18)(V19)(V20), —O—Si(V21)(V22)(V23), —O—C(O)—O—V24, —O—C(O)—NH—V25, —O—C(O)—NV26V27, —NH—C(O)—O—V28, —NH—C(O)—NH—V29, —NH—C(O)—NV30V31, —NV32-C(O)—O—V33, —NV34-C(O)—NH—V35, —NV36-C(O)—NV37V38, —NV39-S(O$_2$)—V40, —NH—S(O$_2$)—V41, —O—S(O$_2$)—V42, —NH—C(O)—V43, —NV44-C(O)—V45, —C(O)—V46, —OC(O)—V47, —S(O)—V48, —S(O$_2$)—NHV49, —S(O$_2$)—NV50V51, —S(O$_2$)—OV52";

with the further proviso that "—N(alkyl)$_2$" is further substituted by at least one substituent selected from the following substituent group (b);

where V4, V5, V6, V7, V8, V9, V10, V11, V12, V13, V14, V15, V16, V17, V18, V19, V20, V21, V22, V23, V24, V25, V26, V27, V28, V29, V30, V31, V32, V33, V34, V35, V36, V37, V38, V39, V40, V41, V42, V43, V44, V45, V46, V47, V48, V49, V50, V51, V52 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, V13, V14 and/or V26, V27 and/or V30, V31 and/or V37, V38 and/or V50, V51 together may also form "heterocyclyl";

where, optionally, additionally one of the Z3, Z4 radicals or additionally both Z3, Z4 radicals may each independently be further substituted by at least one substituent selected identically or differently from the group consisting of:

(b) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHV53, —NV54V55, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—V56, —C(O)O—V57, —C(O)NH—V58, —C(O)NV59V60, —O—V61, —O(—V62-O)$_r$—H (r=1, 2, 3, 4, 5), —O(—V63-O)$_r$—V64 (r=1, 2, 3, 4, 5), —OC(O)—V65, —OC(O)—O—V66, —OC(O)—NHV67, —O—C(O)—NV68V69, —OP(O)(OV70)(OV71), —OSi(V72)(V73)(V74), —OS(O$_2$)—V75, —NHC(O)—V76, —NV77C(O)—V78, —NH—C(O)—O—V79, —NH—C(O)—NH—V80, —NH—C(O)—NV81V82, —NV83-C(O)—O—V84, —NV85-C(O)—NH—V86, —NV87-C(O)—NV88V89, —NHS(O$_2$)—V90, —NV91S(O$_2$)—V92, —S—V93, —S(O)—V94, —S(O$_2$)—V95, —S(O$_2$)NH—V96, —S(O$_2$)NV97V98, —S(O$_2$)O—V99, —P(O)(OV100)(OV101), —Si(V102)(V103)(V104)";

where V53, V54, V55, V56, V57, V58, V59, V60, V61, V62, V63, V64, V65, V66, V67, V68, V69, V70, V71, V72, V73, V74, V75, V76, V77, V78, V79, V80, V81, V82, V83, V84, V85, V86, V87, V88, V89, V90, V91, V92, V93, V94, V95, V96, V97, V98, V99, V100, V101, V102, V103, V104 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, V59, V60 and/or V68, V69 and/or V81, V82 and/or V88, V89 and/or V97, V98 together may also form "heterocyclyl";

where, optionally, the above substituents of substituent group (b) may each independently in turn be substituted by at least one substituent selected identically or differently from the group consisting of:

(ii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHV105, —NV106V107, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—V108, —C(O)O—V109, —C(O)NH—V110, —C(O)NV111V112, —O—V113, —O(—V114-O)$_s$—H (s=1, 2, 3, 4, 5), —O(—V115-O)$_s$—V116 (s=1, 2, 3, 4, 5), —OC(O)—V117, —OC(O)—O—V118, —OC(O)—NHV119, —O—C(O)—NV120V121, —OP(O)(OV122)(OV123), —OSi(V124)(V125)(V126), —OS(O$_2$)—V127, —NHC(O)—V128, —NV129C(O)—V130, —NH—C(O)—O—V131, —NH—C(O)—NH—V132, —NH—C(O)—NV133V134, —NV135-C(O)—O—V136, —NV137-C(O)—NH—V138, —NV139-C(O)—NV140V141, —NHS(O$_2$)—V142, —NV143S(O$_2$)—V144, —S—V145, —S(O)—V146, —S(O$_2$)—V147, —S(O$_2$)NH—V148, —S(O$_2$)NV149V150, —S(O$_2$)O—V151, —P(O)(OV152)(OV153), —Si(V154)(V155)(V156)";

where V105, V106, V107, V108, V109, V110, V111, V112, V113, V114, V115, V116, V117, V118, V119, V120, V121, V122, V123, V124, V125, V126, V127, V128, V129, V130, V131, V132, V133, V134, V135, V136, V137, V138, V139, V140, V141, V142, V143, V144, V145, V146, V147, V148, V149, V150, V151, V152, V153, V154, V155, V156 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, V111, V112 and/or V120, V121 and/or V133, V134 and/or V140, V141 and/or V149, V150 together may also form "heterocyclyl";

where, optionally, the above substituents of substituent group (i) and/or substituent group (ii) may each independently in turn be substituted by at least one substituent selected identically or differently from the group consisting of:

(iii) "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHV157, —NV158V159, —$NO_2$, —OH, —$OCF_3$, —SH, —O—$SO_3H$, —OP(O)(OH)$_2$, —CHO, —COOH, —C(O)NH$_2$, —SO$_3$H, —P(O)(OH)$_2$, —C(O)—V160, —C(O)O—V161, —C(O)NH—V162, —C(O)NV163V164, —O—V165, —O(—V166-O)$_t$—H (t=1, 2, 3, 4, 5), —O(—V167-O)$_t$—V168 (t=1, 2, 3, 4, 5), —OC(O)—V169, —OC(O)—O—V170, —OC(O)—NHV171, —O—C(O)—NV172V173, —OP(O)(OV174)(OV175), —OSi(V176)(V177)(V178), —OS(O$_2$)—V179, —NHC(O)—V180, —NV181C(O)—V182, —NH—C(O)—O—V183, —NH—C(O)—NH—V184, —NH—C(O)—NV185V186, —NV187-C(O)—O—V188, —NV189-C(O)—NH—V190, —NV191-C(O)—NV192V193, —NHS(O$_2$)—V194, —NV195S(O$_2$)—V196, —S—V197, —S(O)—V198, —S(O$_2$)—V199, —S(O$_2$)NH—V200, —S(O$_2$)NV201V202, —S(O$_2$)O—V203, —P(O)(OV204)(OV205), —Si(V206)(V207)(V208)";

where V157, V158, V159, V160, V161, V162, V163, V164, V165, V166, V167, V168, V169, V170, V171, V172, V173, V174, V175, V176, V177, V178, V179, V180, V181, V182, V183, V184, V185, V186, V187, V188, V189, V190, V191, V192, V193, V194, V195, V196, V197, V198, V199, V200, V201, V202, V203, V204, V205, V206, V207, V208 are each independently selected from the group consisting of: "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl" and where, alternatively, V163, V164 and/or V172, V173 and/or V185, V186 and/or V192, V193 and/or V201, V202 together may also form "heterocyclyl";

or one of the Z3, Z4 radicals is, or both Z3, Z4 radicals are, independently "substituted heteroaryl", where "substituted heteroaryl" is substituted by at least one substituent selected identically or differently from the group consisting of:

(c) "$(C_9\text{-}C_{30})$alkyl, —NV209V210, —NH—$(C_9\text{-}C_{30})$alkyl, —NHC(O)-cycloalkylalkyl, —NHC(O)-heterocyclylalkyl, —NHC(O)—$(C_9\text{-}C_{30})$alkyl, —NV211C(O)—V212, —NV213C(O)—$(C_9\text{-}C_{30})$alkyl, —NHC(O)—OV214, —NV215C(O)—OV216, —NHC(O)—NHV217, —NHC(O)—NV218V219, —NV220C(O)—NHV221, —NV222C(O)—NV223V224, —NHS(O$_2$)-cycloalkylalkyl, —NHS(O$_2$)-heterocyclylalkyl, —NV225S(O$_2$)—V226, —O-heterocyclyl, —O—$(C_9\text{-}C_{30})$alkyl, —S-cycloalkyl, —S-heterocyclyl, —S-arylalkyl, —S-heteroarylalkyl, —S-cycloalkylalkyl, —S-heterocyclylalkyl, —S—$(C_9\text{-}C_{30})$alkyl, —OC(O)-cycloalkylalkyl, —OC(O)-heterocyclylalkyl, —OC(O)—$(C_9\text{-}C_{30})$alkyl, —OC(O)—OV227, —OC(O)—NHV228, —OC(O)—NV229V230, —OP(O)(OV231)(OV232), —OS(O$_2$)-cycloalkylalkyl, —OS(O$_2$)-heterocyclylalkyl, —OS(O$_2$)—$(C_9\text{-}C_{30})$alkyl, —C(O)-cycloalkyl, —C(O)-heterocyclyl, —C(O)-arylalkyl, —C(O)-heteroarylalkyl, —C(O)-cycloalkylalkyl, —C(O)-heterocyclylalkyl, —C(O)—$(C_9\text{-}C_{30})$alkyl, —C(O)O—$(C_9\text{-}C_{30})$alkyl, —C(O)NH—$(C_9\text{-}C_{30})$alkyl, —C(O)NV233V234, —C(O)NH—OV235, —C(O)NV236-OV237, —C(O)NH—NV238V239, —C(O)NV240-NV241V242, —S(O)—V243, —S(O$_2$)—V244, —S(O$_2$)NH-cycloalkyl, —S(O$_2$)NH-heterocyclyl, —S(O$_2$)NH-heteroarylalkyl, —S(O$_2$)NH-cycloalkylalkyl, —S(O$_2$)NH-heterocyclylalkyl, —S(O$_2$)NH—$(C_9\text{-}C_{30})$alkyl, —S(O$_2$)O-cycloalkyl, —S(O$_2$)O-heterocyclyl, —S(O$_2$)O-heteroaryl, —S(O$_2$)O-heteroarylalkyl, —S(O$_2$)O-cycloalkylalkyl, —S(O$_2$)O-heterocyclylalkyl, —S(O$_2$)O—$(C_9\text{-}C_{30})$alkyl, —P(O)(OH)$_2$, —P(O)(OV245)(OV246), —Si(V247)(V248)(V249), —O—Si(V250)(V251)(V252)";

where V209, V210, V211, V212, V213, V214, V215, V216, V217, V218, V219, V220, V221, V222, V223, V224, V225, V226, V227, V228, V229, V230, V231, V232, V233, V234, V235, V236, V237, V238, V239, V240, V241, V242, V243, V244, V245, V246, V247, V248, V249, V250, V251, V252 are each independently selected from the group consisting of: "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl" and where, alternatively, V218, V219 and/or V223, V224 and/or V229, V230 and/or V233, V234 and/or V238, V239 and/or V241, V242 together may also form "heterocyclyl";

with the proviso that the substituents "—N(alkyl)$_2$", "—C(O)N(alkyl)$_2$", "—C(O)N(cycloalkyl)$_2$", "—C(O)N(aryl)$_2$", "—C(O)N(heteroaryl)$_2$" are substituted further by at least one substituent selected from the following substituent group (i);

where, optionally, the above substituents of substituent group (c) may each independently in turn be substituted by at least one substituent selected identically or differently from the group consisting of:

(i) "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHV253, —NV254V255, —$NO_2$, —OH, —$OCF_3$, —SH, —O—$SO_3H$, —OP(O)(OH)$_2$, —CHO, —COOH, —C(O)NH$_2$, —SO$_3$H, —P(O)(OH)$_2$, —C(O)—V256, —C(O)O—V257, —C(O)NH—V258, —C(O)NV259V260, —O—V261, —O(—V262-O)$_u$—H (u=1, 2, 3, 4, 5), —O(—V263-O)$_u$—V264 (u=1, 2, 3, 4, 5), —OC(O)—V265, —OC(O)—O—V266, —OC(O)—NHV267, —O—C(O)—NV268V269, —OP(O)(OV270)(OV271), —OSi(V272)(V273)(V274), —OS(O$_2$)—V275, —NHC(O)—V276, —NV277C(O)—V278, —NH—C(O)—O—V279, —NH—C(O)—NH—V280, —NH—C(O)—NV281V282, —NV283-C(O)—O—V284, —NV285-C(O)—NH—V286, —NV287-C(O)—NV288V289, —NHS(O$_2$)—V290, —NV291S(O$_2$)—V292, —S—V293, —S(O)—V294, —S(O$_2$)—V295, —S(O$_2$)NH—V296, —S(O$_2$)NV297V298, —S(O$_2$)O—V299, —P(O)(OV300)(OV301), —Si(V302)(V303)(V304)";

where V253, V254, V255, V256, V257, V258, V259, V260, V261, V262, V263, V264, V265, V266, V267, V268, V269, V270, V271, V272, V273, V274, V275, V276, V277, V278, V279, V280, V281, V282, V283, V284, V285, V286, V287, V288, V289, V290, V291, V292, V293, V294, V295, V296, V297, V298, V299, V300, V301, V302, V303, V304 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, V259, V260 and/or V268, V269 and/or V281, V282 and/or V288, V289 and/or V297, V298 together may also form "heterocyclyl";

where, optionally, additionally one of the Z3, Z4 radicals or additionally both Z3, Z4 radicals may each independently be further substituted by at least one substituent selected identically or differently from the group consisting of:

(d) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHV305, —NV306V307, —$NO_2$, —OH, —$OCF_3$, —SH, —O—$SO_3H$, —OP(O)(OH)$_2$, —CHO, —COOH, —C(O)$NH_2$, —$SO_3H$, —P(O)(OH)$_2$, —C(O)—V308, —C(O)O—V309, —C(O)NH—V310, —C(O)NV311V312, —O—V313, —O(—V314-O)$_v$—H (v=1, 2, 3, 4, 5), —O(—V315-O)$_v$—V316 (v=1, 2, 3, 4, 5), —OC(O)—V317, —OC(O)—O—V318, —OC(O)—NHV319, —O—C(O)—NV320V321, —OP(O)(OV322)(OV323), —OSi(V324)(V325)(V326), —OS($O_2$)—V327, —NHC(O)—V328, —NV329C(O)—V330, —NH—C(O)—O—V331, —NH—C(O)—NH—V332, —NH—C(O)—NV333V334, —NV335-C(O)—O—V336, —NV337-C(O)—NH—V338, —NV339-C(O)—NV340V341, —NHS($O_2$)—V342, —NV343S($O_2$)—V344, —S—V345, —S(O)—V346, —S($O_2$)—V347, —S($O_2$)NH—V348, —S($O_2$)NV349V350, —S($O_2$)O—V351, —P(O)(OV352)(OV353), —Si(V354)(V355)(V356)";

where V305, V306, V307, V308, V309, V310, V311, V312, V313, V314, V315, V316, V317, V318, V319, V320, V321, V322, V323, V324, V325, V326, V327, V328, V329, V330, V331, V332, V333, V334, V335, V336, V337, V338, V339, V340, V341, V342, V343, V344, V345, V346, V347, V348, V349, V350, V351, V352, V353, V354, V355, V356 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, V311, V312 and/or V320, V321 and/or V333, V334 and/or V340, V341 and/or V349, V350 together may also form "heterocyclyl";

where, optionally, the above substituents of substituent group (d) may each independently in turn be substituted by at least one substituent selected identically or differently from the group consisting of:

(ii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHV357, —NV358V359, —$NO_2$, —OH, —$OCF_3$, —SH, —O—$SO_3H$, —OP(O)(OH)$_2$, —CHO, —COOH, —C(O)$NH_2$, —$SO_3H$, —P(O)(OH)$_2$, —C(O)—V360, —C(O)O—V361, —C(O)NH—V362, —C(O)NV363V364, —O—V365, —O(—V366-O)$_w$—H (w=1, 2, 3, 4, 5), —O(—V367-O)$_w$—V368 (w=1, 2, 3, 4, 5), —OC(O)—V369, —OC(O)—O—V370, —OC(O)—NHV371, —O—C(O)—NV372V373, —OP(O)(OV374)(OV375), —OSi(V376)(V377)(V378), —OS($O_2$)—V379, —NHC(O)—V380, —NV381C(O)—V382, —NH—C(O)—O—V383, —NH—C(O)—NH—V384, —NH—C(O)—NV385V386, —NV387-C(O)—O—V388, —NV389-C(O)—NH—V390, —NV391-C(O)—NV392V393, —NHS($O_2$)—V394, —NV395S($O_2$)—V396, —S—V397, —S(O)—V398, —S($O_2$)—V399, —S($O_2$)NH—V400, —S($O_2$)NV401V402, —S($O_2$)O—V403, —P(O)(OV404)(OV405), —Si(V406)(V407)(V408)";

where V357, V358, V359, V360, V361, V362, V363, V364, V365, V366, V367, V368, V369, V370, V371, V372, V373, V374, V375, V376, V377, V378, V379, V380, V381, V382, V383, V384, V385, V386, V387, V388, V389, V390, V391, V392, V393, V394, V395, V396, V397, V398, V399, V400, V401, V402, V403, V404, V405, V406, V407, V408 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, V363, V364 and/or V372, V373 and/or V385, V386 and/or V392, V393 and/or V401, V402 together may also form "heterocyclyl";

where, optionally, the above substituents of substituent group (i) and/or substituent group (ii) may each independently in turn be substituted by at least one substituent selected identically or differently from the group consisting of:

(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHV409, —NV410V411, —$NO_2$, —OH, —$OCF_3$, —SH, —O—$SO_3H$, —OP(O)(OH)$_2$, —CHO, —COOH, —C(O)$NH_2$, —$SO_3H$, —P(O)(OH)$_2$, —C(O)—V412, —C(O)O—V413, —C(O)NH—V414, —C(O)NV415V416, —O—V417, —O(—V418-O)$_x$—H (x=1, 2, 3, 4, 5), —O(—V419-O)$_x$—V420 (x=1, 2, 3, 4, 5), —OC(O)—V421, —OC(O)—O—V422, —OC(O)—NHV423, —O—C(O)—NV424V425, —OP(O)(OV426)(OV427), —OSi(V428)(V429)(V430), —OS($O_2$)—V431, —NHC(O)—V432, —NV433C(O)—V434, —NH—C(O)—O—V435, —NH—C(O)—NH—V436, —NH—C(O)—NV437V438, —NV439-C(O)—O—V440, —NV441-C(O)—NH—V442, —NV443-C(O)—NV444V445, —NHS($O_2$)—V446, —NV447S($O_2$)—V448, —S—V449, —S(O)—V450, —S($O_2$)—V451, —S($O_2$)NH—V452, —S($O_2$)NV453V454, —S($O_2$)O—V455, —P(O)(OV456a)(OV456b), —Si(V456c)(V456d)(V456e)";

where V409, V410, V411, V412, V413, V414, V415, V416, V417, V418, V419, V420, V421, V422, V423, V424, V425, V426, V427, V428, V429, V430, V431, V432, V433, V434, V435, V436, V437, V438, V439, V440, V441, V442, V443, V444, V445, V446, V447, V448, V449, V450, V451, V452, V453, V454, V455, V456a, V456b, V456c, V456d, V456e are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, V415, V416 and/or V424, V425 and/or V437, V438 and/or V444, V445 and/or V453, V454 together may also form "heterocyclyl";

and one of the Z3, Z4 radicals or neither of the Z3, Z4 radicals is independently selected from the group consisting of:
(e) hydrogen;
(f) halogen, F, Cl, Br, I;
(g) unsubstituted or substituted alkyl or ($C_9$-$C_{30}$)alkyl, where, optionally, the alkyl or ($C_9$-$C_{30}$)alkyl radical may be substituted by at least one substituent selected identically or differently from the group consisting of:
(i) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHV457, —NV458V459, —$NO_2$, —OH, —$OCF_3$, —SH, —O—$SO_3H$, —OP(O)(OH)$_2$, —CHO, —COOH, —C(O)$NH_2$, —$SO_3H$, —P(O)(OH)$_2$, —C(O)—V460, —C(O)O—V461, —C(O)NH—V462, —C(O)NV463V464, —O—V465, —O(—V466-O)$_y$—H (y=1, 2, 3, 4, 5), —O(—V467-O)$_y$—V468 (y=1, 2, 3, 4, 5), —OC(O)—V469, —OC(O)—O—V470, —OC(O)—NHV471, —O—C(O)—NV472V473, —OP(O)(OV474)(OV475), —OSi(V476)(V477)(V478), —OS($O_2$)—V479, —NHC(O)—V480, —NV481C(O)—V482, —NH—C(O)—O—V483, —NH—C(O)—NH—V484, —NH—C(O)—NV485V486, —NV487-C(O)—O—V488, —NV489-C(O)—NH—V490, —NV491-C(O)—NV492V493, —NHS($O_2$)—V494, —NV495S($O_2$)—V496, —S—V497, —S(O)—V498, —S($O_2$)—V499, —S($O_2$)NH—V500, —S($O_2$)NV501V502, —S($O_2$)O—V503, —P(O)(OV504)(OV505), —Si(V506)(V507)(V508)";
where V457, V458, V459, V460, V461, V462, V463, V464, V465, V466, V467, V468, V469, V470, V471, V472, V473, V474, V475, V476, V477, V478, V479, V480, V481, V482, V483, V484, V485, V486, V487, V488, V489, V490, V491, V492, V493, V494, V495, V496, V497, V498, V499, V500, V501, V502, V503, V504, V505, V506, V507, V508 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, V463, V464 and/or V472, V473 and/or V485, V486 and/or V492, V493 and/or V501, V502, in each case together, may also form "heterocyclyl";
where, optionally, the above substituents of substituent group (i) may in turn each independently be substituted by at least one substituent selected identically or differently from the group consisting of:
(ii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHV509, —NV510V511, —$NO_2$, —OH, —$OCF_3$, —SH, —O—$SO_3H$, —OP(O)(OH)$_2$, —CHO, —COOH, —C(O)$NH_2$, —$SO_3H$, —P(O)(OH)$_2$, —C(O)—V512, —C(O)O—V513, —C(O)NH—V514, —C(O)NV515V516, —O—V517, —O(—V518-O)$_z$—H (z=1, 2, 3, 4, 5), —O(—V519-O)$_z$—V520 (z=1, 2, 3, 4, 5), —OC(O)—V521, —OC(O)—O—V522, —OC(O)—NHV523, —O—C(O)—NV524V525, —OP(O)(OV526)(OV527), —OSi(V528)(V529)(V530), —OS($O_2$)—V531, —NHC(O)—V532, —NV533C(O)—V534, —NH—C(O)—O—V535, —NH—C(O)—NH—V536, —NH—C(O)—NV537V538, —NV539-C(O)—O—V540, —NV541-C(O)—NH—V542, —NV543-C(O)—NV544V545, —NHS($O_2$)—V546, —NV547S($O_2$)—V548, —S—V549, —S(O)—V550, —S($O_2$)—V551, —S($O_2$)NH—V552, —S($O_2$)NV553V554, —S($O_2$)O—V555, —P(O)(OV556)(OV557), —Si(V558)(V559)(V560)";
where V509, V510, V511, V512, V513, V514, V515, V516, V517, V518, V519, V520, V521, V522, V523, V524, V525, V526, V527, V528, V529, V530, V531, V532, V533, V534, V535, V536, V537, V538, V539, V540, V541, V542, V543, V544, V545, V546, V547, V548, V549, V550, V551, V552, V553, V554, V555, V556, V557, V558, V559, V560 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, V515, V516 and/or V524, V525 and/or V537, V538 and/or V544, V545 and/or V553, V554, in each case together, may also form "heterocyclyl";
where, optionally, the above substituents of substituent group (ii) may in turn each independently be substituted by at least one substituent selected identically or differently from the group consisting of:
(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHV561, —NV562V563, —$NO_2$, —OH, —$OCF_3$, —SH, —O—$SO_3H$, —OP(O)(OH)$_2$, —CHO, —COOH, —C(O)$NH_2$, —$SO_3H$, —P(O)(OH)$_2$, —C(O)—V564, —C(O)O—V565, —C(O)NH—V566, —C(O)NV567V568, —O—V569, —O(—V570-O)$_a$—H (a=1, 2, 3, 4, 5), —O(—V571-O)$_a$—V572 (a=1, 2, 3, 4, 5), —OC(O)—V573, —OC(O)—O—V574, —OC(O)—NHV575, —O—C(O)—NV576V577, —OP(O)(OV578)(OV579), —OSi(V580)(V581)(V582), —OS($O_2$)—V583, —NHC(O)—V584, —NV585C(O)—V586, —NH—C(O)—O—V587, —NH—C(O)—NH—V588, —NH—C(O)—NV589V590, —NV591-C(O)—O—V592, —NV593-C(O)—NH—V594, —NV595-C(O)—NV596V597, —NHS($O_2$)—V598, —NV599S($O_2$)—V600, —S—V601, —S(O)—V602, —S($O_2$)—V603, —S($O_2$)NH—V604, —S($O_2$)NV605V606, —S($O_2$)O—V607, —P(O)(OV608)(OV609), —Si(V610)(V611)(V612)";
where V561, V562, V563, V564, V565, V566, V567, V568, V569, V570, V571, V572, V573, V574, V575, V576, V577, V578, V579, V580, V581, V582, V583, V584, V585, V586, V587, V588, V589, V590, V591, V592, V593, V594, V595, V596, V597, V598, V599, V600, V601, V602, V603, V604, V605, V606, V607, V608, V609, V610, V611, V612 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, V567, V568 and/or V576, V577 and/or V589, V590 and/or V596, V597 and/or V605, V606, in each case together, may also form "heterocyclyl";

(h) unsubstituted or substituted aryl where, optionally, the aryl radical may be substituted by at least one substituent selected identically or differently from the group consisting of:

(i) "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHV613, —NV614V615, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)—V616, —C(O)O—V617, —C(O)NH—V618, —C(O)NV619V620, —O—V621, —O(—V622-O)$_b$—H (b=1, 2, 3, 4, 5), —O(—V623-O)$_b$—V624 (b=1, 2, 3, 4, 5), —OC(O)—V625, —OC(O)—O—V626, —OC(O)—NHV627, —O—C(O)—NV628V629, —OP(O)(OV630)(OV631), —OSi(V632)(V633)(V634), —OS(O$_2$)—V635, —NHC(O)—V636, —NV637C(O)—V638, —NH—C(O)—O—V639, —NH—C(O)—NH—V640, —NH—C(O)—NV641V642, —NV643-C(O)—O—V644, —NV645-C(O)—NH—V646, —NV647-C(O)—NV648V649, —NHS(O$_2$)—V650, —NV651S(O$_2$)—V652, —S—V653, —S(O)—V654, —S(O$_2$)—V655, —S(O$_2$)NH—V656, —S(O$_2$)NV657V658, —S(O$_2$)O—V659, —P(O)(OV660)(OV661), —Si(V662)(V663)(V664)";

where V613, V614, V615, V616, V617, V618, V619, V620, V621, V622, V623, V624, V625, V626, V627, V628, V629, V630, V631, V632, V633, V634, V635, V636, V637, V638, V639, V640, V641, V642, V643, V644, V645, V646, V647, V648, V649, V650, V651, V652, V653, V654, V655, V656, V657, V658, V659, V660, V661, V662, V663, V664 are each independently selected from the group consisting of: "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl" and where, alternatively, V619, V620 and/or V628, V629 and/or V641, V642 and/or V648, V649 and/or V657, V658, in each case together, may also form "heterocyclyl";

where, optionally, the above substituents of substituent group (i) may in turn each independently be substituted by at least one substituent selected identically or differently from the group consisting of:

(ii) "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHV665, —NV666V667, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)—V668, —C(O)O—V669, —C(O)NH—V670, —C(O)NV671V672, —O—V673, —O(—V674-O)$_c$—H (c=1, 2, 3, 4, 5), —O(—V675-O)$_c$—V676 (c=1, 2, 3, 4, 5), —OC(O)—V677, —OC(O)—O—V678, —OC(O)—NHV679, —O—C(O)—NV680V681, —OP(O)(OV682)(OV683), —OSi(V684)(V685)(V686), —OS(O$_2$)—V687, —NHC(O)—V688, —NV689C(O)—V690, —NH—C(O)—O—V691, —NH—C(O)—NH—V692, —NH—C(O)—NV693V694, —NV695-C(O)—O—V696, —NV697-C(O)—NH—V698, —NV699-C(O)—NV700V701, —NHS(O$_2$)—V702, —NV703S(O$_2$)—V704, —S—V705, —S(O)—V706, —S(O$_2$)—V707, —S(O$_2$)NH—V708, —S(O$_2$)NV709V710, —S(O$_2$)O—V711, —P(O)(OV712)(OV713), —Si(V714)(V715)(V716)";

where V665, V666, V667, V668, V669, V670, V671, V672, V673, V674, V675, V676, V677, V678, V679, V680, V681, V682, V683, V684, V685, V686, V687, V688, V689, V690, V691, V692, V693, V694, V695, V696, V697, V698, V699, V700, V701, V702, V703, V704, V705, V706, V707, V708, V709, V710, V711, V712, V713, V714, V715, V716 are each independently selected from the group consisting of: "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl" and where, alternatively, V671, V672 and/or V680, V681 and/or V693, V694 and/or V700, V701 and/or V709, V710, in each case together, may also form "heterocyclyl";

where, optionally, the above substituents of substituent group (ii) may in turn each independently be substituted by at least one substituent selected identically or differently from the group consisting of:

(iii) "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHV717, —NV718V719, —$NO_2$, —OH, —$OCF_3$, —SH, —O—$SO3H$, —OP(O)(OH)$_2$, —CHO, —COOH, —C(O)NH$_2$, —$SO_3H$, —P(O)(OH)$_2$, —C(O)—V720, —C(O)O—V721, —C(O)NH—V722, —C(O)NV723V724, —O—V725, —O(—V726-O)$_d$—H (d=1, 2, 3, 4, 5), —O(—V727-O)$_d$—V728 (d=1, 2, 3, 4, 5), —OC(O)—V729, —OC(O)—O—V730, —OC(O)—NHV731, —O—C(O)—NV732V733, —OP(O)(OV734)(OV735), —OSi(V736)(V737)(V738), —OS(O$_2$)—V739, —NHC(O)—V740, —NV741C(O)—V742, —NH—C(O)—O—V743, —NH—C(O)—NH—V744, —NH—C(O)—NV745V746, —NV747-C(O)—O—V748, —NV749-C(O)—NH—V750, —NV751-C(O)—NV752V753, —NHS(O$_2$)—V754, —NV755S(O$_2$)—V756, —S—V757, —S(O)—V758, —S(O$_2$)—V759, —S(O$_2$)NH—V760, —S(O$_2$)NV761V762, —S(O$_2$)O—V763, —P(O)(OV764)(OV765), —Si(V766)(V767)(V768)";

where V717, V718, V719, V720, V721, V722, V723, V724, V725, V726, V727, V728, V729, V730, V731, V732, V733, V734, V735, V736, V737, V738, V739, V740, V741, V742, V743, V744, V745, V746, V747, V748, V749, V750, V751, V752, V753, V754, V755, V756, V757, V758, V759, V760, V761, V762, V763, V764, V765, V766, V767, V768 are each independently selected from the group consisting of: "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl" and where, alternatively, V723, V724 and/or V732, V733 and/or V745, V746 and/or V752, V753 and/or V761, V762, in each case together, may also form "heterocyclyl";

(j) unsubstituted or substituted heteroaryl where, optionally, the heteroaryl radical may be substituted by at least one substituent selected identically or differently from the group consisting of:

(i) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHV769, —NV770V771, —$NO_2$, —OH, —$OCF_3$, —SH, —O—$SO_3H$, —OP(O)(OH)$_2$, —CHO, —COOH, —C(O)$NH_2$, —$SO_3H$, —P(O)(OH)$_2$, —C(O)—V772, —C(O)O—V773, —C(O)NH—V774, —C(O)NV775V776, —O—V777, —O(—V778-O)$_e$—H (e=1, 2, 3, 4, 5), —O(—V779-O)$_e$—V780 (e=1, 2, 3, 4, 5), —OC(O)—V781, —OC(O)—O—V782, —OC(O)—NHV783, —O—C(O)—NV784V785, —OP(O)(OV786)(OV787), —OSi(V788)(V789)(V790), —OS($O_2$)—V791, —NHC(O)—V792, —NV793C(O)—V794, —NH—C(O)—O—V795, —NH—C(O)—NH—V796, —NH—C(O)—NV797V798, —NV799-C(O)—O—V800, —NV801-C(O)—NH—V802, —NV803-C(O)—NV804V805, —NHS($O_2$)—V806, —NV807S($O_2$)—V808, —S—V809, —S(O)—V810, —S($O_2$)—V811, —S($O_2$)NH—V812, —S($O_2$)NV813V814, —S($O_2$)O—V815, —P(O)(OV816)(OV817), —Si(V818)(V819)(V820)";

where V769, V770, V771, V772, V773, V774, V775, V776, V777, V778, V779, V780, V781, V782, V783, V784, V785, V786, V787, V788, V789, V790, V791, V792, V793, V794, V795, V796, V797, V798, V799, V800, V801, V802, V803, V804, V805, V806, V807, V808, V809, V810, V811, V812, V813, V814, V815, V816, V817, V818, V819, V820 are each independently selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and where, alternatively, V775, V776 and/or V784, V785 and/or V797, V798 and/or V804, V805 and/or V813, V814, in each case together, may also form "heterocyclyl";

where, optionally, the above substituents of substituent group (i) may in turn each independently be substituted by at least one substituent selected identically or differently from the group consisting of:

(ii) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHV821, —NV822V823, —$NO_2$, —OH, —$OCF_3$, —SH, —O—$SO_3H$, —OP(O)(OH)$_2$, —CHO, —COOH, —C(O)$NH_2$, —$SO_3H$, —P(O)(OH)$_2$, —C(O)—V824, —C(O)O—V825, —C(O)NH—V826, —C(O)NV827V828, —O—V829, —O(—V830-O)$_f$—H (f=1, 2, 3, 4, 5), —O(—V831-O)$_f$—V832 (f=1, 2, 3, 4, 5), —OC(O)—V833, —OC(O)—O—V834, —OC(O)—NHV835, —O—C(O)—NV836V837, —OP(O)(OV838)(OV839), —OSi(V840)(V841)(V842), —OS($O_2$)—V843, —NHC(O)—V844, —NV845C(O)—V846, —NH—C(O)—O—V847, —NH—C(O)—NH—V848, —NH—C(O)—NV849V850, —NV851-C(O)—O—V852, —NV853-C(O)—NH—V854, —NV855-C(O)—NV856V857, —NHS($O_2$)—V858, —NV859S($O_2$)—V860, —S—V861, —S(O)—V862, —S($O_2$)—V863, —S($O_2$)NH—V864, —S($O_2$)NV865V866, —S($O_2$)O—V867, —P(O)(OV868)(OV869), —Si(V870)(V871)(V872)";

where V821, V822, V823, V824, V825, V826, V827, V828, V829, V830, V831, V832, V833, V834, V835, V836, V837, V838, V839, V840, V841, V842, V843, V844, V845, V846, V847, V848, V849, V850, V851, V852, V853, V854, V855, V856, V857, V858, V859, V860, V861, V862, V863, V864, V865, V866, V867, V868, V869, V870, V871, V872 are each independently selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and where, alternatively, V827, V828 and/or V836, V837 and/or V849, V850 and/or V856, V857 and/or V865, V866, in each case together, may also form "heterocyclyl";

where, optionally, the above substituents of substituent group (ii) may in turn each independently be substituted by at least one substituent selected identically or differently from the group consisting of:

(iii) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHV873, —NV874V875, —$NO_2$, —OH, —$OCF_3$, —SH, —O—$SO_3H$, —OP(O)(OH)$_2$, —CHO, —COOH, —C(O)$NH_2$, —$SO_3H$, —P(O)(OH)$_2$, —C(O)—V876, —C(O)O—V877, —C(O)NH—V878, —C(O)NV879V880, —O—V881, —O(—V882-O)$_g$—H (g=1, 2, 3, 4, 5), —O(—V883-O)$_g$—V884 (g=1, 2, 3, 4, 5), —OC(O)—V885, —OC(O)—O—V886, —OC(O)—NHV887, —O—C(O)—NV888V889, —OP(O)(OV890)(OV891), —OSi(V892)(V893)(V894), —OS($O_2$)—V895, —NHC(O)—V896, —NV897C(O)—V898, —NH—C(O)—O—V899, —NH—C(O)—NH—V900, —NH—C(O)—NV901V902, —NV903-C(O)—O—V904, —NV905-C(O)—NH—V906, —NV907-C(O)—NV908V909, —NHS($O_2$)—V910, —NV911S($O_2$)—V912, —S—V913, —S(O)—V914, —S($O_2$)—V915, —S($O_2$)NH—V916, —S($O_2$)NV917V918, —S($O_2$)O—V919, —P(O)(OV920)(OV921), —Si(V922)(V923)(V924)";

where V873, V874, V875, V876, V877, V878, V879, V880, V881, V882, V883, V884, V885, V886, V887, V888, V889, V890, V891, V892, V893, V894, V895, V896, V897, V898, V899, V900, V901, V902, V903, V904, V905, V906, V907, V908, V909, V910, V911, V912, V913, V914, V915, V916, V917, V918, V919, V920, V921, V922, V923, V924 are each independently selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and where, alternatively, V879, V880 and/or V888, V889 and/or V901, V902 and/or V908, V909 and/or V917, V918, in each case together, may also form "heterocyclyl";

(k) OZ6 where Z6 is independently selected from the group consisting of:

(i) "hydrogen, alkyl, $(C_9-C_{30})$alkyl, cycloalkyl, cycloalkylalkyl, heterocyclyl, heterocyclylalkyl, aryl, arylalkyl, heteroaryl, heteroarylalkyl";

where, optionally, the above substituents of substituent group (i) may in turn each independently be substituted by at least one substituent selected identically or differently from the group consisting of:

(ii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHV925, —NV926V927, —$NO_2$, —OH, —$OCF_3$, —SH, —O—$SO_3H$, —OP(O)(OH)$_2$, —CHO, —COOH, —C(O)$NH_2$, —$SO_3H$, —P(O)(OH)$_2$, —C(O)—V928, —C(O)O—V929, —C(O)NH—V930, —C(O)NV931V932, —O—V933, —O(—V934-O)$_h$—H (h=1, 2, 3, 4, 5), —O(—V935-O)$_h$—V936 (h=1, 2, 3, 4, 5), —OC(O)—V937, —OC(O)—O—V938, —OC(O)—NHV939, —O—C(O)—NV940V941, —OP(O)(OV942)(OV943), —OSi(V944)(V945)(V946), —OS($O_2$)—V947, —NHC(O)—V948, —NV949C(O)—V950, —NH—C(O)—O—V951, —NH—C(O)—NH—V952, —NH—C(O)—NV953V954, —NV955-C(O)—O—V956, —NV957-C(O)—NH—V958, —NV959-C(O)—NV960V961, —NHS($O_2$)—V962, —NV963S($O_2$)—V964, —S—V965, —S(O)—V966, —S($O_2$)—V967, —S($O_2$)NH—V968, —S($O_2$)NV969V970, —S($O_2$)O—V971, —P(O)(OV972)(OV973), —Si(V974)(V975)(V976)";

where V925, V926, V927, V928, V929, V930, V931, V932, V933, V934, V935, V936, V937, V938, V939, V940, V941, V942, V943, V944, V945, V946, V947, V948, V949, V950, V951, V952, V953, V954, V955, V956, V957, V958, V959, V960, V961, V962, V963, V964, V965, V966, V967, V968, V969, V970, V971, V972, V973, V974, V975, V976 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, V931, V932 and/or V940, V941 and/or V953, V954 and/or V960, V961 and/or V969, V970, in each case together, may also form "heterocyclyl";

where, optionally, the above substituents of substituent group (ii) may in turn each independently be substituted by at least one substituent selected identically or differently from the group consisting of:

(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHV977, —NV978V979, —$NO_2$, —OH, —$OCF_3$, —SH, —O—$SO_3H$, —OP(O)(OH)$_2$, —CHO, —COOH, —C(O)$NH_2$, —$SO_3H$, —P(O)(OH)$_2$, —C(O)—V980, —C(O)O—V981, —C(O)NH—V982, —C(O)NV983V984, —O—V985, —O(—V986-O)$_i$—H (i=1, 2, 3, 4, 5), —O(—V987-O)$_i$—V988 (i=1, 2, 3, 4, 5), —OC(O)—V989, —OC(O)—O—V990, —OC(O)—NHV991, —O—C(O)—NV992V993, —OP(O)(OV994)(OV995), —OSi(V996)(V997)(V998), —OS($O_2$)—V999, —NHC(O)—V1000, —NV1001C(O)—V1002, —NH—C(O)—O—V1003, —NH—C(O)—NH—V1004, —NH—C(O)—NV1005V1006, —NV1007-C(O)—O—V1008, —NV1009-C(O)—NH—V1010, —NV1011-C(O)—NV1012V1013, —NHS($O_2$)—V1014, —NV1015S($O_2$)—V1016, —S—V1017, —S(O)—V1018, —S($O_2$)—V1019, —S($O_2$)NH—V1020-S($O_2$)NV1021V1022, —S($O_2$)O—V1023, —P(O)(OV1024)(OV1025), —Si(V1026)(V1027)(V1028)";

where V977, V978, V979, V980, V981, V982, V983, V984, V985, V986, V987, V988, V989, V990, V991, V992, V993, V994, V995, V996, V997, V998, V999, V1000, V1001, V1002, V1003, V1004, V1005, V1006, V1007, V1008, V1009, V1010, V1011, V1012, V1013, V1014, V1015, V1016, V1017, V1018, V1019, V1020, V1021, V1022, V1023, V1024, V1025, V1026, V1027, V1028 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, V983, V984 and/or V992, V993 and/or V1005, V1006 and/or V1012, V1013 and/or V1021, V1022, in each case together, may also form "heterocyclyl";

(l) SZ7 where Z7 is independently selected from the group consisting of:

(i) "hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl";

where, optionally, the above substituents of substituent group (i) may in turn each independently be substituted by at least one substituent selected identically or differently from the group consisting of:

(ii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHV1029, —NV1030V1031, —$NO_2$, —OH, —$OCF_3$, —SH, —O—$SO_3H$, —OP(O)(OH)$_2$, —CHO, —COOH, —C(O)$NH_2$, —$SO_3H$, —P(O)(OH)$_2$, —C(O)—V1032, —C(O)O—V1033, —C(O)NH—V1034, —C(O)NV1035V1036, —O—V1037, —O(—V1038-O)$_j$—H (j=1, 2, 3, 4, 5), —O(—V1039-O)$_j$—V1040 (j=1, 2, 3, 4, 5), —OC(O)—V1041, —OC(O)—C—V1042, —OC(O)—NHV1043, —O—C(O)—NV1044V1045, —OP(O)(OV1046)(OV1047), —OSi(V1048)(V1049)(V1050), —OS($O_2$)—V1051, —NHC(O)—V1052, —NV1053C(O)—V1054, —NH—C(O)—O—V1055, —NH—C(O)—NH—V1056, —NH—C(O)—NV1057V1058, —NV1059-C(O)—O—V1060, —NV1061-C(O)—NH—V1062, —NV1063-C(O)—NV1064V1065, —NHS($O_2$)—V1066, —NV1067S($O_2$)—V1068, —S—V1069, —S(O)—V1070, —S($O_2$)—V1071, —S($O_2$)NH—V1072, —S($O_2$)NV1073V1074, —S($O_2$)O—V1075, —P(O)(OV1076)(OV1077), —Si(V1078)(V1079)(V1080)";

where V1029, V1030, V1031, V1032, V1033, V1034, V1035, V1036, V1037, V1038, V1039, V1040, V1041, V1042, V1043, V1044, V1045, V1046, V1047, V1048, V1049, V1050, V1051, V1052, V1053, V1054, V1055, V1056, V1057, V1058, V1059, V1060, V1061, V1062, V1063, V1064, V1065, V1066, V1067, V1068, V1069, V1070, V1071, V1072, V1073, V1074, V1075, V1076, V1077, V1078, V1079, V1080 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, V1035, V1036 and/or V1044, V1045 and/or V1057, V1058 and/or V1064, V1065 and/or V1073, V1074, in each case together, may also form "heterocyclyl";

where, optionally, the above substituents of substituent group (ii) may in turn each independently be substituted by at least one substituent selected identically or differently from the group consisting of:

(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHV1081, —NV1082V1083, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)—V1084, —C(O)O—V1085, —C(O)NH—V1086, —C(O)NV1087V1088, —O—V1089, —O(—V1090-O)$_k$—H (k=1, 2, 3, 4, 5), —O(—V1091-O)$_k$—V1092 (k=1, 2, 3, 4, 5), —OC(O)—V1093, —OC(O)—O—V1094, —OC(O)—NHV1095, —O—C(O)—NV1096V1097, —OP(O)(OV1098)(OV1099), —OSi(V1100)(V1101)(V1102), —OS(O$_2$)—, —NHC(O)—V1104, —NV1105C(O)—V1106, —NH—C(O)—O—V1107, —NH—C(O)—NH—V1108, —NH—C(O)—NV1109V1110, —NV1111-C(O)—O—V1112, —NV1113-C(O)—NH—V1114, —NV1115-C(O)—NV1116V1117, —NHS(O$_2$)—V1118, —NV1119S(O$_2$)—V1120, —S—V1121, —S(O)—V1122, —S(O$_2$)—V1123, —S(O$_2$)NH—V1124, —S(O$_2$)NV1125V1126, —S(O$_2$)O—V1127, —P(O)(OV1128)(OV1129), —Si(V1130)(V1131)(V1132)";

where V1081, V1082, V1083, V1084, V1085, V1086, V1087, V1088, V1089, V1090, V1091, V1092, V1093, V1094, V1095, V1096, V1097, V1098, V1099, V1100, V1101, V1102, V1103, V1104, V1105, V1106, V1107, V1108, V1109, V1110, V1111, V1112, V1113, V1114, V1115, V1116, V1117, V1118, V1119, V1120, V1121, V1122, V1123, V1124, V1125, V1126, V1127, V1128, V1129, V1130, V1131, V1132 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, V1087, V1088 and/or V1096, V1097 and/or V1109, V1110 and/or V1116, V1117 and/or V1125, V1126, in each case together, may also form "heterocyclyl";

(m) NZ8Z9 where Z8, Z9 are each independently selected from the group consisting of:

(i) "hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, —C(O)—V1133, —C(O)O—V1134, —C(O)—NV1135V1136, —S(O$_2$)—V1137, —S(O$_2$)O—V1138";

where V1133, V1134, V1135, V1136, V1137, V1138 are each independently selected from the group consisting of: hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, V1135, V1136 together may also form "heterocyclyl";

where, optionally, the above substituents of substituent group (i) may in turn each independently be substituted by at least one substituent selected identically or differently from the group consisting of:

(ii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHV1139, —NV1140V1141, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)—V1142, —C(O)O—V1143, —C(O)NH—V1144, —C(O)NV1145V1146, —O—V1147, —O(—V1148-O)$_l$—H (l=1, 2, 3, 4, 5), —O(—V1149-O)$_l$—V1150 (l=1, 2, 3, 4, 5), —OC(O)—V1151, —OC(O)—O—V1152, —OC(O)—NHV1153, —O—C(O)—NV1154V1155, —OP(O)(OV1156)(OV1157), —OSi(V1158)(V1159)(V1160), —OS(O$_2$)—V1161, —NHC(O)—V1162, —NV1163C(O)—V1164, —NH—C(O)—O—V1165, —NH—C(O)—NH—V1166, —NH—C(O)—NV1167V1168, —NV1169-C(O)—O—V1170, —NV1171-C(O)—NH—V1172, —NV1173-C(O)—NV1174V1175, —NHS(O$_2$)—V1176, —NV1177S(O$_2$)—V1178, —S—V1179, —S(O)—V1180, —S(O$_2$)—V1181, —S(O$_2$)NH—V1182, —S(O$_2$)NV1183V1184, —S(O$_2$)O—V1185, —P(O)(OV1186)(OV1187), —Si(V1188)(V1189)(V1190)";

where V1139, V1140, V1141, V1142, V1143, V1144, V1145, V1146, V1147, V1148, V1149, V1150, V1151, V1152, V1153, V1154, V1155, V1156, V1157, V1158, V1159, V1160, V1161, V1162, V1163, V1164, V1165, V1166, V1167, V1168, V1169, V1170, V1171, V1172, V1173, V1174, V1175, V1176, V1177, V1178, V1179, V1180, V1181, V1182, V1183, V1184, V1185, V1186, V1187, V1188, V1189, V1190 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, V1145, V1146 and/or V1154, V1155 and/or V1167, V1168 and/or V1174, V1175 and/or V1183, V1184, in each case together, may also form "heterocyclyl";

where, optionally, the above substituents of substituent group (ii) may in turn each independently be substituted by at least one substituent selected identically or differently from the group consisting of:

(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHV1191, —NV1192V1193, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)—V1194, —C(O)O—V1195, —C(O)NH—V1196, —C(O)NV1197V1198, —O—V1199, —O(—V1200-O)$_m$—H (m=1, 2, 3, 4, 5), —O(—V1201-O)$_m$—V1202 (m=1, 2, 3, 4, 5), —OC(O)—V1203, —OC(O)—O—V1204, —OC(O)—NHV1205, —O—C(O)—NV1206V1207, —OP(O)(OV1208)(OV1209), —OSi(V1210)(V1211)(V1212), —OS(O$_2$)—V1213, —NHC(O)—V1214, —NV1215C (O)—V1216, —NH—C(O)—O—V1217, —NH—C(O)—NH—V1218, —NH—C(O)—NV1219V1220, —NV1221-C(O)—O—V1222, —NV1223-C(O)—NH—V1224, —NV1225-C(O)—NV1226V1227, —NHS(O$_2$)—V1228, —NV1229S(O$_2$)—V1230, —S—V1231, —S(O)—V1232, —S(O$_2$)—V1233, —S(O$_2$)NH—V1234, —S(O$_2$)NV1235V1236, —S(O$_2$)O—V1237, —P(O)(OV1238)(OV1239), —Si(V1240)(V1241)(V1242)";

where V1191, V1192, V1193, V1194, V1195, V1196, V1197, V1198, V1199, V1200, V1201, V1202, V1203, V1204, V1205, V1206, V1207, V1208, V1209, V1210, V1211, V1212, V1213, V1214, V1215, V1216, V1217, V1218, V1219, V1220, V1221, V1222, V1223, V1224, V1225, V1226, V1227, V1228, V1229, V1230, V1231, V1232, V1233, V1234, V1235, V1236, V1237, V1238, V1239, V1240, V1241, V1242 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, V1197, V1198 and/or V1206, V1207 and/or V1219, V1220 and/or V1226, V1227 and/or V1235, V1236, in each case together, may also form "heterocyclyl"; or (C) one of the Z3, Z4 radicals is, or both Z3, Z4 radicals are, independently "substituted alkyl", where "substituted alkyl" is substituted by at least one substituent selected from the group consisting of:

(a) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHW1, —NW2W3, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—W4, —C(O)O—W5, —C(O)NH—W6, —C(O)NW7W8, —O—W9, —O(—W10-O)$_r$—H (r=1, 2, 3, 4, 5), —O(—W11-O)$_r$—W12 (r=1, 2, 3, 4, 5), —OC(O)—W13, —OC(O)—O—W14, —OC(O)—NHW15, —O—C(O)—NW16W17, —OP(O)(OW18)(OW19), —OSi(W20)(W21)(W22), —OS(O$_2$)—W23, —NHC(O)—W24, —NW25C(O)—W26, —NH—C(O)—O—W27, —NH—C(O)—NH—W28, —NH—C(O)—NW29W30, —NW31-C(O)—O—W32, —NW33-C(O)—NH—W34, —NW35-C(O)—NW36W37, —NHS(O$_2$)—W38, —NW39S(O$_2$)—W40, —S—W41, —S(O)—W42, —S(O$_2$)—W43, —S(O$_2$)NH—W44, —S(O$_2$)NW45W46, —S(O$_2$)O—W47, —P(O)(OW48)(OW49), —Si(W50)(W51)(W52)";

where W1, W2, W3, W4, W5, W6, W7, W8, W9, W10, W11, W12, W13, W14, W15, W16, W17, W18, W19, W20, W21, W22, W23, W24, W25, W26, W27, W28, W29, W30, W31, W32, W33, W34, W35, W36, W37, W38, W39, W40, W41, W42, W43, W44, W45, W46, W47, W48, W49, W50, W51, W52 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, W7, W8 and/or W16, W17 and/or W29, W30 and/or W36, W37 and/or W45, W46, in each case together, may also form "heterocyclyl";

with the proviso that "—C(O)NH-aryl", "—C(O)NH-heteroaryl", "—C(O)NH-cycloalkyl", "—C(O)NH-heterocyclyl" are substituted further by at least one substituent selected from the following substitution group (i);

where, optionally, the above substituents of substituent group (a) may in turn each independently be substituted by at least one substituent selected identically or differently from the group consisting of:

(i) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHW53, —NW54W55, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—W56, —C(O)O—W57, —C(O)NH—W58, —C(O)NW59W60, —O—W61, —O(—W62-O)$_s$—H (s=1, 2, 3, 4, 5), —O(—W63-O)$_t$—W64 (t=1, 2, 3, 4, 5), —OC(O)—W65, —OC(O)—O—W66, —OC(O)—NHW67, —O—C(O)—NW68W69, —OP(O)(OW70)(OW71), —OSi(W72)(W73)(W74), —OS(O$_2$)—W75, —NHC(O)—W76, —NW77C(O)—W78, —NH—C(O)—O—W79, —NH—C(O)—NH—W80, —NH—C(O)—NW81W82, —NW83-C(O)—O—W84, —NW85-C(O)—NH—W86, —NW87-C(O)—NW88W89, —NHS(O$_2$)—W90, —NW91S(O$_2$)—W92, —S—W93, —S(O)—W94, —S(O$_2$)—W95, —S(O$_2$)NH—W96, —S(O$_2$)NW97W98, —S(O$_2$)O—W99, —P(O)(OW100)(OW101), —Si(W102)(W103)(W104)";

where W53, W54, W55, W56, W57, W58, W59, W60, W61, W62, W63, W64, W65, W66, W67, W68, W69, W70, W71, W72, W73, W74, W75, W76, W77, W78, W79, W80, W81, W82, W83, W84, W85, W86, W87, W88, W89, W90, W91, W92, W93, W94, W95, W96, W97, W98, W99, W100, W101, W102, W103, W104 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, W59, W60 and/or W68, W69 and/or W81, W82 and/or W88, W89 and/or W97, W98, in each case together, may also form "heterocyclyl";

where, optionally, the above substituents of substituent group (i) may in turn each independently be substituted by at least one substituent selected identically or differently from the group consisting of:

(ii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHW105, —NW106W107, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—W108, —C(O)O—W109, —C(O)NH—W110, —C(O)NW111W112, —O—W113, —O(—W114-O)$_t$—H (t=1, 2, 3, 4, 5), —O(—W115-O)$_t$—W116 (t=1, 2, 3, 4, 5), —OC(O)—W117, —OC(O)—O—W118, —OC(O)—NHW119, —O—C(O)—NW120W121, —OP(O)(OW122)(OW123), —OSi(W124)(W125)(W126), —OS(O$_2$)—W127, —NHC(O)—W128, —NW129C(O)—W130, —NH—C(O)—O—W131, —NH—C(O)—NH—W132, —NH—C(O)—NW133W134, —NW135-C(O)—O—W136, —NW137-C(O)—NH—W138, —NW139-C(O)—NW140W141, —NHS(O$_2$)—W142, —NW143S(O$_2$)—W144, —S—W145, —S(O)—

W146, —S(O₂)—W147, —S(O₂)NH—W148, —S(O₂)NW149W150, —S(O₂)O—W151, —P(O)(OW152)(OW153), —Si(W154)(W155)(W156)";

where W105, W106, W107, W108, W109, W110, W111, W112, W113, W114, W115, W116, W117, W118, W119, W120, W1211, W22, W123, W124, W125, W126, W127, W128, W129, W130, W131, W132, W133, W134, W135, W136, W137, W138, W139, W140, W141, W142, W143, W144, W145, W146, W147, W148, W149, W150, W151, W152, W153, W154, W155, W156 are each independently selected from the group consisting of: "alkyl, $(C_9-C_{30})$alkyl, cycloalkyl, cycloalkylalkyl, heterocyclyl, heterocyclylalkyl, aryl, aryarylalkyl, heteroaryl, heteroarylalkyl" and where, alternatively, W111, W112 and/or W120, W121 and/or W133, W134 and/or W140, W141 and/or W149, W150, in each case together, may also form "heterocyclyl";

or one of the Z3, Z4 radicals is, or both Z3, Z4 radicals are, independently "$(C_9-C_{30})$alkyl";

where "$(C_9-C_{30})$alkyl" may independently optionally be substituted by at least one substituent selected identically or differently from the group consisting of:

(i) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, CF₃, N₃, NH₂, —NHW157, —NW158W159, —NO₂, —OH, —OCF₃, —SH, —O—SO₃H, —OP(O)(OH)₂, —CHO, —COOH, —C(O)NH₂, —SO₃H, —P(O)(OH)₂, —C(O)—W160, —C(O)O—W161, —C(O)NH—W162, —C(O)NW163W164, —O—W165, —O(—W166-O)$_u$—H (u=1, 2, 3, 4, 5), —O(—W167-O)$_u$—W168 (u=1, 2, 3, 4, 5), —OC(O)—W169, —OC(O)—O—W170, —OC(O)—NHW171, —O—C(O)—NW172W173, —OP(O)(OW174)(OW175), —OSi(W176)(W177)(W178), —OS(O₂)—W179, —NHC(O)—W180, —NW181C(O)—W182, —NH—C(O)—O—W183, —NH—C(O)—NH—W184, —NH—C(O)—NW185W186, —NW187-C(O)—O—W188, —NW189-C(O)—NH—W190, —NW191-C(O)—NW192W193, —NHS(O₂)—W194, —NW195S(O₂)—W196, —S—W197, —S(O)—W198, —S(O₂)—W199, —S(O₂)NH—W200, —S(O₂)NW201W202, —S(O₂)O—W203, —P(O)(OW204)(OW205), —Si(W206)(W207)(W208)";

where W157, W158, W159, W160, W161, W162, W163, W164, W165, W166, W167, W168, W169, W170, W171, W172, W173, W174, W175, W176, W177, W178, W179, W180, W181, W182, W183, W184, W185, W186, W187, W188, W189, W190, W191, W192, W193, W194, W195, W196, W197, W198, W199, W200, W201, W202, W203, W204, W205, W206, W207, W208 are each independently selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and where, alternatively, W163, W164 and/or W172, W173 and/or W185, W186 and/or W192, W193 and/or W201, W202, in each case together, may also form "heterocyclyl";

where, optionally, the above substituents of substituent group (i) may in turn each independently be substituted by at least one substituent selected identically or differently from the group consisting of:

(ii) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, CF₃, N₃, NH₂, —NHW209, —NW210W211, —NO₂, —OH, —OCF₃, —SH, —O—SO₃H, —OP(O)(OH)₂, —CHO, —COOH, —C(O)NH₂, —SO₃H, —P(O)(OH)₂, —C(O)—W212, —C(O)O—W213, —C(O)NH—W214, —C(O)NW215W216, —O—W217, —O(—W218-O)$_v$—H (v=1, 2, 3, 4, 5), —O(—W219-O)$_v$—W220 (v=1, 2, 3, 4, 5), —OC(O)—W221, —OC(O)—O—W222, —OC(O)—NHW223, —O—C(O)—NW224W225, —OP(O)(OW226)(OW227), —OSi(W228)(W229)(W230), —OS(O₂)—W231, —NHC(O)—W232, —NW233C(O)—W234, —NH—C(O)—O—W235, —NH—C(O)—NH—W236, —NH—C(O)—NW237W238, —NW239-C(O)—O—W240, —NW241-C(O)—NH—W242, —NW243-C(O)—NW244W245, —NHS(O₂)—W246, —NW247S(O₂)—W248, —S—W249, —S(O)—W250, —S(O₂)—W251, —S(O₂)NH—W252, —S(O₂)NW253W254, —S(O₂)O—W255, —P(O)(OW256)(OW257), —Si(W258)(W259)(W260)";

where W209, W210, W211, W212, W213, W214, W215, W216, W217, W218, W219, W220, W221, W222, W223, W224, W225, W226, W227, W228, W229, W230, W231, W232, W233, W234, W235, W236, W237, W238, W239, W240, W241, W242, W243, W244, W245, W246, W247, W248, W249, W250, W251, W252, W253, W254, W255, W256, W257, W258, W259, W260 are each independently selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and where, alternatively, W215, W216 and/or W224, W225 and/or W237, W238 and/or W244, W245 and/or W253, W254, in each case together, may also form "heterocyclyl";

and one of the Z3, Z4 radicals or neither of the Z3, Z4 radicals is independently selected from the group consisting of:

(b) hydrogen;
(c) halogen, F, Cl, Br, I;
(d) unsubstituted or substituted alkyl or $(C_9-C_{30})$alkyl, where, optionally, the alkyl or $(C_9-C_{30})$alkyl radical may be substituted by at least one substituent selected identically or differently from the group consisting of:

(i) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, CF₃, N₃, NH₂, —NHW457, —NW458W459, —NO₂, —OH, —OCF₃, —SH, —O—SO₃H, —OP(O)(OH)₂, —CHO, —COOH, —C(O)NH₂, —SO₃H, —P(O)(OH)₂, —C(O)—W460, —C(O)O—W461, —C(O)NH—W462, —C(O)NW463W464, —O—W465, —O(—W466-O)$_x$—H (x=1, 2, 3, 4, 5), —O(—W467-O)$_x$—W468 (x=1, 2, 3, 4, 5), —OC(O)—W469, —OC(O)—O—W470, —OC(O)—NHW471, —O—C(O)—NW472W473, —OP(O)(OW474)(OW475), —OSi(W476)(W477)(W478), —OS(O₂)—W479, —NHC(O)—W480, —NW481C(O)—W482, —NH—C(O)—O—W483, —NH—C(O)—NH—W484, —NH—C(O)—NW485W486, —NW487-C(O)—O—W488, —NW489-C(O)—NH—W490, —NW491-C(O)—NW492W493, —NHS(O₂)—W494, —NW495S(O₂)—W496, —S—W497, —S(O)—W498, —S(O$_2$)—W499, —S(O$_2$)NH—W500, —S(O$_2$)NW501W502, —S(O$_2$)O—W503, —P(O)(OW504)(OW505), —Si(W506)(W507)(W508)";

where W457, W458, W459, W460, W461, W462, W463, W464, W465, W466, W467, W468, W469, W470, W471, W472, W473, W474, W475, W476, W477, W478, W479, W480, W481, W482, W483, W484, W485, W486, W487, W488, W489, W490, W491, W492, W493, W494, W495, W496, W497, W498, W499, W500, W501, W502, W503, W504, W505, W506, W507, W508 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, W463, W464 and/or W472, W473 and/or W485, W486 and/or W492, W493 and/or W501, W502, in each case together, may also form "heterocyclyl";

where, optionally, the above substituents of substituent group (i) may in turn each independently be substituted by at least one substituent selected identically or differently from the group consisting of:

(ii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHW509, —NW510W511, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—W512, —C(O)O—W513, —C(O)NH—W514, —C(O)NW515W516, —O—W517, —O(—W518-O)$_y$—H (y=1, 2, 3, 4, 5), —O(—W519-O)$_y$—W520 (y=1, 2, 3, 4, 5), —OC(O)—W521, —OC(O)—O—W522, —OC(O)—NHW523, —O—C(O)—NW524W525, —OP(O)(OW526)(OW527), —OSi(W528)(W529)(W530), —OS(O$_2$)—W531, —NHC(O)—W532, —NW533C(O)—W534, —NH—C(O)—O—W535, —NH—C(O)—NH—W536, —NH—C(O)—NW537W538, —NW539-C(O)—O—W540, —NW541-C(O)—NH—W542, —NW543-C(O)—NW544W545, —NHS(O$_2$)—W546, —NW547S(O$_2$)—W548, —S—W549, —S(O)—W550, —S(O$_2$)—W551, —S(O$_2$)NH—W552, —S(O$_2$)NW553W554, —S(O$_2$)O—W555, —P(O)(OW556)(OW557), —Si(W558)(W559)(W560)";

where W509, W510, W511, W512, W513, W514, W515, W516, W517, W518, W519, W520, W521, W522, W523, W524, W525, W526, W527, W528, W529, W530, W531, W532, W533, W534, W535, W536, W537, W538, W539, W540, W541, W542, W543, W544, W545, W546, W547, W548, W549, W550, W551, W552, W553, W554, W555, W556, W557, W558, W559, W560 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, W515, W516 and/or W524, W525 and/or W537, W538 and/or W544, W545 and/or W553, W554, in each case together, may also form "heterocyclyl";

where, optionally, the above substituents of substituent group (ii) may in turn each independently be substituted by at least one substituent selected identically or differently from the group consisting of:

(iii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHW561, —NW562W563, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—W564, —C(O)O—W565, —C(O)NH—W566, —C(O)NW567W568, —O—W569, —O(—W570-O)$_z$—H (z=1, 2, 3, 4, 5), —O(—W571-O)$_z$—W572 (z=1, 2, 3, 4, 5), —OC(O)—W573, —OC(O)—O—W574, —OC(O)—NHW575, —O—C(O)—NW576W577, —OP(O)(OW578)(OW579), —OSi(W580)(W581)(W582), —OS(O$_2$)—W583, —NHC(O)—W584, —NW585C(O)—W586, —NH—C(O)—O—W587, —NH—C(O)—NH—W588, —NH—C(O)—NW589W590, —NW591-C(O)—O—W592, —NW593-C(O)—NH—W594, —NW595-C(O)—NW596W597, —NHS(O$_2$)—W598, —NW599S(O$_2$)—W600, —S—W601, —S(O)—W602, —S(O$_2$)—W603, —S(O$_2$)NH—W604, —S(O$_2$)NW605W606, —S(O$_2$)O—W607, —P(O)(OW608)(OW609), —Si(W610)(W611)(W612)";

where W561, W562, W563, W564, W565, W566, W567, W568, W569, W570, W571, W572, W573, W574, W575, W576, W577, W578, W579, W580, W581, W582, W583, W584, W585, W586, W587, W588, W589, W590, W591, W592, W593, W594, W595, W596, W597, W598, W599, W600, W601, W602, W603, W604, W605, W606, W607, W608, W609, W610, W611, W612 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, W567, W568 and/or W576, W577 and/or W589, W590 and/or W596, W597 and/or W605, W606, in each case together, may also form "heterocyclyl";

(e) unsubstituted or substituted aryl where, optionally, the aryl radical may be substituted by at least one substituent selected identically or differently from the group consisting of:

(i) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHW613, —NW614W615, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—W616, —C(O)O—W617, —C(O)NH—W618, —C(O)NW619W620, —O—W621, —O(—W622-O)$_a$—H (a=1, 2, 3, 4, 5), —O(—W623-O)$_a$—W624 (a=1, 2, 3, 4, 5), —OC(O)—W625, —OC(O)—O—W626, —OC(O)—NHW627, —O—C(O)—NW628W629, —OP(O)(OW630)(OW631), —OSi(W632)(W633)(W634), —OS(O$_2$)—W635, —NHC(O)—W636, —NW637C(O)—W638, —NH—C(O)—O—W639, —NH—C(O)—N7H—W640, —NH—C(O)—NW641W642, —NW643-C(O)—O—W644, —NW645-C(O)—NH—W646, —NW647-C(O)—NW648W649, —NHS(O₂)—W650, —NW651S(O₂)—W652, —S—W653, —S(O)—W654, —S(O₂)—W655, —S(O₂)NH—W656, —S(O₂)NW657W658, —S(O₂)O—W659, —P(O)(OW660)(OW661), —Si(W662)(W663)(W664)";

where W613, W614, W615, W616, W617, W618, W619, W620, W621, W622, W623, W624, W625, W626, W627, W628, W629, W630, W631, W632, W633, W634, W635, W636, W637, W638, W639, W640, W641, W642, W643, W644, W645, W646, W647, W648, W649, W650, W651, W652, W653, W654, W655, W656, W657, W658, W659, W660, W661, W662, W663, W664 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, W619, W620 and/or W628, W629 and/or W641, W642 and/or W648, W649 and/or W657, W658, in each case together, may also form "heterocycyl";

where, optionally, the above substituents of substituent group (i) may in turn each independently be substituted by at least one substituent selected identically or differently from the group consisting of:

(ii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHW665, —NW666W667, —NO₂, —OH, —OCF₃, —SH, —O—SO₃H, —OP(O)(OH)₂, —CHO, —COOH, —C(O)NH₂, —SO₃H, —P(O)(OH)₂, —C(O)—W668, —C(O)O—W669, —C(O)NH—W670, —C(O)NW671W672, —O—W673, —O(—W674-O)$_b$—H (b=1, 2, 3, 4, 5), —O(—W675-O)$_b$—W676 (b=1, 2, 3, 4, 5), —OC(O)—W677, —OC(O)—O—W678, —OC(O)—NHW679, —O—C(O)—NW680W681, —OP(O)(OW682)(OW683), —OSi(W684)(W685)(W686), —OS(O₂)—W687, —NHC(O)—W688, —NW689C(O)—W690, —NH—C(O)—O—W691, —NH—C(O)—NH—W692, —NH—C(O)—NW693W694, —NW695-C(O)—O—W696, —NW697-C(O)—NH—W698, —NW699-C(O)—NW700W701, —NHS(O₂)—W702, —NW703S(O₂)—W704, —S—W705, —S(O)—W706, —S(O₂)—W707, —S(O₂)NH—W708, —S(O₂)NW709W710, —S(O₂)O—W711, —P(O)(OW712)(OW713), —Si(W714)(W715)(W716)";

where W665, W666, W667, W668, W669, W670, W671, W672, W673, W674, W675, W676, W677, W678, W679, W680, W681, W682, W683, W684, W685, W686, W687, W688, W689, W690, W691, W692, W693, W694, W695, W696, W697, W698, W699, W700, W701, W702, W703, W704, W705, W706, W707, W708, W709, W710, W711, W712, W713, W714, W715, W716 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, W671, W672 and/or W680, W681 and/or W693, W694 and/or W700, W701 and/or W709, W710, in each case together, may also form "heterocyclyl";

where, optionally, the above substituents of substituent group (ii) may in turn each independently be substituted by at least one substituent selected identically or differently from the group consisting of:

(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHW717, —NW718W719, —NO₂, —OH, —OCF₃, —SH, —O—SO₃H, —OP(O)(OH)₂, —CHO, —COOH, —C(O)NH₂, —SO₃H, —P(O)(OH)₂, —C(O)—W720, —C(O)O—W721, —C(O)NH—W722, —C(O)NW723W724, —O—W725, —O(—W726-O)$_c$—H (c=1, 2, 3, 4, 5), —O(—W727-O)$_c$—W728 (c=1, 2, 3, 4, 5), —OC(O)—W729, —OC(O)—O—W730, —OC(O)—NHW731, —O—C(O)—NW732W733, —OP(O)(OW734)(OW735), —OSi(W736)(W737)(W738), —OS(O₂)—W739, —NHC(O)—W740, —NW741C(O)—W742, —NH—C(O)—O—W743, —NH—C(O)—NH—W744, —NH—C(O)—NW745W746, —NW747-C(O)—O—W748, —NW749-C(O)—NH—W750, —NW751-C(O)—NW752W753, —NHS(O₂)—W754, —NW755S(O₂)—W756, —S—W757, —S(O)—W758, —S(O₂)—W759, —S(O₂)NH—W760, —S(O₂)NW761W762, —S(O₂)O—W763, —P(O)(OW764)(OW765), —Si(W766)(W767)(W768)";

where W717, W718, W719, W720, W721, W722, W723, W724, W725, W726, W727, W728, W729, W730, W731, W732, W733, W734, W735, W736, W737, W738, W739, W740, W741, W742, W743, W744, W745, W746, W747, W748, W749, W750, W751, W752, W753, W754, W755, W756, W757, W758, W759, W760, W761, W762, W763, W764, W765, W766, W767, W768 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, W723, W724 and/or W732, W733 and/or W745, W746 and/or W752, W753 and/or W761, W762, in each case together, may also form "heterocyclyl";

(f) unsubstituted or substituted heteroaryl where, optionally, the heteroaryl radical may be substituted by at least one substituent selected identically or differently from the group consisting of:

(i) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHW769, —NW770W771, —NO₂, —OH, —OCF₃, —SH, —O—SO₃H, —OP(O)(OH)₂, —CHO, —COOH, —C(O)NH₂, —SO₃H, —P(O)(OH)₂, —C(O)—W772, —C(O)O—W773, —C(O)NH—W774, —C(O)NW775W776, —O—W777, —O(—W778-O)$_d$—H (d=1, 2, 3, 4, 5), —O(—W779-O)$_d$—W780 (d=1, 2, 3, 4, 5), —OC(O)—W781, —OC(O)—O—W782, —OC(O)—NHW783, —O—C(O)—NW784W785, —OP(O)(OW786)(OW787), —OSi(W788)(W789)(W790), —OS(O₂)—W791, —NHC(O)—W792, —NW793C(O)—W794, —NH—C(O)—O—W795, —NH—C(O)—NH—W796, —NH—C(O)—NW797W798, —NW799-C(O)—O—W800, —NW801-C(O)—NH—W802, —NW803-C(O)—NW804W805, —NHS(O$_2$)—W806, —NW807S(O$_2$)—W808, —S—W809, —S(O)—W810, —S(O$_2$)—W811, —S(O$_2$)NH—W812, —S(O$_2$)NW813W814, —S(O$_2$)O—W815, —P(O)(OW816)(OW817), —Si(W818)(W819)(W820)";

where W769, W770, W771, W772, W773, W774, W775, W776, W777, W778, W779, W780, W781, W782, W783, W784, W785, W786, W787, W788, W789, W790, W791, W792, W793, W794, W795, W796, W797, W798, W799, W800, W801, W802, W803, W804, W805, W806, W807, W808, W809, W810, W811, W812, W813, W814, W815, W816, W817, W818, W819, W820 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, W775, W776 and/or W784, W785 and/or W797, W798 and/or W804, W805 and/or W813, W814, in each case together, may also form "heterocyclyl";

where, optionally, the above substituents of substituent group (i) may in turn each independently be substituted by at least one substituent selected identically or differently from the group consisting of:

(ii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHW821, —NW822W823, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—W824, —C(O)O—W825, —C(O)NH—W826, —C(O)NW827W828, —O—W829, —O(—W830-O)$_e$—H (e=1, 2, 3, 4, 5), —O(—W831-O)$_e$—W832 (e=1, 2, 3, 4, 5), —OC(O)—W833, —OC(O)—O—W834, —OC(O)—NHW835, —O—C(O)—NW836W837, —OP(O)(OW838)(OW839), —OSi(W840)(W841)(W842), —OS(O$_2$)—W843, —NHC(O)—W844, —NW845C(O)—W846, —NH—C(O)—O—W847, —NH—C(O)—NH—W848, —NH—C(O)—NW849W850, —NW851-C(O)—O—W852, —NW853-C(O)—NH—W854, —NW855-C(O)—NW856W857, —NHS(O$_2$)—W858, —NW859S(O$_2$)—W860, —S—W861, —S(O)—W862, —S(O$_2$)—W863, —S(O$_2$)NH—W864, —S(O$_2$)NW865W866, —S(O$_2$)O—W867, —P(O)(OW868)(OW869), —Si(W870)(W871)(W872)";

where W821, W822, W823, W824, W825, W826, W827, W828, W829, W830, W831, W832, W833, W834, W835, W836, W837, W838, W839, W840, W841, W842, W843, W844, W845, W846, W847, W848, W849, W850, W851, W852, W853, W854, W855, W856, W857, W858, W859, W860, W861, W862, W863, W864, W865, W866, W867, W868, W869, W870, W871, W872 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, W827, W828 and/or W836, W837 and/or W849, W850 and/or W856, W857 and/or W865, W866, in each case together, may also form "heterocyclyl";

where, optionally, the above substituents of substituent group (ii) may in turn each independently be substituted by at least one substituent selected identically or differently from the group consisting of:

(iii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHW873, —NW874W875, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—W876, —C(O)O—W877, —C(O)NH—W878, —C(O)NW879W880, —O—W881, —O(—W882-O)$_f$—H (f=1, 2, 3, 4, 5), —O(—W883-O)$_f$—W884 (f=1, 2, 3, 4, 5), —OC(O)—W885, —OC(O)—O—W886, —OC(O)—NHW887, —O—C(O)—NW888W889, —OP(O)(OW890)(OW891), —OSi(W892)(W893)(W894), —OS(O$_2$)—W895, —NHC(O)—W896, —NW897C(O)—W898, —NH—C(O)—O—W899, —NH—C(O)—NH—W900, —NH—C(O)—NW901W902, —NW903-C(O)—O—W904, —NW905-C(O)—NH—W906, —NW907-C(O)—NW908W909, —NHS(O$_2$)—W910, —NW911S(O$_2$)—W912, —S—W913, —S(O)—W914, —S(O$_2$)—W915, —S(O$_2$)NH—W916, —S(O$_2$)NW917W918, —S(O$_2$)O—W919, —P(O)(OW920)(OW921), —Si(W922)(W923)(W924)";

where W873, W874, W875, W876, W877, W878, W879, W880, W881, W882, W883, W884, W885, W886, W887, W888, W889, W890, W891, W892, W893, W894, W895, W896, W897, W898, W899, W900, W901, W902, W903, W904, W905, W906, W907, W908, W909, W910, W911, W912, W913, W914, W915, W916, W917, W918, W919, W920, W921, W922, W923, W924 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, W879, W880 and/or W888, W889 and/or W901, W902 and/or W908, W909 and/or W917, W918, in each case together, may also form "heterocyclyl";

(g) OZ6 where Z6 is independently selected from the group consisting of:

(i) "hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl";

where, optionally, the above substituents of substituent group (i) may in turn each independently be substituted by at least one substituent selected identically or differently from the group consisting of:

(ii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHW925, —NW926W927, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—W928, —C(O)O—

W929, —C(O)NH—W930, —C(O)NW931W932, —O—W933, —O(—W934-O)$_g$—H (g=1, 2, 3, 4, 5), —O(—W935-O)$_g$—W936 (g=1, 2, 3, 4, 5), —OC(O)—W937, —OC(O)—O—W938, —OC(O)—NHW939, —O—C(O)—NW940W941, —OP(O)(OW942)(OW943), —OSi(W944)(W945)(W946), —OS(O$_2$)—W947, —NHC(O)—W948, —NW949C(O)—W950, —NH—C(O)—O—W951, —NH—C(O)—NH—W952, —NH—C(O)—NW953W954, —NW955-C(O)—O—W956, —NW957-C(O)—NH—W958, —NW959-C(O)—NW960W961, —NHS(O$_2$)—W962, —NW963S(O$_2$)—W964, —S—W965, —S(O)—W966, —S(O$_2$)—W967, —S(O$_2$)NH—W968, —S(O$_2$)NW969W970, —S(O$_2$)O—W971, —P(O)(OW972)(OW973), —Si(W974)(W975)(W976)";

where W925, W926, W927, W928, W929, W930, W931, W932, W933, W934, W935, W936, W937, W938, W939, W940, W941, W942, W943, W944, W945, W946, W947, W948, W949, W950, W951, W952, W953, W954, W955, W956, W957, W958, W959, W960, W961, W962, W963, W964, W965, W966, W967, W968, W969, W970, W971, W972, W973, W974, W975, W976 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, W931, W932 and/or W940, W941 and/or W953, W954 and/or W960, W961 and/or W969, W970, in each case together, may also form "heterocyclyl";

where, optionally, the above substituents of substituent group (ii) may in turn each independently be substituted by at least one substituent selected identically or differently from the group consisting of:

(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHW977, —NW978W979, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—W980, —C(O)O—W981, —C(O)NH—W982, —C(O)NW983W984, —O—W985, —O(—W986-O)$_h$—H (h=1, 2, 3, 4, 5), —O(—W987-O)$_h$—W988 (h=1, 2, 3, 4, 5), —OC(O)—W989, —OC(O)—O—W990, —OC(O)—NHW991, —O—C(O)—NW992W993, —OP(O)(OW994)(OW995), —OSi(W996)(W997)(W998), —OS(O$_2$)—W999, —NHC(O)—W1000, —NW1001C(O)—W1002, —NH—C(O)—O—W1003, —NH—C(O)—NH—W1004, —NH—C(O)—NW1005W1006, —NW1007-C(O)—O—W1008, —NW1009-C(O)—NH—W1010, —NW1011-C(O)—NW1012W1013, —NHS(O$_2$)—W1014, —NW1015S(O$_2$)—W1016, —S—W1017, —S(O)—W1018, —S(O$_2$)—W1019, —S(O$_2$)NH—W1020, —S(O$_2$)NW1021W1022, —S(O$_2$)O—W1023, —P(O)(OW1024)(OW1025), —Si(W1026)(W1027)(W1028)";

where W977, W978, W979, W980, W981, W982, W983, W984, W985, W986, W987, W988, W989, W990, W991, W992, W993, W994, W995, W996, W997, W998, W999, W1000, W1001, W1002, W1003, W1004, W1005, W1006, W1007, W1008, W1009, W1010, W1011, W1012, W1013, W1014, W1015, W1016, W1017, W1018, W1019, W1020, W1021, W1022, W1023, W1024, W1025, W1026, W1027, W1028 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, W983, W984 and/or W992, W993 and/or W1005, W1006 and/or W1012, W1013 and/or W1021, W1022, in each case together, may also form "heterocyclyl";

(h) SZ7 where Z7 is independently selected from the group consisting of:

(i) "hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl";

where, optionally, the above substituents of substituent group (i) may in turn each independently be substituted by at least one substituent selected identically or differently from the group consisting of:

(ii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHW1029, —NW1030W1031, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—W1032, —C(O)O—W1033, —C(O)NH—W1034, —C(O)NW1035W1036, —O—W1037, —O(—W1038-O)$_i$—H (i=1, 2, 3, 4, 5), —O(—W1039-O)$_i$—W1040 (i=1, 2, 3, 4, 5), —OC(O)—W1041, —OC(O)—O—W1042, —OC(O)—NHW1043, —O—C(O)—NW1044W1045, —OP(O)(OW1046)(OW1047), —OSi(W1048)(W1049)(W1050), —OS(O$_2$)—W1051, —NHC(O)—W1052, —NW1053C(O)—W1054, —NH—C(O)—O—W1055, —NH—C(O)—NH—W1056, —NH—C(O)—NW1057W1058, —NW1059-C(O)—O—W1060, —NW1061-C(O)—NH—W1062, —NW1063-C(O)—NW1064W1065, —NHS(O$_2$)—W1066, —NW1067S(O$_2$)—W1068, —S—W1069, —S(O)—W1070, —S(O$_2$)—W1071, —S(O$_2$)NH—W1072, —S(O$_2$)NW1073W1074, —S(O$_2$)O—W1075, —P(O)(OW1076)(OW1077), —Si(W1078)(W1079)(W1080)";

where W1029, W1030, W1031, W1032, W1033, W1034, W1035, W1036, W1037, W1038, W1039, W1040, W1041, W1042, W1043, W1044, W1045, W1046, W1047, W1048, W1049, W1050, W1051, W1052, W1053, W1054, W1055, W1056, W1057, W1058, W1059, W1060, W1061, W1062, W1063, W1064, W1065, W1066, W1067, W1068, W1069, W1070, W1071, W1072, W1073, W1074, W1075, W1076, W1077, W1078, W1079, W1080 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, W1035, W1036 and/or W1044, W1045 and/or W1057, W1058 and/or W1064, W1065 and/or W1073, W1074, in each case together, may also form "heterocyclyl";

where, optionally, the above substituents of substituent group (ii) may in turn each independently be substituted by at least one substituent selected identically or differently from the group consisting of:

(iii) "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHW1081, —NW1082W1083, —$NO_2$, —OH, —$OCF_3$, —SH, —O—$SO_3H$, —OP(O)$(OH)_2$, —CHO, —COOH, —C(O)$NH_2$, —$SO_3H$, —P(O)$(OH)_2$, —C(O)—W1084, —C(O)O—W1085, —C(O)NH—W1086, —C(O)NW1087W1088, —O—W1089, —O(—W1090-O)$_j$—H (j=1, 2, 3, 4, 5), —O(—W1091-O)$_j$—W1092 (j=1, 2, 3, 4, 5), —OC(O)—W1093, —OC(O)—O—W1094 —OC(O)—NHW1095, —O—C(O)—NW1096W1097, —OP(O)(OW1098)(OW1099), —OSi(W1100)(W1101)(W1102), —OS$(O_2)$—W1103, —NHC(O)—W1104, —NW1105C(O)—W1106, —NH—C(O)—O—W1107, —NH—C(O)—NH—W1108, —NH—C(O)—NW1109W1110, —NW1111-C(O)—O—W1112, —NW1113-C(O)—NH—W1114, —NW1115-C(O)—NW1116W1117, —NHS$(O_2)$—W1118, —NW1119S$(O_2)$—W1120, —S—W1121, —S(O)—W1122, —S$(O_2)$—W1123, —S$(O_2)$NH—W1124, —S$(O_2)$NW1125W1126, —S$(O_2)$O—W1127, —P(O)(OW1128)(OW1129), —Si(W1130)(W1131)(W1132)";

where W1081, W1082, W1083, W1084, W1085, W1086, W1087, W1088, W1089, W1090, W1091, W1092, W1093, W1094, W1095, W1096, W1097, W1098, W1099, W1100, W1101, W1102, W1103, W1104, W1105, W1106, W1107, W1108, W1109, W1110, W1111, W1112, W1113, W1114, W1115, W1116, W1117, W1118, W1119, W1120, W1121, W1122, W1123, W1124, W1125, W1126, W1127, W1128, W1129, W1130, W1131, W1132 are each independently selected from the group consisting of: "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl" and where, alternatively, W1087, W1088 and/or W1096, W1097 and/or W1109, W1110 and/or W1116, W1117 and/or W1125, W1126, in each case together, may also form "heterocyclyl";

(j) NZ8Z9 where Z8, Z9 are each independently selected from the group consisting of:

(i) "hydrogen, alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl, —C(O)—W1133, —C(O)O—W1134, —C(O)—NW1135W1136, —S$(O_2)$—W1137, —S$(O_2)$O—W1138";

where W1133, W1134, W1135, W1136, W1137, W1138 are each independently selected from the group consisting of: hydrogen, alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl" and where, alternatively, W1135, W1136 together may also form "heterocyclyl";

where, optionally, the above substituents of substituent group (i) may in turn each independently be substituted by at least one substituent selected identically or differently from the group consisting of:

(ii) "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHW1139, —NW1140W1141, —$NO_2$, —OH, —$OCF_3$, —SH, —O—$SO_3H$, —OP(O)$(OH)_2$, —CHO, —COOH, —C(O)$NH_2$, —$SO_3H$, —P(O)$(OH)_2$, —C(O)—W1142, —C(O)O—W1143, —C(O)NH—W1144, —C(O)NW1145W1146, —O—W1147, —O(—W1148-O)$_k$—H (k=1, 2, 3, 4, 5), —O(—W1149-O)$_k$—W1150 (k=1, 2, 3, 4, 5), —OC(O)—W1151, —OC(O)—O—W1152, —OC(O)—NHW1153, —O—C(O)—NW1154W1155, —OP(O)(OW1156)(OW1157), —OSi(W1158)(W1159)(W1160), —OS$(O_2)$—W1161, —NHC(O)—W1162, —NW1163C(O)—W1164, —NH—C(O)—O—W1165, —NH—C(O)—NH—W1166, —NH—C(O)—NW1167W1168, —NW1169-C(O)—O—W1170, —NW1171-C(O)—NH—W1172, —NW1173-C(O)—NW1174W1175, —NHS$(O_2)$—W1176, —NW1177S$(O_2)$—W1178, —S—W1179, —S(O)—W1180, —S$(O_2)$—W1181, —S$(O_2)$NH—W1182, —S$(O_2)$NW1183W1184, —S$(O_2)$O—W1185, —P(O)(OW1186)(OW1187), —Si(W1188)(W1189)(W1190)";

where W1139, W1140, W1141, W1142, W1143, W1144, W1145, W1146, W1147, W1148, W1149, W1150, W1151, W1152, W1153, W1154, W1155, W1156, W1157, W1158, W1159, W1160, W1161, W1162, W1163, W1164, W1165, W1166, W1167, W1168, W1169, W1170, W1171, W1172, W1173, W1174, W1175, W1176, W1177, W1178, W1179, W1180, W1181, W1182, W1183, W1184, W1185, W1186, W1187, W1188, W1189, W1190 are each independently selected from the group consisting of: "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl" and where, alternatively, W1145, W1146 and/or W1154, W1155 and/or W1167, W1168 and/or W1174, W1175 and/or W1183, W1184, in each case together, may also form "heterocyclyl";

where, optionally, the above substituents of substituent group (ii) may in turn each independently be substituted by at least one substituent selected identically or differently from the group consisting of:

(iii) "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHW1191, —NW1192W1193, —$NO_2$, —OH, —$OCF_3$, —SH, —O—$SO_3H$, —OP(O)$(OH)_2$, —CHO, —COOH, —C(O)$NH_2$, —$SO_3H$, —P(O)$(OH)_2$, —C(O)—W1194, —C(O)O—W1195, —C(O)NH—W1196, —C(O)NW1197W1198, —O—W1199, —O(—W1200-O)$_l$—H (l=1, 2, 3, 4, 5), —O(—W1201-O)$_l$—W1202 (l=1, 2, 3, 4, 5), —OC(O)—W1203, —OC(O)—O—W1204, —OC(O)—NHW1205, —O—C(O)—

NW1206W1207, —OP(O)(OW1208)
(OW1209), —OSi(W1210)(W1211)(W1212),
—OS(O$_2$)—W1213, —NHC(O)—W1214,
—NW1215C(O)—W1216, —NH—C(O)—
O—W1217, —NH—C(O)—NH—W1218,
—NH—C(O)—NW1219W1220, —NW1221-
C(O)—O—W1222, —NW1223-C(O)—NH—
W1224, —NW1225-C(O)—NW1226W1227,
—NHS(O$_2$)—W1228, —NW1229S(O$_2$)—
W1230, —S—W1231, —S(O)—W1232,
—S(O$_2$)—W1233, —S(O$_2$)NH—W1234,
—S(O$_2$)NW1235W1236, —S(O$_2$)O—W1237,
—P(O)(OW1238)(OW1239), —Si(W1240)
(W1241)(W1242)";
where W1191, W1192, W1193, W1194, W1195, W1196, W1197, W1198, W1199, W1200, W1201, W1202, W1203, W1204, W1205, W1206, W1207, W1208, W1209, W1210, W1211, W1212, W1213, W1214, W1215, W1216, W1217, W1218, W1219, W1220, W1221, W1222, W1223, W1224, W1225, W1226, W1227, W1228, W1229, W1230, W1231, W1232, W1233, W1234, W1235, W1236, W1237, W1238, W1239, W1240, W1241, W1242 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, W1197, W1198 and/or W1206, W1207 and/or W1219, W1220 and/or W1226, W1227 and/or W1235, W1236, in each case together, may also form "heterocyclyl"; or (D) one of the Z3, Z4 radicals or both Z3, Z4 radicals are each independently selected from the group consisting of:
(1) "—NZ10Z11, —OZ12, —SZ13";
where one of the Z10, Z11 radicals or both Z10, Z11 radicals and Z12, Z13 radicals are each independently selected from the group consisting of:
(a) "hydrogen, alkyl, cycloalkyl, cycloalkylalkyl, aryl, arylalkyl, heteroaryl, heteroarylalkyl, heterocyclyl, heterocyclylalkyl";
with the proviso that both Z10, Z11 radicals are not simultaneously hydrogen;
with the further proviso that the Z12 radical is not hydrogen;
with the further proviso that the above substituents of substituent group (a), when they are not hydrogen, are each independently substituted further by at least one substituent selected identically or differently from the group consisting of:
(i) "(C$_9$-C$_{30}$)alkyl, cycloalkyl, cycloalkylalkyl, heterocyclyl, heterocyclylalkyl, aryl, arylalkyl, heteroaryl, heteroarylalkyl, N$_3$, —NH-cycloalkyl, —NH-cycloalkylalkyl, —NH-heteroaryl, —NH-heteroarylalkyl, —NH-arylalkyl, —NH-heterocyclyl, —NH-heterocyclylalkyl, —NQ1Q2, —S-cycloalkyl, —S-cycloalkylalkyl, —S-aryl, —S-arylalkyl, —S-heteroaryl, —S-heteroarylalkyl, —S-heterocyclyl, —S-heterocyclylalkyl, —O-cycloalkyl, —O-cycloalkylalkyl, —O-arylalkyl, —O-heteroaryl, —O-heteroarylalkyl, —O-heterocyclyl, —O-heterocyclylalkyl, —O(-Q3-O)$_p$—H (p=1, 2, 3, 4, 5), —O(-Q4-O)$_p$-Q5 (p=1, 2, 3, 4, 5), —OP(O)(OQ6)(OQ7), —C(O)O-Q8, —C(O)NH$_2$, —C(O)NH-Q9, —C(O)NQ10Q11, —S(O$_2$)-Q12, —P(O)(OH)$_2$, —P(O)(OQ13)(OQ14), —Si(Q15)(Q16)(Q17), —O—Si (Q18)(Q19)(Q20), —O—C(O)—O-Q21, —O—C(O)—NH-Q22, —O—C(O)—NQ23Q24, —NH—C(O)—O-Q25, —NH—C(O)—NH-Q26, —NH—C(O)—NQ27Q28, —NQ29-C(O)—O-Q30, —NQ31-C(O)—NH-Q32, —NQ33-C(O)—NQ34Q35, —NQ36-S(O$_2$)-Q37, —NH—S(O$_2$)-Q38, —O—S(O$_2$)-Q39, —NH—C(O)-Q40, —NQ41-C(O)-Q42, —C(O)-Q43, —OC(O)-Q44, —S(O)-Q45, —S(O$_2$)—NHQ46, —S(O$_2$)—NQ47Q48, —S(O$_2$)—OQ49";
with the further proviso that "—N(alkyl)$_2$" is further substituted by at least one substituent selected from the following substituent group (ii);
where Q1, Q2, Q3, Q4, Q5, Q6, Q7, Q8, Q9, Q10, Q11, Q12, Q13, Q14, Q15, Q16, Q17, Q18, Q19, Q20, Q21, Q22, Q23, Q24, Q25, Q26, Q27, Q28, Q29, Q30, Q31, Q32, Q33, Q34, Q35, Q36, Q37, Q38, Q39, Q40, Q41, Q42, Q43, Q44, Q45, Q46, Q47, Q48, Q49 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, Q10, Q11 and/or Q23, Q24 and/or Q27, Q28 and/or Q34, Q35 and/or Q47, Q48, in each case together, may also form "heterocyclyl";
where, optionally, the above substituents of substituent group (a) and/or of substituent group (i) may in turn each independently be substituted by at least one substituent selected identically or differently from the group consisting of:
(ii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHQ50, —NQ51Q52, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)-Q53, —C(O)O-Q54, —C(O)NH-Q55, —C(O)NQ56Q57, —O-Q58, —O(-Q59-O)$_r$—H (r=1, 2, 3, 4, 5), -Q(-Q60-O)$_r$-Q61 (r=1, 2, 3, 4, 5), —OC(O)-Q62, —OC(O)—O-Q63, —OC(O)—NHQ64, —O—C(O)—NQ65Q66, —OP(O)(OQ67)(OQ68), —OSi(Q69)(Q70)(Q71), —OS(O$_2$)-Q72, —NHC(O)-Q73, —NQ74C(O)-Q75, —NH—C(O)—O-Q76, —NH—C(O)—NH-Q77, —NH—C(O)—NQ78Q79, —NQ80-C(O)—O-Q81, —NQ82-C(O)—NH-Q83, —NQ84-C(O)—NQ85Q86, —NHS(O$_2$)-Q87, —NQ88S(O$_2$)-Q89, —S-Q90, —S(O)-Q91, —S(O$_2$)-Q92, —S(O$_2$)NH-Q93, —S(O$_2$)NQ94Q95, —S(O$_2$)O-Q96, —P(O)(OQ97)(OQ98), —Si(Q99)(Q100)(Q101)";
where Q50, Q51, Q52, Q53, Q54, Q55, Q56, Q57, Q58, Q59, Q60, Q61, Q62, Q63, Q64, Q65, Q66, Q67, Q68, Q69, Q70, Q71, Q72, Q73, Q74, Q75, Q76, Q77, Q78, Q79, Q80, Q81, Q82, Q83, Q84, Q85, Q86, Q87, Q88, Q89, Q90, Q91, Q92, Q93, Q94, Q95, Q96, Q97, Q98, Q99, Q100, Q101 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, Q56, Q57 and/or Q65, Q66 and/or Q78, Q79 and/or Q85, Q86 and/or Q94, Q95, in each case together, may also form "heterocyclyl";
where, optionally, the above substituents of substituent group (ii) may in turn each independently be substituted by at least one substituent selected identically or differently from the group consisting of:
(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —$NHQ102$, —$NQ103Q104$, —$NO_2$, —OH, —$OCF_3$, —SH, —O—$SO_3H$, —OP(O)(OH)$_2$, —CHO, —COOH, —C(O)$NH_2$, —$SO_3H$, —P(O)(OH)$_2$, —C(O)-Q105, —C(O)O-Q106, —C(O)NH-Q107, —C(O)NQ108Q109, —O-Q110, —O(-Q111-O)$_s$—H (s=1, 2, 3, 4, 5), —O(-Q112-O)$_s$-Q113 (s=1, 2, 3, 4, 5), —OC(O)-Q114, —OC(O)—O-Q115, —OC(O)—NHQ116, —O—C(O)—NQ117Q118, —OP(O)(OQ119)(OQ120), —OSi(Q121)(Q122)(Q123), —OS($O_2$)-Q124, —NHC(O)-Q125, —NQ126C(O)-Q127, —NH—C(O)—O-Q128, —NH—C(O)—NH-Q129, —NH—C(O)—NQ130Q131, —NQ132-C(O)—O-Q133, —NQ134-C(O)—NH-Q135, —NQ136-C(O)—NQ137Q138, —NHS($O_2$)-Q139, —NQ140S($O_2$)-Q141, —S-Q142, —S(O)-Q143, —S($O_2$)-Q144, —S($O_2$)NH-Q145, —S($O_2$)NQ146Q147, —S($O_2$)O-Q148, —P(O)(OQ149)(OQ150), —Si(Q151)(Q152)(Q153)";
where Q102, Q103, Q104, Q105, Q106, Q107, Q108, Q109, Q110, Q111, Q112, Q113, Q114, Q115, Q116, Q117, Q118, Q119, Q120, Q121, Q122, Q123, Q124, Q125, Q126, Q127, Q128, Q129, Q130, Q131, Q132, Q133, Q134, Q135, Q136, Q137, Q138, Q139, Q140, Q141, Q142, Q143, Q144, Q145, Q146, Q147, Q148, Q149, Q150, Q151, Q152, Q153 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, Q108, Q109 and/or Q117, Q118 and/or Q130, Q131 and/or Q137, Q138 and/or Q146, Q147, in each case together, may also form "heterocyclyl";
(b) "($C_9$-$C_{30}$)alkyl, —C(O)-Q154, —C(O)O-Q155, —C(O)—NQ156Q157, —S($O_2$)-Q158, —S($O_2$)O-Q159";
where Q154, Q155, Q156, Q157, Q158, Q159 are each independently selected from the group consisting of: "hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, Q156, Q157 together may also form "heterocyclyl";
where, optionally, the above substituents of substituent group (b) may in turn each independently be substituted by at least one substituent selected identically or differently from the group consisting of:
(i) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHQ160, —NQ161Q162, —$NO_2$, —OH, —$OCF_3$, —SH, —O—$SO_3H$, —OP(O)(OH)$_2$, —CHO, —COOH, —C(O)$NH_2$, —$SO_3H$, —P(O)(OH)$_2$, —C(O)-Q163, —C(O)O-Q164, —C(O)NH-Q165, —C(O)NQ166Q167, —O-Q168, —O(-Q169-O)$_t$—H (t=1, 2, 3, 4, 5), —O(-Q170-O)$_t$-Q171 (t=1, 2, 3, 4, 5), —OC(O)-Q172, —OC(O)—O-Q173, —OC(O)—NHQ174, —O—C(O)—NQ175Q176, —OP(O)(OQ177)(OQ178), —OSi(Q179)(Q180)(Q181), —OS($O_2$)-Q182, —NHC(O)-Q183, —NQ184C(O)-Q185, —NH—C(O)—O-Q186, —NH—C(O)—NH-Q187, —NH—C(O)—NQ188Q189, —NQ190-C(O)—O-Q191, —NQ192-C(O)—NH-Q193, —NQ194-C(O)—NQ195Q196, —NHS($O_2$)-Q197, —NQ198S($O_2$)-Q199, —S-Q200, —S(O)-Q201, —S($O_2$)-Q202, —S($O_2$)NH-Q203, —S($O_2$)NQ204Q205, —S($O_2$)O-Q206, —P(O)(OQ207)(OQ208), —Si(Q209)(Q210)(Q211)";
where Q160, Q161, Q162, Q163, Q164, Q165, Q166, Q167, Q168, Q169, Q170, Q171, Q172, Q173, Q174, Q175, Q176, Q177, Q178, Q179, Q180, Q181, Q182, Q183, Q184, Q185, Q186, Q187, Q188, Q189, Q190, Q191, Q192, Q193, Q194, Q195, Q196, Q197, Q198, Q199, Q200, Q201, Q202, Q203, Q204, Q205, Q206, Q207, Q208, Q209, Q210, Q211 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, Q166, Q167 and/or Q175, Q176 and/or Q188, Q189 and/or Q195, Q196 and/or Q204, Q205, in each case together, may also form "heterocyclyl";
where, optionally, the above substituents of substituent group (i) may in turn each independently be substituted by at least one substituent selected identically or differently from the group consisting of:
(ii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHQ212, —NQ213Q214, —$NO_2$, —OH, —$OCF_3$, —SH, —O—$SO_3H$, —OP(O)(OH)$_2$, —CHO, —COOH, —C(O)$NH_2$, —$SO_3H$, —P(O)(OH)$_2$, —C(O)-Q215, —C(O)O-Q216, —C(O)NH-Q217, —C(O)NQ218Q219, —O-Q220, —O(-Q221-O)$_u$—H (u=1, 2, 3, 4, 5), —O(-Q222-O)$_u$-Q223 (u=1, 2, 3, 4, 5), —OC(O)-Q224, —OC(O)—O-Q225, —OC(O)—NHQ226, —O—C(O)—NQ227Q228, —OP(O)(OQ229)(OQ230), —OSi(Q231)(Q232)(Q233), —OS($O_2$)-Q234, —NHC(O)-Q235, —NQ236C(O)-Q237, —NH—C(O)—O-Q238, —NH—C(O)—NH-Q239, —NH—C(O)—NQ240Q241, —NQ242-C(O)—O-Q243, —NQ244-C(O)—NH-Q245, —NQ246-C(O)—NQ247Q248, —NHS($O_2$)-Q249, —NQ250S($O_2$)-Q251, —S-Q252, —S(O)-Q253, —S($O_2$)-Q254, —S($O_2$)NH-Q255, —S($O_2$)NQ256Q257, —S($O_2$)O-Q258, —P(O)(OQ259)(OQ260), —Si(Q261)(Q262)(Q263)";
where Q212, Q213, Q214, Q215, Q216, Q217, Q218, Q219, Q220, Q221, Q222, Q223, Q224, Q225, Q226, Q227, Q228, Q229, Q230, Q231, Q232, Q233, Q234, Q235, Q236, Q237, Q238, Q239, Q240, Q241, Q242, Q243, Q244, Q245, Q246, Q247, Q248, Q249, Q250, Q251, Q252, Q253, Q254, Q255, Q256, Q257, Q258, Q259, Q260, Q261, Q262, Q263 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, Q218, Q219 and/or Q227, Q228 and/or Q240, Q241 and/or Q247, Q248 and/or Q256, Q257, in each case together, may also form "heterocyclyl";

where, optionally, the above substituents of substituent group (ii) may in turn each independently be substituted by at least one substituent selected identically or differently from the group consisting of:

(iii) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHQ264, —NQ265Q266, —$NO_2$, —OH, —$OCF_3$, —SH, —O—$SO_3H$, —OP(O)(OH)$_2$, —CHO, —COOH, —C(O)NH$_2$, —SO$_3$H, —P(O)(OH)$_2$, —C(O)-Q267, —C(O)O-Q268, —C(O)NH-Q269, —C(O)NQ270Q271, —O-Q272, —O(-Q273-O)$_v$—H (v=1, 2, 3, 4, 5), —O(-Q274-O)$_v$-Q275 (v=1, 2, 3, 4, 5), —OC(O)-Q276, —OC(O)—O-Q277, —OC(O)—NHQ278, —O—C(O)—NQ279Q280, —OP(O)(OQ281)(OQ282), —OSi(Q283)(Q284)(Q285), —OS(O$_2$)-Q286, —NHC(O)-Q287, —NQ288C(O)-Q289, —NH—C(O)—O-Q290, —NH—C(O)—NH-Q291, —NH—C(O)—NQ292Q293, —NQ294-C(O)—O-Q295, —NQ296-C(O)—NH-Q297, —NQ298-C(O)—NQ299Q300, —NHS(O$_2$)-Q301, —NQ302S(O$_2$)-Q303, —S-Q304, —S(O)-Q305, —S(O$_2$)-Q306, —S(O$_2$)NH-Q307, —S(O$_2$)NQ308Q309, —S(O$_2$)O-Q310, —P(O)(OQ311)(OQ312), —Si(Q313)(Q314)(Q315)";

where Q264, Q265, Q266, Q267, Q268, Q269, Q270, Q271, Q272, Q273, Q274, Q275, Q276, Q277, Q278, Q279, Q280, Q281, Q282, Q283, Q284, Q285, Q286, Q287, Q288, Q289, Q290, Q291, Q292, Q293, Q294, Q295, Q296, Q297, Q298, Q299, Q300, Q301, Q302, Q303, Q304, Q305, Q306, Q307, Q308, Q309, Q310, Q311, Q312, Q313, Q314, Q315 are each independently selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and where, alternatively, Q270, Q271 and/or Q279, Q280 and/or Q292, Q293 and/or Q299, Q300 and/or Q308, Q309, in each case together, may also form "heterocyclyl";

or one of the Z10, Z11 radicals or neither of the Z10, Z11 radicals are each independently selected from the group consisting of:

(c) "hydrogen, alkyl, $(C_9-C_{30})$alkyl, cycloalkyl, cycloalkylalkyl, aryl, arylalkyl, heteroaryl, heteroarylalkyl, heterocyclyl, heterocyclylalkyl, —C(O)-Q316, —C(O)O-Q317, —C(O)—NQ318Q319, —S(O$_2$)-Q320, —S(O$_2$)O-Q321";

where Q316, Q317, Q318, Q319, Q320, Q321 are each independently selected from the group consisting of: "hydrogen, alkyl, $(C_9-C_{30})$alkyl, cycloalkyl, cycloalkylalkyl, heterocyclyl, heterocyclylalkyl, aryl, arylalkyl, heteroaryl, heteroarylalkyl" and where, alternatively, Q318, Q319 together may also form "heterocyclyl";

where, optionally, the above substituents of substituent group (c), when they are not hydrogen, may in turn each independently be substituted by at least one substituent selected identically or differently from the group consisting of:

(i) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHQ322, —NQ323Q324, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)-Q325, —C(O)O-Q326, —C(O)NH-Q327, —C(O)NQ328Q329, —O-Q330, —O(-Q331-O)$_w$—H (w=1, 2, 3, 4, 5), —O(-Q332-O)$_w$-Q333 (w=1, 2, 3, 4, 5), —OC(O)-Q334, —OC(O)—O-Q335, —OC(O)—NHQ336, —O—C(O)—NQ337Q338, —OP(O)(OQ339)(OQ340), —OSi(Q341)(Q342)(Q343), —OS(O$_2$)-Q344, —NHC(O)-Q345, —NQ346C(O)-Q347, —NH—C(O)—O-Q348, —NH—C(O)—NH-Q349, —NH—C(O)—NQ350Q351, —NQ352-C(O)—O-Q353, —NQ354-C(O)—NH-Q355, —NQ356-C(O)—NQ357Q358, —NHS(O$_2$)-Q359, —NQ360S(O$_2$)-Q361, —S-Q362, —S(O)-Q363, —S(O$_2$)-Q364, —S(O$_2$)NH-Q365, —S(O$_2$)NQ366Q367, —S(O$_2$)O-Q368, —P(O)(OQ369)(OQ370), —Si(Q371)(Q372)(Q373)";

where Q322, Q323, Q324, Q325, Q326, Q327, Q328, Q329, Q330, Q331, Q332, Q333, Q334, Q335, Q336, Q337, Q338, Q339, Q340, Q341, Q342, Q343, Q344, Q345, Q346, Q347, Q348, Q349, Q350, Q351, Q352, Q353, Q354, Q355, Q356, Q357, Q358, Q359, Q360, Q361, Q362, Q363, Q364, Q365, Q366, Q367, Q368, Q369, Q370, Q371, Q372, Q373 are each independently selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and where, alternatively, Q328, Q329 and/or Q337, Q338 and/or Q350, Q351 and/or Q357, Q358 and/or Q366, Q367, in each case together, may also form "heterocyclyl";

where, optionally, the above substituents of substituent group (i) may in turn each independently be substituted by at least one substituent selected identically or differently from the group consisting of:

(ii) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHQ374, —NQ375Q376, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)-Q377, —C(O)O-Q378, —C(O)NH-Q379, —C(O)NQ380Q381, —O-Q382, —O(-Q383-O)$_x$—H (x=1, 2, 3, 4, 5), —O(-Q384-O)$_x$-Q385 (x=1, 2, 3, 4, 5), —OC(O)-Q386, —OC(O)—O-Q387, —OC(O)—NHQ388, —O—C(O)—NQ389Q390, —OP(O)(OQ391)(OQ392), —OSi(Q393)(Q394)(Q395), —OS(O$_2$)-Q396, —NHC(O)-Q397, —NQ398C(O)-Q399, —NH—C(O)—O-Q400, —NH—C(O)—NH-Q401, —NH—C(O)—NQ402Q403, —NQ404-C(O)—O-Q405, —NQ406-C(O)—NH-Q407, —NQ408-C(O)—NQ409Q410, —NHS(O$_2$)-Q411, —NQ412S(O$_2$)-Q413, —S-Q414, —S(O)-Q415, —S(O$_2$)-Q416, —S(O$_2$)NH-Q417, —S(O$_2$)NQ418Q419, —S(O$_2$)O-Q420, —P(O)(OQ421)(OQ422), —Si(Q423)(Q424)(Q425)";

where Q374, Q375, Q376, Q377, Q378, Q379, Q380, Q381, Q382, Q383, Q384, Q385, Q386, Q387, Q388, Q389, Q390, Q391, Q392, Q393, Q394, Q395, Q396, Q397, Q398, Q399, Q400, Q401, Q402, Q403, Q404, Q405, Q406, Q407, Q408, Q409, Q410, Q411, Q412, Q413, Q414, Q415, Q416, Q417, Q418, Q419, Q420, Q421, Q422, Q423, Q424, Q425 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, Q380, Q381 and/or Q389, Q390 and/or Q402, Q403 and/or Q409, Q410 and/or Q418, Q419, in each case together, may also form "heterocyclyl";

where, optionally, the above substituents of substituent group (ii) may in turn each independently be substituted by at least one substituent selected identically or differently from the group consisting of:

(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHQ426, —NQ427Q428, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)-Q429, —C(O)O-Q430, —C(O)NH-Q431, —C(O)NQ432Q433, —O-Q434, —O(-Q435-O)$_y$—H (y=1, 2, 3, 4, 5), —O(-Q436-O)$_y$-Q437 (y=1, 2, 3, 4, 5), —OC(O)-Q438, —OC(O)—O-Q439, —OC(O)—NHQ440, —O—C(O)—NQ441Q442, —OP(O)(OQ443)(OQ444), —OSi(Q445)(Q446)(Q447), —OS(O$_2$)-Q448, —NHC(O)-Q449, —NQ450C(O)-Q451, —NH—C(O)—O-Q452, —NH—C(O)—NH-Q453, —NH—C(O)—NQ454Q455, —NQ456a—C(O)—O-Q456b, —NQ456c—C(O)—NH-Q456d, —NQ456e—C(O)—NQ456fQ456g, —NHS(O$_2$)-Q456h, —NQ456iS(O$_2$)-Q456j, —S-Q456k, —S(O)-Q456l, —S(O$_2$)-Q456m, —S(O$_2$)NH-Q456n, —S(O$_2$)NQ456oQ456p, —S(O$_2$)O-Q456q, —P(O)(OQ456r)(OQ456s), —Si(Q456t)(Q456u)(Q456v)";

where Q426, Q427, Q428, Q429, Q430, Q431, Q432, Q433, Q434, Q435, Q436, Q437, Q438, Q439, Q440, Q441, Q442, Q443, Q444, Q445, Q446, Q447, Q448, Q449, Q450, Q451, Q452, Q453, Q454, Q455, Q456a, Q456b, Q456c, Q456d, Q456e, Q456f, Q456g, Q456h, Q456i, Q456j, Q456k, Q456l, Q456m, Q456n, Q456o, Q456p, Q456q, Q456r, Q456s, Q456t, Q456u, Q456v are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, Q432, Q433 and/or Q441, Q442 and/or Q454, Q455 and/or Q456f, Q456g and/or Q456o, Q456p, in each case together, may also form "heterocyclyl";

and one of the Z3, Z4 radicals or neither of the Z3, Z4 radicals is independently selected from the group consisting of:

(d) hydrogen;

(e) halogen, F, Cl, Br, I;

(f) unsubstituted or substituted alkyl or ($C_9$-$C_{30}$)alkyl, where, optionally, the alkyl or ($C_9$-$C_{30}$)alkyl radical may be substituted by at least one substituent selected identically or differently from the group consisting of:

(i) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHQ457, —NQ458Q459, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)-Q460, —C(O)O-Q461, —C(O)NH-Q462, —C(O)NQ463Q464, —O-Q465, —O(-Q466-O)$_z$—H (z=1, 2, 3, 4, 5), —O(-Q467-O)$_z$-Q468 (z=1, 2, 3, 4, 5), —OC(O)-Q469, —OC(O)—O-Q470, —OC(O)—NHQ471, —O—C(O)—NQ472Q473, —OP(O)(OQ474)(OQ475), —OSi(Q476)(Q477)(Q478), —OS(O$_2$)-Q479, —NHC(O)-Q480, —NQ481C(O)-Q482, —NH—C(O)—O-Q483, —NH—C(O)—NH-Q484, —NH—C(O)—NQ485Q486, —NQ487-C(O)—O-Q488, —NQ489-C(O)—NH-Q490, —NQ491-C(O)—NQ492Q493, —NHS(O$_2$)-Q494, —NQ495S(O$_2$)-Q496, —S-Q497, —S(O)-Q498, —S(O$_2$)-Q499, —S(O$_2$)NH-Q500, —S(O$_2$)NQ501Q502, —S(O$_2$)O-Q503, —P(O)(OQ504)(OQ505), —Si(Q506)(Q507)(Q508)";

where Q457, Q458, Q459, Q460, Q461, Q462, Q463, Q464, Q465, Q466, Q467, Q468, Q469, Q470, Q471, Q472, Q473, Q474, Q475, Q476, Q477, Q478, Q479, Q480, Q481, Q482, Q483, Q484, Q485, Q486, Q487, Q488, Q489, Q490, Q491, Q492, Q493, Q494, Q495, Q496, Q497, Q498, Q499, Q500, Q501, Q502, Q503, Q504, Q505, Q506, Q507, Q508 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, Q463, Q464 and/or Q472, Q473 and/or Q485, Q486 and/or Q492, Q493 and/or Q501, Q502, in each case together, may also form "heterocyclyl";

where, optionally, the above substituents of substituent group (i) may in turn each independently be substituted by at least one substituent selected identically or differently from the group consisting of:

(ii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHQ509, —NQ510Q511, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)-Q512, —C(O)O-Q513, —C(O)NH-Q514, —C(O)NQ515Q516, —O-Q517, —O(-Q518-O)$_a$—H (a=1, 2, 3, 4, 5), —O(-Q519-O)$_a$-Q520 (a=1, 2, 3, 4, 5), —OC(O)-Q521, —OC(O)—O-Q522, —OC(O)—NHQ523, —O—C(O)—NQ524Q525, —OP(O)(OQ526)(OQ527), —OSi(Q528)(Q529)(Q530), —OS(O$_2$)-Q531, —NHC(O)-Q532, —NQ533C(O)-Q534, —NH—C(O)—O-Q535, —NH—C(O)—NH-Q536, —NH—C(O)—NQ537Q538, —NQ539-C(O)—O-Q540, —NQ541-C(O)—NH-Q542, —NQ543-C(O)—NQ544Q545, —NHS(O$_2$)-Q546, —NQ547S(O$_2$)-Q548, —S-Q549, —S(O)-Q550, —S(O$_2$)-Q551, —S(O$_2$)NH-Q552, —S(O$_2$)NQ553Q554, —S(O$_2$)O-Q555, —P(O)(OQ556)(OQ557), —Si(Q558)(Q559)(Q560)";

where Q509, Q510, Q511, Q512, Q513, Q514, Q515, Q516, Q517, Q518, Q519, Q520, Q521, Q522, Q523, Q524, Q525, Q526, Q527, Q528, Q529, Q530, Q531, Q532, Q533, Q534, Q535, Q536, Q537, Q538, Q539, Q540, Q541, Q542, Q543, Q544, Q545, Q546, Q547, Q548, Q549, Q550, Q551, Q552, Q553, Q554, Q555, Q556, Q557, Q558, Q559, Q560 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, Q515, Q516 and/or Q524, Q525 and/or Q537, Q538 and/or Q544, Q545 and/or Q553, Q554, in each case together, may also form "heterocyclyl";

where, optionally, the above substituents of substituent group (ii) may in turn each independently be substituted by at least one substituent selected identically or differently from the group consisting of:

(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHQ561, —NQ562Q563, —$NO_2$, —OH, —$OCF_3$, —SH, —O—$SO_3H$, —OP(O)$(OH)_2$, —CHO, —COOH, —C(O)$NH_2$, —$SO_3H$, —P(O)$(OH)_2$, —C(O)-Q564, —C(O)O-Q565, —C(O)NH-Q566, —C(O)NQ567Q568, —O-Q569, —O(-Q570-O)$_b$—H (b=1, 2, 3, 4, 5), —O(-Q571-O)$_b$-Q572 (b=1, 2, 3, 4, 5), —OC(O)-Q573, —OC(O)—O-Q574, —OC(O)—NHQ575, —O—C(O)—NQ576Q577, —OP(O)(OQ578)(OQ579), —OSi(Q580)(Q581)(Q582), —OS($O_2$)-Q583, —NHC(O)-Q584, —NQ585C(O)-Q586, —NH—C(O)—O-Q587, —NH—C(O)—NH-Q588, —NH—C(O)—NQ589Q590, —NQ591-C(O)—O-Q592, —NQ593-C(O)—NH-Q594, —NQ595-C(O)—NQ596Q597, —NHS($O_2$)-Q598, —NQ599S($O_2$)-Q600, —S-Q601, —S(O)-Q602, —S($O_2$)-Q603, —S($O_2$)NH-Q604, —S($O_2$)NQ605Q606, —S($O_2$)O-Q607, —P(O)(OQ608)(OQ609), —Si(Q610)(Q611)(Q612)";

where Q561, Q562, Q563, Q564, Q565, Q566, Q567, Q568, Q569, Q570, Q571, Q572, Q573, Q574, Q575, Q576, Q577, Q578, Q579, Q580, Q581, Q582, Q583, Q584, Q585, Q586, Q587, Q588, Q589, Q590, Q591, Q592, Q593, Q594, Q595, Q596, Q597, Q598, Q599, Q600, Q601, Q602, Q603, Q604, Q605, Q606, Q607, Q608, Q609, Q610, Q611, Q612 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, Q567, Q568 and/or Q576, Q577 and/or Q589, Q590 and/or Q596, Q597 and/or Q605, Q606, in each case together, may also form "heterocyclyl";

(g) unsubstituted or substituted aryl where, optionally, the aryl radical may be substituted by at least one substituent selected identically or differently from the group consisting of:

(i) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHQ613, —NQ614Q615, —$NO_2$, —OH, —$OCF_3$, —SH, —O—$SO_3H$, —OP(O)$(OH)_2$, —CHO, —COOH, —C(O)$NH_2$, —$SO_3H$, —P(O)$(OH)_2$, —C(O)-Q616, —C(O)O-Q617, —C(O)NH-Q618, —C(O)NQ619Q620, —O-Q621, —O(-Q622-O)$_c$—H (c=1, 2, 3, 4, 5), —O(-Q623-O)$_c$-Q624 (c=1, 2, 3, 4, 5), —OC(O)-Q625, —OC(O)—O-Q626, —OC(O)—NHQ627, —O—C(O)—NQ628Q629, —OP(O)(OQ630)(OQ631), —OSi(Q632)(Q633)(Q634), —OS($O_2$)-Q635, —NHC(O)-Q636, —NQ637C(O)-Q638, —NH—C(O)—O-Q639, —NH—C(O)—NH-Q640, —NH—C(O)—NQ641Q642, —NQ643-C(O)—O-Q644, —NQ645-C(O)—NH-Q646, —NQ647-C(O)—NQ648Q649, —NHS($O_2$)-Q650, —NQ651S($O_2$)-Q652, —S-Q653, —S(O)-Q654, —S($O_2$)-Q655, —S($O_2$)NH-Q656, —S($O_2$)NQ657Q658, —S($O_2$)O-Q659, —P(O)(OQ660)(OQ661), —Si(Q662)(Q663)(Q664)";

where Q613, Q614, Q615, Q616, Q617, Q618, Q619, Q620, Q621, Q622, Q623, Q624, Q625, Q626, Q627, Q628, Q629, Q630, Q631, Q632, Q633, Q634, Q635, Q636, Q637, Q638, Q639, Q640, Q641, Q642, Q643, Q644, Q645, Q646, Q647, Q648, Q649, Q650, Q651, Q652, Q653, Q654, Q655, Q656, Q657, Q658, Q659, Q660, Q661, Q662, Q663, Q664 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, Q619, Q620 and/or Q628, Q629 and/or Q641, Q642 and/or Q648, Q649 and/or Q657, Q658, in each case together, may also form "heterocyclyl";

where, optionally, the above substituents of substituent group (i) may in turn each independently be substituted by at least one substituent selected identically or differently from the group consisting of:

(ii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHQ665, —NQ666Q667, —$NO_2$, —OH, —$OCF_3$, —SH, —O—$SO_3H$, —OP(O)$(OH)_2$, —CHO, —COOH, —C(O)$NH_2$, —$SO_3H$, —P(O)$(OH)_2$, —C(O)-Q668, —C(O)O-Q669, —C(O)NH-Q670, —C(O)NQ671Q672, —O-Q673, —O(-Q674-O)$_d$—H (d=1, 2, 3, 4, 5), —O(-Q675-O)$_d$-Q676 (d=1, 2, 3, 4, 5), —OC(O)-Q677, —OC(O)—O-Q678, —OC(O)—NHQ679, —O—C(O)—NQ680Q681, —OP(O)(OQ682)(OQ683), —OSi(Q684)(Q685)(Q686), —OS($O_2$)-Q687, —NHC(O)-Q688, —NQ689C(O)-Q690, —NH—C(O)—O-Q691, —NH—C(O)—NH-Q692, —NH—C(O)—NQ693Q694, —NQ695-C(O)—O-Q696, —NQ697-C(O)—NH-Q698, —NQ699-C(O)—NQ700Q701, —NHS($O_2$)-Q702, —NQ703S($O_2$)-Q704, —S-Q705, —S(O)-Q706, —S($O_2$)-Q707, —S($O_2$)NH-Q708, —S($O_2$)NQ709Q710, —S($O_2$)O-Q711, —P(O)(OQ712)(OQ713), —Si(Q714)(Q715)(Q716)";

where Q665, Q666, Q667, Q668, Q669, Q670, Q671, Q672, Q673, Q674, Q675, Q676, Q677, Q678, Q679, Q680, Q681, Q682, Q683, Q684, Q685, Q686, Q687, Q688, Q689, Q690, Q691, Q692, Q693, Q694, Q695, Q696, Q697, Q698, Q699, Q700, Q701, Q702, Q703, Q704, Q705, Q706, Q707, Q708, Q709, Q710, Q711, Q712, Q713, Q714, Q715, Q716 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, Q671, Q672 and/or Q680, Q681 and/or Q693, Q694 and/ or Q700, Q701 and/or Q709, Q710, in each case together, may also form "heterocyclyl";

where, optionally, the above substituents of substituent group (ii) may in turn each independently be substituted by at least one substituent selected identically or differently from the group consisting of:

(iii) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHQ717, —NQ718Q719, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)-Q720, —C(O)O-Q721, —C(O)NH-Q722, —C(O)NQ723Q724, —O-Q725, —O(-Q726-O)$_e$—H (e=1, 2, 3, 4, 5), —O(-Q727-O)$_e$-Q728 (e=1, 2, 3, 4, 5), —OC(O)-Q729, —OC(O)—O-Q730, —OC(O)—NHQ731, —O—C(O)—NQ732Q733, —OP(O)(OQ734)(OQ735), —OSi(Q736)(Q737)(Q738), —OS(O$_2$)-Q739, —NHC(O)-Q740, —NQ741C(O)-Q742, —NH—C(O)—O-Q743, —NH—C(O)—NH-Q744, —NH—C(O)—NQ745Q746, —NQ747-C(O)—O-Q748, —NQ749-C(O)—NH-Q750, —NQ751-C(O)—NQ752Q753, —NHS(O$_2$)-Q754, —NQ755S(O$_2$)-Q756, —S-Q757, —S(O)-Q758, —S(O$_2$)-Q759, —S(O$_2$)NH-Q760, —S(O$_2$)NQ761Q762, —S(O$_2$)O-Q763, —P(O)(OQ764)(OQ765), —Si(Q766)(Q767)(Q768)";

where Q717, Q718, Q719, Q720, Q721, Q722, Q723, Q724, Q725, Q726, Q727, Q728, Q729, Q730, Q731, Q732, Q733, Q734, Q735, Q736, Q737, Q738, Q739, Q740, Q741, Q742, Q743, Q744, Q745, Q746, Q747, Q748, Q749, Q750, Q751, Q752, Q753, Q754, Q755, Q756, Q757, Q758, Q759, Q760, Q761, Q762, Q763, Q764, Q765, Q766, Q767, Q768 are each independently selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and where, alternatively, Q723, Q724 and/or Q732, Q733 and/or Q745, Q746 and/or Q752, Q753 and/or Q761, Q762, in each case together, may also form "heterocyclyl";

(h) unsubstituted or substituted heteroaryl where, optionally, the heteroaryl radical may be substituted by at least one substituent selected identically or differently from the group consisting of:

(i) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHQ769, —NQ770Q771, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)-Q772, —C(O)O-Q773, —C(O)NH-Q774, —C(O)NQ775Q776, —O-Q777, —O(-Q778-O)$_f$—H (f=1, 2, 3, 4, 5), —O(-Q779-O)$_f$-Q780 (f=1, 2, 3, 4, 5), —OC(O)-Q781, —OC(O)—O-Q782, —OC(O)—NHQ783, —O—C(O)—NQ784Q785, —OP(O)(OQ786)(OQ787), —OSi(Q788)(Q789)(Q790), —OS(O$_2$)-Q791, —NHC(O)-Q792, —NQ793C(O)-Q794, —NH—C(O)—O-Q795, —NH—C(O)—NH-Q796, —NH—C(O)—NQ797Q798, —NQ799-C(O)—O-Q800, —NQ801-C(O)—NH-Q802, —NQ803-C(O)—NQ804Q805, —NHS(O$_2$)-Q806, —NQ807S(O$_2$)-Q808, —S-Q809, —S(O)-Q810, —S(O$_2$)-Q811, —S(O$_2$)NH-Q812, —S(O$_2$)NQ813Q814, —S(O$_2$)O-Q815, —P(O)(OQ816)(OQ817), —Si(Q818)(Q819)(Q820)";

where Q769, Q770, Q771, Q772, Q773, Q774, Q775, Q776, Q777, Q778, Q779, Q780, Q781, Q782, Q783, Q784, Q785, Q786, Q787, Q788, Q789, Q790, Q791, Q792, Q793, Q794, Q795, Q796, Q797, Q798, Q799, Q800, Q801, Q802, Q803, Q804, Q805, Q806, Q807, Q808, Q809, Q810, Q811, Q812, Q813, Q814, Q815, Q816, Q817, Q818, Q819, Q820 are each independently selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and where, alternatively, Q775, Q776 and/or Q784, Q785 and/or Q797, Q798 and/or Q804, Q805 and/or Q813, Q814, in each case together, may also form "heterocyclyl";

where, optionally, the above substituents of substituent group (i) may in turn each independently be substituted by at least one substituent selected identically or differently from the group consisting of:

(ii) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHQ821, —NQ822Q823, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)-Q824, —C(O)O-Q825, —C(O)NH-Q826, —C(O)NQ827Q828, —O-Q829, —O(-Q830-O)$_g$—H (g=1, 2, 3, 4, 5), —O(-Q831-O)$_g$-Q832 (g=1, 2, 3, 4, 5), —OC(O)-Q833, —OC(O)—O-Q834, —OC(O)—NHQ835, —O—C(O)—NQ836Q837, —OP(O)(OQ838)(OQ839), —OSi(Q840)(Q841)(Q842), —OS(O$_2$)-Q843, —NHC(O)-Q844, —NQ845C(O)-Q846, —NH—C(O)—O-Q847, —NH—C(O)—NH-Q848, —NH—C(O)—NQ849Q850, —NQ851-C(O)—O-Q852, —NQ853-C(O)—NH-Q854, —NQ855-C(O)—NQ856Q857, —NHS(O$_2$)-Q858, —NQ859S(O$_2$)-Q860, —S-Q861, —S(O)-Q862, —S(O$_2$)-Q863, —S(O$_2$)NH-Q864, —S(O$_2$)NQ865Q866, —S(O$_2$)O-Q867, —P(O)(OQ868)(OQ869), —Si(Q870)(Q871)(Q872)";

where Q821, Q822, Q823, Q824, Q825, Q826, Q827, Q828, Q829, Q830, Q831, Q832, Q833, Q834, Q835, Q836, Q837, Q838, Q839, Q840, Q841, Q842, Q843, Q844, Q845, Q846, Q847, Q848, Q849, Q850, Q851, Q852, Q853, Q854, Q855, Q856, Q857, Q858, Q859, Q860, Q861, Q862, Q863, Q864, Q865, Q866, Q867, Q868, Q869, Q870, Q871, Q872 are each independently selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and where, alternatively, Q827, Q828 and/or Q836, Q837 and/or Q849, Q850 and/or Q856, Q857 and/or Q865, Q866, in each case together, may also form "heterocyclyl";

where, optionally, the above substituents of substituent group (ii) may in turn each independently be substituted by at least one substituent selected identically or differently from the group consisting of:

(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHQ873, —NQ874Q875, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)-Q876, —C(O)O-Q877, —C(O)NH-Q878, —C(O)NQ879Q880, —O-Q881, —O(-Q882-O)$_h$—H (h=1, 2, 3, 4, 5), —O(-Q883-O)$_h$-Q884 (h=1, 2, 3, 4, 5), —OC(O)-Q885, —OC(O)—O-Q886, —OC(O)—NHQ887, —O—C(O)—NQ888Q889, —(P(O)(OQ890)(OQ891), —OSi(Q892)(Q893)(Q894), —OS(O$_2$)-Q895, —NHC(O)-Q896, —NQ897C(O)-Q898, —NH—C(O)—O-Q899, —NH—C(O)—NH-Q900, —NH—C(O)—NQ901Q902, —NQ903-C(O)—O-Q904, —NQ905-C(O)—NH-Q906, —NQ907-C(O)—NQ908Q909, —NHS(O$_2$)-Q910, —NQ911S(O$_2$)-Q912, —S-Q913, —S(O)-Q914, —S(O$_2$)-Q915, —S(O$_2$)NH-Q916, —S(O$_2$)NQ917Q918, —S(O$_2$)O-Q919, —P(O)(OQ920)(OQ921), —Si(Q922)(Q923)(Q924)";

where Q873, Q874, Q875, Q876, Q877, Q878, Q879, Q880, Q881, Q882, Q883, Q884, Q885, Q886, Q887, Q888, Q889, Q890, Q891, Q892, Q893, Q894, Q895, Q896, Q897, Q898, Q899, Q900, Q901, Q902, Q903, Q904, Q905, Q906, Q907, Q908, Q909, Q910, Q911, Q912, Q913, Q914, Q915, Q916, Q917, Q918, Q919, Q920, Q921, Q922, Q923, Q924 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, Q879, Q880 and/or Q888, Q889 and/or Q901, Q902 and/or Q908, Q909 and/or Q917, Q918, in each case together, may also form "heterocyclyl";

(j) OZ6 where Z6 is independently selected from the group consisting of:

(i) "hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl";

where, optionally, the above substituents of substituent group (i) may in turn each independently be substituted by at least one substituent selected identically or differently from the group consisting of:

(ii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHQ925, —NQ926Q927, —$NO_2$, —OH, —$OCF_3$, —SH, —O—SO3H, —OP(O)(OH)$_2$, —CHO, —COOH, —C(O)NH$_2$, —$SO_3H$, —P(O)(OH)$_2$, —C(O)-Q928, —C(O)O-Q929, —C(O)NH-Q930, —C(O)NQ931Q932, —O-Q933, —O(-Q934-O)$_i$—H (i=1, 2, 3, 4, 5), —O(-Q935-O)$_i$-Q936 (i=1, 2, 3, 4, 5), —OC(O)-Q937, —OC(O)—O-Q938, —OC(O)—NHQ939, —O—C(O)—NQ940Q941, —OP(O)(OQ942)(OQ943), —OSi(Q944)(Q945)(Q946), —OS(O$_2$)-Q947, —NHC(O)-Q948, —NQ949C(O)-Q950, —NH—C(O)—O-Q951, —NH—C(O)—NH-Q952, —NH—C(O)—NQ953Q954, —NQ955-C(O)—O-Q956, —NQ957-C(O)—NH-Q958, —NQ959-C(O)—NQ960Q961, —NHS(O$_2$)-Q962, —NQ963S(O$_2$)-Q964, —S-Q965, —S(O)-Q966, —S(O$_2$)-Q967, —S(O$_2$)NH-Q968, —S(O$_2$)NQ969Q970, —S(O$_2$)O-Q971, —P(O)(OQ972)(OQ973), —Si(Q974)(Q975)(Q976)";

where Q925, Q926, Q927, Q928, Q929, Q930, Q931, Q932, Q933, Q934, Q935, Q936, Q937, Q938, Q939, Q940, Q941, Q942, Q943, Q944, Q945, Q946, Q947, Q948, Q949, Q950, Q951, Q952, Q953, Q954, Q955, Q956, Q957, Q958, Q959, Q960, Q961, Q962, Q963, Q964, Q965, Q966, Q967, Q968, Q969, Q970, Q971, Q972, Q973, Q974, Q975, Q976 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, Q931, Q932 and/or Q940, Q941 and/or Q953, Q954 and/or Q960, Q961 and/or Q969, Q970, in each case together, may also form "heterocyclyl";

where, optionally, the above substituents of substituent group (ii) may in turn each independently be substituted by at least one substituent selected identically or differently from the group consisting of:

(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHQ977, —NQ978Q979, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)-Q980, —C(O)O-Q981, —C(O)NH-Q982, —C(O)NQ983Q984, —O-Q985, —O(-Q986-O)$_j$—H (j=1, 2, 3, 4, 5), —O(-Q987-O)$_j$-Q988 (j=1, 2, 3, 4, 5), —OC(O)-Q989, —OC(O)—O-Q990, —OC(O)—NHQ991, —O—C(O)—NQ992Q993, —OP(O)(OQ994)(OQ995), —OSi(Q996)(Q997)(Q998), —OS(O$_2$)-Q999, —NHC(O)-Q1000, —NQ1001C(O)-Q1002, —NH—C(O)—O-Q1003, —NH—C(O)—NH-Q1004, —NH—C(O)—NQ1005Q1006, —NQ1007-C(O)—O-Q1008, —NQ1009-C(O)—NH-Q1010, —NQ1011-C(O)—NQ1012Q1013, —NHS(O$_2$)-Q1014, —NQ1015S(O$_2$)-Q1016, —S-Q1017, —S(O)-Q1018, —S(O$_2$)-Q1019, —S(O$_2$)NH-Q1020, —S(O$_2$)NQ1021Q1022, —S(O$_2$)O-Q1023, —P(O)(OQ1024)(OQ1025), —Si(Q1026)(Q1027)(Q1028)";

where Q977, Q978, Q979, Q980, Q981, Q982, Q983, Q984, Q985, Q986, Q987, Q988, Q989, Q990, Q991, Q992, Q993, Q994, Q995, Q996, Q997, Q998, Q999, Q1000, Q1001, Q1002, Q1003, Q1004, Q1005, Q1006, Q1007, Q1008, Q1009, Q1010, Q1011, Q1012, Q1013, Q1014, Q1015, Q1016, Q1017, Q1018, Q1019, Q1020, Q1021, Q1022, Q1023, Q1024, Q1025, Q1026, Q1027, Q1028 are each independently selected from the group consisting of: "alkyl, ($C_9$-$C_{30}$) alkyl, cycloalkyl, cycloalkylalkyl, heterocyclyl, heterocyclylalkyl, aryl, arylalkyl, heteroaryl, heteroarylalkyl" and where, alternatively, Q983, Q984 and/or Q992, Q993 and/or Q1005, Q1006 and/or Q1012, Q1013 and/or Q1021, Q1022, in each case together, may also form "heterocyclyl";

(k) SZ7 where Z7 is independently selected from the group consisting of:
  (i) "hydrogen, alkyl, $(C_9$-$C_{30})$alkyl, cycloalkyl, cycloalkylalkyl, heterocyclyl, heterocyclylalkyl, aryl, arylalkyl, heteroaryl, heteroarylalkyl";
    where, optionally, the above substituents of substituent group (i) may in turn each independently be substituted by at least one substituent selected identically or differently from the group consisting of:
  (ii) "alkyl, $(C_9$-$C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHQ1029, —NQ1030Q1031, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)-Q1032, —C(O)O-Q1033, —C(O)NH-Q1034, —C(O)NQ1035Q1036, —O-Q1037, —O(-Q1038-O)$_k$—H (k=1, 2, 3, 4, 5), —O(-Q1039-O)$_k$-Q1040 (k=1, 2, 3, 4, 5), —OC(O)-Q1041, —OC(O)—O-Q1042, —OC(O)—NHQ1043, —O—C(O)—NQ1044Q1045, —OP(O)(OQ1046)(OQ1047), —OSi(Q1048)(Q1049)(Q1050), —OS(O$_2$)-Q1051, —NHC(O)-Q1052, —NQ1053C(O)-Q1054, —NH—C(O)—O-Q1055, —NH—C(O)—NH-Q1056, —NH—C(O)—NQ1057Q1058, —NQ1059-C(O)—O-Q1060, —NQ1061-C(O)—NH-Q1062, —NQ1063-C(O)—NQ1064Q1065, —NHS(O$_2$)-Q1066, —NQ1067S(O$_2$)-Q1068, —S-Q1069, —S(O)-Q1070, —S(O$_2$)-Q1071, —S(O$_2$)NH-Q1072, —S(O$_2$)NQ1073Q1074, —S(O$_2$)O-Q1075, —P(O)(OQ1076)(OQ1077), —Si(Q1078)(Q1079)(Q1080)";
    where Q1029, Q1030, Q1031, Q1032, Q1033, Q1034, Q1035, Q1036, Q1037, Q1038, Q1039, Q1040, Q1041, Q1042, Q1043, Q1044, Q1045, Q1046, Q1047, Q1048, Q1049, Q1050, Q1051, Q1052, Q1053, Q1054, Q1055, Q1056, Q1057, Q1058, Q1059, Q1060, Q1061, Q1062, Q1063, Q1064, Q1065, Q1066, Q1067, Q1068, Q1069, Q1070, Q1071, Q1072, Q1073, Q1074, Q1075, Q1076, Q1077, Q1078, Q1079, Q1080 are each independently selected from the group consisting of: "alkyl, $(C_9$-$C_{30})$alkyl, cycloalkyl, cycloalkylalkyl, heterocyclyl, heterocyclylalkyl, aryl, arylalkyl, heteroaryl, heteroarylalkyl" and where, alternatively, Q1035, Q1036 and/or Q1044, Q1045 and/or Q1057, Q1058 and/or Q1064, Q1065 and/or Q1073, Q1074, in each case together, may also form "heterocyclyl";
    where, optionally, the above substituents of substituent group (ii) may in turn each independently be substituted by at least one substituent selected identically or differently from the group consisting of:
  (iii) "alkyl, $(C_9$-$C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHQ1081, —NQ1082Q1083, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)-Q1084, —C(O)O-Q1085, —C(O)NH-Q1086, —C(O)NQ1087Q1088, —O-Q1089, —O(-Q1090-O)$_l$—H (l=1, 2, 3, 4, 5), —O(-Q1091-O)$_l$-Q1092 (l=1, 2, 3, 4, 5), —OC(O)-Q1093, —OC(O)—O-Q1094, —OC(O)—NHQ1095, —O—C(O)—NQ1096Q1097, —OP(O)(OQ1098)(OQ1099), —OSi(Q1100)(Q1101)(Q1102), —OS(O$_2$)-Q1103, —NHC(O)-Q1104, —NQ1105C(O)-Q1106, —NH—C(O)—O-Q1107, —NH—C(O)—NH-Q1108, —NH—C(O)—NQ1109Q1110, —NQ1111-C(O)—O-Q1112, —NQ1113-C(O)—NH-Q1114, —NQ1115-C(O)—NQ1116Q1117, —NHS(O$_2$)-Q1118, —NQ1119S(O$_2$)-Q1120, —S-Q1121, —S(O)-Q1122, —S(O$_2$)-Q1123, —S(O$_2$)NH-Q1124, —S(O$_2$)NQ1125Q1126, —S(O$_2$)O-Q1127, —P(O)(OQ1128)(OQ1129), —Si(Q1130)(Q1131)(Q1132)";
    where Q1081, Q1082, Q1083, Q1084, Q1085, Q1086, Q1087, Q1088, Q1089, Q1090, Q1091, Q1092, Q1093, Q1094, Q1095, Q1096, Q1097, Q1098, Q1099, Q1100, Q1101, Q1102, Q1103, Q1104, Q1105, Q1106, Q1107, Q1108, Q1109, Q1110, Q1111, Q1112, Q1113, Q1114, Q1115, Q1116, Q1117, Q1118, Q1119, Q1120, Q1121, Q1122, Q1123, Q1124, Q1125, Q1126, Q1127, Q1128, Q1129, Q1130, Q1131, Q1132 are each independently selected from the group consisting of: "alkyl, $(C_9$-$C_{30})$alkyl, cycloalkyl, cycloalkylalkyl, heterocyclyl, heterocyclylalkyl, aryl, arylalkyl, heteroaryl, heteroarylalkyl" and where, alternatively, Q1087, Q1088 and/or Q1096, Q1097 and/or Q1109, Q1110 and/or Q1116, Q1117 and/or Q1125, Q1126, in each case together, may also form "heterocyclyl";
(l) NZ8Z9 where Z8, Z9 are each independently selected from the group consisting of:
  (i) "hydrogen, alkyl, $(C_9$-$C_{30})$alkyl, cycloalkyl, cycloalkylalkyl, heterocyclyl, heterocyclylalkyl, aryl, arylalkyl, heteroaryl, heteroarylalkyl, —C(O)-Q1133, —C(O)O-Q1134, —C(O)—NQ1135Q1136, —S(O$_2$)-Q1137, —S(O$_2$)O-Q1138";
    where Q1133, Q1134, Q1135, Q1136, Q1137, Q1138 are each independently selected from the group consisting of: hydrogen, alkyl, $(C_9$-$C_{30})$alkyl, cycloalkyl, cycloalkylalkyl, heterocyclyl, heterocyclylalkyl, aryl, arylalkyl, heteroaryl, heteroarylalkyl" and where, alternatively, Q1135, Q1136 together may also form "heterocyclyl";
    where, optionally, the above substituents of substituent group (i) may in turn each independently be substituted by at least one substituent selected identically or differently from the group consisting of:
  (ii) "alkyl, $(C_9$-$C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHQ1139, —NQ1140Q1141, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)-Q1142, —C(O)O-Q1143, —C(O)NH-Q1144, —C(O)NQ1145Q1146, —O-Q1147, —O(-Q1148-O)$_m$—H (m=1, 2, 3, 4, 5), —O(-Q1149-O)$_m$-Q1150 (m=1, 2, 3, 4, 5), —OC(O)-Q1151, —OC(O)—O-Q1152, —OC(O)—NHQ1153, —O—C(O)—NQ1154Q1155, —OP(O)(OQ1156)(OQ1157), —OSi(Q1158)(Q1159)(Q1160), —OS(O$_2$)-Q1161, —NHC(O)-Q1162, —NQ1163C(O)-Q1164, —NH—C(O)—O-Q1165, —NH—C(O)—NH-Q1166, —NH—C(O)—NQ1167Q1168, —NQ1169-C(O)—O-Q1170, —NQ1171-C(O)—NH-Q1172, —NQ1173-C(O)—NQ1174Q1175, —NHS(O$_2$)-

Q1176, —NQ1177S(O$_2$)-Q1178, —S-Q1179, —S(O)-Q1180, —S(O$_2$)-Q1181, —S(O$_2$)NH-Q1182, —S(O$_2$)NQ1183Q1184, —S(O$_2$)O-Q1185, —P(O)(OQ1186)(OQ1187), —Si(Q1188)(Q1189)(Q1190)";

where Q1139, Q1140, Q1141, Q1142, Q1143, Q1144, Q1145, Q1146, Q1147, Q1148, Q1149, Q1150, Q1151, Q1152, Q1153, Q1154, Q1155, Q1156, Q1157, Q1158, Q1159, Q1160, Q1161, Q1162, Q1163, Q1164, Q1165, Q1166, Q1167, Q1168, Q1169, Q1170, Q1171, Q1172, Q1173, Q1174, Q1175, Q1176, Q1177, Q1178, Q1179, Q1180, Q1181, Q1182, Q1183, Q1184, Q1185, Q1186, Q1187, Q1188, Q1189, Q1190 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, Q1145, Q1146 and/or Q1154, Q1155 and/or Q1167, Q1168 and/or Q1174, Q1175 and/or Q1183, Q1184, in each case together, may also form "heterocyclyl";

where, optionally, the above substituents of substituent group (ii) may in turn each independently be substituted by at least one substituent selected identically or differently from the group consisting of:

(iii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHQ1191, —NQ1192Q1193, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)-Q1194, —C(O)O-Q1195, —C(O)NH-Q1196, —C(O)NQ1197Q1198, —O-Q1199, —O(-Q1200-O)$_n$—H (n=1, 2, 3, 4, 5), —O(-Q1201-O)$_n$-Q1202 (n=1, 2, 3, 4, 5), —OC(O)-Q1203, —OC(O)—O-Q1204, —OC(O)—NHQ1205, —O—C(O)—NQ1206Q1207, —OP(O)(OQ1208)(OQ1209), —OSi(Q1210)(Q1211)(Q1212), —OS(O$_2$)-Q1213, —NHC(O)-Q1214, —NQ1215C(O)-Q1216, —NH—C(O)—O-Q1217, —NH—C(O)—NH-Q1218, —NH—C(O)—NQ1219Q1220, —NQ1221-C(O)—O-Q1222, —NQ1223-C(O)—NH-Q1224, —NQ1225-C(O)—NQ1226Q1227, —NHS(O$_2$)-Q1228, —NQ1229S(O$_2$)-Q1230, —S-Q1231, —S(O)-Q1232, —S(O$_2$)-Q1233, —S(O$_2$)NH-Q1234, —S(O$_2$)NQ1235Q1236, —S(O$_2$)O-Q1237, —P(O)(OQ1238)(OQ1239), —Si(Q1240)(Q1241)(Q1242)";

where Q1191, Q1192, Q1193, Q1194, Q1195, Q1196, Q1197, Q1198, Q1199, Q1200, Q1201, Q1202, Q1203, Q1204, Q1205, Q1206, Q1207, Q1208, Q1209, Q1210, Q1211, Q1212, Q1213, Q1214, Q1215, Q1216, Q1217, Q1218, Q1219, Q1220, Q1221, Q1222, Q1223, Q1224, Q1225, Q1226, Q1227, Q1228, Q1229, Q1230, Q1231, Q1232, Q1233, Q1234, Q1235, Q1236, Q1237, Q1238, Q1239, Q1240, Q1241, Q1242 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, Q1197, Q1198 and/or Q1206, Q1207 and/or Q1219, Q1220 and/or Q1226, Q1227 and/or Q1235, Q1236, in each case together, may also form "heterocyclyl";

and

Z1, Z2 radicals are each independently selected from the group consisting of: "hydrogen, NZ14Z15";

with the proviso that when Z1=H, Z2=NZ14Z15, and when Z1=NZ14Z15, Z2=H;

where Z14, Z15 are each independently selected from the group consisting of:

(a) "hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, —C(Y1)NZ16Z17, —C(=NZ18)-Z19, —C(Y2)NZ20-Y3-Z21";

with the proviso that Z14, Z15 are not simultaneously hydrogen or "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl";

with the further proviso that when one of the Z14, Z15 radicals is hydrogen or "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl", the other Z14, Z15 radical in each case is "—C(Y1)NZ16Z17", "—C(=NZ18)-Z19" or "—C(Y2)NZ20-Y3-Z21";

where Y1, Y2, Y3 are each independently selected from the group consisting of "O, S, =NH, =NZ22";

where Z16, Z17, Z18, Z19, Z20, Z21, Z22 are each independently selected from the group consisting of:

(1) hydrogen (2) "alkyl, (C$_9$-C$_{30}$)alkyl, cycloalkyl, cycloalkylalkyl, aryl, arylalkyl, heteroaryl, heteroarylalkyl, heterocyclyl, heterocyclylalkyl";

where the above substituents of substitution group (a) and/or substitution group (2) may optionally each independently be substituted by at least one substituent selected identically or differently from the group consisting of:

(i) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHU1, —NU2U3, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—U4, —C(O)O—U5, —C(O)NH—U6, —C(O)NU7U8, —O—U9, —O(—U10-O)$_r$—H (r=1, 2, 3, 4, 5), —O(—U11-O)$_r$—U12 (r=1, 2, 3, 4, 5), —OC(O)—U13, —OC(O)—O—U14, —OC(O)—NHU15, —O—C(O)—NU16U17, —OP(O)(OU18)(OU19), —OSi(U20)(U21)(U22), —OS(O$_2$)—U23, —NHC(O)—U24, —NU25C(O)—U26, —NH—C(O)—O—U27, —NH—C(O)—NH—U28, —NH—C(O)—NU29U30, —NU31-C(O)—O—U32, —NU33-C(O)—NH—U34, —NU35-C(O)—NU36U37, —NHS(O$_2$)—U38, —NU39S(O$_2$)—U40, —S—U41, —S(O)—U42, —S(O$_2$)—U43, —S(O$_2$)NH—U44, —S(O$_2$)NU45U46, —S(O$_2$)O—U47, —P(O)(OU48)(OU49), —Si(U50)(U51)(U52)";

where U1, U2, U3, U4, U5, U6, U7, U8, U9, U10, U11, U12, U13, U14, U15, U16, U17, U18, U19, U20, U21, U22, U23, U24, U25, U26, U27, U28, U29, U30, U31, U32, U33, U34, U35, U36, U37, U38, U39, U40, U41, U42, U43, U44, U45, U46, U47, U48, U49, U50, U51, U52 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, U7, U8 and/or U16, U17 and/or U29, U30 and/or U36, U37 and/or U45, U46, in each case together, may also form "heterocyclyl";

where, optionally, the above substituents of substituent group (i) may in turn each independently be substituted by at least one substituent selected identically or differently from the group consisting of:

(iii) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHU53, —NU54U55, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)—U56, —C(O)O—U57, —C(O)NH—U58, —C(O)NU59U60, —O—U61, —O(—U62-O)$_r$—H (r=1, 2, 3, 4, 5), —O(—U63-O)$_r$—U64 (r=1, 2, 3, 4, 5), —OC(O)—U65, —OC(O)—O—U66, —OC(O)—NHU67, —O—C(O)—NU68U69, —OP(O)(OU70)(OU71), —OSi(U72)(U73)(U74), —OS(O$_2$)—U75, —NHC(O)—U76, —NU77C(O)—U78, —NH—C(O)—O—U79, —NH—C(O)—NH—U80, —NH—C(O)—NU81U82, —NU83-C(O)—O—U84, —NU85-C(O)—NH—U86, —NU87-C(O)—NU88U89, —NHS(O$_2$)—U90, —NU91S(O$_2$)—U92, —S—U93, —S(O)—U94, —S(O$_2$)—U95, —S(O$_2$)NH—U96, —S(O$_2$)NU97U98, —S(O$_2$)O—U99, —P(O)(OU100)(OU101), —Si(U102)(U103)(U104)";

where U53, U54, U55, U56, U57, U58, U59, U60, U61, U62, U63, U64, U65, U66, U67, U68, U69, U70, U71, U72, U73, U74, U75, U76, U77, U78, U79, U80, U81, U82, U83, U84, U85, U86, U87, U88, U89, U90, U91, U92, U93, U94, U95, U96, U97, U98, U99, U100, U101, U102, U103, U104 are each independently selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and where, alternatively, U59, U60 and/or U68, U69 and/or U81, U82 and/or U88, U89 and/or U97, U98, in each case together, may also form "heterocyclyl";

where, optionally, the above substituents of substituent group (ii) may in turn each independently be substituted by at least one substituent selected identically or differently from the group consisting of:

(iii) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHU105, —NU106U107, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)—U108, —C(O)O—U109, —C(O)NH—U110, —C(O)NU111U112, —O—U113, —O(—U114-O)$_s$—H (s=1, 2, 3, 4, 5), —O(—U115-O)$_s$—U116 (s=1, 2, 3, 4, 5), —OC(O)—U117, —OC(O)—O—U118, —OC(O)—NHU119, —O—C(O)—NU120U121, —OP(O)(OU122)(OU123), —OSi(U124)(U125)(U126), —OS(O$_2$)—U127, —NHC(O)—U128, —NU129C(O)—U130, —NH—C(O)—O—U131, —NH—C(O)—NH—U132, —NH—C(O)—NU133U134, —NU135-C(O)—O—U136, —NU137-C(O)—NH—U138, —NU139-C(O)—NU140U141, —NHS(O$_2$)—U142, —NU143S(O$_2$)—U144, —S—U145, —S(O)—U146, —S(O$_2$)—U147, —S(O$_2$)NH—U148, —S(O$_2$)NU149U150, —S(O$_2$)O—U151, —P(O)(OU152)(OU153), —Si(U154)(U155)(U156)";

where U105, U106, U107, U108, U109, U110, U111, U112, U113, U114, U115, U116, U117, U118, U119, U120, U121, U122, U123, U124, U125, U126, U127, U128, U129, U130, U131, U132, U133, U134, U135, U136, U137, U138, U139, U140, U141, U142, U143, U144, U145, U146, U147, U148, U149, U150, U151, U152, U153, U154, U155, U156 are each independently selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and where, alternatively, U111, U112 and/or U120, U121 and/or U133, U134 and/or U140, U141 and/or U149, U150, in each case together, may also form "heterocyclyl";

(3) —C(O)—Z23, where Z23 is independently selected from the group consisting of:

(a) "hydrogen, alkyl, $(C_9-C_{30})$alkyl, cycloalkyl, cycloalkylalkyl, heterocyclyl, heterocyclylalkyl, aryl, arylalkyl, heteroaryl, heteroarylalkyl";

where the above substituents of substitution group (a) may optionally each independently be substituted by at least one substituent selected identically or differently from the group consisting of:

(i) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHU157, —NU158U159, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)—U160, —C(O)O—U161, —C(O)NH—U162, —C(O)NU163U164, —O—U165, —O(—U166-O)$_t$—H (t=1, 2, 3, 4, 5), —O(—U167-O)$_t$—U168 (t=1, 2, 3, 4, 5), —OC(O)—U169, —OC(O)—O—U170, —OC(O)—NHU171, —O—C(O)—NU172U173, —OP(O)(OU174)(OU175), —OSi(U176)(U177)(U178), —OS(O$_2$)—U179, —NHC(O)—U180, —NU181C(O)—U182, —NH—C(O)—O—U183, —NH—C(O)—NH—U184, —NH—C(O)—NU185U186, —NU187-C(O)—O—U188, —NU189-C(O)—NH—U190, —NU191-C(O)—NU192U193, —NHS(O$_2$)—U194, —NU195S(O$_2$)—U196, —S—U197, —S(O)—U198, —S(O$_2$)—U199, —S(O$_2$)NH—U200, —S(O$_2$)NU201U202, —S(O$_2$)O—U203, —P(O)(OU204)(OU205), —Si(U206)(U207)(U208)";

where U157, U158, U159, U160, U161, U162, U163, U164, U165, U166, U167, U168, U169, U170, U171, U172, U173, U174, U175, U176, U177, U178, U179, U180, U181, U182, U183, U184, U185, U186, U187, U188, U189, U190, U191, U192, U193, U194, U195, U196, U197, U198, U199, U200, U201, U202, U203, U204, U205, U206, U207, U208 are each independently selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and where, alternatively, U163, U164 and/or U172, U173 and/or U185, U186 and/or U192, U193 and/or U201, U202, in each case together, may also form "heterocyclyl";

where, optionally, the above substituents of substituent group (i) may in turn each independently be substituted by at least one substituent selected identically or differently from the group consisting of:

(ii) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHU209, —NU210U211, —$NO_2$, —OH, —$OCF_3$, —SH, —O—$SO_3$H, —OP(O)(OH)$_2$, —CHO, —COOH, —C(O)$NH_2$, —$SO_3$H, —P(O)(OH)$_2$, —C(O)—U212, —C(O)O—U213, —C(O)NH—U214, —C(O)NU215U216, —O—U217, —O(—U218-O)$_u$—H (u=1, 2, 3, 4, 5), —O(—U219-O)$_u$—U220 (u=1, 2, 3, 4, 5), —OC(O)—U221, —OC(O)—O—U222, —OC(O)—NHU223, —O—C(O)—NU224U225, —OP(O)(OU226)(OU227), —OSi(U228)(U229)(U230), —OS($O_2$)—U231, —NHC(O)—U232, —NU233C(O)—U234, —NH—C(O)—O—U235, —NH—C(O)—NH—U236, —NH—C(O)—NU237U238, —NU239-C(O)—O—U240, —NU241-C(O)—NH—U242, —NU243-C(O)—NU244U245, —NHS($O_2$)—U246, —NU247S($O_2$)—U248, —S—U249, —S(O)—U250, —S($O_2$)—U251, —S($O_2$)NH—U252, —S($O_2$)NU253U254, —S($O_2$)O—U255, —P(O)(OU256)(OU257), —Si(U258)(U259)(U260)";

where U209, U210, U211, U212, U213, U214, U215, U216, U217, U218, U219, U220, U221, U222, U223, U224, U225, U226, U227, U228, U229, U230, U231, U232, U233, U234, U235, U236, U237, U238, U239, U240, U241, U242, U243, U244, U245, U246, U247, U248, U249, U250, U251, U252, U253, U254, U255, U256, U257, U258, U259, U260 are each independently selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and where, alternatively, U215, U216 and/or U224, U225 and/or U237, U238 and/or U244, U245 and/or U253, U254, in each case together, may also form "heterocyclyl";

where, optionally, the above substituents of substituent group (ii) may in turn each independently be substituted by at least one substituent selected identically or differently from the group consisting of:

(iii) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHU261, —NU262U263, —$NO_2$, —OH, —$OCF_3$, —SH, —O—$SO_3$H, —OP(O)(OH)$_2$, —CHO, —COOH, —C(O)$NH_2$, —$SO_3$H, —P(O)(OH)$_2$, —C(O)—U264, —C(O)O—U265, —C(O)NH—U266, —C(O)NU267U268, —O—U269, —O(—U270-O)$_v$—H (v=1, 2, 3, 4, 5), —O(—U271-O)$_v$—U272 (v=1, 2, 3, 4, 5), —OC(O)—U273, —OC(O)—O—U274, —OC(O)—NHU275, —O—C(O)—NU276U277, —OP(O)(OU278)(OU279), —OSi(U280)(U281)(U282), —OS($O_2$)—U283, —NHC(O)—U284, —NU285C(O)—U286, —NH—C(O)—O—U287, —NH—C(O)—NH—U288, —NH—C(O)—NU289U290, —NU291-C(O)—O—U292, —NU293-C(O)—NH—U294, —NU295-C(O)—NU296U297, —NHS($O_2$)—U298, —NU299S($O_2$)—U300, —S—U301, —S(O)—U302, —S($O_2$)—U303, —S($O_2$)NH—U304, —S($O_2$)NU305U306, —S($O_2$)O—U307, —P(O)(OU308)(OU309), —Si(U310)(U311)(U312)";

where U261, U262, U263, U264, U265, U266, U267, U268, U269, U270, U271, U272, U273, U274, U275, U276, U277, U278, U279, U280, U281, U282, U283, U284, U285, U286, U287, U288, U289, U290, U291, U292, U293, U294, U295, U296, U297, U298, U299, U300, U301, U302, U303, U304, U305, U306, U307, U308, U309, U310, U311, U312 are each independently selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and where, alternatively, U267, U268 and/or U276, U277 and/or U289, U290 and/or U296, U297 and/or U305, U306, in each case together, may also form "heterocyclyl";

(4) Z16, Z17 may independently optionally also form "heterocyclyl" together;

(5) "—C(O)—C(O)—U313, —S($O_2$)—NU314U315"; where U313, U314, U315 are each independently selected from the group consisting of:

(I) "hydrogen, alkyl, $(C_9-C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHU316, —NU317U318, —$NO_2$, —OH, —$OCF_3$, —SH, —O—$SO_3$H, —OP(O)(OH)$_2$, —CHO, —COOH, —C(O)$NH_2$, —$SH_3$H, —P(O)(OH)$_2$, —C(O)—U319, —C(O)O—U320, —C(O)NH—U321, —C(O)NU322U323, —O—U324, —O(—U325-O)$_w$—H (w=1, 2, 3, 4, 5), —O(—U326-O)$_w$—U327 (w=1, 2, 3, 4, 5), —OC(O)—U328, —OC(O)—O—U329, —OC(O)—NHU330, —O—C(O)—NU331U332, —OP(O)(OU333)(OU334), —OSi(U335)(U336)(U337), —OS($O_2$)—U338, —NHC(O)—U339, —NU340C(O)—U341, —NH—C(O)—O—U342, —NH—C(O)—NH—U343, —NH—C(O)—NU344U345, —NU346-C(O)—O—U347, —NU348-C(O)—NH—U349, —NU350-C(O)—NU351U352, —NHS($O_2$)—U353, —NU354S($O_2$)—U355, —S—U356, —S(O)—U357, —S($O_2$)—U358, —S($O_2$)NH—U359, —S($O_2$)NU360U361, —S($O_2$)O—U362, —P(O)(OU363)(OU364), —Si(U365)(U366)(U367)";

where U316, U317, U318, U319, U320, U321, U322, U323, U324, U325, U326, U327, U328, U329, U330, U331, U332, U333, U334, U335, U336, U337, U338, U339, U340, U341, U342, U343, U344, U345, U346, U347, U348, U349, U350, U351, U352, U353, U354, U355, U356, U357, U358, U359, U360, U361, U362, U363, U364, U365, U366, U367 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, U322, U323 and/or U331, U332 and/or U344, U345 and/or U351, U352 and/or U360, U361, in each case together, may also form "heterocyclyl";

where, optionally, the above substituents of substitution group (I) may each independently be further substituted by at least one substituent selected identically or differently from the group consisting of:

(i) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHU368, —NU369U370, —$NO_2$, —OH, —$OCF_3$, —SH, —O—$SO_3$H, —OP(O)(OH)$_2$, —CHO, —COOH, —C(O)NH$_2$, —SO$_3$H, —P(O)(OH)$_2$, —C(O)—U371, —C(O)O—U372, —C(O)NH—U373, —C(O)NU374U375, —O—U376, —O(—U377-O)$_x$—H (x=1, 2, 3, 4, 5), —O(—U378-O)$_x$—U379 (x=1, 2, 3, 4, 5), —OC(O)—U380, —OC(O)—O—U381, —OC(O)—NHU382, —O—C(O)—NU383U384, —OP(O)(OU385)(OU386), —OSi(U387)(U388)(U389), —OS(O$_2$)—U390, —NHC(O)—U391, —NU392C(O)—U393, —NH—C(O)—O—U394, —NH—C(O)—NH—U395, —NH—C(O)—NU396U397, —NU398-C(O)—O—U399, —NU400-C(O)—NH—U401, —NU402-C(O)—NU403U404, —NHS(O$_2$)—U405, —NU406S(O$_2$)—U407, —S—U408, —S(O)—U409, —S(O$_2$)—U410, —S(O$_2$)NH—U411, —S(O$_2$)NU412U413, —S(O$_2$)O—U414, —P(O)(OU415)(OU416), —Si(U417)(U418)(U419)";

where U368, U369, U370, U371, U372, U373, U374, U375, U376, U377, U378, U379, U380, U381, U382, U383, U384, U385, U386, U387, U388, U389, U390, U391, U392, U393, U394, U395, U396, U397, U398, U399, U400, U401, U402, U403, U404, U405, U406, U407, U408, U409, U410, U411, U412, U413, U414, U415, U416, U417, U418, U419 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, U374, U375 and/or U383, U384 and/or U396, U397 and/or U403, U404 and/or U412, U413, in each case together, may also form "heterocyclyl";

where, optionally, the above substituents of substituent group (i) may in turn each independently be substituted by at least one substituent selected identically or differently from the group consisting of:

(ii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHU420, —NU421U422, —$NO_2$, —OH, —$OCF_3$, —SH, —O—$SO_3$H, —OP(O)(OH)$_2$, —CHO, —COOH, —C(O)NH$_2$, —SO$_3$H, —P(O)(OH)$_2$, —C(O)—U423, —C(O)O—U424, —C(O)NH—U425, —C(O)NU426U427, —O—U428, —O(—U429-O)$_y$—H (y=1, 2, 3, 4, 5), —O(—U430-O)$_y$—U431 (y=1, 2, 3, 4, 5), —OC(O)—U432, —OC(O)—O—U433, —OC(O)—NHU434, —O—C(O)—NU435U436, —OP(O)(OU437)(OU438), —OSi(U439)(U440)(U441), —OS(O$_2$)—U442, —NHC(O)—U443, —NU444C(O)—U445, —NH—C(O)—O—U446, —NH—C(O)—NH—U447, —NH—C(O)—NU448U449, —NU450-C(O)—O—U451, —NU452-C(O)—NH—U453, —NU454-C(O)—NU455U456, —NHS(O$_2$)—U457, —NU458S(O$_2$)—U459, —S—U460, —S(O)—U461, —S(O$_2$)—U462, —S(O$_2$)NH—U463, —S(O$_2$)NU464U465, —S(O$_2$)O—U466, P(O)(OU467)(OU468), —Si(U469)(U470)(U471)";

where U420, U421, U422, U423, U424, U425, U426, U427, U428, U429, U430, U431, U432, U433, U434, U435, U436, U437, U438, U439, U440, U441, U442, U443, U444, U445, U446, U447, U448, U449, U450, U451, U452, U453, U454, U455, U456, U457, U458, U459, U460, U461, U462, U463, U464, U465, U466, U467, U468, U469, U470, U471 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, U426, U427 and/or U435, U436 and/or U448, U449 and/or U455, U456 and/or U464, U465, in each case together, may also form "heterocyclyl";

where, optionally, the above substituents of substituent group (ii) may in turn each independently be substituted by at least one substituent selected identically or differently from the group consisting of:

(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHU472, —NU473U474, —$NO_2$, —OH, —$OCF_3$, —SH, —O—$SO_3$H, —OP(O)(OH)$_2$, —CHO, —COOH, —C(O)NH$_2$, —SO$_3$H, —P(O)(OH)$_2$, —C(O)—U475, —C(O)O—U476, —C(O)NH—U477, —C(O)NU478U479, —O—U480, —O(—U481-O)$_z$—H (z=1, 2, 3, 4, 5), —O(—U482-O)$_z$—U483 (z=1, 2, 3, 4, 5), —OC(O)—U484, —OC(O)—O—U485, —OC(O)—NHU486, —O—C(O)—NU487U488, —OP(O)(OU489)(OU490), —OSi(U491)(U492)(U493), —OS(O$_2$)—U494, —NHC(O)—U495, —NU496C(O)—U497, —NH—C(O)—O—U498, —NH—C(O)—NH—U499, —NH—C(O)—NU500U501, —NU502-C(O)—O—U503, —NU504-C(O)—NH—U505, —NU506-C(O)—NU507U508, —NHS(O$_2$)—U509, —NU510S(O$_2$)—U511, —S—U512, —S(O)—U513, —S(O$_2$)—U514, —S(O$_2$)NH—U515, —S(O$_2$)NU516U517, —S(O$_2$)O—U518, —P(O)(OU519)(OU520), —Si(U521)(U522)(U523)";

where U472, U473, U474, U475, U476, U477, U478, U479, U480, U481, U482, U483, U484, U485, U486, U487, U488, U489, U490, U491, U492, U493, U494, U495, U496, U497, U498, U499, U500, U501, U502, U503, U504, U505, U506, U507, U508, U509, U510, U511, U512, U513, U514, U515, U516, U517, U518, U519, U520, U521, U522, U523 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, U478, U479 and/or U487, U488 and/or U500, U501 and/or U507, U508 and/or U516, U517, in each case together, may also form "heterocyclyl";

and where, alternatively, U314, U315 together may also form "heterocyclyl";

and the Z5 radical is independently selected from the group consisting of:

(i) "hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHA1, —NA2A3, —$NO_2$, —OH, —$OCF_3$, —SH, —O—$SO_3H$, —OP(O)(OH)$_2$, —CHO, —COOH, —C(O)$NH_2$, —$SO_3H$, —P(O)(OH)$_2$, —C(O)-A4, —C(O)O-A5, —C(O)NH-A6, —C(O)NA7A8, —O-A9, —O(-A10-O)$_r$-—H (r=1, 2, 3, 4, 5), —O(-A11-O)$_r$-A12 (r=1, 2, 3, 4, 5), —OC(O)-A13, —OC(O)—O-A14, —OC(O)—NHA15, —O—C(O)—NA16A17, —OP(O)(OA18)(OA19), —OSi(A20)(A21)(A22), —OS($O_2$)-A23, —NHC(O)-A24, —NA25C(O)-A26, —NH—C(O)—O-A27, —NH—C(O)—NH-A28, —NH—C(O)—NA29A30, —NA31-C(O)—O-A32, —NA33-C(O)—NH-A34, —NA35-C(O)—NA36A37, —NHS($O_2$)-A38, —NA39S($O_2$)-A40, —S-A41, —S(O)-A42, —S($O_2$)-A43, —S($O_2$)NH-A44, —S($O_2$)NA45A46, —S($O_2$)O-A47, —P(O)(OA48)(OA49), —Si(A50)(A51)(A52)";

where A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, A36, A37, A38, A39, A40, A41, A42, A43, A44, A45, A46, A47, A48, A49, A50, A51, A52 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, A7, A8 and/or A16, A17 and/or A29, A30 and/or A36, A37 and/or A45, A46, in each case together, may also form "heterocyclyl";

where, optionally, the above substituents of substituent group (i) may in turn each independently be substituted by at least one substituent selected identically or differently from the group consisting of:

(ii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHA53, —NA54A55, —$NO_2$, —OH, —$OCF_3$, —SH, —O—$SO_3H$, —OP(O)(OH)$_2$, —CHO, —COOH, —C(O)$NH_2$, —$SO_3H$, —P(O)(OH)$_2$, —C(O)-A56, —C(O)O-A57, —C(O)NH-A58, —C(O)NA59A60, —O-A61, —O(-A62-O)$_s$-—H (s=1, 2, 3, 4, 5), —O(-A63-O)$_t$-A64 (t=1, 2, 3, 4, 5), —OC(O)-A65, —OC(O)—O-A66, —OC(O)—NHA67, —O—C(O)—NA68A69, —OP(O)(OA70)(OA71), —OSi(A72)(A73)(A74), —OS($O_2$)-A75, —NHC(O)-A76, —NA77C(O)-A78, —NH—C(O)—O-A79, —NH—C(O)—NH-A80, —NH—C(O)—NA81A82, —NA83-C(O)—O-A84, —NA85-C(O)—NH-A86, —NA87-C(O)—NA88A89, —NHS($O_2$)-A90, —NA91S($O_2$)-A92, —S-A93, —S(O)-A94, —S($O_2$)-A95, —S($O_2$)NH-A96, —S($O_2$)NA97A98, —S($O_2$)O-A99, —P(O)(OA100)(OA101), —Si(A102)(A103)(A104)";

where A53, A54, A55, A56, A57, A58, A59, A60, A61, A62, A63, A64, A65, A66, A67, A68, A69, A70, A71, A72, A73, A74, A75, A76, A77, A78, A79, A80, A81, A82, A83, A84, A85, A86, A87, A88, A89, A90, A91, A92, A93, A94, A95, A96, A97, A98, A99, A100, A101, A102, A103, A104 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, A59, A60 and/or A68, A69 and/or A81, A82 and/or A88, A89 and/or A97, A98, in each case together, may also form "heterocyclyl";

where, optionally, the above substituents of substituent group (ii) may in turn each independently be substituted by at least one substituent selected identically or differently from the group consisting of:

(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHA105, —NA106A107, —$NO_2$, —OH, —$OCF_3$, —SH, —O—$SO_3H$, —OP(O)(OH)$_2$, —CHO, —COOH, —C(O)$NH_2$, —$SO_3H$, —P(O)(OH)$_2$, —C(O)-A108, —C(O)O-A109, —C(O)NH-A110, —C(O)NA111A112, —O-A113, —O(-A114-O)$_t$-—H (t=1, 2, 3, 4, 5), —O(-A115-O)$_t$-A116 (t=1, 2, 3, 4, 5), —OC(O)-A117, —OC(O)—O-A118, —OC(O)—NHA119, —O—C(O)—NA120A121, —OP(O)(OA122)(OA123), —OSi(A124)(A125)(A126), —OS($O_2$)-A127, —NHC(O)-A128, —NA129C(O)-A130, —NH—C(O)—O-A131, —NH—C(O)—NH-A132, —NH—C(O)—NA133A134, —NA135-C(O)—O-A136, —NA137-C(O)—NH-A138, —NA139-C(O)—NA140A141, —NHS($O_2$)-A142, —NA143S($O_2$)-A144, —S-A145, —S(O)-A146, —S($O_2$)-A147, —S($O_2$)NH-A148, —S($O_2$)NA149A150, —S($O_2$)O-A151, —P(O)(OA152)(OA153), —Si(A154)(A155)(A156)";

where A105, A106, A107, A108, A109, A110, A111, A112, A113, A114, A115, A116, A117, A118, A119, A120, A121, A122, A123, A124, A125, A126, A127, A128, A129, A130, A131, A132, A133, A134, A135, A136, A137, A138, A139, A140, A141, A142, A143, A144, A145, A146, A147, A148, A149, A150, A151, A152, A153, A154, A155, A156 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, A111, A112 and/or A120, A121 and/or A133, A134 and/or A140, A141 and/or A149, A150, in each case together, may also form "heterocyclyl";

or (E) one of the Z1, Z2 radicals or both Z1, Z2 radicals are each independently selected from the group consisting of:

(a) —NZ24Z25;

with the proviso that one of the Z24, Z25 radicals or both Z24, Z25 radicals are each independently selected from the group consisting of:

(1) "—C(O)—C(O)-T1, —S(O$_2$)—NT2T3";
where T1, T2, T3 are each independently selected from the group consisting of:
(I) "hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHT4, —NT5T6, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)-T7, —C(O)O-T8, —C(O)NH-T9, —C(O)NT10T11, —O-T12, —O(-T13-O)$_p$—H (p=1, 2, 3, 4, 5), —O(-T14-O)$_p$-T15 (p=1, 2, 3, 4, 5), —OC(O)-T16, —OC(O)—O-T17, —OC(O)—NHT18, —O—C(O)—NT19T20, —OP(O)(OT21)(OT22), —OSi(T23)(T24)(T25), —OS(O$_2$)-T26, —NHC(O)-T27, —NT28C(O)-T29, —NH—C(O)—O-T30, —NH—C(O)—NH-T31, —NH—C(O)—NT32T33, —NT34-C(O)—O-T35, —NT36-C(O)—NH-T37, —NT38-C(O)—NT39T40, —NHS(O$_2$)-T41, —NT42S(O$_2$)-T43, —S-T44, —S(O)-T45, —S(O$_2$)-T46, —S(O$_2$)NH-T47, —S(O$_2$)NT48T49, —S(O$_2$)O-T50, —P(O)(OT51)(OT52), —Si(T53)(T54)(T55)";
where T4, T5, T6, T7, T8, T9, T10, T11, T12, T13, T14, T15, T16, T17, T18, T19, T20, T21, T22, T23, T24, T25, T26, T27, T28, T29, T30, T31, T32, T33, T34, T35, T36, T37, T38, T39, T40, T41, T42, T43, T44, T45, T46, T47, T48, T49, T50, T51, T52, T53, T54, T55 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, T10, T11 and/or T19, T20 and/or T32, T33 and/or T39, T40 and/or T48, T49, in each case together, may also form "heterocyclyl";
where, optionally, the above substituents of substitution group (I) may each independently be further substituted by at least one substituent selected identically or differently from the group consisting of:
(i) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHT56, —NT57T58, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)-T59, —C(O)O-T60, —C(O)NH-T61, —C(O)NT62T63, —O-T64, —O(-T65-O)$_r$—H (r=1, 2, 3, 4, 5), —O(-T66-O)$_r$-T67 (r=1, 2, 3, 4, 5), —OC(O)-T68, —OC(O)—O-T69, —OC(O)—NHT70, —O—C(O)—NT71T72, —OP(O)(OT73)(OT74), —OSi(T75)(T76)(T77), —OS(O$_2$)-T78, —NHC(O)-T79, —NT80C(O)-T81, —NH—C(O)—O-T82, —NH—C(O)—NH-T83, —NH—C(O)—NT84T85, —NT86-C(O)—O-T87, —NT88-C(O)—NH-T89, —NT90-C(O)—NT91T92, —NHS(O$_2$)-T93, —NT94S(O$_2$)-T95, —S-T96, —S(O)-T97, —S(O$_2$)-T98, —S(O$_2$)NH-T99, —S(O$_2$)NT100T101, —S(O$_2$)O-T102, —P(O)(OT103)(OT104), —Si(T105)(T106)(T107)";
where T56, T57, T58, T59, T60, T61, T62, T63, T64, T65, T66, T67, T68, T69, T70, T71, T72, T73, T74, T75, T76, T77, T78, T79, T80, T81, T82, T83, T84, T85, T86, T87, T88, T89, T90, T91, T92, T93, T94, T95, T96, T97, T98, T99, T100, T101, T102, T103, T104, T105, T106, T107 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, T62, T63 and/or T71, T72 and/or T84, T85 and/or T91, T92 and/or T100, T101, in each case together, may also form "heterocyclyl";
where, optionally, the above substituents of substituent group (i) may in turn each independently be substituted by at least one substituent selected identically or differently from the group consisting of:
(ii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHT108, —NT109T110, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)-T111, —C(O)O-T112, —C(O)NH-T113, —C(O)NT114T115, —O-T116, —O(-T117-O)$_s$—H (s=1, 2, 3, 4, 5), —O(-T118-O)$_s$-T119 (s=1, 2, 3, 4, 5), —OC(O)-T120, —OC(O)—O-T121, —OC(O)—NHT122, —O—C(O)—NT123T124, —OP(O)(OT125)(OT126), —OSi(T127)(T128)(T129), —OS(O$_2$)-T130, —NHC(O)-T131, —NT132C(O)-T133, —NH—C(O)—O-T134, —NH—C(O)—NH-T135, —NH—C(O)—NT136T137, —NT138-C(O)—O-T139, —NT140-C(O)—NH-T141, —NT142-C(O)—NT143T144, —NHS(O$_2$)-T145, —NT146S(O$_2$)-T147, —S-T148, —S(O)-T149, —S(O$_2$)-T150, —S(O$_2$)NH-T151, —S(O$_2$)NT152T153, —S(O$_2$)O-T154, —P(O)(OT155)(OT156), —Si(T157)(T158)(T159)";
where T108, T109, T110, T111, T112, T113, T114, T115, T116, T117, T118, T119, T120, T121, T122, T123, T124, T125, T126, T127, T128, T129, T130, T131, T132, T133, T134, T135, T136, T137, T138, T139, T140, T141, T142, T143, T144, T145, T146, T147, T148, T149, T150, T151, T152, T153, T154, T155, T156, T157, T158, T159 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, T114, T115 and/or T123, T124 and/or T136, T137 and/or T143, T144 and/or T152, T153, in each case together, may also form "heterocyclyl";
where, optionally, the above substituents of substituent group (ii) may in turn each independently be substituted by at least one substituent selected identically or differently from the group consisting of:
(iii) "alkyl, (C$_9$-C$_{30}$)alkyl, cycloalkyl, cycloalkylalkyl, heterocyclyl, heterocyclylalkyl, aryl, arylalkyl, heteroaryl, heteroaryl alkyl, F, Cl, Br, I, CN, CF$_3$, N$_3$, NH$_2$, —NHT160, —NT161T162, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)-T163, —C(O)O-T164, —C(O)NH-T165, —C(O)NT166T167, —O-T168, —O(-T169-O)$_t$—H (t=1, 2, 3, 4, 5), —O(-T170-O)$_t$-T171 (t=1, 2, 3, 4, 5), —OC(O)-T172, —OC(O)—O-T173, —OC(O)—NHT174, —O—C(O)—NT175T176, —OP(O)(OT177)(OT178), —OSi(T179)(T180)(T181), —OS(O$_2$)-T182, —NHC(O)-T183, —NT184C(O)-T185, —NH—C(O)—O-T186, —NH—C(O)—NH-T187, —NH—C(O)—NT188T189, —NT190-C(O)—O-T191, —NT192-C(O)—NH-T193, —NT194-C(O)—NT195T196, —NHS(O$_2$)-T197, —NT198S(O$_2$)-T199, —S-T200, —S(O)-T201, —S(O$_2$)-T202, —S(O$_2$)NH-T203, —S(O$_2$)NT204T205, —S(O$_2$)O-T206, —P(O)(OT207)(OT208), —Si(T209)(T210)(T211)";

where T160, T161, T162, T163, T164, T165, T166, T167, T168, T169, T170, T171, T172, T173, T174, T175, T176, T177, T178, T179, T180, T181, T182, T183, T184, T185, T186, T187, T188, T189, T190, T191, T192, T193, T194, T195, T196, T197, T198, T199, T200, T201, T202, T203, T204, T205, T206, T207, T208, T209, T210, T211 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, T166, T167 and/or T175, T176 and/or T188, T189 and/or T195, T196 and/or T204, T205, in each case together, may also form "heterocyclyl";

where, alternatively, T2, T3 together may also form "heterocyclyl";

and one of the Z24, Z25 radicals or neither of the Z24, Z25 radicals is also independently selected from the group consisting of:

(2) "hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl";

where, optionally, the above substituents of substitution group (2) may each independently be further substituted by at least one substituent selected identically or differently from the group consisting of:

(i) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHT212, —NT213T214, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)-T215, —C(O)O-T216, —C(O)NH-T217, —C(O)NT218T219, —O-T220, —O(-T221-O)$_u$—H (u=1, 2, 3, 4, 5), —O(-T222-O)$_u$-T223 (u=1, 2, 3, 4, 5), —OC(O)-T224, —OC(O)—O-T225, —OC(O)—NHT226, —O—C(O)—NT227T228, —OP(O)(OT229)(OT230), —OSi(T231)(T232)(T233), —OS(O$_2$)-T234, —NHC(O)-T235, —NT236C(O)-T237, —NH—C(O)—O-T238, —NH—C(O)—NH-T239, —NH—C(O)—NT240T241, —NT242-C(O)—O-T243, —NT244-C(O)—NH-T245, —NT246-C(O)—NT247T248, —NHS(O$_2$)-T249, —NT250S(O$_2$)-T251, —S-T252, —S(O)-T253, —S(O$_2$)-T254, —S(O$_2$)NH-T255, —S(O$_2$)NT256T257, —S(O$_2$)O-T258, —P(O)(OT259)(OT260), —Si(T261)(T262)(T263)";

where T212, T213, T214, T215, T216, T217, T218, T219, T220, T221, T222, T223, T224, T225, T226, T227, T228, T229, T230, T231, T232, T233, T234, T235, T236, T237, T238, T239, T240, T241, T242, T234, T244, T245, T246, T247, T248, T249, T250, T251, T252, T253, T254, T255, T256, T257, T258, T259, T260, T261, T262, T263 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, T218, T219 and/or T227, T228 and/or T240, T241 and/or T247, T248 and/or T256, T257, in each case together, may also form "heterocyclyl";

where, optionally, the above substituents of substituent group (i) may in turn each independently be substituted by at least one substituent selected identically or differently from the group consisting of:

(ii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHT264, —NT265T266, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)-T267, —C(O)O-T268, —C(O)NH-T269, —C(O)NT270T271, —O-T272, —O(-T273-O)$_v$—H (v=1, 2, 3, 4, 5), —O(-T274-O)$_v$-T275 (v=1, 2, 3, 4, 5), —OC(O)-T276, —OC(O)—O-T277, —OC(O)—NHT278, —O—C(O)—NT279T280, —OP(O)(OT281)(OT282), —OSi(T283)(T284)(T285), —OS(O$_2$)-T286, —NHC(O)-T287, —NT288C(O)-T289, —NH—C(O)—O-T290, —NH—C(O)—NH-T291, —NH—C(O)—NT292T293, —NT294-C(O)—O-T295, —NT296-C(O)—NH-T297, —NT298-C(O)—NT299T300, —NHS(O$_2$)-T301, —NT302S(O$_2$)-T303, —S-T304, —S(O)-T305, —S(O$_2$)-T306, —S(O$_2$)NH-T307, —S(O$_2$)NT308T309, —S(O$_2$)O-T310, —P(O)(OT311)(OT312), —Si(T313)(T314)(T315)";

where T264, T265, T266, T267, T268, T269, T270, T271, T272, T273, T274, T275, T276, T277, T278, T279, T280, T281, T282, T283, T284, T285, T286, T287, T288, T289, T290, T291, T292, T293, T294, T295, T296, T297, T298, T299, T300, T301, T302, T303, T304, T305, T306, T307, T308, T309, T310, T311, T312, T313, T314, T315 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, T270, T271 and/or T279, T280 and/or T292, T293 and/or T299, T300 and/or T308, T309, in each case together, may also form "heterocyclyl";

where, optionally, the above substituents of substituent group (ii) may in turn each independently be substituted by at least one substituent selected identically or differently from the group consisting of:

(iii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHT316, —NT317T318, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)-T319, —C(O)O-T320, —C(O)NH-T321, —C(O)NT322T323, —O-T324, —O(-T325-O)$_w$—H (w=1, 2, 3, 4, 5), —O(-T326-O)$_w$-T327 (w=1, 2, 3, 4, 5), —OC(O)-T328, —OC(O)—O-T329, —OC(O)—NHT330, —O—C(O)—NT331T332, —OP(O)(OT333)(OT334), —OSi(T335)(T336)(T337), —OS(O$_2$)-T338, —NHC(O)-T339, —NT340C(O)-T341, —NH—C(O)—O-T342, —NH—C(O)—NH-T343, —NH—C(O)—NT344T345, —NT346-C(O)—O-T347, —NT348-C(O)—NH-T349, —NT350-C(O)—NT351T352, —NHS(O$_2$)-T353, —NT354S(O$_2$)-T355, —S-T356, —S(O)-T357, —S(O$_2$)-T358, —S(O$_2$)NH-T359, —S(O$_2$)NT360T361, —S(O$_2$)O-T362, —P(O)(OT363)(OT364), —Si(T365)(T366)(T367)";

where T316, T317, T318, T319, T320, T321, T322, T323, T324, T325, T326, T327, T328, T329, T330, T331, T332, T333, T334, T335, T336, T337, T338, T339, T340, T341, T342, T343, T344, T345, T346, T347, T348, T349, T350, T351, T352, T353, T354, T355, T356, T357, T358, T359, T360, T361, T362, T363, T364, T365, T366, T367 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, T322, T323 and/or T331, T332 and/or T344, T345 and/or T351, T352 and/or T360, T361, in each case together, may also form "heterocyclyl";

(b) —NZ26Z27 where one of the Z26, Z27 radicals or both Z26, Z27 radicals are each independently selected from the group consisting of:

(1) "—C(Y4)NZ28Z29, —C(=NZ30)-Z31";
where Y4 is independently selected from the group consisting of "O, S, =NH, =NZ32";
with the proviso that at least one of the Z28, Z29 radicals and at least one of the Z30, Z31 radicals is independently selected from the group consisting of:
(I) "alkyl, cycloalkyl, heterocyclyl, aryl, heteroaryl, —C(O)-alkyl, —C(O)-aryl, —C(O)-heteroaryl";
with the further proviso that the above substituents of substituent group (I) are each independently substituted further by at least one substituent selected identically or differently from the group consisting of:
(i) "(C$_9$-C$_{30}$)alkyl, cycloalkylalkyl, heterocyclylalkyl, arylalkyl, heteroarylalkyl, N$_3$, —NT368T369, —NHC(O)-cycloalkylalkyl, —NHC(O)-heterocyclylalkyl, —NT370C(O)-T371, —NH—C(O)—O-T372, —NH—C(O)—NH-T373, —NH—C(O)—NT374T375, —NT376-C(O)—O-T377, —NT378-C(O)—NH-T379, —NT380-C(O)—NT381T382, —NHS(O$_2$)-Cycloalkylalkyl, —NHS(O$_2$)-heterocyclylalkyl, —NT383S(O$_2$)-T384, —O-T385, —O(-T386-O)$_x$-T387 (x=1, 2, 3, 4, 5), —O(-T388-O)$_x$—H (x=1, 2, 3, 4, 5), —OC(O)-cycloalkylalkyl, —OC(O)-heterocyclylalkyl, —OC(O)—O-T389, —OC(O)—NHT390, —O—C(O)—NT391T392, —OS(O$_2$)-cycloalkylalkyl, —OS(O$_2$)-heterocyclylalkyl, —OP(O)(OT393)(OT394), —OSi(T395)(T396)(T397), —CHO, —C(O)-cycloalkyl, —C(O)-heterocyclyl, —C(O)-cycloalkylalkyl, —C(O)-heterocyclylalkyl, —C(O)-arylalkyl, —C(O)-heteroarylalkyl, —S-cycloalkylalkyl, —S-heterocyclylalkyl, —S-arylalkyl, —S-heteroarylalkyl, —S(O)-cycloalkyl, —S(O)-heterocyclyl, —S(O)-heteroaryl, —S(O)-cycloalkylalkyl, —S(O)-heterocyclylalkyl, —S(O)-arylalkyl, —S(O)-heteroarylalkyl, —S(O$_2$)-cycloalkyl, —S(O$_2$)-heterocyclyl, —S(O$_2$)-heteroaryl, —S(O$_2$)-cycloalkylalkyl, —S(O$_2$)-heterocyclylalkyl, —S(O$_2$)-arylalkyl, —S(O$_2$)-heteroarylalkyl, —S(O$_2$)NH-cycloalkyl, —S(O$_2$)NH-heterocyclyl, —S(O$_2$)NH-cycloalkylalkyl, —S(O$_2$)NH-heterocyclylalkyl, —S(O$_2$)NH-heteroarylalkyl, —S(O$_2$)NT398T399, —S(O$_2$)O-cycloalkyl, —S(O$_2$)O-heterocyclyl, —S(O$_2$)O-heteroaryl, —S(O$_2$)O-cycloalkylalkyl, —S(O$_2$)O-heterocyclylalkyl, —S(O$_2$)O-heteroarylalkyl, —P(O)(OH)$_2$, —P(O)(OT400)(OT401), —Si(T402)(T403)(T404)"; with the further proviso that "—N(alkyl)$_2$", "—C(O)N(alkyl)$_2$", "—C(O)N(cycloalkyl)$_2$", "—C(O)N(Aryl)$_2$", "—C(O)N(heteroaryl)$_2$" are substituted further by at least one substituent selected from the following substituent group (ii);

where T368, T369, T370, T371, T372, T373, T374, T375, T376, T377, T378, T379, T380, T381, T382, T383, T384, T385, T386, T387, T388, T389, T390, T391, T392, T393, T394, T395, T396, T397, T398, T399, T400, T401, T402, T403, T404 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, T374, T375 and/or T381, T382 and/or T391, T392 and/or T398, T399, in each case together, may also form "heterocyclyl";

where, optionally, the above substituents of substituent group (i) may in turn each independently be further substituted by at least one substituent selected identically or differently from the group consisting of:

(ii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHT405, —NT406T407, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)-T408, —C(O)O-T409, —C(O)NH-T410, —C(O)NT411T412, —O-T413, —O(-T414-O)$_y$—H (y=1, 2, 3, 4, 5), —O(-T415-O)$_y$-T416 (y=1, 2, 3, 4, 5), —OC(O)-T417, —OC(O)—O-T418, —OC(O)—NHT419, —O—C(O)—NT420T421, —OP(O)(OT422)(OT423), —OSi(T424)(T425)(T426), —OS(O$_2$)-T427, —NHC(O)-T428, —NT429C(O)-T430, —NH—C(O)—O-T431, —NH—C(O)—NH-T432, —NH—C(O)—NT433T434, —NT435-C(O)—O-T436, —NT437-C(O)—NH-T438, —NT439-C(O)—NT440T441, —NHS(O$_2$)-T442, —NT443S(O$_2$)-T444, —S-T445, —S(O)-T446, —S(O$_2$)-T447, —S(O$_2$)NH-T448, —S(O$_2$)NT449T450, —S(O$_2$)O-T451, —P(O)(OT452)(OT453), —Si(T454)(T455)(T456)";

where T405, T406, T407, T408, T409, T410, T411, T412, T413, T414, T415, T416, T417, T418, T419, T420, T421, T422, T423, T424, T425, T426, T427, T428, T429, T430, T431, T432, T433, T434, T435, T436, T437, T438, T439, T440, T441, T442, T443, T444, T445, T446, T447, T448, T449, T450, T451, T452, T453, T454, T455, T456 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, T411, T412 and/or T420, T421 and/or T433, T434 and/or T440, T441 and/or T449, T450, in each case together, may also form "heterocyclyl";

where, optionally, the above substituents of substituent group (ii) may in turn each independently be substituted by at least one substituent selected identically or differently from the group consisting of:

(iii) "alkyl, (C$_9$-C$_{30}$)alkyl, cycloalkyl, cycloalkylalkyl, heterocyclyl, heterocyclylalkyl, aryl, arylalkyl, heteroaryl, heteroaryl alkyl, F, Cl, Br, I, CN, CF$_3$, N$_3$, NH$_2$, —NHT457, —NT458T459, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)-T460, —C(O)O-T461, —C(O)NH-T462, —C(O)NT463T464, —O-T465, —O(-T466-O)$_z$—H (z=1, 2, 3, 4, 5), —O(-T467-O)$_z$-T468 (z=1, 2, 3, 4, 5), —OC(O)-T469, —OC(O)—O-T470, —OC(O)—NHT471, —O—C(O)—NT472T473, —OP(O)(OT474)(OT475), —OSi(T476)(T477)(T478), —OS(O$_2$)-T479, —NHC(O)-T480, —NT481C(O)-T482, —NH—C(O)—O-T483, —NH—C(O)—NH-T484, —NH—C(O)—NT485T486, —NT487-C(O)—O-T488, —NT489-C(O)—NH-T490, —NT491-C(O)—NT492T493, —NHS(O$_2$)-T494, —NT495S(O$_2$)-T496, —S-T497, —S(O)-T498, —S(O$_2$)-T499, —S(O$_2$)NH-T500, —S(O$_2$)NT501T502, —S(O$_2$)O-T503, —P(O)(OT504)(OT505), —Si(T506)(T507)(T508)";

where T457, T458, T459, T460, T461, T462, T463, T464, T465, T466, T467, T468, T469, T470, T471, T472, T473, T474, T475, T476, T477, T478, T479, T480, T481, T482, T483, T484, T485, T486, T487, T488, T489, T490, T491, T492, T493, T494, T495, T496, T497, T498, T499, T500, T501, T502, T503, T504, T505, T506, T507, T508 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, T463, T464 and/or T472, T473 and/or T485, T486 and/or T492, T493 and/or T501, T502, in each case together, may also form "heterocyclyl";

or with the proviso that at least one of the Z28, Z29 radicals and at least one of the Z30, Z31 radicals is independently selected from the group consisting of:

(II) "(C$_9$-C$_{30}$)alkyl, cycloalkylalkyl, heterocyclylalkyl, arylalkyl, heteroarylalkyl, —C(O)—(C$_9$-C$_{30}$)alkyl, —C(O)-cycloalkyl, —C(O)-cycloalkylalkyl, —C(O)-arylalkyl, —C(O)-heteroarylalkyl, —C(O)-heterocyclyl, —C(O)-heterocyclylalkyl, —S(O$_2$)-alkyl, —S(O$_2$)—(C$_9$-C$_{30}$)alkyl, —S(O$_2$)-cycloalkyl, —S(O$_2$)-cycloalkylalkyl, —S(O$_2$)-aryl, —S(O$_2$)-arylalkyl, —S(O$_2$)-heteroaryl, —S(O$_2$)-heteroarylalkyl, —S(O$_2$)-heterocyclyl, —S(O$_2$)-heterocyclylalkyl";

where, optionally, the above substituents of substitution group (II) may each independently be further substituted by at least one substituent selected identically or differently from the group consisting of:

(i) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHT509, —NT510T511, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)-T512, —C(O)O-T513, —C(O)NH-T514, —C(O)NT515T516, —O-T517, —O(-T518-O)$_a$—H (a=1, 2, 3, 4, 5), —O(-T519-O)$_a$-T520 (a=1, 2, 3, 4, 5), —OC(O)-T521, —OC(O)—O-T522, —OC(O)—NHT523, —O—C(O)—NT524T525, —OP(O)(OT526)(OT527), —OSi(T528)(T529)(T530), —OS(O$_2$)-T531, —NHC(O)-T532, —NT533C(O)-T534, —NH—C(O)—O-T535, —NH—C(O)—NH-T536, —NH—C(O)—NT537T538, —NT539-C(O)—O-T540, —NT541-C(O)—NH-T542, —NT543-C(O)—NT544T545, —NHS(O$_2$)-T546, —NT547S(O$_2$)-T548, —S-T549, —S(O)-T550, —S(O$_2$)-T551, —S(O$_2$)NH-T552, —S(O$_2$)NT553T554, —S(O$_2$)O-T555, —P(O)(OT556)(OT557), —Si(T558)(T559)(T560)";

where T509, T510, T511, T512, T513, T514, T515, T516, T517, T518, T519, T520, T521, T522, T523, T524, T525, T526, T527, T528, T529, T530, T531, T532, T533, T534, T535, T536, T537, T538, T539, T540, T541, T542, T543, T544, T545, T546, T547, T548, T549, T550, T551, T552, T553, T554, T555, T556, T557, T558, T559, T560 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, T515, T516 and/or T524, T525 and/or T537, T538 and/or T544, T545 and/or T553, T554, in each case together, may also form "heterocyclyl";

where, optionally, the above substituents of substituent group (i) may in turn each independently be substituted by at least one substituent selected identically or differently from the group consisting of:

(ii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHT561, —NT562T563, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)-T564, —C(O)O-T565, —C(O)NH-T566, —C(O)NT567T568, —O-T569, —O(-T570-O)$_b$—H (b=1, 2, 3, 4, 5), —O(-T571-O)$_b$-T572 (b=1, 2, 3, 4, 5), —OC(O)-T573, —OC(O)—O-T574, —OC(O)—NHT575, —O—C(O)—NT576T577, —OP(O)(OT578)(OT579), —OSi(T580)(T581)(T582), —OS(O$_2$)-T583, —NHC(O)-T584, —NT585C(O)-T586, —NH—C(O)—O-T587, —NH—C(O)—NH-T588, —NH—C(O)—NT589T590, —NT591-C(O)—O-T592, —NT593-C(O)—NH-T594, —NT595-C(O)—NT596T597, —NHS(O$_2$)-T598, —NT599S(O$_2$)-T600, —S-T601, —S(O)-T602, —S(O$_2$)-T603, —S(O$_2$)NH-T604, —S(O$_2$)NT605T606, —S(O$_2$)O-T607, —P(O)(OT608)(OT609), —Si(T610)(T611)(T612)";

where T561, T562, T563, T564, T565, T566, T567, T568, T569, T570, T571, T572, T573, T574, T575, T576, T577, T578, T579, T580, T581, T582, T583, T584, T585, T586, T587, T588, T589, T590, T591, T592, T593, T594, T595, T596, T597, T598, T599, T600, T601, T602, T603, T604, T605, T606, T607, T608, T609, T610, T611, T612 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, T567, T568 and/or T576, T577 and/or T589, T590 and/or T596, T597 and/or T605, T606, in each case together, may also form "heterocyclyl";

where, optionally, the above substituents of substituent group (ii) may in turn each independently be substituted by at least one substituent selected identically or differently from the group consisting of:

(iii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHT613, —NT614T615, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)-T616, —C(O)O-T617, —C(O)NH-T618, —C(O)NT619T620, —O-T621, —O(-T622-O)$_c$—H (c=1, 2, 3, 4, 5), —O(-T623-O)$_c$-T624 (c=1, 2, 3, 4, 5), —OC(O)-T625, —OC(O)—O-T626, —OC(O)—NHT627, —O—C(O)—NT628T629, —OP(O)(OT630)(OT631), —OSi(T632)(T633)(T634), —OS(O$_2$)-T635, —NHC(O)-T636, —NT637C(O)-T638, —NH—C(O)—O-T639, —NH—C(O)—NH-T640, —NH—C(O)—NT641T642, —NT643-C(O)—O-T644, —NT645-C(O)—NH-T646, —NT647-C(O)—NT648T649, —NHS(O$_2$)-T650, —NT651S(O$_2$)-T652, —S-T653, —S(O)-T654, —S(O$_2$)-T655, —S(O$_2$)NH-T656, —S(O$_2$)NT657T658, —S(O$_2$)O-T659, —P(O)(OT660)(OT661), —Si(T662)(T663)(T664)";

where T613, T614, T615, T616, T617, T618, T619, T620, T621, T622, T623, T624, T625, T626, T627, T628, T629, T630, T631, T632, T633, T634, T635, T636, T637, T638, T639, T640, T641, T642, T643, T644, T645, T646, T647, T648, T649, T650, T651, T652, T653, T654, T655, T656, T657, T658, T659, T660, T661, T662, T663, T664 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, T619, T620 and/or T628, T629 and/or T641, T642 and/or T648, T649 and/or T657, T658, in each case together, may also form "heterocyclyl";

and one of the Z28, Z29 radicals or neither of the Z28, Z29 radicals and one of the Z30, Z31 radicals or neither of the Z30, Z31 radicals and the Z32 radical is independently selected from the group consisting of:

(III) "hydrogen, alkyl, cycloalkyl, heterocyclyl, aryl, heteroaryl, —C(O)-alkyl, —C(O)-aryl, —C(O)-heteroaryl";

where, optionally, the above substituents of substituent group (III) may each independently in turn be substituted by at least one substituent selected identically or differently from the group consisting of:

(i) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHT665, —NT666T667, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)-T668, —C(O)O-T669, —C(O)NH-T670, —C(O)NT671T672, —O-T673, —O(-T674-O)$_d$—H (d=1, 2, 3, 4, 5), —O(-T675-O)$_d$-T676 (d=1, 2, 3, 4, 5), —OC(O)-T677, —OC(O)—O-T678, —OC(O)—NHT679, —O—C(O)—NT680T681, —OP(O)(OT682)(OT683), —OSi(T684)(T685)(T686), —OS(O$_2$)-T687, —NHC(O)-T688, —NT689C(O)-T690, —NH—C(O)—O-T691, —NH—C(O)—NH-T692, —NH—C(O)—NT693T694, —NT695-C(O)—O-T696, —NT697-C(O)—NH-T698, —NT699-C(O)—NT700T701, —NHS(O$_2$)-T702, —NT703S(O$_2$)-T704, —S-T705, —S(O)-T706, —S(O$_2$)-T707, —S(O$_2$)NH-T708, —S(O$_2$)NT709T710, —S(O$_2$)O-T711, —P(O)(OT712)(OT713), —Si(T714)(T715)(T716)";

where T665, T666, T667, T668, T669, T670, T671, T672, T673, T674, T675, T676, T677, T678, T679, T680, T681, T682, T683, T684, T685, T686, T687, T688, T689, T690, T691, T692, T693, T694, T695, T696, T697, T698, T699, T700, T701, T702, T703, T704, T705, T706, T707, T708, T709, T710, T711, T712, T713, T714, T715, T716 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, T671, T672 and/or T680, T681 and/or T693, T694 and/or T700, T701 and/or T709, T710, in each case together, may also form "heterocyclyl";

where, optionally, the above substituents of substituent group (i) may in turn each independently be further substituted by at least one substituent selected identically or differently from the group consisting of:

(ii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHT717, —NT718T719, —$NO_2$, —OH, —$OCF_3$, —SH, —O—$SO_3H$, —OP(O)$(OH)_2$, —CHO, —COOH, —C(O)$NH_2$, —$SO_3H$, —P(O)$(OH)_2$, —C(O)-T720, —C(O)O-T721, —C(O)NH-T722, —C(O)NT723T724, —O-T725, —O(-T726-O)$_e$—H (e=1, 2, 3, 4, 5), —O(-T727-O)$_e$-T728 (e=1, 2, 3, 4, 5), —OC(O)-T729, —OC(O)—O-T730, —OC(O)—NHT731, —O—C(O)—NT732T733, —OP(O)(OT734)(OT735), —OSi(T736)(T737)(T738), —OS($O_2$)-T739, —NHC(O)-T740, —NT741C(O)-T742, —NH—C(O)—O-T743, —NH—C(O)—NH-T744, —NH—C(O)—NT745T746, —NT747-C(O)—O-T748, —NT749-C(O)—NH-T750, —NT751-C(O)—NT752T753, —NHS($O_2$)-T754, —NT755S($O_2$)-T756, —S-T757, —S(O)-T758, —S($O_2$)-T759, —S($O_2$)NH-T760, —S($O_2$)NT761T762, —S($O_2$)O-T763, —P(O)(OT764)(OT765), —Si(T766)(T767)(T768)";

where T717, T718, T719, T720, T721, T722, T723, T724, T725, T726, T727, T728, T729, T730, T731, T732, T733, T734, T735, T736, T737, T738, T739, T740, T741, T742, T743, T744, T745, T746, T747, T748, T749, T750, T751, T752, T753, T754, T755, T756, T757, T758, T759, T760, T761, T762, T763, T764, T765, T766, T767, T768 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, T723, T724 and/or T732, T733 and/or T745, T746 and/or T752, T753 and/or T761, T762, in each case together, may also form "heterocyclyl";

where, optionally, the above substituents of substituent group (ii) may in turn each independently be substituted by at least one substituent selected identically or differently from the group consisting of:

(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHT769, —NT770T771, —$NO_2$, —OH, —$OCF_3$, —SH, —O—$SO_3H$, OP(O)$(OH)_2$, —CHO, —COOH, —C(O)$NH_2$, —$SO_3H$, —P(O)$(OH)_2$, —C(O)-T772, —C(O)O-T773, —C(O)NH-T774, —C(O)NT775T776, —O-T777, —O(-T778-O)$_f$—H (f=1, 2, 3, 4, 5), —O(-T779-O)$_f$-T780 (f=1, 2, 3, 4, 5), —OC(O)-T781, —OC(O)—O-T782, —OC(O)—NHT783, —O—C(O)—NT784T785, —OP(O)(OT786)(OT787), —OSi(T788)(T789)(T790), —OS($O_2$)-T791, —NHC(O)-T792, —NT793C(O)-T794, —NH—C(O)—O-T795, —NH—C(O)—NH-T796, —NH—C(O)—NT797T798, —NT799-C(O)—O-T800, —NT801-C(O)—NH-T802, —NT803-C(O)—NT804T805, —NHS($O_2$)-T806, —NT807S($O_2$)-T808, —S-T809, —S(O)-T810, —S($O_2$)-T811, —S($O_2$)NH-T812, —S($O_2$)NT813T814, —S($O_2$)O-T815, —P(O)(OT816)(OT817), —Si(T818)(T819)(T820)";

where T769, T770, T771, T772, T773, T774, T775, T776, T777, T778, T779, T780, T781, T782, T783, T784, T785, T786, T787, T788, T789, T790, T791, T792, T793, T794, T795, T796, T797, T798, T799, T800, T801, T802, T803, T804, T805, T806, T807, T808, T809, T810, T811, T812, T813, T814, T815, T816, T817, T818, T819, T820 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, T775, T776 and/or T784, T785 and/or T797, T798 and/or T804, T805 and/or T813, T814, in each case together, may also form "heterocyclyl";

(2) "—C(Y5)NZ33-Y6-Z34";

where Y5, Y6 are each independently selected from the group consisting of "O, S, =NH, =NZ35";

where Z33, Z34, Z35 are each independently selected from the group consisting of:

(I) "hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, —C(O)-alkyl, —C(O)—($C_9$-$C_{30}$)alkyl, —C(O)-cycloalkyl, —C(O)-cycloalkylalkyl, —C(O)-aryl, —C(O)-arylalkyl, —C(O)-heteroaryl, —C(O)-heteroarylalkyl, —C(O)-heterocyclyl, —C(O)-heterocyclylalkyl, —S($O_2$)-alkyl, —S($O_2$)—($C_9$-$C_{30}$)alkyl, —S($O_2$)-cycloalkyl, —S($O_2$)-cycloalkylalkyl, —S($O_2$)-aryl, —S($O_2$)-arylalkyl, —S($O_2$)-heteroaryl, —S($O_2$)-heteroarylalkyl, —S($O_2$)-heterocyclyl, —S($O_2$)-heterocyclylalkyl";

where, optionally, the above substituents of substituent group (I) may each independently in turn be substituted by at least one substituent selected identically or differently from the group consisting of:

(i) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHT821, —NT822T823, —$NO_2$, —OH, —$OCF_3$, —SH, —O—$SO_3H$, —OP(O)$(OH)_2$, —CHO, —COOH, —C(O)$NH_2$, —$SO_3H$, —P(O)$(OH)_2$, —C(O)-T824, —C(O)O-T825, —C(O)NH-T826, —C(O)NT827T828, —O-T829, —O(-T830-O)$_g$—H (g=1, 2, 3, 4, 5), —O(-T831-O)$_g$-T832 (g=1, 2, 3, 4, 5), —OC(O)-T833, —OC(O)—O-T834, —OC(O)—NHT835, —O—C(O)—NT836T837, —OP(O)(OT838)(OT839), —OSi(T840)(T814)(T842), —OS($O_2$)-T843, —NHC(O)-T844, —NT845C(O)-T846, —NH—C(O)—O-T847, —NH—C(O)—NH-T848, —NH—C(O)—NT849T850, —NT851-C(O)—O-T852, —NT853-C(O)—NH-T854, —NT855-C(O)—NT856T857, —NHS($O_2$)-T858, —NT859S($O_2$)-T860, —S-T861, —S(O)-T862, —S($O_2$)-T863, —S($O_2$)NH- T864, —S(O$_2$)NT865T866, —S(O$_2$)O-T867, —P(O)(OT868)(OT869), —Si(T870)(T871)(T872)";

where T821, T822, T823, T824, T825, T826, T827, T828, T829, T830, T831, T832, T833, T834, T835, T836, T837, T838, T839, T840, T841, T842, T843, T844, T845, T846, T847, T848, T849, T850, T851, T852, T853, T854, T855, T856, T857, T858, T859, T860, T861, T862, T863, T864, T865, T866, T867, T868, T869, T870, T871, T872 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, T827, T828 and/or T836, T837 and/or T849, T850 and/or T856, T857 and/or T865, T866, in each case together, may also form "heterocyclyl";

where, optionally, the above substituents of substituent group (i) may in turn each independently be further substituted by at least one substituent selected identically or differently from the group consisting of:

(ii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHT873, —NT874T875, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)-T876, —C(O)O-T877, —C(O)NH-T878, —C(O)NT879T880, —O-T881, —O(-T882-O)$_h$—H (h=1, 2, 3, 4, 5), —O(-T883-O)$_h$-T884 (h=1, 2, 3, 4, 5), —OC(O)-T885, —OC(O)—O-T886, —OC(O)—NHT887, —O—C(O)—NT888T889, —OP(O)(OT890)(OT891), —OSi(T892)(T893)(T894), —OS(O$_2$)-T895, —NHC(O)-T896, —NT897C(O)-T898, —NH—C(O)—O-T899, —NH—C(O)—NH-T900, —NH—C(O)—NT901T902, —NT903-C(O)—O-T904, —NT905-C(O)—NH-T906, —NT907-C(O)—NT908T909, —NHS(O$_2$)-T910, —NT911S(O$_2$)-T912, —S-T913, —S(O)-T914, —S(O$_2$)-T915, —S(O$_2$)NH-T916, —S(O$_2$)NT917T918, —S(O$_2$)O-T919, —P(O)(OT920)(OT921), —Si(T922)(T923)(T924)";

where T873, T874, T875, T876, T877, T878, T879, T880, T881, T882, T883, T884, T885, T886, T887, T888, T889, T890, T891, T892, T893, T894, T895, T896, T897, T898, T899, T900, T901, T902, T903, T904, T905, T906, T907, T908, T909, T910, T911, T912, T913, T914, T915, T916, T917, T918, T919, T920, T921, T922, T923, T924 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, T879, T880 and/or T888, T889 and/or T901, T902 and/or T908, T909 and/or T917, T918, in each case together, may also form "heterocyclyl";

where, optionally, the above substituents of substituent group (ii) may in turn each independently be substituted by at least one substituent selected identically or differently from the group consisting of:

(iii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHT925, —NT926T927, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)-T928, —C(O)O-T929, —C(O)NH-T930, —C(O)NT931T932, —O-T933, —O(-T934-O)$_i$—H (i=1, 2, 3, 4, 5), -Q(-T935-O)$_i$-T936 (i=1, 2, 3, 4, 5), —OC(O)-T937, —OC(O)—O-T938, —OC(O)—NHT939, —O—C(O)—NT940T941, —OP(O)(OT942)(OT943), —OSi(T944)(T945)(T946), —OS(O$_2$)-T947, —NHC(O)-T948, —NT949C(O)-T950, —NH—C(O)—O-T951, —NH—C(O)—NH-T952, —NH—C(O)—NT953T954, —NT955-C(O)—O-T956, —NT957-C(O)—NH-T958, —NT959-C(O)—NT960T961, —NHS(O$_2$)-T962, —NT963S(O$_2$)-T964, —S—T965, —S(O)-T966, —S(O$_2$)-T967, —S(O$_2$)NH-T968, —S(O$_2$)NT969T970, —S(O$_2$)O-T971, —P(O)(OT972)(OT973), —Si(T974)(T975)(T976)";

where T925, T926, T927, T928, T929, T930, T931, T932, T933, T934, T935, T936, T937, T938, T939, T940, T941, T942, T943, T944, T945, T946, T947, T948, T949, T950, T951, T952, T953, T954, T955, T956, T957, T958, T959, T960, T961, T962, T963, T964, T965, T966, T967, T968, T969, T970, T971, T972, T973, T974, T975, T976 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, T931, T932 and/or T940, T941 and/or T953, T954 and/or T960, T961 and/or T969, T970, in each case together, may also form "heterocyclyl";

and one of the Z26, Z27 radicals or neither of the Z26, Z27 radicals is also independently selected from the group consisting of:

(2) "hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, —C(O)-alkyl, —C(O)—(C$_9$-C$_{30}$)alkyl, —C(O)-cycloalkyl, —C(O)-cycloalkylalkyl, —C(O)-aryl, —C(O)-arylalkyl, —C(O)-heteroaryl, —C(O)-heteroarylalkyl, —C(O)-heterocyclyl, —C(O)-heterocyclylalkyl, —C(Y7)NZ36Z37, —C(=NZ38)-Z39, —S(O$_2$)-alkyl, —S(O$_2$)—(C$_9$-C$_{30}$)alkyl, —S(O$_2$)-cycloalkyl, —S(O$_2$)-cycloalkylalkyl, —S(O$_2$)-aryl, —S(O$_2$)-arylalkyl, —S(O$_2$)-heteroaryl, —S(O$_2$)-heteroarylalkyl, —S(O$_2$)-heterocyclyl, —S(O$_2$)-heterocyclylalkyl";

where Y7 is independently selected from the group consisting of "O, S, =NH, =NZ40";

where the Z36, Z37, Z38, Z39, Z40 radicals are each independently selected from the group consisting of:

(I) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, —C(O)-alkyl, —C(O)—(C$_9$-C$_{30}$)alkyl, —C(O)-cycloalkyl, —C(O)-cycloalkylalkyl, —C(O)-aryl, —C(O)-arylalkyl, —C(O)-heteroaryl, —C(O)-heteroarylalkyl, —C(O)-heterocyclyl, —C(O)-heterocyclylalkyl, —S(O$_2$)-alkyl, —S(O$_2$)-(C$_9$-C$_{30}$)alkyl, —S(O$_2$)-Cycloalkyl, —S(O$_2$)-Cycloalkylalkyl, —S(O$_2$)-aryl, —S(O$_2$)-arylalkyl, —S(O$_2$)-heteroaryl, —S(O$_2$)-heteroarylalkyl, —S(O$_2$)-heterocyclyl, —S(O$_2$)-heterocyclylalkyl";

where, optionally, the above substituents of substituent group (3) and/or substituent group (I) may each independently in turn be substituted by at least one substituent selected identically or differently from the group consisting of:

(i) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHT977, —NT978T979, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)-T980, —C(O)O-T981, —C(O)NH-T982, —C(O)NT983T984, —O-T985, —O(-T986-O)$_j$—H (j=1, 2, 3, 4, 5), —O(-T987-O)$_j$-T988 (j=1, 2, 3, 4, 5), —OC(O)-T989, —OC(O)—O-T990, —OC(O)—NHT991, —O—C(O)—NT992T993, —OP(O)(OT994)(OT995), —OSi(T996)(T997)(T998), —OS(O$_2$)-T999, —NHC(O)-T1000, —NT1001C(O)-T1002, —NH—C(O)—O-T1003, —NH—C(O)—NH-T1004, —NH—C(O)—NT1005T1006, —NT1007-C(O)—O-T1008, —NT1009-C(O)—NH-T1000, —NT1011-C(O)—NT1012T1003, —NHS(O$_2$)-T1014, —NT1015S(O$_2$)-T1016, —S-T1017, —S(O)-T1018, —S(O$_2$)-T1019, —S(O$_2$)NH-T1020, —S(O$_2$)NT1021T1022, —S(O$_2$)O-T1023, —P(O)(OT1024)(OT1025), —Si(T1026)(T1027)(T1028)";

where T977, T978, T979, T980, T981, T982, T983, T984, T985, T986, T987, T988, T989, T990, T991, T992, T993, T994, T995, T996, T997, T998, T999, T1000, T1001, T1002, T1003, T1004, T1005, T1006, T1007, T1008, T1009, T1001, T101, T1012, T1003, T1014, T1005, T1006, T1007, T1008, T1009, T1020, T1021, T1022, T1023, T1024, T1025, T1026, T1027, T1028 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, T983, T984 and/or T992, T993 and/or T1005, T1006 and/or T1012, T1013 and/or T1021, T1022, in each case together, may also form "heterocyclyl";

where, optionally, the above substituents of substituent group (i) may in turn each independently be further substituted by at least one substituent selected identically or differently from the group consisting of:

(ii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHT1029, —NT1030T1031, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)-T1032, —C(O)O-T1033, —C(O)NH-T1034, —C(O)NT1035T1036, —O-T1037, —O(-T1038-O)$_k$—H (k=1, 2, 3, 4, 5), —O(-T1039-O)$_k$-T1040 (k=1, 2, 3, 4, 5), —OC(O)-T1041, —OC(O)—O-T1042, —OC(O)—NHT1043, —O—C(O)—NT1044T1045, —OP(O)(OT1046)(OT1047), —OSi(T1048)(T1049)(T1050), —OS(O$_2$)-T1051, —NHC(O)-T1052, —NT1053C(O)-T1054, —NH—C(O)—O-T1055, —NH—C(O)—NH-T1056, —NH—C(O)—NT1057T1058, —NT1059-C(O)—O-T1060, —NT1061-C(O)—NH-T1062, —NT1063-C(O)—NT1064T1065, —NHS(O$_2$)-T1066, —NT1067S(O$_2$)-T1068, —S-T1069, —S(O)-T1070, —S(O$_2$)-T1071, —S(O$_2$)NH-T1072, —S(O$_2$)NT1073T1074, —S(O$_2$)O-T1075, —P(O)(OT1076)(OT1077), —Si(T1078)(T1079)(T1080)";

where T1029, T1030, T1031, T1032, T1033, T1034, T1035, T1036, T1037, T1038, T1039, T1040, T1041, T1042, T1043, T1044, T1045, T1046, T1047, T1048, T1049, T1050, T1051, T1052, T1053, T1054, T1055, T1056, T1057, T1058, T1059, T1060, T1061, T1062, T1063, T1064, T1065, T1066, T1067, T1068, T1069, T1070, T1071, T1072, T1073, T1074, T1075, T1076, T1077, T1078, T1079, T1080 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, T1035, T1036 and/or T1044, T1045 and/or T1057, T1058 and/or T1064, T1065 and/or T1073, T1074, in each case together, may also form "heterocyclyl";

where, optionally, the above substituents of substituent group (ii) may in turn each independently be substituted by at least one substituent selected identically or differently from the group consisting of:

(iii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHT1081, —NT1082T1083, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)-T1084, —C(O)O-T1085, —C(O)NH-T1086, —C(O)NT1087T1088, —O-T1089, —O(-T1090-O)$_l$—H (l=1, 2, 3, 4, 5), —O(-T1091-O)$_l$-T1092 (l=1, 2, 3, 4, 5), —OC(O)-T1093, —OC(O)—O-T1094, —OC(O)—NHT1095, —O—C(O)—NT1096T1097, —OP(O)(OT1098)(OT1099), —OSi(T1100)(T1101)(T1102), —OS(O$_2$)-T1103, —NHC(O)-T1104, —NT1105C(O)-T1106, —NH—C(O)—O-T1107, —NH—C(O)—NH-T1108, —NH—C(O)—NT1109T1110, —NT1111-C(O)—O-T1112, —NT1113-C(O)—NH-T1114, —NT1115-C(O)—NT1116T1117, —NHS(O$_2$)-T1118, —NT1119S(O$_2$)-T1120, —S-T1121, —S(O)-T1122, —S(O$_2$)-T1123, —S(O$_2$)NH-T1124, —S(O$_2$)NT1125T1126, —S(O$_2$)O-T1127, —P(O)(OT1128)(OT1129), —Si(T1130)(T1131)(T1132)";

where T1081, T1082, T1083, T1084, T1085, T1086, T1087, T1088, T1089, T1090, T1091, T1092, T1093, T1094, T1095, T1096, T1097, T1098, T1099, T1100, T1101, T1102, T1103, T1104, T1105, T1106, T1107, T1108, T1109, T1110, T1111, T1112, T1113, T1114, T1115, T1116, T1117, T1118, T1119, T1120, T1121, T1122, T1123, T1124, T1125, T1126, T1127, T1128, T1129, T1130, T1131, T1132 are each independently selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and where, alternatively, T1087, T1088 and/or T1096, T1097 and/or T1109, T1110 and/or T1116, T1117 and/or T1125, T1126, in each case together, may also form "heterocyclyl";

and one of the Z1, Z2 radicals or neither of the Z1, Z2 radicals is independently selected from the group consisting of:

(c) hydrogen, alkyl, $(C_9-C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHT1133, —NT1134T1135, —$NO_2$, —OH, —$OCF_3$, —SH, —O—$SO_3H$, —OP(O)(OH)$_2$, —CHO, —COOH, —C(O)NH$_2$, —SO$_3$H, —P(O)(OH)$_2$, —C(O)-T1136, —C(O)O-T1137, —C(O)NH-T1138, —C(O)NT1139T1140, —O-T1141, —O(-T1142-O)$_m$—H (m=1, 2, 3, 4, 5), —O(-T1143-O)$_m$-T1144 (m=1, 2, 3, 4, 5), —OC(O)-T1145, —OC(O)—O-T1146, —OC(O)—NHT1147, —O—C(O)—NT1148T1149, —OP(O)(OT1150)(OT1151), —OSi(T1152)(T1153)(T1154), —OS(O$_2$)-T1155, —NHC(O)-T1156, —NT1157C(O)-T1158, —NH—C(O)—O-T1159, —NH—C(O)—NH-T1160, —NH—C(O)—NT1161T1162, —NT1163-C(O)—O-T1164, —NT1165-C(O)—NH-T1166, —NT1167-C(O)—NT1168T1169, —NHS(O$_2$)-T1170, —NT1171S(O$_2$)-T1172, —S-T1173, —S(O)-T1174, —S(O$_2$)-T1175, —S(O$_2$)NH-T1176, —S(O$_2$)NT1177T1178, —S(O$_2$)O-T1179, —P(O)(OT1180)(OT1181), —Si(T1182)(T1183)(T1184)";

where T1133, T1134, T1135, T1136, T1137, T1138, T1139, T1140, T1141, T1142, T1143, T1144, T1145, T1146, T1147, T1148, T1149, T1150, T1151, T1152, T1153, T1154, T1155, T1156, T1157, T1158, T1159, T1160, T1161, T1162, T1163, T1164, T1165, T1166, T1167, T1168, T1169, T1170, T1171, T1172, T1173, T1174, T1175, T1176, T1177, T1178, T1179, T1180, T1181, T1182, T1183, T1184 are each independently selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and where, alternatively, T1139, T1140 and/or T1148, T1149 and/or T1161, T1162 and/or T1168, T1169 and/or T1177, T1178, in each case together, may also form "heterocyclyl";

where, optionally, the above substituents of substituent group (c) may in turn each independently be further substituted by at least one substituent selected identically or differently from the group consisting of:

(i) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHT1185, —NT1186T1187, —$NO_2$, —OH, —$OCF_3$, —SH, —O—$SO_3H$, —OP(O)(OH)$_2$, —CHO, —COOH, —C(O)NH$_2$, —SO$_3$H, —P(O)(OH)$_2$, —C(O)-T1188, —C(O)O-T1189, —C(O)NH-T1190, —C(O)NT1191T1192, —O-T1193, —O(-T1194-O)$_n$—H (n=1, 2, 3, 4, 5), —O(-T1195-O)$_n$-T1196 (n=1, 2, 3, 4, 5), —OC(O)-T1197, —OC(O)—O-T1198, —OC(O)—NHT1199, —O—C(O)—NT1200T1201, —OP(O)(OT1202)(OT1203), —OSi(T1204)(T1205)(T1206), —OS(O$_2$)-T1207, —NHC(O)-T1208, —NT1209C(O)-T1210, —NH—C(O)—O-T1211, —NH—C(O)—NH-T1212, —NH—C(O)—NT1213T1214, —NT1215-C(O)—O-T1216, —NT1217-C(O)—NH-T1218, —NT1219-C(O)—NT1220T1221, —NHS(O$_2$)-T1222, —NT1223S(O$_2$)-T1224, —S-T1225, —S(O)-T1226, —S(O$_2$)-T1227, —S(O$_2$)NH-T1228, —S(O$_2$)NT1229T1230, —S(O$_2$)O-T1231, —P(O)(OT1232)(OT1233), —Si(T1234)(T1235)(T1236)";

where T1185, T1186, T1187, T1188, T1189, T1190, T1191, T1192, T1193, T1194, T1195, T1196, T1197, T1198, T1199, T1200, T1201, T1202, T1203, T1204, T1205, T1206, T1207, T1208, T1209, T1210, T1211, T1212, T1213, T1214, T1215, T1216, T1217, T1218, T1219, T1220, T1221, T1222, T1223, T1224, T1225, T1226, T1227, T1228, T1229, T1230, T1231, T1232, T1233, T1234, T1235, T1236 are each independently selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and where, alternatively, T1191, T1192 and/or T1200, T1201 and/or T1213, T1214 and/or T1220, T1221 and/or T1229, T1230, in each case together, may also form "heterocyclyl";

where, optionally, the above substituents of substituent group (i) may in turn each independently be substituted by at least one substituent selected identically or differently from the group consisting of:

(ii) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHT1237, —NT1238T1239, —$NO_2$, —OH, —$OCF_3$, —SH, —O—$SO_3H$, —OP(O)(OH)$_2$, —CHO, —COOH, —C(O)NH$_2$, —SO$_3$H, —P(O)(OH)$_2$, —C(O)-T1240, —C(O)O-T1241, —C(O)NH-T1242, —C(O)NT1243T1244, —O-T1245, —O(-T1246-O)$_o$—H (o=1, 2, 3, 4, 5), —O(-T1247-O)$_o$-T1248 (o=1, 2, 3, 4, 5), —OC(O)-T1249, —OC(O)—O-T1250, —OC(O)—NHT1251, —O—C(O)—NT1252T1253, —OP(O)(OT1254)(OT1255), —OSi(T1256)(T1257)(T1258), —OS(O$_2$)-T1259, —NHC(O)-T1260, —NT1261C(O)-T1262, —NH—C(O)—O-T1263, —NH—C(O)—NH-T1264, —NH—C(O)—NT1265T1266, —NT1267-C(O)—O-T1268, —NT1269-C(O)—NH-T1270, —NT1271-C(O)—NT1272T1273, —NHS(O$_2$)-T1274, —NT1275S(O$_2$)-T1276, —S-T1277, —S(O)-T1278, —S(O$_2$)-T1279, —S(O$_2$)NH-T1280, —S(O$_2$)NT1281T1282, —S(O$_2$)O-T1283, —P(O)(OT1284)(OT1285), —Si(T1286)(T1287)(T1288)";

where T1237, T1238, T1239, T1240, T1241, T1242, T1243, T1244, T1245, T1246, T1247, T1248, T1249, T1250, T1251, T1252, T1253, T1254, T1255, T1256, T1257, T1258, T1259, T1260, T1261, T1262, T1263, T1264, T1265, T1266, T1267, T1268, T1269, T1270, T1271, T1272, T1273, T1274, T1275, T1276, T1277, T1278, T1279, T1280, T1281, T1282, T1283, T1284, T1285, T1286, T1287, T1288 are each independently selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and where, alternatively, T1243, T1244 and/or T1252, T1253 and/or T1265, T1266 and/or T1272, T1273 and/or T1281, T1282, in each case together, may also form "heterocyclyl";

(d) —NZ41Z42 where the Z41, Z42 radicals are each independently selected from the group consisting of:

(1) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, —C(O)-alkyl, —C(O)—($C_9$-$C_{30}$)alkyl, —C(O)-cycloalkyl, —C(O)-cycloalkylalkyl, —C(O)-aryl, —C(O)-arylalkyl, —C(O)-heteroaryl, —C(O)-heteroarylalkyl, —C(O)-heterocyclyl, —C(O)-heterocyclylalkyl";

where, optionally, the above substituents of substituent group (1) may each independently be substituted further by at least one substituent selected identically or differently from the group consisting of:

(i) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHT1289, —NT1290T1291, —$NO_2$, —OH, —$OCF_3$, —SH, —O—$SO_3H$, —OP(O)(OH)$_2$, —CHO, —COOH, —C(O)$NH_2$, —$SO_3H$, —P(O)(OH)$_2$, —C(O)-T1292, —C(O)O-T1293, —C(O)NH-T1294, —C(O)NT1295T1296, —O-T1297, —O(-T1298-O)$_{rr}$—H (rr=1, 2, 3, 4, 5), —O(-T1299-O)$_{rr}$-T1300 (rr=1, 2, 3, 4, 5), —OC(O)-T1301, —OC(O)—O-T1302, —OC(O)—NHT1303, —O—C(O)—NT1304T1305, —OP(O)(OT1306)(OT1307), —OSi(T1308)(T1309)(T1310), —OS($O_2$)-T1311, —NHC(O)-T1312, —NT1313C(O)-T1314, —NH—C(O)—O-T1315, —NH—C(O)—NH-T1316, —NH—C(O)—NT1317T1318, —NT1319-C(O)—O-T1320, —NT1321-C(O)—NH-T1322, —NT1323-C(O)—NT1324T1325, —NHS($O_2$)-T1326, —NT1327S($O_2$)-T1328, —S-T1329, —S(O)-T1330, —S($O_2$)-T1331, —S($O_2$)NH-T1332, —S($O_2$)NT1333T1334, —S($O_2$)O-T1335, —P(O)(OT1336)(OT1337), —Si(T1338)(T1339)(T1340)";

where T1289, T1290, T1291, T1292, T1293, T1294, T1295, T1296, T1297, T1298, T1299, T1300, T1301, T1302, T1303, T1304, T1305, T1306, T1307, T1308, T1309, T1310, T1311, T1312, T1313, T1314, T1315, T1316, T1317, T1318, T1319, T1320, T1321, T1322, T1323, T1324, T1325, T1326, T1327, T1328, T1329, T1330, T1331, T1332, T1333, T1334, T1335, T1336, T1337, T1338, T1339, T1340 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, T1295, T1296 and/or T1304, T1305 and/or T1317, T1318 and/or T1324, T1325 and/or T1333, T1334, in each case together, may also form "heterocyclyl";

where, optionally, the above substituents of substituent group (i) may in turn each independently be further substituted by at least one substituent selected identically or differently from the group consisting of:

(ii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHT1341, —NT1342T1343, —$NO_2$, —OH, —$OCF_3$, —SH, —O—$SO_3H$, —OP(O)(OH)$_2$, —CHO, —COOH, —C(O)$NH_2$, —$SO_3H$, —P(O)(OH)$_2$, —C(O)-T1344, —C(O)O-T1345, —C(O)NH-T1346, —C(O)NT1347T1348, —O-T1349, —O(-T1350-O)$_{rs}$—H (rs=1, 2, 3, 4, 5), —O(-T1351-O)$_{rs}$-T1352 (rs=1, 2, 3, 4, 5), —OC(O)-T1353, —OC(O)—O-T1354, —OC(O)—NHT1355, —O—C(O)—NT1356T1357, —OP(O)(OT1358)(OT1359), —OSi(T1360)(T1361)(T1362), —OS($O_2$)-T1363, —NHC(O)-T1364, —NT1365C(O)-T1366, —NH—C(O)—O-T1367, —NH—C(O)—NH-T1368, —NH—C(O)—NT1369T1370, —NT1371-C(O)—O-T1372, —NT1373-C(O)—NH-T1374, —NT1375-C(O)—NT1376T1377, —NHS($O_2$)-T1378, —NT1379S($O_2$)-T1380, —S-T1381, —S(O)-T1382, —S($O_2$)-T1383, —S($O_2$)NH-T1384, —S($O_2$)NT1385T1386, —S($O_2$)O-T1387, —P(O)(OT1388)(OT1389), —Si(T1390)(T1391)(T1392)";

where T1341, T1342, T1343, T1344, T1345, T1346, T1347, T1348, T1349, T1350, T1351, T1352, T1353, T1354, T1355, T1356, T1357, T1358, T1359, T1360, T1361, T1362, T1363, T1364, T1365, T1366, T1367, T1368, T1369, T1370, T1371, T1372, T1373, T1374, T1375, T1376, T1377, T1378, T1379, T1380, T1381, T1382, T1383, T1384, T1385, T1386, T1387, T1388, T1389, T1390, T1391, T1392 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, T1347, T1348 and/or T1356, T1357 and/or T1369, T1370 and/or T1376, T1377 and/or T1385, T1386, in each case together, may also form "heterocyclyl";

where, optionally, the above substituents of substituent group (ii) may in turn each independently be substituted by at least one substituent selected identically or differently from the group consisting of:

(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHT1393, —NT1394T1395, —$NO_2$, —OH, —$OCF_3$, —SH, —O—$SO_3H$, —OP(O)(OH)$_2$, —CHO, —COOH, —C(O)$NH_2$, —$SO_3H$, —P(O)(OH)$_2$, —C(O)-T1396, —C(O)O-T1397, —C(O)NH-T1398, —C(O)NT1399T1400, —O-T140, —O(-T1402-O)$_{rt}$—H (rt=1, 2, 3, 4, 5), —O(-T1403-O)$_{rt}$-T1404 (rt=1, 2, 3, 4, 5), —OC(O)-T1405, —OC(O)—O-T1406, —OC(O)—NHT1407, —O—C(O)—NT1408T1409, —OP(O)(OT1410)(OT1411), —OSi(T1412)(T1413)(T1414), —OS($O_2$)-T1415, —NHC(O)-T1416, —NT1417C(O)-T1418, —NH—C(O)—O-T1419, —NH—C(O)—NH-T1420, —NH—C(O)—NT1421T1422, —NT1423-C(O)—O-T1424, —NT1425-C(O)—NH-T1426, —NT1427-C(O)—NT1428T1429, —NHS($O_2$)-T1430, —NT1431S($O_2$)-T1432, —S-T1433, —S(O)-T1434, —S($O_2$)-T1435, —S($O_2$)NH-T4436, —S($O_2$)NT1437T1438, —S(O₂)OT1439, —P(O)(OT1440)(OT1441), —Si(T1442)(T1443)(T1444)";

where T1393, T1394, T1395, T1396, T1397, T1398, T1399, T1400, T140, T1402, T1403, T1404, T1405, T1406, T1407, T1408, T1409, T1410, T1411, T1412, T1413, T1414, T1415, T1416, T1417, T1418, T1419, T1420, T1421, T1422, T1423, T1424, T1425, T1426, T1427, T1428, T1429, T1430, T1431, T1432, T1433, T1434, T1435, T1436, T1437, T1438, T1439, T1440, T1441, T1442, T1443, T1444 are each independently selected from the group consisting of: "alkyl, (C₉-C₃₀)alkyl, cycloalkyl, cycloalkylalkyl, heterocyclyl, heterocyclylalkyl, aryl, arylalkyl, heteroaryl, heteroarylalkyl" and where, alternatively, T1399, T1400 and/or T1408, T1409 and/or T1421, T1422 and/or T1428, T1429 and/or T1437, T1438, in each case together, may also form "heterocyclyl";

(2) "—C(O)—C(O)-T1445, —S(O₂)—NT1446T1447";

where T1445, T1446, T1447 are each independently selected from the group consisting of:

(I) "hydrogen, alkyl, (C₉-C₃₀)alkyl, cycloalkyl, cycloalkylalkyl, heterocyclyl, heterocyclylalkyl, aryl, arylalkyl, heteroaryl, heteroarylalkyl, F, Cl, Br, I, CN, CF₃, N₃, NH₂, —NHT1448, —NT1449T1450, —NO₂, —OH, —OCF₃, —SH, —O—SO₃H, —OP(O)(OH)₂, —CHO, —COOH, —C(O)NH₂, —SO₃H, —P(O)(OH)₂, —C(O)-T1451, —C(O)O-T1452, —C(O)NH-T1453, —C(O)NT1454T1455, —O-T1456, —O(-T1457-O)$_{ru}$—H (ru=1, 2, 3, 4, 5), —O(-T1458-O)$_{ru}$-T1459 (ru=1, 2, 3, 4, 5), —OC(O)-T1460, —OC(O)—O-T1461, —OC(O)—NHT1462, —O—C(O)—NT1463T1464, —OP(O)(OT1465)(OT1466), —OSi(T1467)(T1468)(T1469), —OS(O₂)-T1470, —NHC(O)-T1471, —NT1472C(O)-T1473, —NH—C(O)—O-T1474, —NH—C(O)—NH-T1475, —NH—C(O)—NT1476T1477, —NT1478-C(O)—O-T1479, —NT1480-C(O)—NH-T1481, —NT1482-C(O)—NT1483T1484, —NHS(O₂)-T1485, —NT1486S(O₂)-T1487, —S-T1488, —S(O)-T1489, —S(O₂)-T1490, —S(O₂)NH-T1491, —S(O₂)NT1492T1493, —S(O₂)O-T1494, —P(O)(OT1495)(OT1496), —Si(T1497)(T1498)(T1499)";

where T1448, T1449, T1450, T1451, T1452, T1453, T1454, T1455, T1456, T1457, T1458, T1459, T1460, T1461, T1462, T1463, T1464, T1465, T1466, T1467, T1468, T1469, T1470, T1471, T1472, T1473, T1474, T1475, T1476, T1477, T1478, T1479, T1480, T1481, T1482, T1483, T1484, T1485, T1486, T1487, T1488, T1489, T1490, T1491, T1492, T1493, T1494, T1495, T1496, T1497, T1498, T1499 are each independently selected from the group consisting of: "alkyl, (C₉-C₃₀)alkyl, cycloalkyl, cycloalkylalkyl, heterocyclyl, heterocyclylalkyl, aryl, arylalkyl, heteroaryl, heteroarylalkyl" and where, alternatively, T1454, T1455 and/or T1463, T1464 and/or T1476, T1477 and/or T1483, T1484 and/or T1492, T1493, in each case together, may also form "heterocyclyl";

where, optionally, the above substituents of substitution group (i) may each independently be further substituted by at least one substituent selected identically or differently from the group consisting of:

(i) "alkyl, (C₉-C₃₀)alkyl, cycloalkyl, cycloalkylalkyl, heterocyclyl, heterocyclylalkyl, aryl, arylalkyl, heteroaryl, heteroarylalkyl, F, Cl, Br, I, CN, CF₃, N₃, NH₂, —NHT1500, —NT1501T1502, —NO₂, —OH, —OCF₃, —SH, —O—SO₃H, —OP(O)(OH)₂, —CHO, —COOH, —C(O)NH₂, —SO₃H, —P(O)(OH)₂, —C(O)-T1503, —C(O)O-T1504, —C(O)NH-T1505, —C(O)NT1506T1507, —O-T1508, —O(-T1509-O)$_{rv}$—H (rv=1, 2, 3, 4, 5), —O(-T1510-O)$_{rv}$-T1511 (rv=1, 2, 3, 4, 5), —OC(O)-T1512, —OC(O)—O-T1513, —OC(O)—NHT1514, —O—C(O)—NT1515T1516, —OP(O)(OT1517)(OT1518), —OSi(T1519)(T1520)(T1521), —OS(O₂)-T1522, —NHC(O)-T1523, —NT1524C(O)-T1525, —NH—C(O)—O-T1526, —NH—C(O)—NH-T1527, —NH—C(O)—NT1528T1529, —NT1530-C(O)—O-T1531, —NT1532-C(O)—NH-T1533, —NT1534-C(O)—NT1535T1536, —NHS(O₂)-T1537, —NT1538S(O₂)-T1539, —S-T1540, —S(O)-T1541, —S(O₂)-T1542, —S(O₂)NH-T1543, —S(O₂)NT1544T1545, —S(O₂)O-T1546, —P(O)(OT1547)(OT1548), —Si(T1549)(T1550)(T1551)";

where T1500, T1501, T1502, T1503, T1504, T1505, T1506, T1507, T1508, T1509, T1510, T1511, T1512, T1513, T1514, T1515, T1516, T1517, T1518, T1519, T1520, T1521, T1522, T1523, T1524, T1525, T1526, T1527, T1528, T1529, T1530, T1531, T1532, T1533, T1534, T1535, T1536, T1537, T1538, T1539, T1540, T1541, T1542, T1543, T1544, T1545, T1546, T1547, T1548, T1549, T1550, T1551 are each independently selected from the group consisting of: "alkyl, (C₉-C₃₀)alkyl, cycloalkyl, cycloalkylalkyl, heterocyclyl, heterocyclylalkyl, aryl, arylalkyl, heteroaryl, heteroarylalkyl" and where, alternatively, T1506, T1507 and/or T1515, T1516 and/or T1528, T1529 and/or T1535, T1536 and/or T1544, T1545, in each case together, may also form "heterocyclyl";

where, optionally, the above substituents of substituent group (i) may in turn each independently be substituted by at least one substituent selected identically or differently from the group consisting of:

(ii) "alkyl, (C₉-C₃₀)alkyl, cycloalkyl, cycloalkylalkyl, heterocyclyl, heterocyclylalkyl, aryl, arylalkyl, heteroaryl, heteroarylalkyl, F, Cl, Br, I, CN, CF₃, N₃, NH₂, —NHT1552, —NT1553T1554, —NO₂, —OH, —OCF₃, —SH, —O—SO₃H, —OP(O)(OH)₂, —CHO, —COOH, —C(O)NH₂, —SO₃H, —P(O)(OH)₂, —C(O)-T1555, —C(O)O-T1556, —C(O)NH-T1557, —C(O)NT1558T1559, —O-T1560, —O(-T1561-O)$_{rw}$—H (rw=1, 2, 3, 4, 5), —O(-T1562-O)$_{rw}$-T1563 (rw=1, 2, 3, 4, 5), —OC(O)-T1564, —OC(O)—O-T1565, —OC(O)—NHT1566, —O—C(O)—NT1567T1568, —OP(O)(OT1569)(OT1570), —OSi(T1571)(T1572)(T1573), —OS(O₂)-T1574, —NHC(O)-T1575, —NT1576C(O)-T1577, —NH—C(O)—O-T1578, —NH—C(O)—NH-T1579, —NH—C(O)—NT1580T1581, —NT1582-C(O)—O-

T1583, —NT1584-C(O)—NH-T1585, —NT1586-C(O)—NT1587T1588, —NHS(O$_2$)-T1589, —NT1590S(O$_2$)-T1591, —S-T1592, —S(O)-T1593, —S(O$_2$)-T1594, —S(O$_2$)NH-T1595, —S(O$_2$)NT1596T1597, —S(O$_2$)O-T1598, —P(O)(OT1599)(OT1600), —Si(T160)(T1602)(T1603)";

where T1552, T1553, T1554, T1555, T1556, T1557, T1558, T1559, T1560, T1561, T1562, T1563, T1564, T1565, T1566, T1567, T1568, T1569, T1570, T1571, T1572, T1573, T1574, T1575, T1576, T1577, T1578, T1579, T1580, T1581, T1582, T1583, T1584, T1585, T1586, T1587, T1588, T1589, T1590, T1591, T1592, T1593, T1594, T1595, T1596, T1597, T1598, T1599, T1600, T1601, T1602, T1603 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, T1558, T1559 and/or T1567, T1568 and/or T1580, T1581 and/or T1587, T1588 and/or T1596, T1597, in each case together, may also form "heterocyclyl";

where, optionally, the above substituents of substituent group (ii) may in turn each independently be substituted by at least one substituent selected identically or differently from the group consisting of:

(iii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHT1604, —NT1605T1606, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)-T1607, —C(O)O-T1608, —C(O)NH-T1609, —C(O)NT1610T1611, —O-T1612, —O(-T1613-O)$_{rx}$—H (rx=1, 2, 3, 4, 5), —O(-T1614-O)$_{rx}$-T1615 (rx=1, 2, 3, 4, 5), —OC(O)-T1616, —OC(O)—O-T1617, —OC(O)—NHT1618, —O—C(O)—NT1619T1620, —OP(O)(OT1621)(OT1622), —OSi(T1623)(T1624)(T1625), —OS(O$_2$)-T1626, —NHC(O)-T1627, —NT1628C(O)-T1629, —NH—C(O)—O-T1630, —NH—C(O)—NH-T1631, —NH—C(O)—NT1632T1633, —NT1634-C(O)—O-T1635, —NT1636-C(O)—NH-T1637, —NT1638-C(O)—NT1639T1640, —NHS(O$_2$)-T1641, —NT1642S(O$_2$)-T1643, —S-T1644, —S(O)-T1645, —S(O$_2$)-T1646, —S(O$_2$)NH-T1647, —S(O$_2$)NT1648T1649, —S(O$_2$)O-T1650, —P(O)(OT1651)(OT1652), —Si(T1653)(T1654)(T1655)";

where T1604, T1605, T1606, T1607, T1608, T1609, T1610, T1611, T1612, T1613, T1614, T1615, T1616, T1617, T1618, T1619, T1620, T1621, T1622, T1623, T1624, T1625, T1626, T1627, T1628, T1629, T1630, T1631, T1632, T1633, T1634, T1635, T1636, T1637, T1638, T1639, T1640, T1641, T1642, T1643, T1644, T1645, T1646, T1647, T1648, T1649, T1650, T1651, T1652, T1653, T1654, T1655 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl"

and where, alternatively, T1610, T1611 and/or T1619, T1620 and/or T1632, T1633 and/or T1639, T1640 and/or T1648, T1649, in each case together, may also form "heterocyclyl";

where, alternatively, T1446, T1447 together may also form "heterocyclyl";

(3) "—C(Y8)NZ43Z44, —C(=NZ45)-Z46, —C(Y9)NZ47-Y10-Z48";

where Y8, Y9, Y10 are each independently selected from the group consisting of "O, S, =NH, =NZ49" where the Z43, Z44, Z45, Z46, Z47, Z48, Z49 radicals are each independently selected from the group consisting of:

(I) "hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, —C(O)-alkyl, —C(O)—(C$_9$-C$_{30}$)alkyl, —C(O)-cycloalkyl, —C(O)-cycloalkylalkyl, —C(O)-aryl, —C(O)-arylalkyl, —C(O)-heteroaryl, —C(O)-heteroarylalkyl, —C(O)-heterocyclyl, —C(O)-heterocyclylalkyl, —S(O$_2$)-alkyl, —S(O$_2$)—(C$_9$-C$_{30}$)alkyl, —S(O$_2$)-cycloalkyl, —S(O$_2$)-cycloalkylalkyl, —S(O$_2$)-aryl, —S(O$_2$)-arylalkyl, —S(O$_2$)-heteroaryl, —S(O$_2$)-heteroarylalkyl, —S(O$_2$)-heterocyclyl, —S(O$_2$)-heterocyclylalkyl";

where, optionally, the above substituents of substituent group (I) may also each independently be substituted by at least one substituent selected identically or differently from the group consisting of:

(i) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHT1656, —NT1657T1658, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)-T1659, —C(O)O-T1660, —C(O)NH-T1661, —C(O)NT1662T1663, —O-T1664, —O(-T1665-O)$_{ry}$—H (ry=1, 2, 3, 4, 5), —O(-T1666-O)$_{ry}$-T1667 (ry=1, 2, 3, 4, 5), —OC(O)-T1668, —OC(O)—O-T1669, —OC(O)—NHT1670, —O—C(O)—NT1671T1672, —OP(O)(OT1673)(OT1674), —OSi(T1675)(T1676)(T1677), —OS(O$_2$)-T1678, —NHC(O)-T1679, —NT1680C(O)-T1681, —NH—C(O)—O-T1682, —NH—C(O)—NH-T1683, —NH—C(O)—NT1684T1685, —NT1686-C(O)—O-T1687, —NT1688-C(O)—NH-T1689, —NT1690-C(O)—NT1691T1692, —NHS(O$_2$)-T1693, —NT1694S(O$_2$)-T1695, —S-T1696, —S(O)-T1697, —S(O$_2$)-T1698, —S(O$_2$)NH-T1699, —S(O$_2$)NT1700T1701, —S(O$_2$)O-T1702, —P(O)(OT1703)(OT1704), —Si(T1705)(T1706)(T1707)";

where T1656, T1657, T1658, T1659, T1660, T1661, T1662, T1663, T1664, T1665, T1666, T1667, T1668, T1669, T1670, T1671, T1672, T1673, T1674, T1675, T1676, T1677, T1678, T1679, T1680, T1681, T1682, T1683, T1684, T1685, T1686, T1687, T1688, T1689, T1690, T1691, T1692, T1693, T1694, T1695, T1696, T1697, T1698, T1699, T1700, T1701, T1702, T1703, T1704, T1705, T1706, T1707 are each independently selected from the group consisting of: "alkyl, (C$_9$-C$_{30}$)alkyl, cycloalkyl, cycloalkylalkyl, heterocyclyl, heterocyclalkyl, aryl, arylalkyl, heteroaryl, heteroarylalkyl" and where, alternatively, T1662, T1663 and/or T1671, T1672 and/or T1684, T1685 and/or T1691, T1692 and/or T1700, T1701, in each case together, may also form "heterocyclyl";
where, optionally, the above substituents of substituent group (i) may also in turn each independently be further substituted by at least one substituent selected identically or differently from the group consisting of:

(ii) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHT1708, —NT1709T1710, —$NO_2$, —OH, —$OCF_3$, —SH, —O—$SO_3H$, —OP(O)(OH)$_2$, —CHO, —COOH, —C(O)NH$_2$, —SO$_3$H, —P(O)(OH)$_2$, —C(O)-T1711, —C(O)O-T1712, —C(O)NH-T1713, —C(O)NT1714T1715, —O-T1716, —O(-T1717-O)$_{rz}$—H (rz=1, 2, 3, 4, 5), —O(-T1718-O)$_{rz}$H-T1719 (rz=1, 2, 3, 4, 5), —OC(O)-T1720, —OC(O)—O-T1721, —OC(O)—NHT1722, —O—C(O)—NT1723T1724, —OP(O)(OT1725)(OT1726), —OSi(T1727)(T1728)(T1729), —OS(O$_2$)-T1730, —NHC(O)-T1731, —NT1732C(O)-T1733, —NH—C(O)—O-T1734, —NH—C(O)—NH-T1735, —NH—C(O)—NT1736T1737, —NT1738-C(O)—O-T1739, —NT1740-C(O)—NH-T1741, —NT1742-C(O)—NT1743T1744, —NHS(O$_2$)-T1745, —NT1746S(O$_2$)-T1747, —S-T1748, —S(O)-T1749, —S(O$_2$)-T1750, —S(O$_2$)NH-T1751, —S(O$_2$)NT1752T1753, —S(O$_2$)O-T1754, —P(O)(OT1755)(OT1756), —Si(T1757)(T1758)(T1759)";
where T1708, T1709, T1710, T1711, T1712, T1713, T1714, T1715, T1716, T1717, T1718, T1719, T1720, T1721, T1722, T1723, T1724, T1725, T1726, T1727, T1728, T1729, T1730, T1731, T1732, T1733, T1734, T1735, T1736, T1737, T1738, T1739, T1740, T1741, T1742, T1743, T1744, T1745, T1746, T1747, T1748, T1749, T1750, T1751, T1752, T1753, T1754, T1755, T1756, T1757, T1758, T1759 are each independently selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and where, alternatively, T1714, T1715 and/or T1723, T1724 and/or T1736, T1737 and/or T1743, T1744 and/or T1752, T1753, in each case together, may also form "heterocyclyl";
where, optionally, the above substituents of substituent group (ii) may in turn each independently be substituted by at least one substituent selected identically or differently from the group consisting of:

(iii) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHT1760, —NT1761T1762, —$NO_2$, —OH, —$OCF_3$, —SH, —O—$SO_3H$, —OP(O)(OH)$_2$, —CHO, —COOH, —C(O)NH$_2$, —SO$_3$H, —P(O)(OH)$_2$, —C(O)-T1763, —C(O)O-T1764, —C(O)NH-T1765, —C(O)NT1766T1767, —O-T1768, —O(-T1769-O)$_{ra}$—H (ra=1, 2, 3, 4, 5), —O(-T1770-O)$_{ra}$-T1771 (ra=1, 2, 3, 4, 5), —OC(O)-T1772, —OC(O)—O-T1773, —OC(O)—NHT1774, —O—C(O)—NT1775T1776, —OP(O)(OT1777)(OT1778), —OSi(T1779)(T1780)(T1781), —OS(O$_2$)-T1782, —NHC(O)-T1783, —NT1784C(O)-T1785, —NH—C(O)—O-T1786, —NH—C(O)—NH-T1787, —NH—C(O)—NT1788T1789, —NT1790-C(O)—O-T1791, —NT1792-C(O)—NH-T1793, —NT1794-C(O)—NT1795T1796, —NHS(O$_2$)-T1797, —NT1798S(O$_2$)-T1799, —S-T1800, —S(O)-T1801, —S(O$_2$)-T1802, —S(O$_2$)NH-T1803, —S(O$_2$)NT1804T1805, —S(O$_2$)O-T1806, —P(O)(OT1807)(OT1808), —Si(T1809)(T1810)(T1811)";
where T1760, T1761, T1762, T1763, T1764, T1765, T1766, T1767, T1768, T1769, T1770, T1771, T1772, T1773, T1774, T1775, T1776, T1777, T1778, T1779, T1780, T1781, T1782, T1783, T1784, T1785, T1786, T1787, T1788, T1789, T1790, T1791, T1792, T1793, T1794, T1795, T1796, T1797, T1798, T1799, T1800, T1801, T1802, T1803, T1804, T1805, T1806, T1807, T1808, T1809, T1810, T1811 are each independently selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and where, alternatively, T1766, T1767 and/or T1775, T1776 and/or T1788, T1789 and/or T1795, T1796 and/or T1804, T1805, in each case together, may also form "heterocyclyl";

and the Z3, Z4 radicals are each independently selected from the group consisting of:

(e) hydrogen;

(f) halogen, F, Cl, Br, I;

(g) unsubstituted or substituted alkyl or $(C_9-C_{30})$alkyl, where, optionally, the alkyl or $(C_9-C_{30})$alkyl radical may be substituted by at least one substituent selected identically or differently from the group consisting of:

(i) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHB457, —NB458B459, —$NO_2$, —OH, —$OCF_3$, —SH, —O—$SO_3H$, —OP(O)(OH)$_2$, —CHO, —COOH, —C(O)NH$_2$, —SO$_3$H, —P(O)(OH)$_2$, —C(O)—B460, —C(O)O—B461, —C(O)NH—B462, —C(O)NB463B464, —O—B465, —O(—B466-O)$_x$—H (x=1, 2, 3, 4, 5), —O(—B467-O)$_x$—B468 (x=1, 2, 3, 4, 5), —OC(O)—B469, —OC(O)—O—B470, —OC(O)—NHB471, —O—C(O)—NB472B473, —OP(O)(OB474)(OB475), —OSi(B476)(B477)(B478), —OS(O$_2$)—B479, —NHC(O)—B480, —NB481C(O)—B482, —NH—C(O)—O—B483, —NH—C(O)—NH—B484, —NH—C(O)—NB485B486, —NB487-C(O)—O—B488, —NB489-C(O)—NH—B490, —NB491-C(O)—NB492B493, —NHS(O$_2$)—B494, —NB495S(O$_2$)—B496, —S—B497, —S(O)—B498, —S(O$_2$)—B499, —S(O$_2$)NH—B500, —S(O$_2$)NB501B502, —S(O$_2$)O—B503, —P(O)(OB504)(OB505), —Si(B506)(B507)(B508)";
where B457, B458, B459, B460, B461, B462, B463, B464, B465, B466, B467, B468, B469, B470, B471, B472, B473, B474, B475, B476, B477, B478, B479, B480, B481, B482, B483, B484, B485, B486, B487, B488, B489, B490, B491, B492, B493, B494, B495, B496, B497, B498, B499, B500, B501, B502, B503, B504, B505, B506, B507, B508 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, B463, B464 and/or B472, B473 and/or B485, B486 and/or B492, B493 and/or B501, B502, in each case together, may also form "heterocyclyl";

where, optionally, the above substituents of substituent group (i) may in turn each independently be substituted by at least one substituent selected identically or differently from the group consisting of:

(ii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHB509, —NB510B511, —$NO_2$, —OH, —$OCF_3$, —SH, —O—$SO_3$H, —OP(O)(OH)$_2$, —CHO, —COOH, —C(O)NH$_2$, —$SO_3$H, —P(O)(OH)$_2$, —C(O)—B512, —C(O)O—B513, —C(O)NH—B514, —C(O)NB515B516, —O—B517, —O(—B518-O)$_y$—H (y=1, 2, 3, 4, 5), —O(—B519-O)$_y$—B520 (y=1, 2, 3, 4, 5), —OC(O)—B521, —OC(O)—O—B522, —OC(O)—NHB523, —O—C(O)—NB524B525, —OP(O)(OB526)(OB527), —OSi(B528)(B529)(B530), —OS(O$_2$)—B531, —NHC(O)—B532, —NB533C(O)—B534, —NH—C(O)—O—B535, —NH—C(O)—NH—B536, —NH—C(O)—NB537B538, —NB539-C(O)—O—B540, —NB541-C(O)—NH—B542, —NB543-C(O)—NB544B545, —NHS(O$_2$)—B546, —NB547S(O$_2$)—B548, —S—B549, —S(O)—B550, —S(O$_2$)—B551, —S(O$_2$)NH—B552, —S(O$_2$)NB553B554, —S(O$_2$)O—B555, —P(O)(OB556)(OB557), —Si(B558)(B559)(B560)";

where B509, B510, B511, B512, B513, B514, B515, B516, B517, B518, B519, B520, B521, B522, B523, B524, B525, B526, B527, B528, B529, B530, B531, B532, B533, B534, B535, B536, B537, B538, B539, B540, B541, B542, B543, B544, B545, B546, B547, B548, B549, B550, B551, B552, B553, B554, B555, B556, B557, B558, B559, B560 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, B515, B516 and/or B524, B525 and/or B537, B538 and/or B544, B545 and/or B553, B554, in each case together, may also form "heterocyclyl";

where, optionally, the above substituents of substituent group (ii) may in turn each independently be substituted by at least one substituent selected identically or differently from the group consisting of:

(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHB561, —NB562B563, —$NO_2$, —OH, —$OCF_3$, —SH, —O—$SO_3$H, —OP(O)(OH)$_2$, —CHO, —COOH, —C(O)NH$_2$, —$SO_3$H, —P(O)(OH)$_2$, —C(O)—B564, —C(O)O—B565, —C(O)NH—B566, —C(O)NB567B568, —O—B569, —O(—B570-O)$_z$—H (z=1, 2, 3, 4, 5), —O(—B571-O)$_z$—B572 (z=1, 2, 3, 4, 5), —OC(O)—B573, —OC(O)—O—B574, —OC(O)—NHB575, —O—C(O)—NB576B577, —OP(O)(OB578)(OB579), —OSi(B580)(B581)(B582), —OS(O$_2$)—B583, —NHC(O)—B584, —NB585C(O)—B586, —NH—C(O)—O—B587, —NH—C(O)—NH—B588, —NH—C(O)—NB589B590, —NB591-C(O)—O—B592, —NB593-C(O)—NH—B594, —NB595-C(O)—NB596B597, —NHS(O$_2$)—B598, —NB599S(O$_2$)—B600, —S—B601, —S(O)—B602, —S(O$_2$)—B603, —S(O$_2$)NH—B604, —S(O$_2$)NB605B606, —S(O$_2$)O—B607, —P(O)(OB608)(OB609), —Si(B610)(B611)(B612)";

where B561, B562, B563, B564, B565, B566, B567, B568, B569, B570, B571, B572, B573, B574, B575, B576, B577, B578, B579, B580, B581, B582, B583, B584, B585, B586, B587, B588, B589, B590, B591, B592, B593, B594, B595, B596, B597, B598, B599, B600, B601, B602, B603, B604, B605, B606, B607, B608, B609, B610, B611, B612 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, B567, B568 and/or B576, B577 and/or B589, B590 and/or B596, B597 and/or B605, B606, in each case together, may also form "heterocyclyl";

(h) unsubstituted or substituted aryl where, optionally, the aryl radical may be substituted by at least one substituent selected identically or differently from the group consisting of:

(i) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHB613, —NB614B615, —$NO_2$, —OH, —$OCF_3$, —SH, —O—$SO_3$H, —OP(O)(OH)$_2$, —CHO, —COOH, —C(O)NH$_2$, —$SO_3$H, —P(O)(OH)$_2$, —C(O)—B616, —C(O)O—B617, —C(O)NH—B618, —C(O)NB619B620, —O—B621, —O(—B622-O)$_a$—H (a=1, 2, 3, 4, 5), —O(—B623-O)$_a$—B624 (a=1, 2, 3, 4, 5), —OC(O)—B625, —OC(O)—O—B626, —OC(O)—NHB627, —O—C(O)—NB628B629, —OP(O)(OB630)(OB631), —OSi(B632)(B633)(B634), —OS(O$_2$)—B635, —NHC(O)—B636, —NB637C(O)—B638, —NH—C(O)—O—B639, —NH—C(O)—NH—B640, —NH—C(O)—NB641B642, —NB643-C(O)—O—B644, —NB645-C(O)—NH—B646, —NB647-C(O)—NB648B649, —NHS(O$_2$)—B650, —NB651S(O$_2$)—B652, —S—B653, —S(O)—B654, —S(O$_2$)—B655, —S(O$_2$)NH—B656, —S(O$_2$)NB657B658, —S(O$_2$)O—B659, —P(O)(OB660)(OB661), —Si(B662)(B663)(B664)";

where B613, B614, B615, B616, B617, B618, B619, B620, B621, B622, B623, B624, B625, B626, B627, B628, B629, B630, B631, B632, B633, B634, B635, B636, B637, B638, B639, B640, B641, B642, B643, B644, B645, B646, B647, B648, B649, B650, B651, B652, B653, B654, B655, B656, B657, B658, B659, B660, B661, B662, B663, B664 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, B619, B620 and/or B628, B629 and/or B641, B642 and/or B648, B649 and/or B657, B658, in each case together, may also form "heterocyclyl";

where, optionally, the above substituents of substituent group (i) may in turn each independently be substituted by at least one substituent selected identically or differently from the group consisting of:

(ii) "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHB665, —NB666B667, —$NO_2$, —OH, —$OCF_3$, —SH, —O—$SO_3H$, —OP(O)(OH)$_2$, —CHO, —COOH, —C(O)NH$_2$, —SO$_3$H, —P(O)(OH)$_2$, —C(O)—B668, —C(O)O—B669, —C(O)NH—B670, —C(O)NB671B672, —O—B673, —O(—B674-O)$_b$—H (b=1, 2, 3, 4, 5), —O(—B675-O)$_b$—B676 (b=1, 2, 3, 4, 5), —OC(O)—B677, —OC(O)—O—B678, —OC(O)—NHB679, —O—C(O)—NB680B681, —OP(O)(OB682)(OB683), —OSi(B684)(B685)(B686), —OS(O$_2$)—B687, —NHC(O)—B688, —NB689C(O)—B690, —NH—C(O)—O—B691, —NH—C(O)—NH—B692, —NH—C(O)—NB693B694, —NB695-C(O)—O—B696, —NB697-C(O)—NH—B698, —NB699-C(O)—NB700B701, —NHS(O$_2$)—B702, —NB703S(O$_2$)—B704, —S—B705, —S(O)—B706, —S(O$_2$)—B707, —S(O$_2$)NH—B708, —S(O$_2$)NB709B710, —S(O$_2$)O—B711, —P(O)(OB712)(OB713), —Si(B714)(B715)(B716)";

where B665, B666, B667, B668, B669, B670, B671, B672, B673, B674, B675, B676, B677, B678, B679, B680, B681, B682, B683, B684, B685, B686, B687, B688, B689, B690, B691, B692, B693, B694, B695, B696, B697, B698, B699, B700, B701, B702, B703, B704, B705, B706, B707, B708, B709, B710, B711, B712, B713, B714, B715, B716 are each independently selected from the group consisting of: "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl" and where, alternatively, B671, B672 and/or B680, B681 and/or B693, B694 and/or B700, B701 and/or B709, B710, in each case together, may also form "heterocyclyl";

where, optionally, the above substituents of substituent group (ii) may in turn each independently be substituted by at least one substituent selected identically or differently from the group consisting of:

(iii) "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHB717, —NB718B719, —$NO_2$, —OH, —$OCF_3$, —SH, —O—$SO_3H$, —OP(O)(OH)$_2$, —CHO, —COOH, —C(O)NH$_2$, —SO$_3$H, —P(O)(OH)$_2$, —C(O)—B720, —C(O)O—B721, —C(O)NH—B722, —C(O)NB723B724, —O—B725, —O(—B726-O)$_c$—H (c=1, 2, 3, 4, 5), —O(—B727-O)$_c$—B728 (c=1, 2, 3, 4, 5), —OC(O)—B729, —OC(O)—O—B730, —OC(O)—NHB731, —O—C(O)—NB732B733, —OP(O)(OB734)(OB735), —OSi(B736)(B737)(B738), —OS(O$_2$)—B739, —NHC(O)—B740, —NB741C(O)—B742, —NH—C(O)—O—B743, —NH—C(O)—NH—B744, —NH—C(O)—NB745B746, —NB747-C(O)—O—B748, —NB749-C(O)—NH—B750, —NB751-C(O)—NB752B753, —NHS(O$_2$)—B754, —NB755S(O$_2$)—B756, —S—B757, —S(O)—B758, —S(O$_2$)—B759, —S(O$_2$)NH—B760, —S(O$_2$)NB761B762, —S(O$_2$)O—B763, —P(O)(OB764)(OB765), —Si(B766)(B767)(B768)";

where B717, B718, B719, B720, B721, B722, B723, B724, B725, B726, B727, B728, B729, B730, B731, B732, B733, B734, B735, B736, B737, B738, B739, B740, B741, B742, B743, B744, B745, B746, B747, B748, B749, B750, B751, B752, B753, B754, B755, B756, B757, B758, B759, B760, B761, B762, B763, B764, B765, B766, B767, B768 are each independently selected from the group consisting of: "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl" and where, alternatively, B723, B724 and/or B732, B733 and/or B745, B746 and/or B752, B753 and/or B761, B762, in each case together, may also form "heterocyclyl";

(j) unsubstituted or substituted heteroaryl where, optionally, the heteroaryl radical may be substituted by at least one substituent selected identically or differently from the group consisting of:

(i) "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHB769, —NB770B771, —$NO_2$, —OH, —$OCF_3$, —SH, —O—$SO_3H$, —OP(O)(OH)$_2$, —CHO, —COOH, —C(O)NH$_2$, —SO$_3$H, —P(O)(OH)$_2$, —C(O)—B772, —C(O)O—B773, —C(O)NH—B774, —C(O)NB775B776, —O—B777, —O(—B778-O)$_d$—H (d=1, 2, 3, 4, 5), —O(—B779-O)$_d$—B780 (d=1, 2, 3, 4, 5), —OC(O)—B781, —OC(O)—O—B782, —OC(O)—NHB783, —O—C(O)—NB784B785, —OP(O)(OB786)(OB787), —OSi(B788)(B789)(B790), —OS(O$_2$)—B791, —NHC(O)—B792, —NB793C(O)—B794, —NH—C(O)—O—B795, —NH—C(O)—NH—B796, —NH—C(O)—NB797B798, —NB799-C(O)—O—B800, —NB801-C(O)—NH—B802, —NB803-C(O)—NB804B805, —NHS(O$_2$)—B806, —NB807S(O$_2$)—B808, —S—B809, —S(O)—B810, —S(O$_2$)—B811, —S(O$_2$)NH—B812, —S(O$_2$)NB813B814, —S(O$_2$)O—B815, —P(O)(OB816)(OB817), —Si(B818)(B819)(B820)";

where B769, B770, B771, B772, B773, B774, B775, B776, B777, B778, B779, B780, B781, B782, B783, B784, B785, B786, B787, B788, B789, B790, B791, B792, B793, B794, B795, B796, B797, B798, B799, B800, B801, B802, B803, B804, B805, B806, B807, B808, B809, B810, B811, B812, B813, B814, B815, B816, B817, B818, B819, B820 are each independently selected from the group consisting of: "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl" and where, alternatively, B775, B776 and/or B784, B785 and/or B797, B798 and/or B804, B805 and/or B813, B814, in each case together, may also form "heterocyclyl";

where, optionally, the above substituents of substituent group (i) may in turn each independently be substituted by at least one substituent selected identically or differently from the group consisting of:

(ii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHB821, —NB822B823, —$NO_2$, —OH, —$OCF_3$, —SH, —O—$SO_3H$, —OP(O)(OH)$_2$, —CHO, —COOH, —C(O)$NH_2$, —$SO_3H$, —P(O)(OH)$_2$, —C(O)—B824, —C(O)O—B825, —C(O)NH—B826, —C(O)NB827B828, —O—B829, —O(—B830-O)$_e$—H (e=1, 2, 3, 4, 5), —O(—B831-O)$_e$—B832 (e=1, 2, 3, 4, 5), —OC(O)—B833, —OC(O)—O—B834, —OC(O)—NHB835, —O—C(O)—NB836B837, —OP(O)(OB838)(OB839), —OSi(B840)(B841)(B842), —OS($O_2$)—B843, —NHC(O)—B844, —NB845C(O)—B846, —NH—C(O)—O—B847, —NH—C(O)—NH—B848, —NH—C(O)—NB849B850, —NB851-C(O)—O—B852, —NB853-C(O)—NH—B854, —NB855-C(O)—NB856B857, —NHS($O_2$)—B858, —NB859S($O_2$)—B860, —S—B861, —S(O)—B862, —S($O_2$)—B863, —S($O_2$)NH—B864, —S($O_2$)NB865B866, —S($O_2$)O—B867, —P(O)(OB868)(OB869), —Si(B870)(B871)(B872)";

where B821, B822, B823, B824, B825, B826, B827, B828, B829, B830, B831, B832, B833, B834, B835, B836, B837, B838, B839, B840, B841, B842, B843, B844, B845, B846, B847, B848, B849, B850, B851, B852, B853, B854, B855, B856, B857, B858, B859, B860, B861, B862, B863, B864, B865, B866, B867, B868, B869, B870, B871, B872 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, B827, B828 and/or B836, B837 and/or B849, B850 and/or B856, B857 and/or B865, B866, in each case together, may also form "heterocyclyl";

where, optionally, the above substituents of substituent group (ii) may in turn each independently be substituted by at least one substituent selected identically or differently from the group consisting of:

(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHB873, —NB874B875, —$NO_2$, —OH, —$OCF_3$, —SH, —O—$SO_3H$, —OP(O)(OH)$_2$, —CHO, —COOH, —C(O)$NH_2$, —$SO_3H$, —P(O)(OH)$_2$, —C(O)—B876, —C(O)O—B877, —C(O)NH—B878, —C(O)NB879B880, —O—B881, —O(—B882-O)$_f$—H (f=1, 2, 3, 4, 5), —O(—B883-O)$_f$—B884 (f=1, 2, 3, 4, 5), —OC(O)—B885, —OC(O)—O—B886, —OC(O)—NHB887, —O—C(O)—NB888B889, —OP(O)(OB890)(OB891), —OSi(B892)(B893)(B894), —OS($O_2$)—B895, —NHC(O)—B896, —NB897C(O)—B898, —NH—C(O)—O—B899, —NH—C(O)—NH—B900, —NH—C(O)—NB901B902, —NB903-C(O)—O—B904, —NB905-C(O)—NH—B906, —NB907-C(O)—NB908B909, —NHS($O_2$)—B910, —NB911S($O_2$)—B912, —S—B913, —S(O)—B914, —S($O_2$)—B915, —S($O_2$)NH—B916, —S($O_2$)NB917B918, —S($O_2$)O—B919, —P(O)(OB920)(OB921), —Si(B922)(B923)(B924)";

where B873, B874, B875, B876, B877, B878, B879, B880, B881, B882, B883, B884, B885, B886, B887, B888, B889, B890, B891, B892, B893, B894, B895, B896, B897, B898, B899, B900, B901, B902, B903, B904, B905, B906, B907, B908, B909, B910, B911, B912, B913, B914, B915, B916, B917, B918, B919, B920, B921, B922, B923, B924 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, B879, B880 and/or B888, B889 and/or B901, B902 and/or B908, B909 and/or B917, B918, in each case together, may also form "heterocyclyl";

(k) OZ6 where Z6 is independently selected from the group consisting of:

(i) "hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl";

where, optionally, the above substituents of substituent group (i) may in turn each independently be substituted by at least one substituent selected identically or differently from the group consisting of:

(ii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHB925, —NB926B927, —$NO_2$, —OH, —$OCF_3$, —SH, —O—$SO_3H$, —OP(O)(OH)$_2$, —CHO, —COOH, —C(O)$NH_2$, —$SO_3H$, —P(O)(OH)$_2$, —C(O)—B928, —C(O)O—B929, —C(O)NH—B930, —C(O)NB931B932, —O—B933, —O(—B934-O)$_g$—H (g=1, 2, 3, 4, 5), —O(—B935-O)$_g$—B936 (g=1, 2, 3, 4, 5), —OC(O)—B937, —OC(O)—O—B938, —OC(O)—NHB939, —O—C(O)—NB940B941, —OP(O)(OB942)(OB943), —OSi(B944)(B945)(B946), —OS($O_2$)—B947, —NHC(O)—B948, —NB949C(O)—B950, —NH—C(O)—O—B951, —NH—C(O)—NH—B952, —NH—C(O)—NB953B954, —NB955-C(O)—O—B956, —NB957-C(O)—NH—B958, —NB959-C(O)—NB960B961, —NHS($O_2$)—B962, —NB963S($O_2$)—B964, —S—B965, —S(O)—B966, —S($O_2$)—B967, —S($O_2$)NH—B968, —S($O_2$)NB969B970, —S($O_2$)O—B971, —P(O)(OB972)(OB973), —Si(B974)(B975)(B976)";

where B925, B926, B927, B928, B929, B930, B931, B932, B933, B934, B935, B936, B937, B938, B939, B940, B941, B942, B943, B944, B945, B946, B947, B948, B949, B950, B951, B952, B953, B954, B955, B956, B957, B958, B959, B960, B961, B962, B963, B964, B965, B966, B967, B968, B969, B970, B971, B972, B973, B974, B975, B976 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, B931, B932 and/or B940, B941 and/or B953, B954 and/or B960, B961 and/or B969, B970, in each case together, may also form "heterocyclyl";

where, optionally, the above substituents of substituent group (ii) may in turn each independently be substituted by at least one substituent selected identically or differently from the group consisting of:
(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHB977, —NB978B979, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)—B980, —C(O)O—B981, —C(O)NH—B982, —C(O)NB983B984, —O—B985, —O(—B986-O)$_h$—H (h=1, 2, 3, 4, 5), —O(—B987-O)$_h$—B988 (h=1, 2, 3, 4, 5), —OC(O)—B989, —OC(O)—O—B990, —OC(O)—NHB991, —O—C(O)—NB992B993, —OP(O)(OB994)(OB995), —OSi(B996)(B997)(B998), —OS(O$_2$)—B999, —NHC(O)—B1000, —NB1001C(O)—B1002, —NH—C(O)—O—B1003, —NH—C(O)—NH—B1004, —NH—C(O)—NB1005B1006, —NB1007-C(O)—O—B1008, —NB1009-C(O)—NH—B1010, —NB1011-C(O)—NB1012B1013, —NHS(O$_2$)—B1014, —NB1015S(O$_2$)—B1016, —S—B1017, —S(O)—B1018, —S(O$_2$)—B1019, —S(O$_2$)NH—B1020, —S(O$_2$)NB1021B1022, —S(O$_2$)O—B1023, —P(O)(OB1024)(OB1025), —Si(B1026)(B1027)(B1028)";

where B977, B978, B979, B980, B981, B982, B983, B984, B985, B986, B987, B988, B989, B990, B991, B992, B993, B994, B995, B996, B997, B998, B999, B1000, B1001, B1002, B1003, B1004, B1005, B1006, B1007, B1008, B1009, B1010, B1011, B1012, B1013, B1014, B1015, B1016, B1017, B1018, B1019, B1020, B1021, B1022, B1023, B1024, B1025, B1026, B1027, B1028 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, B983, B984 and/or B992, B993 and/or B1005, B1006 and/or B1012, B1013 and/or B1021, B1022, in each case together, may also form "heterocyclyl";

(l) SZ7 where Z7 is independently selected from the group consisting of:
(i) "hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl";
where, optionally, the above substituents of substituent group (i) may in turn each independently be substituted by at least one substituent selected identically or differently from the group consisting of:
(ii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHB1029, —NB1030B1031, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)—B1032, —C(O)O—B1033, —C(O)NH—B1034, —C(O)NB1035B1036, —O—B1037, —O(—B1038-O)$_i$—H (i=1, 2, 3, 4, 5), —O(—B1039-O)$_i$—B1040 (i=1, 2, 3, 4, 5), —OC(O)—B1041, —OC(O)—O—B1042, —OC(O)—NHB1043, —O—C(O)—NB1044B1045, —OP(O)(OB1046)(OB1047), —OSi(B1048)(B1049)(B1050), —OS(O$_2$)—B1051, —NHC(O)—B1052, —NB1053C(O)—B1054, —NH—C(O)—O—B1055, —NH—C(O)—NH—B1056, —NH—C(O)—NB1057B1058, —NB1059-C(O)—O—B1060, —NB1061-C(O)—NH—B1062, —NB1063-C(O)—NB1064B1065, —NHS(N$_2$)—B1066, —NB1067S(O$_2$)—B1068, —S—B1069, —S(O)—B1070, —S(O$_2$)—B1071, —S(O$_2$)NH—B1072, —S(O$_2$)NB1073B1074, —S(O$_2$)O—B1075, —P(O)(OB1076)(OB1077), —Si(B1078)(B1079)(B1080)";

where B1029, B1030, B1031, B1032, B1033, B1034, B1035, B1036, B1037, B1038, B1039, B1040, B1041, B1042, B1043, B1044, B1045, B1046, B1047, B1048, B1049, B1050, B1051, B1052, B1053, B1054, B1055, B1056, B1057, B1058, B1059, B1060, B1061, B1062, B1063, B1064, B1065, B1066, B1067, B1068, B1069, B1070, B1071, B1072, B1073, B1074, B1075, B1076, B1077, B1078, B1079, B1080 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, B1035, B1036 and/or B1044, B1045 and/or B1057, B1058 and/or B1064, B1065 and/or B1073, B1074, in each case together, may also form "heterocyclyl";

where, optionally, the above substituents of substituent group (ii) may in turn each independently be substituted by at least one substituent selected identically or differently from the group consisting of:
(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, $CF_3$, $N_3$, $NH_2$, —NHB1081, —NB1082B1083, —$NO_2$, —OH, —$OCF_3$, —SH, —O—$SO_3H$, —OP(O)(OH)$_2$, —CHO, —COOH, —C(O)NH$_2$, —$SO_3H$, —P(O)(OH)$_2$, —C(O)—B1084, —C(O)O—B1085, —C(O)NH—B1086, —C(O)NB1087B1088, —O—B1089, —O(—B1090-O)$_j$—H (j=1, 2, 3, 4, 5), —O(—B1091-O)$_j$—B1092 (j=1, 2, 3, 4, 5), —OC(O)—B1093, —OC(O)—O—B1094, —OC(O)—NHB1095, —O—C(O)—NB1096B1097, —OP(O)(OB1098)(OB1099), —OSi(B1100)(B1101)(B1102), —OS(O$_2$)—B1103, —NHC(O)—B1104, —NB1105C(O)—B1106, —NH—C(O)—O—B1107, —NH—C(O)—NH—B1108, —NH—C(O)—NB1109B1110, —NB1111-C(O)—O—B1112, —NB1113-C(C)—NH—B1114, —NB1115-C(O)—NB1116B1117, —NHS(O$_2$)—B1118, —NB1119S(O$_2$)—B1120, —S—B1121, —S(O)—B1122, —S(O$_2$)—B1123, —S(O$_2$)NH—B1124, —S(O$_2$)NB1125B1126, —S(O$_2$)O—B1127, —P(O)(OB1128)(OB1129), —Si(B1130)(B1131)(B1132)";

where B1081, B1082, B1083, B1084, B1085, B1086, B1087, B1088, B1089, B1090, B1091, B1092, B1093, B1094, B1095, B1096, B1097, B1098, B1099, B1100, B1101, B1102, B1103, B1104, B1105, B1106, B1107, B1108, B1109, B1110, B1111, B1112, B1113, B1114, B1115, B1116, B1117, B1118, B1119, B1120, B1121, B1122, B1123, B1124, B1125, B1126, B1127, B1128, B1129, B1130, B1131, B1132 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, B1087, B1088 and/or B1096, B1097 and/or B1109, B1110 and/or B1116, B1117 and/or B1125, B1126, in each case together, may also form "heterocyclyl";

(m) NZ8Z9 where Z8, Z9 are each independently selected from the group consisting of:
(i) "hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, —C(O)—B1133, —C(O)O—B1134, —C(O)—NB1135B1136, —S(O$_2$)—B1137, —S(O$_2$)O—B1138";

where B1133, B1134, B1135, B1136, B1137, B1138 are each independently selected from the group consisting of: hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, B1135, B1136 together may also form "heterocyclyl";

where, optionally, the above substituents of substituent group (i) may in turn each independently be substituted by at least one substituent selected identically or differently from the group consisting of:

(ii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHB1139, —NB1140B1141, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—B1142, —C(O)O—B1143, —C(O)NH—B1144, —C(O)NB1145B1146, —O—B1147, —O(—B1148-O)$_k$—H (k=1, 2, 3, 4, 5), —O(—B1149-O)$_k$—B1150 (k=1, 2, 3, 4, 5), —OC(O)—B1151, —OC(O)—O—B1152, —OC(O)—NHB1153, —O—C(O)—NB1154B1155, —OP(O)(OB1156)(OB1157), —OSi(B1158)(B1159)(B1160), —OS(O$_2$)—B1161, —NHC(O)—B1162, —NB1163C(O)—B1164, —NH—C(O)—O—B1165, —NH—C(O)—NH—B1166, —NH—C(O)—NB1167B1168, —NB1169-C(O)—O—B1170, —NB1171-C(O)—NH—B1172, —NB1173-C(O)—NB1174B1175, —NHS(O$_2$)—B1176, —NB1177S(O$_2$)—B1178, —S—B1179, —S(O)—B1180, —S(O$_2$)—B1181, —S(O$_2$)NH—B1182, —S(O$_2$)NB1183B1184, —S(O$_2$)O—B1185, —P(O)(OB1186)(OB1187), —Si(B1188)(B1189)(B1190)";

where B1139, B1140, B1141, B1142, B1143, B1144, B1145, B1146, B1147, B1148, B1149, B1150, B151, B1152, B1153, B1154, B1155, B1156, B1157, B1158, B1159, B1160, B1161, B1162, B1163, B1164, B1165, B1166, B1167, B1168, B1169, B1170, B1171, B1172, B1173, B1174, B1175, B1176, B1177, B1178, B1179, B1180, B1181, B1182, B1183, B1184, B1185, B1186, B1187, B1188, B1189, B1190 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, B1145, B1146 and/or B1154, B1155 and/or B1167, B1168 and/or B1174, B1175 and/or B1183, B1184, in each case together, may also form "heterocyclyl";

where, optionally, the above substituents of substituent group (ii) may in turn each independently be substituted by at least one substituent selected identically or differently from the group consisting of:

(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHB1191, —NB1192B1193, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—B1194, —C(O)O—B1195, —C(O)NH—B1196, —C(O)NB1197B1198, —O—B1199, —O(—B1200-O)$_l$—H (l=1, 2, 3, 4, 5), —O(—B1201-O)$_l$—B1202 (l=1, 2, 3, 4, 5), —OC(O)—B1203, —OC(O)—O—B1204, —OC(O)—NHB1205, —O—C(O)—NB1206B1207, —OP(O)(OB1208)(OB1209), —OSi(B1210)(B1211)(B1212), —OS(O$_2$)—B1213, —NHC(O)—B1214, —NB1215C(O)—B1216, —NH—C(O)—O—B1217, —NH—C(O)—NH—B1218, —NH—C(O)—NB1219B1220, —NB1221-C(O)—O—B1222, —NB1223-C(O)—NH—B1224, —NB1225-C(O)—NB1226B1227, —NHS(O$_2$)—B1228, —NB1229S(O$_2$)—B1230, —S—B1231, —S(O)—B1232, —S(O$_2$)—B1233, —S(O$_2$)NH—B1234, —S(O$_2$)NB1235B1236, —S(O$_2$)O—B1237, —P(O)(OB1238)(OB1239), —Si(B1240)(B1241)(B1242)";

where B1191, B1192, B1193, B1194, B1195, B1196, B1197, B1198, B1199, B1200, B1201, B1202, B1203, B1204, B1205, B1206, B1207, B1208, B1209, B1210, B1211, B1212, B1213, B1214, B1215, B1216, B1217, B1218, B1219, B1220, B1221, B1222, B1223, B1224, B1225, B1226, B1227, B1228, B1229, B1230, B1231, B1232, B1233, B1234, B1235, B1236, B1237, B1238, B1239, B1240, B1241, B1242 are each independently selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and where, alternatively, B1197, B1198 and/or B1206, B1207 and/or B1219, B1220 and/or B1226, B1227 and/or B1235, B1236, in each case together, may also form "heterocyclyl"; and the Z5 radical is independently selected from the group consisting of:
(i) "hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHD1, —ND2D3, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)-D4, —C(O)O-D5, —C(O)NH-D6, —C(O)ND7D8, —O-D9, —O(-D10-O)$_r$—H (r=1, 2, 3, 4, 5), —O(-D11-O)$_r$-D12 (r=1, 2, 3, 4, 5), —OC(O)-D13, —OC(O)—O-D14, —OC(O)—NHD15, —O—C(O)—ND16D17, —OP(O)(OD18)(OD19), —OSi(D20)(D21)(D22), —OS(O$_2$)-D23, —NHC(O)-D24, —ND25C(O)-D26, —NH—C(O)—O-D27, —NH—C (O)—NH-D28, —NH—C(O)—ND29D30, —ND31-C(O)—O-D32, —ND33-C(O)—NH-D34, —ND35-C(O)—ND36D37, —NHS(O$_2$)-D38, —ND39S(O$_2$)-D40, —S-D41, —S(O)-D42, —S(O$_2$)-D43, —S(O$_2$)NH-D44, —S(O$_2$)ND45D46, —S(O$_2$)O-D47, —P(O)(OD48)(OD49), —Si(D50)(D51)(D52)";

where D1, D2, D3, D4, D5, D6, D7, D8, D9, D10, D11, D12, D13, D14, D15, D16, D17, D18, D19, D20, D21, D22, D23, D24, D25, D26, D27, D28, D29, D30, D31, D32, D33, D34, D35, D36, D37, D38, D39, D40, D41, D42, D43, D44, D45, D46, D47, D48, D49, D50, D51, D52 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, D7, D8 and/or D16, D17 and/or D29, D30 and/or D36, D37 and/or D45, D46, in each case together, may also form "heterocyclyl";

where, optionally, the above substituents of substituent group (i) may in turn each independently be substituted by at least one substituent selected identically or differently from the group consisting of:

(ii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHD53, —ND54D55, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)-D56, —C(O)O-D57, —C(O)NH-D58, —C(O)ND59D60, —O-D61, —O(-D62-O)$_s$—H (s=1, 2, 3, 4, 5), —O(-D63-O)$_t$-D64 (t=1, 2, 3, 4, 5), —OC(O)-D65, —OC(O)—O-D66, —OC(O)—NHD67, —O—C(O)—ND68D69, —OP(O)(OD70)(OD71), —OSi(D72)(D73)(D74), —OS(O$_2$)-D75, —NHC(O)-D76, —ND77C(O)-D78, —NH—C(O)—O-D79, —NH—C(O)—NH-D80, —NH—C(O)—ND81D82, —ND83-C(O)—O-D84, —ND85-C(O)—NH-D86, —ND87-C(O)—ND88D89, —NHS(O$_2$)-D90, —ND91S(O$_2$)-D92, —S-D93, —S(O)-D94, —S(O$_2$)-D95, —S(O$_2$)NH-D96, —S(O$_2$)ND97D98, —S(O$_2$)O-D99, —P(O)(CD100)(OD101), —Si(D102)(D103)(D104)";

where D53, D54, D55, D56, D57, D58, D59, D60, D61, D62, D63, D64, D65, D66, D67, D68, D69, D70, D71, D72, D73, D74, D75, D76, D77, D78, D79, D80, D81, D82, D83, D84, D85, D86, D87, D88, D89, D90, D91, D92, D93, D94, D95, D96, D97, D98, D99, D100, D101, D102, D103, D104 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, D59, D60 and/or D68, D69 and/or D81, D82 and/or D88, D89 and/or D97, D98, in each case together, may also form "heterocyclyl";

where, optionally, the above substituents of substituent group (ii) may in turn each independently be substituted by at least one substituent selected identically or differently from the group consisting of:

(iii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, F, Cl, Br, I, CN, CF$_3$, N$_3$, NH$_2$, —NHD105, —ND106D107, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)-D108, —C(O)O-D109, —C(O)NH-D110, —C(O)ND111D112, —O-D113, —O(-D114-O)$_t$—H (t=1, 2, 3, 4, 5), —O(-D15-O)$_t$-D116 (t=1, 2, 3, 4, 5), —OC(O)-D117, —OC(O)—O-D118, —OC(O)—NHD119, —O—C(O)—ND120D121, —OP(O)(OD122)(OD123), —OSi(D124)(D125)(D126), —OS(O$_2$)-D127, —NHC(O)-D128, —ND129C(O)-D130, —NH—C(O)—O-D131, —NH—C(O)—NH-D132, —NH—C(O)—ND133D134, —ND135-C(O)—O-D136, —ND137-C(O)—NH-D138, —ND139-C(O)—ND140D141, —NHS(O$_2$)-D142, —ND143S(O$_2$)-D144, —S-D145, —S(O)-D146, —S(O$_2$)-D147, —S(O$_2$)NH-D148, —S(O$_2$)ND149D150, —S(O$_2$)O-D151, —P(O)(OD152)(OD153), —Si(D154)(D155)(D156)";

where D105, D106, D107, D108, D109, D10, D111, D112, D113, D114, D115, D116, D117, D118, D119, D120, D121, D122, D123, D124, D125, D126, D127, D128, D129, D130, D131, D132, D133, D134, D135, D136, D137, D138, D139, D140, D141, D142, D143, D144, D145, D146, D147, D148, D149, D150, D151, D152, D153, D154, D155, D156 are each independently selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and where, alternatively, D111, D112 and/or D120, D121 and/or D133, D134 and/or D140, D141 and/or D149, D150, in each case together, may also form "heterocyclyl".

In order to avoid ambiguities, the cases (A) to (E) detailed above for the general formula (I) are explained below:

In case (A), the novel pyrido[2,3-b]pyrazine derivatives may be substituted by "substituted aryl" in at least one of their Z3, Z4 radicals, the novelty arising either by virtue of sub-case (a) or by virtue of sub-case (c). If only one Z3, Z4 radical is novel "substituted aryl", the other Z3, Z4 radical in each case may have any substitution within the maximum range stated [("and" linkage in subcase (d)]. Optionally, both Z3, Z4 radicals may also have further substitution [sub-case (b) or (d)]. The Z1, Z2 and Z5 radicals may have any substitution within the maximum range stated [("and" linkage in cases (A) to (D)].

In case (B), the novel pyrido[2,3-b]pyrazine derivatives may be substituted by "substituted heteroaryl" in at least one of their Z3, Z4 radicals, the novelty arising either by virtue of sub-case (a) or by virtue of sub-case (c). If only one Z3, Z4 radical is novel "substituted heteroaryl", the other Z3, Z4 radical in each case may have any substitution within the maximum range stated [("and" linkage in subcase (d)]. Optionally, both Z3, Z4 radicals may also have further substitution [sub-case (b) or (d)]. The Z1, Z2 and Z5 radicals may have any substitution within the maximum range stated [("and" linkage in cases (A) to (D)].

In case (C), the novel pyrido[2,3-b]pyrazine derivatives may be substituted in a novel manner by "substituted alkyl" or "(C$_9$-C$_{30}$)alkyl" in at least one of their Z3, Z4 radicals. If only one Z3, Z4 radical is novel "substituted alkyl" or "(C$_9$-C$_{30}$)alkyl", the other Z3, Z4 radical in each case may have any desired substitution within the maximum range stated [("and" linkage in sub-case "(C$_9$-C$_{30}$)alkyl"]. Z1, Z2 and Z5 radicals have any substitution within the maximum range stated [("and" linkage in cases (A) to (D)].

In case (D), the novel pyrido[2,3-b]pyrazine derivatives may be substituted by "—NZ10Z11, —OZ12, —SZ13" in at least one of their Z3, Z4 radicals, the novelty arising either by virtue of sub-case (a) or by virtue of sub-case (b). If only one Z3, Z4 radical is novel "—NZ10Z11, —OZ12, —SZ13", the other Z3, Z4 radical in each case may have any desired substitution within the maximum range stated [("and" linkage in sub-case (b)]. Z1, Z2 and Z5 radicals have any desired substitution within the maximum range stated [("and" linkage in cases (A) to (D)].

In case (E), the novel pyrido[2,3-b]pyrazine derivatives may be substituted by "—NZ24Z25, —NZ26Z27" in at least one of their Z1, Z2 radicals, the novelty arising either by virtue of sub-case (a)(1), sub-case (b)(1)(I), sub-case (b)(1)(II) or sub-case (b)(2). If only one Z1, Z2 radical is novel "—NZ24Z25, —NZ26Z27", the other Z1, Z2 radical in each case may have any substitution within the maximum range stated [sub-cases (c), (d)] [("and" linkage in sub-case (b)(2)]. Z3, Z4 and Z5 radicals have any substitution within the maximum range stated [("and" linkage in sub-case (d)].

In a preferred embodiment, novel pyrido[2,3-b]pyrazine derivatives of the general formula (I) are provided, where, in (A),
- the Z1 radical is independently "NZ14Z15"; where Z14 is hydrogen or "aryl" and Z15 is "—C(O)NH-alkyl"; where "—C(O)NH-alkyl" may additionally, optionally, be substituted by "—OH";
- the Z2 radical is independently hydrogen;
- the Z3 radical is independently "substituted aryl", where "substituted aryl" is substituted by at least one substituent selected identically or differently from the group consisting of:
  (a) "alkyl, —OC(O)-alkyl, —Oalkyl, —NHC(O)-alkyl";
  with the proviso that the above substituents of substituent group (a) are each independently substituted further by at least one substituent selected identically or differently from the group consisting of:
  (i) "aryl, heterocyclyl, —O-alkyl-O-alkyl, —O-arylalkyl";
- or the Z3 radical is independently "substituted aryl", where "substituted aryl" is substituted by at least one substituent selected identically or differently from the group consisting of:
  (c) "—OC(O)—O-alkyl, —OC(O)—O-aryl, —OC(O)—N(alkyl)$_2$, —OC(O)—NH-alkyl, —OC(O)—(C$_9$-C$_{30}$)alkyl, —NHC(O)—O-alkyl, —NHC(O)—NH-alkyl, —NHC(O)—N(alkyl)$_2$, —Si(alkyl)$_3$";
  where, optionally, the above substituents of substituent group (c) may in turn each independently be substituted by at least one substituent selected identically or differently from the group consisting of:
  (i) "—O-alkyl, —O-arylalkyl";
- where, optionally, the Z3 radical may also independently be substituted by at least one substituent selected identically or differently from the group consisting of:
  (d) "halogen, F, Cl, Br, I, —O-alkyl";
- the Z4 radical is independently hydrogen;
- the Z5 radical is independently hydrogen.

In a preferred embodiment, novel pyrido[2,3-b]pyrazine derivatives of the general formula (I) are provided, where, in (A),
- the Z1 radical is independently selected from the group consisting of "—NHC(O)NH-ethyl, —NHC(O)NH-butyl-OH";
- the Z2 radical is independently hydrogen;
- the Z3 radical is independently selected from the group consisting of "4-phenyl methyl carbonate, 3-phenyl 2-methoxyethyl carbonate, 4-phenyl 2-methoxyethyl carbonate, 4-phenyl phenyl carbonate, 4-phenyl N-diethylcarbamate, 4-phenyl 3-phenylacrylate, 4-phenyl nonadecanoate, 4-phenyl isobutyl carbonate, 4-phenyl but-2-ynyl carbonate, 4-phenyl N-dimethylcarbamate, 4-phenyl N-ethylcarbamate, tert-butyl N-(4-phenyl)carbamate, 2-methoxyethyl N-(4-phenyl)carbamate, 4-(3-ethylurea)phenyl, 4-(3,3-methylurea)phenyl, 4-morpholin-4-ylmethylphenyl, 4-[2-(2-methoxyethoxy)ethoxy]phenyl, N-(4-phenyl)-2-(2-methoxyethoxy)acetamide, 4-(2-methoxy)phenyl 2-methoxyethyl carbonate, 4-phenyl 2-benzyloxyethyl carbonate, 4-(2-methoxy)phenyl 2-benzyloxyethyl carbonate, N-(4-phenyl)-2-benzyloxyacetamide, 3-trimethylsilanylphenyl, 4-(2-methoxy)phenyl N-diethylcarbamate, 4-(2-chloro-6-methoxy)phenyl N-diethylcarbamate, 4-(2-methoxy)phenyl 2-[2-(2-methoxyethoxy)ethoxy]ethyl carbonate";
- the Z4 radical is independently hydrogen;
- the Z5 radical is independently hydrogen.

In a further preferred embodiment, novel pyrido[2,3-b]pyrazine derivatives of the general formula (I) are provided, where, in (B),
- the Z1 radical is independently "NZ14Z15"; where Z14 is hydrogen and Z15 is "—C(O)NH-alkyl";
- the Z2 radical is independently hydrogen;
- the Z3 radical is independently "substituted heteroaryl", where "substituted heteroaryl" is substituted by at least one substituent selected identically or differently from the group consisting of:
  (a) "—NHC(O)—NH-alkyl";
- the Z4 radical is independently hydrogen;
- the Z5 radical is independently hydrogen.

In a further preferred embodiment, novel pyrido[2,3-b]pyrazine derivatives of the general formula (I) are provided, where, in (B),
- the Z1 radical is independently selected from the group consisting of "—NHC(O)NH-ethyl";
- the Z2 radical is independently hydrogen;
- the Z3 radical is independently selected from the group consisting of "6-(3-ethylurea)pyridin-3-yl";
- the Z4 radical is independently hydrogen;
- the Z5 radical is independently hydrogen.

In a further preferred embodiment, novel pyrido[2,3-b]pyrazine derivatives of the general formula (I) are provided, where, in (C),
- the Z1 radical is independently "NZ14Z15"; where Z14 is hydrogen and Z15 is "—C(O)NH-alkyl";
- the Z2 radical is independently hydrogen;
- the Z3 radical is independently "substituted alkyl", where "substituted alkyl" is substituted by at least one substituent selected identically or differently from the group consisting of:
  (a) "aryl, heteroaryl, cycloalkyl, —N(alkyl)$_2$, —O-alkyl";
  where, optionally, the above substituents of substituent group (a) may in turn each independently be substituted by at least one substituent selected identically or differently from the group consisting of:
  (i) "halogen, F, Cl, Br, I";
- the Z4 radical is independently hydrogen;
- the Z5 radical is independently hydrogen.

In a further preferred embodiment, novel pyrido[2,3-b]pyrazine derivatives of the general formula (I) are provided, where, in (C),
- the Z1 radical is independently selected from the group consisting of "—NHC(O)NH-ethyl";
- the Z2 radical is independently hydrogen;
- the Z3 radical is independently selected from the group consisting of "phenylethynyl, thiophen-3-ylethynyl, cyclopropylethynyl, N-dimethylaminoprop-1-ynyl, 2-cyclohexylvinyl, 3-methoxypropenyl, benzyl, 2-(4-fluorophenyl)ethyl, 2-(4-fluorophenyl)vinyl";
the Z4 radical is independently hydrogen;
the Z5 radical is independently hydrogen.

In a further preferred embodiment, novel pyrido[2,3-b]pyrazine derivatives of the general formula (I) are provided, where, in (D),
the Z1 radical is independently "NZ14Z15"; where Z14 is hydrogen and Z15 is "—C(O)NH-alkyl";
the Z2 radical is independently hydrogen;
the Z3 radical is independently selected from the group consisting of:
  (1) "—NZ10Z11";
    where the Z10, Z11 radicals are each independently selected from the group consisting of:
    (a) "hydrogen, aryl";
      with the proviso that the above substituents of substituent group (a), when they are not hydrogen, are each independently substituted further by at least one substituent selected identically or differently from the group consisting of:
        (i) "cycloalkyl, heteroaryl, heterocyclylalkyl, —S(O)$_2$-alkyl, —NH—S(O)$_2$-alkyl, —C(O)NH-alkyl, —NH—C(O)-alkyl, —C(O)O-alkyl";
    (b) "—C(O)-aryl";
      where, optionally, the above substituents of substituent group (a) and/or substituent group (b) may each independently be substituted by at least one substituent selected identically or differently from the group consisting of:
        (i) "alkyl";
the Z4 radical is independently hydrogen;
the Z5 radical is independently hydrogen.

In a further preferred embodiment, novel pyrido[2,3-b]pyrazine derivatives of the general formula (I) are provided, where, in (D),
the Z1 radical is independently selected from the group consisting of "—NHC(O)NH-ethyl";
the Z2 radical is independently hydrogen;
the Z3 radical is independently selected from the group consisting of "4-methylbenzamide, 4-cyclohexylphenylamino, 4-methanesulphonylphenylamino, 3-(N-methanesulphonamide)-4-methylphenylamino, 3-N-methylbenzamideamino, 4-piperidin-1-ylmethylphenylamino, 4-thiophen-3-ylphenylamino, 4-N-acetamidophenylamino, 3-(ethyl benzoate)amino";
the Z4 radical is independently hydrogen;
the Z5 radical is independently hydrogen.

In a further preferred embodiment, novel pyrido[2,3-b]pyrazine derivatives of the general formula (I) are provided, where, in (E),
the Z1 radical is independently selected from the group consisting of:
  (a) "NZ24Z25"; where Z24 is hydrogen and Z25 is "—C(O)—C(O)—O-alkyl" or "—C(O)—C(O)—NH-alkyl" or "—C(O)—NH—O-alkyl";
    where, optionally, the above substituents of substituent group (a) may each independently be substituted by at least one substituent selected identically or differently from the group consisting of:
      (i) "—OSi(alkyl)$_3$, —OC(O)—NH-alkyl, —OC(O)—O-alkyl, —P(O)(O-alkyl)$_2$, —P(O)(OH)$_2$, —O-alkyl";
      where, optionally, the above substituents of substituent group (i) may also each independently be substituted further by at least one substituent selected identically or differently from the group consisting of:
        (ii) "heterocyclyl, OH, —N(alkyl)$_2$, —OC(O)-alkyl";
        where, optionally, the above substituents of substituent group (ii) may also each independently be substituted further by at least one substituent selected identically or differently from the group consisting of:
          (iii) "alkyl";
  (b) "NZ26Z27"; where Z26 is hydrogen and Z27 is "—C(O)—NH-alkyl";
    with the proviso that the above substituents of substituent group (b) are each independently substituted further by at least one substituent selected identically or differently from the group consisting of:
      (i) "—OSi(alkyl)$_3$, —OC(O)—NH-alkyl, —OC(O)—O-alkyl, —P(O)(O-alkyl)$_2$, —P(O)(OH)$_2$, —O-alkyl";
      where, optionally, the above substituents of substituent group (i) may also each independently be substituted further by at least one substituent selected identically or differently from the group consisting of:
        (ii) "heterocyclyl, OH, —N(alkyl)$_2$, —OC(O)-alkyl";
        where, optionally, the above substituents of substituent group (ii) may also each independently be substituted further by at least one substituent selected identically or differently from the group consisting of:
          (iii) "alkyl";
the Z2 radical is independently hydrogen;
the Z3 radical is independently selected from the group consisting of:
  (a) "aryl";
    where, optionally, the above substituents of substituent group (a) may each independently be substituted by at least one substituent selected identically or differently from the group consisting of:
      (i) "—O-alkyl, OH";
the Z4 radical is independently hydrogen;
the Z5 radical is independently hydrogen.

In a further preferred embodiment, novel pyrido[2,3-b]pyrazine derivatives of the general formula (I) are provided, where, in (E),
the Z1 radical is independently selected from the group consisting of "3-methoxy-1-ylurea, 3-(prop-1-yn-3-yl)-1-ylurea, 3-[4-(tert-butyldimethylsilanyloxy)butyl]-1-ylurea, 4-(N-ethyl carbamate)butyl-1-ylurea, 4-(methyl carbonate)butyl-1-ylurea, 4-(2,3-dihydroxypropyl carbonate)butyl-1-ylurea, 4-(2,2-dimethyl-[1,3]dioxolan-4-ylmethyl carbonate)butyl-1-ylurea, 4-(diethyl phosphate)butyl-1-ylurea, 4-(butyl phosphate)-1-ylurea, N-oxalic monoamide ethyl ester, N-ethyl-N'-oxalamide, 2-(diethyl phosphate)ethyl-1-ylurea, 2-(ethyl phosphate)-1-ylurea, 3-(2-diethylamino-ethoxy)propyl-1-ylurea, 4-[(2,2-dimethylpropionyloxymethoxy)phosphinoyloxymethyl 2,2-dimethylpropanoate]butyl-1-ylurea, 4-[1-(1-acetoxyethoxy)ethoxyphosphinoyloxy acetate]butyl-1-ylurea";
the Z2 radical is independently hydrogen;
the Z3 radical is independently selected from the group consisting of "phenyl, 4-hydroxy-3-methoxyphenyl";
the Z4 radical is independently hydrogen;
the Z5 radical is independently hydrogen.

A further aspect of the present application relates to novel compounds from the group of the pyrido[2,3-b]pyrazines of the general formula (II),

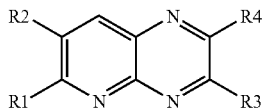

in which the substituents R1-R4 are each defined as follows:

R1 and R2 may each independently be hydrogen or NR5R6, with the prerequisite that when R1=NR5R6, R2=H, and when R2=NR5R6, R1=H, where R5 may be hydrogen, alkyl, R38, cycloalkyl, heterocyclyl, aryl, heteroaryl, alkylcycloalkyl, alkylheterocyclyl, alkylaryl or alkylheteroaryl, and the alkyl, cycloalkyl, heterocyclyl, aryl and heteroaryl, alkylcycloalkyl, alkylheterocyclyl, alkylaryl or alkylheteroaryl substituents may themselves in turn be mono- or polysubstituted, identically or differently, by F, Cl, Br, I, CN, $CF_3$, $NH_2$, NH-alkyl, NH-aryl, N(alkyl)$_2$, $NO_2$, SH, S-alkyl, OH, $OCF_3$, O(-alkylO)$_p$-alkyl, O-aryl, $OSO_3H$, $OP(O)(OH)_2$, $OP(O)(Oalkyl)_2$, $OP(O)(Oaryl)_2$, CHO, C(O)OH, C(O)OR12, C(O)NH$_2$, C(O)NHR12, C(O)NR12R13, $SO_3H$, $SO_2$alkyl, $SO_2$aryl, $P(O)(OH)_2$, $P(O)(Oalkyl)_2$, $P(O)(Oaryl)_2$, alkyl, cycloalkyl, heterocyclyl, aryl, heteroaryl, p may assume the value of 0, 1, 2, 3, 4 or 5 and the R12 and R13 radicals may each independently be alkyl, cycloalkyl, heterocyclyl, aryl, heteroaryl, alkylcycloalkyl, alkylheterocyclyl, alkylaryl or alkylheteroaryl, or R12 and R13 together may form a heterocyclyl ring and R6:

may be —C(Y)NR7R8 where Y may independently be O or S and R7 and R8 may each independently be hydrogen, unsubstituted or substituted alkyl, where the alkyl radical may be mono- or polysubstituted, identically or differently, by F, Cl, Br, I, $CF_3$, CN, $NH_2$, NH-alkyl, NH-cycloalkyl, NH-heterocyclyl, NH-aryl, NH-heteroaryl, NH-alkylcycloalkyl, NH-alkylheterocyclyl, NH-alkylaryl, NH-alkylheteroaryl, N(alkyl)$_2$, NHC(O)-alkyl, NHC(O)-cycloalkyl, NHC(O)-heterocyclyl, NHC(O)-aryl, NHC(O)-heteroaryl, NHC(O)-alkylaryl, NHC(O)-alkylheteroaryl, $NHSO_2$-alkyl, $NHSO_2$-cycloalkyl, $NHSO_2$-heterocyclyl, $NHSO_2$-aryl, $NHSO_2$-heteroaryl, $NHSO_2$-alkylaryl, $NHSO_2$-alkylheteroaryl, $NO_2$, SH, S-alkyl, S-cycloalkyl, S-heterocyclyl, S-aryl, S-heteroaryl, OH, $OCF_3$, O(-alkylO)$_p$-alkyl, O-cycloalkyl, O-heterocyclyl, O-aryl, O-heteroaryl, O-alkylcycloalkyl, O-alkylheterocyclyl, O-alkylaryl, O-alkylheteroaryl, OC(O)-alkyl, OC(O)-cycloalkyl, OC(O)-heterocyclyl, OC(O)-aryl, OC(O)-heteroaryl, OC(O)-alkylaryl, OC(O)-alkylheteroaryl, $OSO_3H$, $OSO_2$-alkyl, $OSO_2$-cycloalkyl, $OSO_2$-heterocyclyl, $OSO_2$-aryl, $OSO_2$-heteroaryl, $OSO_2$-alkylaryl, $OSO_2$-alkylheteroaryl, $OP(O)(OH)_2$, C(O)-alkyl, C(O)-aryl, C(O)-heteroaryl, $CO_2H$, $CO_2$-alkyl, $CO_2$-cycloalkyl, $CO_2$-heterocyclyl, $CO_2$-aryl, $CO_2$-heteroaryl, $CO_2$-alkylcycloalkyl, $CO_2$-alkylheterocyclyl, $CO_2$-alkylaryl, $CO_2$-alkylheteroaryl, C(O)—$NH_2$, C(O)NH-alkyl, C(O)NH-cycloalkyl, C(O)NH-heterocyclyl, C(O)NH-aryl, C(O)NH-heteroaryl, C(O)NH-alkylcycloalkyl, C(O)NH-alkylheterocyclyl, C(O)NH-alkylaryl, C(O)

NH-alkylheteroaryl, C(O)N(alkyl)$_2$, C(O)N(cycloalkyl)$_2$, C(O)N(aryl)$_2$, C(O)N(heteroaryl)$_2$, SO-alkyl, SO-aryl, $SO_2$-alkyl, $SO_2$-aryl, $SO_2NH_2$, $SO_2$NH-alkyl, $SO_2$NH-aryl, $SO_2$NH-heteroaryl, $SO_2$NH-alkylaryl, $SO_3H$, $SO_2O$-alkyl, $SO_2O$-aryl, $SO_2O$-alkylaryl, cycloalkyl, heterocyclyl, aryl or heteroaryl, where p may assume the value of 0, 1, 2, 3, 4 or 5, unsubstituted or substituted cycloalkyl, where the cycloalkyl radical may be mono- or polysubstituted, identically or differently, by F, Cl, Br, I, $NH_2$, NH-alkyl, NH-cycloalkyl, NH-heterocyclyl, NH-aryl, NH-heteroaryl, NH-alkylaryl, NH-alkylheteroaryl, N(alkyl)$_2$, NHC(O)-alkyl, NHC(O)-cycloalkyl, NHC(O)-heterocyclyl, NHC(O)-aryl, NHC(O)-heteroaryl, NHC(O)-alkylaryl, NHC(O)-alkylheteroaryl, $NHSO_2$-alkyl, $NHSO_2$-cycloalkyl, $NHSO_2$-heterocyclyl, $NHSO_2$-aryl, $NHSO_2$-heteroaryl, $NHSO_2$-alkylaryl, $NHSO_2$-alkylheteroaryl, OH, O(-alkylO)$_p$-alkyl, O-cycloalkyl, O-heterocyclyl, O-aryl, O-heteroaryl, O-alkylaryl, O-alkylheteroaryl, OC(O)-alkyl, OC(O)-cycloalkyl, OC(O)-heterocyclyl, OC(O)-aryl, OC(O)-heteroaryl, OC(O)-alkylaryl, OC(O)-alkylheteroaryl, $OSO_3H$, $OSO_2$-alkyl, $OSO_2$-cycloalkyl, $OSO_2$-heterocyclyl, $OSO_2$-aryl, $OSO_2$-heteroaryl, $OSO_2$-alkylaryl, $OSO_2$-alkylheteroaryl, $OP(O)(OH)_2$, $CO_2H$, $CO_2$-alkyl, $CO_2$-cycloalkyl, $CO_2$-heterocyclyl, $CO_2$-aryl, $CO_2$-heteroaryl, $CO_2$-alkylcycloalkyl, $CO_2$-alkylheterocyclyl, $CO_2$-alkylaryl, $CO_2$-alkylheteroaryl, C(O)—$NH_2$, C(O)NH-alkyl, C(O)NH-cycloalkyl, C(O)NH-heterocyclyl, C(O)NH-aryl, C(O)NH-heteroaryl, C(O)NH-alkylcycloalkyl, C(O)NH-alkylheterocyclyl, C(O)NH-alkylaryl, C(O)NH-alkylheteroaryl, C(O)N(alkyl)$_2$, C(O)N(cycloalkyl)$_2$, C(O)N(aryl)$_2$, C(O)N(heteroaryl)$_2$, alkyl, or aryl, where p may assume the value of 0, 1, 2, 3, 4 or 5, unsubstituted or substituted heterocyclyl, where the heterocyclyl radical may be mono- or polysubstituted, identically or differently, by OH, O-alkyl, O-aryl, $NH_2$, NH-alkyl, NH-aryl, alkyl, alkylaryl or aryl, unsubstituted or substituted aryl, where the aryl radical may be mono- or polysubstituted, identically or differently, by F, Cl, Br, I, $CF_3$, CN, $NH_2$, NH-alkyl, NH—R38, NH-cycloalkyl, NH-heterocyclyl, NH-aryl, NH-heteroaryl, NH-alkylcycloalkyl, NH-alkylheterocyclyl, NH-alkylaryl, NH-alkylheteroaryl, NH-alkylNH$_2$, NH-alkylOH, N(alkyl)$_2$, NHC(O)-alkyl, NHC(O)—R38, NHC(O)-cycloalkyl, NHC(O)-heterocyclyl, NHC(O)-aryl, NHC(O)-heteroaryl, NHC(O)-alkylaryl, NHC(O)-alkylheteroaryl, $NHSO_2$-alkyl, $NHSO_2$-cycloalkyl, $NHSO_2$-heterocyclyl, $NHSO_2$-aryl, $NHSO_2$-heteroaryl, $NHSO_2$-alkylaryl, $NHSO_2$-alkylheteroaryl, $NO_2$, SH, S-alkyl, S-cycloalkyl, S-heterocyclyl, S-aryl, S-heteroaryl, OH, $OCF_3$, O(-alkylO)$_p$-alkyl, O—R38, O-cycloalkyl, O-heterocyclyl, O-aryl, O-heteroaryl, O-alkylcycloalkyl, O-alkylheterocyclyl, O-alkylaryl, O-alkylheteroaryl, O-alkylOH, O—(CH$_2$), —O, OC(O)-alkyl, OC(O)—R38, OC(O)-cycloalkyl, OC(O)-heterocyclyl, OC(O)-aryl, OC(O)-heteroaryl, OC(O)-alkylaryl, OC(O)-alkylheteroaryl, $OSO_3H$, $OSO_2$-alkyl, $OSO_2$-cycloalkyl, $OSO_2$-heterocyclyl, $OSO_2$-aryl, $OSO_2$-heteroaryl, $OSO_2$-alkylaryl, $OSO_2$-alkylheteroaryl, $OP(O)(OH)_2$, C(O)-alkyl, C(O)-aryl, C(O)-heteroaryl, $CO_2H$, $CO_2$-alkyl, $CO_2$—R38, $CO_2$-cycloalkyl, $CO_2$-heterocyclyl, $CO_2$-aryl, $CO_2$-heteroaryl, $CO_2$-alkylcycloalkyl, $CO_2$-alkylheterocyclyl, $CO_2$-alkylaryl, $CO_2$-alkylheteroaryl, C(O)—$NH_2$, C(O)

NH-alkyl, C(O)NH—R38, C(O)NH-cycloalkyl, C(O)NH-heterocyclyl, C(O)NH-aryl, C(O)NH-heteroaryl, C(O)NH-alkylcycloalkyl, C(O)NH-alkylheterocyclyl, C(O)NH-alkylaryl, C(O)NH-alkylheteroaryl, C(O)N(alkyl)$_2$, C(O)N(cycloalkyl)$_2$, C(O)N(aryl)$_2$, C(O)N(heteroaryl)$_2$, SO-alkyl, SO-aryl, SO$_2$-alkyl, SO$_2$-aryl, SO$_2$NH$_2$, SO$_2$NH-alkyl, SO$_2$NH-aryl, SO$_2$NH-heteroaryl, SO$_2$NH-alkylaryl, SO3H, SO$_2$O-alkyl, SO$_2$O-aryl, SO$_2$O-alkylaryl, alkyl, cycloalkyl, heterocyclyl, aryl or heteroaryl, where p may assume the value of 0, 1, 2, 3, 4 or 5 and n the value of 1, 2 or 3, unsubstituted or substituted heteroaryl, where the heteroaryl radical may be mono- or polysubstituted, identically or differently, by F, Cl, Br, I, CF$_3$, CN, NH$_2$, NH-alkyl, NH—R38, NH-cycloalkyl, NH-heterocyclyl, NH-aryl, NH-heteroaryl, NH-alkylcycloalkyl, NH-alkylheterocyclyl, NH-alkylaryl, NH-alkylheteroaryl, NH-alkylNH$_2$, NH-alkylOH, N(alkyl)$_2$, NHC(O)-alkyl, NHC(O)—R38, NHC(O)-cycloalkyl, NHC(O)-heterocyclyl, NHC(O)-aryl, NHC(O)-heteroaryl, NHC(O)-alkylaryl, NHC(O)-alkylheteroaryl, NHSO$_2$-alkyl, NHSO$_2$-cycloalkyl, NHSO$_2$-heterocyclyl, NHSO$_2$-aryl, NHSO$_2$-heteroaryl, NHSO$_2$-alkylaryl, NHSO$_2$-alkylheteroaryl, NO$_2$, SH, S-alkyl, S-aryl, S-heteroaryl, OH, OCF$_3$, O(-alkylO)$_p$-alkyl, O—R38, O-cycloalkyl, O-heterocyclyl, O-aryl, O-heteroaryl, O-alkylcycloalkyl, O-alkylheterocyclyl, O-alkylaryl, O-alkylheteroaryl, OC(O)-alkyl, OC(O)—R38, OC(O)-cycloalkyl, OC(O)-heterocyclyl, OC(O)-aryl, OC(O)-heteroaryl, OC(O)-alkylaryl, OC(O)-alkylheteroaryl, OSO$_3$H, OSO$_2$-alkyl, OSO$_2$-cycloalkyl, OSO$_2$-heterocyclyl, OSO$_2$-aryl, OSO$_2$-heteroaryl, OSO$_2$-alkylaryl, OSO$_2$-alkylheteroaryl, OP(O)(OH)$_2$, C(O)-alkyl, C(O)-aryl, C(O)-heteroaryl, CO$_2$H, CO$_2$-alkyl, CO$_2$—R38, CO$_2$-cycloalkyl, CO$_2$-heterocyclyl, CO$_2$-aryl, CO$_2$-heteroaryl, CO$_2$-alkylcycloalkyl, CO$_2$-alkylheterocyclyl, CO$_2$-alkylaryl, CO$_2$-alkylheteroaryl, C(O)—NH$_2$, C(O)NH-alkyl, C(O)NH—R38, C(O)NH-cycloalkyl, C(O)NH-heterocyclyl, C(O)NH-aryl, C(O)NH-heteroaryl, C(O)NH-alkylcycloalkyl, C(O)NH-alkylheterocyclyl, C(O)NH-alkylaryl, C(O)NH-alkylheteroaryl, C(O)N(alkyl)$_2$, C(O)N(cycloalkyl)$_2$, C(O)N(aryl)$_2$, C(O)N(heteroaryl)$_2$, SO$_2$NH$_2$, SO$_2$NH-alkyl, SO$_2$NH-aryl, SO$_2$NH-heteroaryl, SO$_2$NH-alkylaryl, SO$_3$H, SO$_2$O-alkyl, SO$_2$O-aryl, SO$_2$O-alkylaryl, alkyl, cycloalkyl, heterocyclyl, aryl or heteroaryl, where p may assume the value of 0, 1, 2, 3, 4 or 5, —C(O)—R39 where R39 may be alkyl, aryl or heteroaryl, and the alkyl, aryl and heteroaryl substituents may themselves in turn be substituted, or R7 and R8 together may form a heterocyclyl ring, R3 and R4 may each independently be:

hydrogen, where R3 and R4 are not simultaneously hydrogen, substituted alkyl, where the alkyl radical may be mono- or polysubstituted, identically or differently, by F, Cl, Br, I, CN, CF$_3$, NH$_2$, NH-alkyl, NH-aryl, N(alkyl)$_2$, SH, S-alkyl, OH, OCF$_3$, O(-alkylO)$_p$-alkyl, O-aryl, OSO$_3$H, OP(O)(OH)$_2$, OP(O)(Oalkyl)$_2$, OP(O)(Oaryl)$_2$, C(O)OH, C(O)OR14, C(O)NH$_2$, C(O)NHR14, C(O)NR14R15, SO$_3$H, SO$_2$alkyl, SO$_2$aryl, P(O)(OH)$_2$, P(O)(Oalkyl)$_2$, P(O)(Oaryl)$_2$, cycloalkyl, heterocyclyl, aryl or heteroaryl, where p may assume the value of 0, 1, 2, 3, 4 or 5 and the R14 and R15 radicals may each independently be alkyl, cycloalkyl, heterocyclyl, aryl, heteroaryl, alkylcycloalkyl, alkylheterocyclyl, alkylaryl or alkylheteroaryl, or R14 and R15 together may form a heterocyclyl ring, substituted aryl, where the aryl radical is mono- or polysubstituted, identically or differently, by substituents selected from the group of NH-alkyl, NH-cycloalkyl, NH-heterocyclyl, NH-aryl, NH-heteroaryl, NH-alkylcycloalkyl, NH-alkylheterocyclyl, NH-alkylaryl, NH-alkylheteroaryl, N(alkyl)$_2$, N(aryl)$_2$, NHC(O)-alkyl, NHC(O)-cycloalkyl, NHC(O)-heterocyclyl, NHC(O)-aryl, NHC(O)-heteroaryl, NHC(O)-alkylaryl, NHC(O)-alkylheteroaryl, NHSO$_2$-alkyl, NHSO$_2$-cycloalkyl, NHSO$_2$-heterocyclyl, NHSO$_2$-aryl, NHSO$_2$-heteroaryl, NHSO$_2$-alkylaryl, NHSO$_2$-alkylheterocyclyl, S-alkyl, S-aryl, S-heteroaryl, O-alkyl, O-cycloalkyl, O-heterocyclyl, O-aryl, O-heteroaryl, O-alkylcycloalkyl, O-alkylheterocyclyl, O-alkylaryl, O-alkylheteroaryl, OC(O)-alkyl, OC(O)-cycloalkyl, OC(O)-heterocyclyl, OC(O)-aryl, OC(O)-heteroaryl, OC(O)-alkylaryl, OC(O)-alkylheterocyclyl, OSO$_2$-alkyl, OSO$_2$-cycloalkyl, OSO$_2$-heterocyclyl, OSO$_2$-aryl, OSO$_2$-heteroaryl, OSO$_2$-alkylaryl, OSO$_2$-alkylheterocyclyl, C(O)-alkyl, C(O)-aryl, C(O)-heteroaryl, CO$_2$-alkyl, CO$_2$-cycloalkyl, CO$_2$-heterocyclyl, CO$_2$-aryl, CO$_2$-heteroaryl, CO$_2$-alkylcycloalkyl, CO$_2$-alkylheterocyclyl, CO$_2$-alkylaryl, CO$_2$-alkylheteroaryl, C(O)NH-alkyl, C(O)NH-cycloalkyl, C(O)NH-heterocyclyl, C(O)NH-aryl, C(O)NH-heteroaryl, C(O)NH-alkylcycloalkyl, C(O)NH-alkylheterocyclyl, C(O)NH-alkylaryl, C(O)NH-alkylheteroaryl, C(O)N(alkyl)$_2$, C(O)N(cycloalkyl)$_2$, C(O)N(aryl)$_2$, C(O)N(heteroaryl)$_2$, SO-alkyl, SO-aryl, SO$_2$-alkyl, SO$_2$-aryl, SO$_2$NH-alkyl, SO$_2$NH-aryl, SO$_2$NH-heteroaryl, SO$_2$NH-alkylaryl, SO$_2$O-alkyl, SO$_2$O-aryl, SO$_2$O-alkylaryl, alkyl, cycloalkyl, heterocyclyl, aryl, heteroaryl and the alkyl, cycloalkyl, heterocyclyl, aryl, heteroaryl, alkylcycloalkyl, alkylheterocyclyl, alkylaryl and alkylheteroaryl substituents are themselves in turn substituted by O(-alkylO)$_p$-alkyl, OP(O)(Oalkyl)$_2$, OP(O)(Oaryl)$_2$, C(O)OR16, C(O)NH$_2$, C(O)NHR16, C(O)NR16R17, SO$_2$alkyl, SO$_2$aryl, P(O)(OH)$_2$, P(O)(Oalkyl)$_2$, P(O)(Oaryl)$_2$, cycloalkyl, heterocyclyl, aryl, heteroaryl or alkylaryl, where p may assume the value of 1, 2, 3, 4 or 5, and the R16 and R17 radicals may each independently be alkyl, cycloalkyl, heterocyclyl, aryl, heteroaryl, alkylcycloalkyl, alkylheterocyclyl, alkylaryl or alkylheteroaryl, or R16 and R17 together may form a heterocyclyl ring, with the prerequisite that when R3 or R4 is alkylheterocyclyl-substituted aryl, R4 or R3 is correspondingly≠aryl, and where the aryl radical is mono- or polysubstituted, identically or differently, by substituents selected from the group of NR20-alkyl, NH—R38, NHC(O)—R38, NR19C(O)-alkyl, NR19C(O)-cycloalkyl, NR19C(O)-heterocyclyl, NR19C(O)-aryl, NR19C(O)-heteroaryl, NR18C(O)-alkylcycloalkyl, NR18C(O)-alkylheterocyclyl, NR19C(O)-alkylaryl, NR19C(O)-alkylheteroaryl, NR18C(O)O—R19, NR18C(O)NR18R18, O—R38, OC(O)—R38, OC(O)-alkylcycloalkyl, OC(O)-alkylheterocyclyl, OC(O)O—R19, OC(O)NR18R18, OP(O)(Oalkyl)$_2$, OP(O)(Oaryl)$_2$, C(O)O—R38, C(O)NH—R38, C(O)NR20-alkyl, C(O)NR19-alkylR21, C(O)NR18O—R18, C(O)NR18NR18R18 and the alkyl, cycloalkyl, heterocyclyl, aryl, heteroaryl, alkylcycloalkyl, alkylheterocyclyl, alkylaryl and alkylheteroaryl substituents may themselves in turn be substituted by F, Cl, Br, I, CN, CF$_3$, NH$_2$, NH-alkyl, NH-aryl, N(alkyl)$_2$, NO$_2$, SH, S-alkyl, OH, OCF$_3$, O(-alkylO)$_p$-alkyl, O-aryl, OSO$_3$H, OP(O)(OH)$_2$, OP(O)(Oalkyl)$_2$, OP(O)(Oaryl)$_2$, CHO, C(O)OH, C(O)OR22, C(O)NH$_2$, C(O)NHR22, C(O)NR22R23, SO$_3$H, SO$_2$alkyl, SO$_2$aryl, P(O)(OH)$_2$, P(O)(Oalkyl)$_2$, P(O)(Oaryl)$_2$, alkyl, cycloalkyl, heterocyclyl, aryl, heteroaryl or alkylaryl, where p may assume the value of 0, 1, 2, 3, 4 or 5 and the R22 and R23 radicals may each independently be alkyl, cycloalkyl, heterocyclyl, aryl, heteroaryl, alkylcycloalkyl, alkylheterocyclyl, alkylaryl or alkylheteroaryl, or R22 and R23 together may form a heterocyclyl ring, substituted heteroaryl, where the heteroaryl radical is mono- or polysubstituted, identically or differently, by substituents selected from the group of NH-alkyl, NH-cycloalkyl, NH-heterocyclyl, NH-aryl, NH-heteroaryl, NH-alkylcycloalkyl, NH-alkylheterocyclyl, NH-alkylaryl, NH-alkylheteroaryl, N(alkyl)$_2$, N(aryl)$_2$, NHC(O)-alkyl, NHC(O)-cycloalkyl, NHC(O)-heterocyclyl, NHC(O)-aryl, NHC(O)-heteroaryl, NHC(O)-alkylaryl, NHC(O)-alkylheteroaryl, NHSO$_2$-alkyl, NHSO$_2$-cycloalkyl, NHSO$_2$-heterocyclyl, NHSO$_2$-aryl, NHSO$_2$-heteroaryl, NHSO$_2$-alkylaryl, NHSO$_2$-alkylheteroaryl, S-alkyl, S-aryl, S-heteroaryl, O-alkyl, O-cycloalkyl, O-aryl, O-heteroaryl, O-alkylcycloalkyl, O-alkylheterocyclyl, O-alkylaryl, O-alkylheteroaryl, OC(O)-alkyl, OC(O)-cycloalkyl, OC(O)-heterocyclyl, OC(O)-aryl, OC(O)-heteroaryl, OC(O)-alkylaryl, OC(O)-alkylheteroaryl, OSO$_2$-alkyl, OSO$_2$-cycloalkyl, OSO$_2$-heterocyclyl, OSO$_2$-aryl, OSO$_2$-heteroaryl, OSO$_2$-alkylaryl, OSO$_2$-alkylheteroaryl, C(O)-alkyl, C(O)-aryl, C(O)-heteroaryl, CO$_2$-alkyl, CO$_2$-cycloalkyl, CO$_2$-heterocyclyl, CO$_2$-aryl, CO$_2$-heteroaryl, CO$_2$-alkylcycloalkyl, CO$_2$-alkylheterocyclyl, CO$_2$-alkylaryl, CO$_2$-alkylheteroaryl, C(O)NH-alkyl, C(O)NH-cycloalkyl, C(O)NH-heterocyclyl, C(O)NH-aryl, C(O)NH-heteroaryl, C(O)NH-alkylcycloalkyl, C(O)NH-alkylheterocyclyl, C(O)NH-alkylaryl, C(O)NH-alkylheteroaryl, C(O)N(alkyl)$_2$, C(O)N(cycloalkyl)$_2$, C(O)N(aryl)$_2$, C(O)N(heteroaryl)$_2$, SO$_2$NH-alkyl, SO$_2$NH-aryl, SO$_2$NH-heteroaryl, SO$_2$NH-alkylaryl, SO$_2$O-alkyl, SO$_2$O-aryl, SO$_2$O-alkylaryl, alkyl, cycloalkyl, heterocyclyl, aryl, heteroaryl, and the alkyl, cycloalkyl, heterocyclyl, aryl, heteroaryl, alkylcycloalkyl, alkylheterocyclyl, alkylaryl and alkylheteroaryl substituents are themselves in turn substituted by O(-alkylO)$_p$-alkyl, OP(O)(Oalkyl)$_2$, OP(O)(Oaryl)$_2$, C(O)OR16, C(O)NH$_2$, C(O)NHR16, C(O)NR16R17, SO$_2$alkyl, SO$_2$aryl, P(O)(OH)$_2$, P(O)(Oalkyl)$_2$, P(O)(Oaryl)$_2$, cycloalkyl, heterocyclyl, aryl, heteroaryl or alkylaryl, where p may assume the value of 1, 2, 3, 4 or 5 and the R16 and R17 radicals may each independently be alkyl, cycloalkyl, heterocyclyl, aryl, heteroaryl, alkylcycloalkyl, alkylheterocyclyl, alkylaryl or alkylheteroaryl, or R16 and R17 together may form a heterocyclyl ring, and where the heteroaryl radical is mono- or polysubstituted, identically or differently, by substituents selected from the group of NR20-alkyl, NH—R38, NHC(O)—R38, NR19C(O)-alkyl, NR19C(O)-cycloalkyl, NR19C(O)-heterocyclyl, NR19C(O)-aryl, NR19C(O)-heteroaryl, NR18C(O)-alkylcycloalkyl, NR18C(O)-alkylheterocyclyl, NR19C(O)-alkylaryl, NR19C(O)-alkylheteroaryl, NR18C(O)O—R19, NR18C(O)NR18R18, NHSO$_2$-alkylheterocyclyl, O—R38, O-heterocyclyl, OC(O)—R38, OC(O)-alkylcycloalkyl, OC(O)-alkylheterocyclyl, OC(O)O—R19, OC(O)NR18R18, OP(O)(Oalkyl)$_2$, OP(O)(Oaryl)$_2$, C(O)O—R38, C(O)NH—R38, C(O)NR20-alkyl, C(O)NR19-alkylR21, C(O)NR18O—R18, C(O)NR18NR18R18, and the alkyl, cycloalkyl, heterocyclyl, aryl, heteroaryl, alkylcycloalkyl, alkylheterocyclyl, alkylaryl and alkylheteroaryl substituents may themselves in turn be substituted by F, Cl, Br, I, CN, CF$_3$, NH$_2$, NH-alkyl, NH-aryl, N(alkyl)$_2$, NO$_2$, SH, S-alkyl, OH, OCF$_3$, O(-alkylO)$_p$-alkyl, O-aryl, OSO$_3$H, OP(O)(OH)$_2$, OP(O)(Oalkyl)$_2$, OP(O)(Oaryl)$_2$, CHO, C(O)OH, C(O)OR22, C(O)NH$_2$, C(O)NHR22, C(O)NR22R23, SO$_3$H, SO$_2$alkyl, SO$_2$aryl, P(O)(OH)$_2$, P(O)(Oalkyl)$_2$, P(O)(Oaryl)$_2$, alkyl, cycloalkyl, heterocyclyl, aryl, heteroaryl or alkylaryl, where p may assume the value of 0, 1, 2, 3, 4 or 5 and the R22 and R23 radicals may each independently be alkyl, cycloalkyl, heterocyclyl, aryl, heteroaryl, alkylcycloalkyl, alkylheterocyclyl, alkylaryl or alkylheteroaryl, or R22 and R23 together may form a heterocyclyl ring, NR24R25 where R24 may be—C(O)—R26, —SO$_2$R26, —C(O)OR26 or —C(O)—NR27R28 and where R25 may be hydrogen, alkyl, cycloalkyl, aryl or heteroaryl and where R26 may be alkyl, cycloalkyl, heterocyclyl, aryl, heteroaryl, alkylcycloalkyl, alkylheterocyclyl, alkylaryl, alkylheteroaryl, and R27 and R28 may each independently be hydrogen, alkyl, cycloalkyl, heterocyclyl, aryl, heteroaryl, alkylcycloalkyl, alkylheterocyclyl, alkylaryl, alkylheteroaryl, or R27 and R28 together may form a heterocyclyl ring and the alkyl, cycloalkyl, heterocyclyl, aryl and heteroaryl, alkylcycloalkyl, alkylheterocyclyl, alkylaryl or alkylheteroaryl substituents may themselves in turn be substituted, and R18 may be hydrogen, alkyl, cycloalkyl, heterocyclyl, aryl, heteroaryl, alkylcycloalkyl, alkylheterocyclyl, alkylaryl or alkylheteroaryl, and R19 may be alkyl, cycloalkyl, heterocyclyl, aryl, heteroaryl, alkylcycloalkyl, alkylheterocyclyl, alkylaryl or alkylheteroaryl, and R20 may be cycloalkyl, heterocyclyl, aryl, heteroaryl, alkylcycloalkyl, alkylheterocyclyl, alkylaryl or alkylheteroaryl, and R21 may be cycloalkyl, heterocyclyl, aryl, heteroaryl, and R38 may be alkyl, where the alkyl radical may be saturated or unsaturated, straight-chain or branched, having from 9 to 30 carbon atoms, i.e. C$_{9-30}$-alkanyls, C$_{9-30}$-alkenyls and C$_{9-30}$-alkynyls. Alkenyls have at least one C—C double bond and alkynyls have at least one C—C triple bond, where the alkenyls may be present either in (E)- or in (Z)-conformation. It is preferred that the alkyl radical is selected from the group which comprises nonyl, decyl, dodecyl, hexadecyl, octadecyl, eicosyl, henicosyl, docosyl, tetracosyl, nonacosyl, octadecenyl, docosenyl, tetracosenyl and octadecynyl.

In a further aspect, the present application describes novel compounds from the group of the pyrido[2,3-b]pyrazines of the general formula (II),

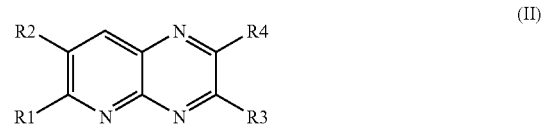

which the substituents R1-R4 are each defined as follows:

R1 and R2 may each independently be hydrogen or NR5R6, with the prerequisite that when R1=NR5R6, R2=H, and when R2=NR5R6, R1=H, where R5 may be hydrogen, alkyl, R38, cycloalkyl, heterocyclyl, aryl, heteroaryl, alkylcycloalkyl, alkylheterocyclyl, alkylaryl or alkylheteroaryl, and the alkyl, cycloalkyl, heterocyclyl, aryl and heteroaryl, alkylcycloalkyl, alkylheterocyclyl, alkylaryl or alkylheteroaryl substituents may themselves in turn be mono- or polysubstituted, identically or differently, by F, Cl, Br, I, CN, CF$_3$, NH$_2$, NH-alkyl, NH-aryl, N(alkyl)$_2$, NO$_2$, SH, S-alkyl, OH, OCF$_3$, O(-alkylO)$_p$-alkyl, O-aryl, OSO$_3$H, OP(O)(OH)$_2$, OP(O)(Oalkyl)$_2$, OP(O)(Oaryl)$_2$, CHO, C(O)OH, C(O)NH$_2$, C(O)OR12, C(O)NHR12, C(O)NR12R13, SO$_3$H, SO$_2$alkyl, SO$_2$aryl, P(O)(OH)$_2$, P(O)(Oalkyl)$_2$, P(O)(Oaryl)$_2$, alkyl, cycloalkyl, heterocyclyl, aryl, heteroaryl, p may assume the value of 0, 1, 2, 3, 4 or 5 and the R12 and R13 radicals may each independently be alkyl, cycloalkyl, heterocyclyl, aryl, heteroaryl, alkylcycloalkyl, alkylheterocyclyl, alkylaryl or alkylheteroaryl, or R12 and R13 together may form a heterocyclyl ring and R6:

may be —C(O)NR9-Y—R10 where Y may independently be O or NR11 and R9 may be hydrogen, alkyl, cycloalkyl, heterocyclyl, aryl, heteroaryl, alkylcycloalkyl, alkylheterocyclyl, alkylaryl, alkylheteroaryl, and the alkyl, cycloalkyl, heterocyclyl, aryl and heteroaryl, alkylcycloalkyl, alkylheterocyclyl, alkylaryl or alkylheteroaryl substituents may themselves be substituted, and R10 and R11 may each independently be hydrogen, unsubstituted or substituted alkyl, unsubstituted or substituted cycloalkyl, unsubstituted or substituted heterocyclyl, where the heterocyclyl radical may be mono- or polysubstituted, identically or differently, by OH, O-alkyl, O-aryl, NH$_2$, NH-alkyl, NH-aryl, alkyl, alkylaryl or aryl, unsubstituted or substituted aryl, where the aryl radical may be mono- or polysubstituted, identically or differently, by F, Cl, Br, I, CF$_3$, CN, NH$_2$, NH-alkyl, NH—R38, NH-cycloalkyl, NH-heterocyclyl, NH-aryl, NH-heteroaryl, NH-alkylcycloalkyl, NH-alkylheterocyclyl, NH-alkylaryl, NH-alkylheteroaryl, NH-alkylNH$_2$, NH-alkylOH, N(alkyl)$_2$, NHC(O)-alkyl, NHC(O)—R38, NHC(O)-cycloalkyl, NHC(O)-heterocyclyl, NHC(O)-aryl, NHC(O)-heteroaryl, NHC(O)-alkylaryl, NHC(O)-alkylheteroaryl, NHSO$_2$-alkyl, NHSO$_2$-cycloalkyl, NHSO$_2$-heterocyclyl, NHSO$_2$-aryl, NHSO$_2$-heteroaryl, NHSO$_2$-alkylaryl, NHSO$_2$-alkylheteroaryl, NO$_2$, SH, S-alkyl, S-cycloalkyl, S-heterocyclyl, S-aryl, S-heteroaryl, OH, OCF$_3$, O(-alkylO)$_p$-alkyl, O—R38, O-cycloalkyl, O-heterocyclyl, O-aryl, O-heteroaryl, O-alkylcycloalkyl, O-alkylheterocyclyl, O-alkylaryl, O-alkylheteroaryl, O-alkylOH, O—(CH$_2$)$_n$—O, OC(O)-alkyl, OC(O)—R38, OC(O)-cycloalkyl, OC(O)-heterocyclyl, OC(O)-aryl, OC(O)-heteroaryl, OC(O)-alkylaryl, OC(O)-alkylheteroaryl, OSO$_3$H, OSO$_2$-alkyl, OSO$_2$-cycloalkyl, OSO$_2$-heterocyclyl, OSO$_2$-aryl, OSO$_2$-heteroaryl, OSO$_2$-alkylaryl, OSO$_2$-alkylheteroaryl, OP(O)(OH)$_2$, C(O)-alkyl, C(O)-aryl, C(O)-heterocyclyl, CO$_2$H, CO$_2$-alkyl, CO$_2$—R38, CO$_2$-cycloalkyl, CO$_2$-heterocyclyl, CO$_2$-aryl, CO$_2$-heteroaryl, CO$_2$-alkylcycloalkyl, CO$_2$-alkylheterocyclyl, CO$_2$-alkylaryl, CO$_2$-alkylheteroaryl, C(O)—NH$_2$, C(O)NH-alkyl, C(O)NH—R38, C(O)NH-cycloalkyl, C(O)NH-heterocyclyl, C(O)NH-aryl, C(O)NH-heteroaryl, C(O)NH-alkylcycloalkyl, C(O)NH-alkylheterocyclyl, C(O)NH-alkylaryl, C(O)NH-alkylheteroaryl, C(O)N(alkyl)$_2$, C(O)N(cycloalkyl)$_2$, C(O)N(aryl)$_2$, C(O)N(heteroaryl)$_2$, SO$_2$NH$_2$, SO$_2$NH-alkyl, SO$_2$NH-aryl, SO$_2$NH-heteroaryl, SO$_2$NH-alkylaryl, SO$_3$H, SO$_2$O-alkyl, SO$_2$O-aryl, SO$_2$O-alkylaryl, alkyl, cycloalkyl, heterocyclyl, aryl or heteroaryl, where p may assume the value of 0, 1, 2, 3, 4 or 5 and n the value of 1, 2 or 3, unsubstituted or substituted heteroaryl, where the heteroaryl radical may be mono- or polysubstituted, identically or differently, by F, Cl, Br, I, CF$_3$, CN, NH$_2$, NH-alkyl, NH—R38, NH-cycloalkyl, NH-heterocyclyl, NH-aryl, NH-heteroaryl, NH-alkylcycloalkyl, NH-alkylheterocyclyl, NH-alkylaryl, NH-alkylheteroaryl, NH-alkylNH$_2$, NH-alkylOH, N(alkyl)$_2$, NHC(O)-alkyl, NHC(O)—R38, NHC(O)-cycloalkyl, NHC(O)-heterocyclyl, NHC(O)-aryl, NHC(O)-heteroaryl, NHC(O)-alkylaryl, NHC(O)-alkylheteroaryl, NHSO$_2$-alkyl, NHSO$_2$-cycloalkyl, NHSO$_2$-heterocyclyl, NHSO$_2$-aryl, NHSO$_2$-heteroaryl, NHSO$_2$-alkylaryl, NHSO$_2$-alkylheteroaryl, NO$_2$, SH, S-alkyl, S-aryl, S-heteroaryl, OH, OCF$_3$, O(-alkylO)$_p$-alkyl, O—R38, O-cycloalkyl, O-heterocyclyl, O-aryl, O-heteroaryl, O-alkylcycloalkyl, O-alkylheterocyclyl, O-alkylaryl, O-alkylheteroaryl, OC(O)-alkyl, OC(O)—R38, OC(O)-cycloalkyl, OC(O)-heterocyclyl, OC(O)-aryl, OC(O)-heteroaryl, OC(O)-alkylaryl, OC(O)-alkylheteroaryl, OSO$_3$H, OSO$_2$-alkyl, OSO$_2$-cycloalkyl, OSO$_2$-heterocyclyl, OSO$_2$-aryl, OSO$_2$-heteroaryl, OSO$_2$-alkylaryl, OSO$_2$-alkylheteroaryl, OP(O)(OH)$_2$, C(O)-alkyl, C(O)-aryl, C(O)-heterocyclyl, CO$_2$H, CO$_2$-alkyl, CO$_2$—R38, CO$_2$-cycloalkyl, CO$_2$-heterocyclyl, CO$_2$-aryl, CO$_2$-heteroaryl, CO$_2$-alkylcycloalkyl, CO$_2$-alkylheterocyclyl, CO$_2$-alkylaryl, CO$_2$-alkylheteroaryl, C(O)—NH$_2$, C(O)NH-alkyl, C(O)NH—R38, C(O)NH-cycloalkyl, C(O)NH-heterocyclyl, C(O)NH-aryl, C(O)NH-heteroaryl, C(O)NH-alkylcycloalkyl, C(O)NH-alkylheterocyclyl, C(O)NH-alkylaryl, C(O)NH-alkylheteroaryl, C(O)N(alkyl)$_2$, C(O)N(cycloalkyl)$_2$, C(O)N(aryl)$_2$, C(O)N(heteroaryl)$_2$, SO$_2$NH$_2$, SO$_2$NH-alkyl, SO$_2$NH-aryl, SO$_2$NH-heteroaryl, SO$_2$NH-alkylaryl, SO$_3$H, SO$_2$O-alkyl, SO$_2$O-aryl, SO$_2$O-alkylaryl, alkyl, cycloalkyl, heterocyclyl, aryl or heteroaryl, where p may assume the value of 0, 1, 2, 3, 4 or 5, or R10 and R11 together may form a heterocyclyl ring, R3 and R4 may each independently be:

hydrogen hydroxyl halogen such as fluorine, chlorine, bromine, iodine unsubstituted or substituted alkyl, where the alkyl radical may be mono- or polysubstituted, identically or differently, by F, Cl, Br, I, CN, CF$_3$, NH$_2$, NH-alkyl, NH-aryl, N(alkyl)$_2$, SH, S-alkyl, OH, OCF$_3$, O(-alkylO)$_p$-alkyl, O-aryl, OSO$_3$H, OP(O)(OH)$_2$, OP(O)(Oalkyl)$_2$, OP(O)(Oaryl)$_2$, C(O)OH, C(O)OR14, C(O)NH$_2$, C(O)NHR14, C(O)NR14R15, SO$_3$H, SO$_2$alkyl, SO$_2$aryl, P(O)(OH)$_2$, P(O)(Oalkyl)$_2$, P(O)(Oaryl)$_2$, cycloalkyl, heterocyclyl, aryl or heteroaryl, where p may assume the value of 0, 1, 2, 3, 4 or 5 and the R14 and R15 radicals may each independently be alkyl, cycloalkyl, heterocyclyl, aryl, heteroaryl, alkylcycloalkyl, alkylheterocyclyl, alkylaryl or alkylheteroaryl, or R14 and R15 together may form a heterocyclyl ring, unsubstituted or substituted aryl, where the aryl radical may be mono- or polysubstituted, identically or differently, by F, Cl, Br, I, CF$_3$, CN, NH$_2$, NH-alkyl, NH—R38, NH-cycloalkyl, NH-heterocyclyl, NH-aryl, NH-heteroaryl, NH-alkylcycloalkyl, NH-alkylheterocyclyl, NH-alkylaryl, NH-alkylheteroaryl, N(alkyl)$_2$, N(aryl)$_2$, NR20-alkyl, NHC(O)-alkyl, NHC(O)—R38, NR19(O)-alkyl, NHC(O)-cycloalkyl, NR19C(O)-cycloalkyl, NHC(O)-heterocyclyl, NR19C(O)-heterocyclyl, NHC(O)-aryl, NR19C(O)-aryl, NHC(O)-heteroaryl, NR19C(O)-heteroaryl, NR18C(O)-alkylcycloalkyl, NR18C(O)-alkylheterocyclyl, NHC(O)-alkylaryl, NR19C(O)-alkylaryl, NHC(O)-alkylheteroaryl, NR19C(O)-alkylheteroaryl, NR18C(O)O—R19, NR18C(O)NR18R18, NHSO$_2$-alkyl, NHSO$_2$-cycloalkyl, NHSO$_2$-heterocyclyl, NHSO$_2$-aryl, NHSO$_2$-heteroaryl, NHSO$_2$-alkylheterocyclyl, NHSO$_2$-alkylaryl, NHSO$_2$-alkylheteroaryl, NO$_2$, SH, S-alkyl, S-aryl, S-heteroaryl, OH, OCF$_3$, O-alkyl, O—R38, O-cycloalkyl, O-heterocyclyl, O-aryl, O-heteroaryl, O-alkylcycloalkyl, O-alkylheterocyclyl, O-alkylaryl, O-alkylheteroaryl, O—(CH$_2$)$_n$—O, OC(O)-alkyl, OC(O)—R38, OC(O)-cycloalkyl, OC(O)-heterocyclyl, OC(O)-aryl, OC(O)-heteroaryl, OC(O)-alkylcycloalkyl, OC(O)-alkylheterocyclyl OC(O)-alkylaryl, OC(O)-alkylheteroaryl, OC(O)O—R19, OC(O)NR18R18, OSO$_3$H, OSO$_2$-alkyl, OSO$_2$-cycloalkyl, OSO$_2$-heterocyclyl, OSO$_2$-aryl, OSO$_2$-heteroaryl, OSO$_2$-alkylaryl, OSO$_2$-alkylheteroaryl, OP(O)(OH)$_2$, OP(O)(Oalkyl)$_2$, OP(O)(Oaryl)$_2$, C(O)-alkyl, C(O)-aryl, C(O)-heteroaryl, CO$_2$H, CO$_2$-alkyl, CO$_2$—R38, CO$_2$-cycloalkyl, CO$_2$-heterocyclyl, CO$_2$-aryl, CO$_2$-heteroaryl, CO$_2$-alkylcycloalkyl, CO$_2$-alkylheterocyclyl, CO$_2$-alkylaryl, CO$_2$-alkylheteroaryl, C(O)—NH$_2$, C(O)NH-alkyl, C(O)NH—R38, C(O)NH-cycloalkyl, C(O)NH-heterocyclyl, C(O)NH-aryl, C(O)NH-heteroaryl, C(O)NH-alkylcycloalkyl, C(O)NH-alkylheterocyclyl, C(O)NH-alkylaryl, C(O)NH-alkylheteroaryl, C(O)N(alkyl)$_2$, C(O)N(cycloalkyl)$_2$, C(O)N(aryl)$_2$, C(O)N(heteroaryl)$_2$, C(O)NR20-alkyl, C(O)NR19-alkylR21, —C(O)NR18O—R18, —C(O)NR18NR18R18, SO-alkyl, SO-aryl, SO$_2$-alkyl, SO$_2$-aryl, SO$_2$NH$_2$, SO$_2$NH-alkyl, SO$_2$NH-aryl, SO$_2$NH-heteroaryl, SO$_2$NH-alkylaryl, SO$_3$H, SO$_2$O-alkyl, SO$_2$O-aryl, SO$_2$O-alkylaryl, alkyl, alkylcycloalkyl, alkylheterocyclyl, alkylaryl, alkylheteroaryl, cycloalkyl, heterocyclyl, aryl or heteroaryl, n may assume the value of 1, 2 or 3, and the alkyl, cycloalkyl, heterocyclyl, aryl, heteroaryl, alkylcycloalkyl, alkylheterocyclyl, alkylaryl and alkylheteroaryl substituents may themselves in turn be substituted, unsubstituted or substituted heteroaryl, where the heteroaryl radical may be mono- or polysubstituted, identically or differently, by F, Cl, Br, I, CF$_3$, CN, NH$_2$, NH-alkyl, NH—R38, NH-cycloalkyl, NH-heterocyclyl, NH-aryl, NH-heteroaryl, NH-alkylcycloalkyl, NH-alkylheterocyclyl, NH-alkylaryl, NH-alkylheteroaryl, N(alkyl)$_2$, N(aryl)$_2$, NR20-alkyl, NHC(O)-alkyl, NHC(O)—R38, NR19C(O)-alkyl, NHC(O)-cycloalkyl, NR19C(O)-cycloalkyl, NHC(O)-heterocyclyl, NR19C(O)-heterocyclyl, NHC(O)-aryl, NR19C(O)-aryl, NHC(O)-heteroaryl, NR19C(O)-heteroaryl, NR18C(O)-alkylcycloalkyl, NR18C(O)-alkylheterocyclyl, NHC(O)-alkylaryl, NR19C(O)-alkylaryl, NHC(O)-alkylheteroaryl, NR19C(O)-alkylheteroaryl, NR18C(O)O—R19, NR18C(O)NR18R18, NHSO$_2$-alkyl, NHSO$_2$-cycloalkyl, NHSO$_2$-heterocyclyl, NHSO$_2$-aryl, NHSO$_2$-heteroaryl, NHSO$_2$-alkylheterocyclyl, NHSO$_2$-alkylaryl, NHSO$_2$-alkylheteroaryl, NO$_2$, SH, S-alkyl, S-aryl, S-heteroaryl, OH, OCF$_3$, O-alkyl, O—R38, O-cycloalkyl, O-heterocyclyl, O-aryl, O-heteroaryl, O-alkylcycloalkyl, O-alkylheterocyclyl, O-alkylaryl, O-alkylheteroaryl, OC(O)-alkyl, OC(O)—R38, OC(O)-cycloalkyl, OC(O)-heterocyclyl, OC(O)-aryl, OC(O)-heteroaryl, OC(O)-alkylcycloalkyl, OC(O)-alkylheterocyclyl OC(O)-alkylaryl, OC(O)-alkylheteroaryl, OC(O)O—R19, OC(O)NR18R18, OSO$_3$H, OSO$_2$-alkyl, OSO$_2$-cycloalkyl, OSO$_2$-heterocyclyl, OSO$_2$-aryl, OSO$_2$-heteroaryl, OSO$_2$-alkylaryl, OSO$_2$-alkylheteroaryl, OP(O)(OH)$_2$, OP(O)(Oalkyl)$_2$, OP(O)(Oaryl)$_2$, C(O)-alkyl, C(O)-aryl, C(O)-heteroaryl, CO$_2$H, CO$_2$-alkyl, CO$_2$—R38, CO$_2$-cycloalkyl, CO$_2$-heterocyclyl, CO$_2$-aryl, CO$_2$-heteroaryl, CO$_2$-alkylcycloalkyl, CO$_2$-alkylheterocyclyl, CO$_2$-alkylaryl, CO$_2$-alkylheteroaryl, C(O)—NH$_2$, C(O)NH-alkyl, C(O)NH—R38, C(O)NH-cycloalkyl, C(O)NH-heterocyclyl, C(O)NH-aryl, C(O)NH-heteroaryl, C(O)NH-alkylcycloalkyl, C(O)NH-alkylheterocyclyl, C(O)NH-alkylaryl, C(O)NH-alkylheteroaryl, C(O)N(alkyl)$_2$, C(O)N(cycloalkyl)$_2$, C(O)N(aryl)$_2$, C(O)N(heteroaryl)$_2$, C(O)NR20-alkyl, C(O)NR19-alkylR21, —C(O)NR18O—R18, —C(O)NR18NR18R18, SO$_2$NH$_2$, SO$_2$NH-alkyl, SO$_2$NH-aryl, SO$_2$NH-heteroaryl, SO$_2$NH-alkylaryl, SO$_3$H, SO$_2$O-alkyl, SO$_2$O-aryl, SO$_2$O-alkylaryl, alkyl, alkylcycloalkyl, alkylheterocyclyl, alkylaryl, alkylheteroaryl, cycloalkyl, heterocyclyl, aryl or heteroaryl, and the alkyl, cycloalkyl, heterocyclyl, aryl, heteroaryl, alkylcycloalkyl, alkylheterocyclyl, alkylaryl and alkylheteroaryl substituents may themselves in turn be substituted, OR29 where R29 may be alkyl, cycloalkyl, heterocyclyl, aryl, heteroaryl, alkylcycloalkyl, alkylheterocyclyl, alkylaryl or alkylheteroaryl, and the alkyl, cycloalkyl, heterocyclyl, aryl, heteroaryl, alkylcycloalkyl, alkylheterocyclyl, alkylaryl or alkylheteroaryl substituents may themselves in turn be substituted, SR30 where R30 may be alkyl, cycloalkyl, heterocyclyl, aryl, heteroaryl, alkylcycloalkyl, alkylheterocyclyl, alkylaryl or alkylheteroaryl, and the alkyl, cycloalkyl, heterocyclyl, aryl and heteroaryl, alkylcycloalkyl, alkylheterocyclyl, alkylaryl or alkylheteroaryl substituents may themselves in turn be substituted, NR31R32 where R31 and R32 may each independently be hydrogen, alkyl, cycloalkyl, heterocyclyl, aryl, heteroaryl, alkylcycloalkyl, alkylheterocyclyl, alkylaryl, alkylheteroaryl, —C(O)—R33, —SO$_2$R33, —C(O)OR33 and —C(O)—NR34R35, where R33 may be alkyl, cycloalkyl, heterocyclyl, aryl, heteroaryl, alkylcycloalkyl, alkylheterocyclyl, alkylaryl, alkylheteroaryl, and R34 and R35 may each independently be hydrogen, alkyl, cycloalkyl, heterocyclyl, aryl, heteroaryl, alkylcycloalkyl, alkylheterocyclyl, alkylaryl, alkylheteroaryl, or R34 and R35 together may form a heterocyclyl ring, or R31 and R32 together may form a heterocyclyl ring, and the alkyl, cycloalkyl, heterocyclyl, aryl and heteroaryl, alkylcycloalkyl, alkylheterocyclyl, alkylaryl or alkylheteroaryl substituents may themselves in turn be substituted, and R18 may be hydrogen, alkyl, cycloalkyl, heterocyclyl, aryl, heteroaryl, alkylcycloalkyl, alkylheterocyclyl, alkylaryl or alkylheteroaryl, and R19 may be alkyl, cycloalkyl, heterocyclyl, aryl, heteroaryl, alkylcycloalkyl, alkylheterocyclyl, alkylaryl or alkylheteroaryl, and R20 may be cycloalkyl, heterocyclyl, aryl, heteroaryl, alkylcycloalkyl, alkylheterocyclyl, alkylaryl or alkylheteroaryl, and R21 may be cycloalkyl, heterocyclyl, aryl, heteroaryl, and R38 may be alkyl, where the alkyl radical may be saturated or unsaturated, straight-chain or branched, having from 9 to 30 carbon atoms, i.e. $C_{9-30}$-alkanyls, $C_{9-3}$-alkenyls and $C_{9-30}$-alkynyls. Alkenyls have at least one C—C double bond and alkynyls have at least one C—C triple bond, where the alkenyls may be present either in (E)- or in (Z)-conformation. It is preferred that the alkyl radical is selected from the group which comprises nonyl, decyl, dodecyl, hexadecyl, octadecyl, eicosyl, henicosyl, docosyl, tetracosyl, nonacosyl, octadecenyl, docosenyl, tetracosenyl and octadecynyl.

Particular preference is given to pyrido[2,3-b]pyrazine derivatives of the general formula (II), where R2=H.

Particular preference is further given to pyrido[2,3-b]pyrazine derivatives of the general formula (II), where R2 and R4=H.

Particular preference is given to the following pyrido[2,3-b]pyrazine derivatives of the general formulae (I) and (II) which may be present in the form of their free base or else as pharmaceutically acceptable salts of physiologically tolerated acids:

Compound 1

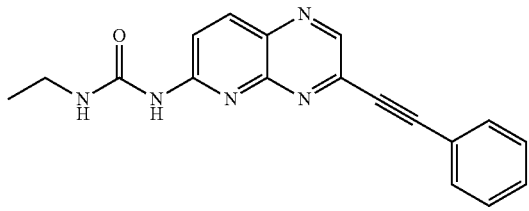

1-ethyl-3-(3-phenylethynylpyrido[2,3-b]pyrazin-6-yl)urea

Compound 2

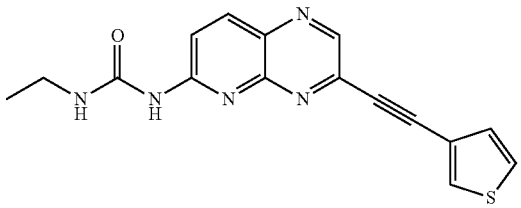

1-ethyl-3-(3-thiophen-3-ylethynylpyrido[2,3-b]pyrazin-6-yl)urea

Compound 3

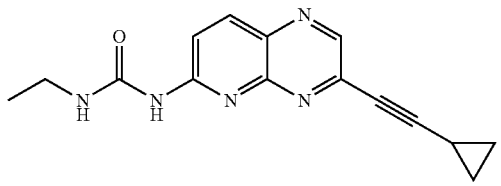

1-(3-cyclopropylethynylpyrido[2,3-b]pyrazin-6-yl)-3-ethylurea

Compound 4

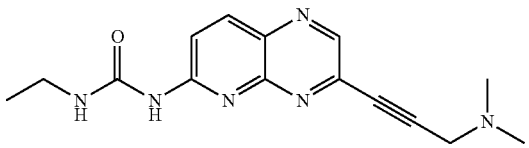

1-[3-(3-dimethylaminoprop-1-ynyl)pyrido[2,3-b]pyrazin-6-yl)-3-ethylurea

Compound 5

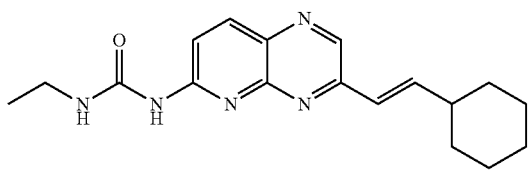

1-[3-((E)-2-cyclohexylvinyl)pyrido[2,3-b]pyrazin-6-yl)-3-ethylurea

Compound 6

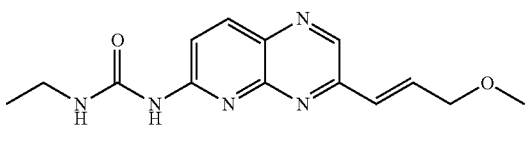

1-ethyl-3-[3-((E)-3-methoxypropenyl)pyrido[2,3-b]pyrazin-6-yl)urea

Compound 7

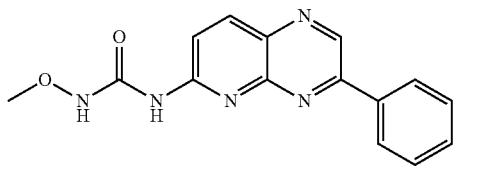

Compound 8

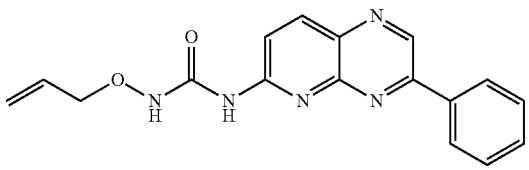

Compound 9

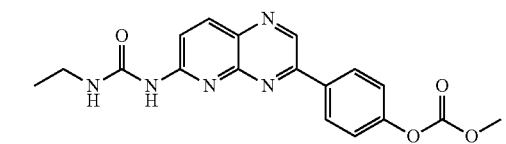

4-[6-(3-ethylurea)pyrido[2,3-b]pyrazin-3-yl]phenyl methyl carbonate

Compound 10

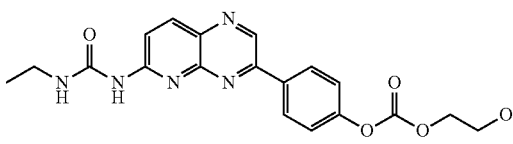

4-[6-(3-ethylurea)pyrido[2,3-b]pyrazin-3-yl]phenyl 2-methoxyethyl carbonate

-continued

Compound 11

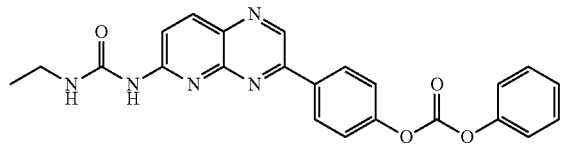

4-[6-(3-ethylurea)pyrido[2,3-b]pyrazin-3-yl]phenyl
phenyl carbonate

Compound 12

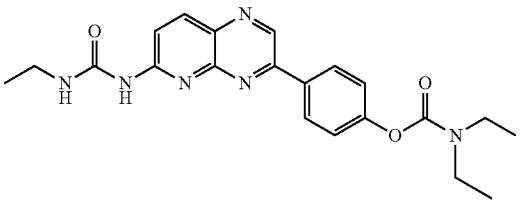

4-[6-(3-ethylurea)pyrido[2,3-b]pyrazin-3-yl]phenyl
diethylcarbamate

Compound 13

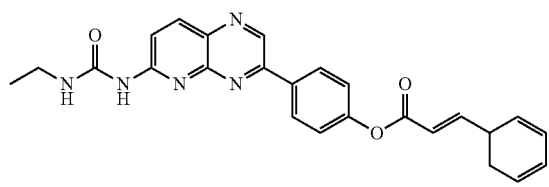

4-[6-(3-ethylurea)pyrido[2,3-b]pyrazin-3-yl]phenyl
(E)-3-phenylacrylate

Compound 14

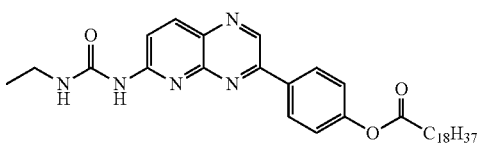

4-[6-(3-ethylurea)pyrido[2,3-b]pyrazin-3-yl]phenyl
nonadecanoate

Compound 15

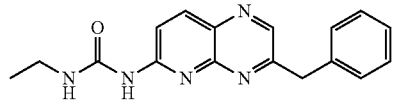

1-(3-benzylpyrido[2,3-b]pyrazin-6-yl)-3-ethylurea

Compound 16

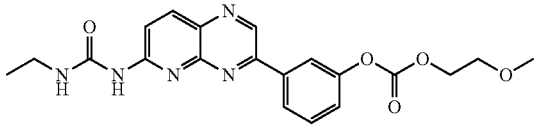

3-[6-(3-ethylurea)pyrido[2,3-b]pyrazin-3-yl]phenyl
2-methoxyethyl carbonate

Compound 17

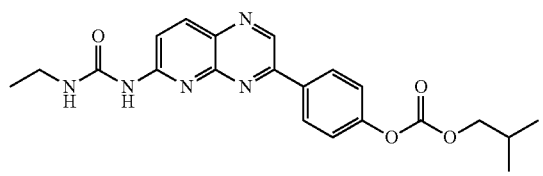

4-[6-(3-ethylurea)pyrido[2,3-b]pyrazin-3-yl]phenyl
isobutyl carbonate

Compound 18

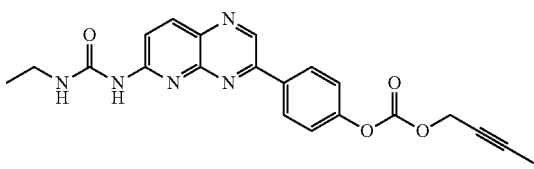

but-2-ynyl 4-[6-(3-ethylurea)pyrido[2,3-b]pyrazin-3-yl]phenyl carbonate

Compound 19

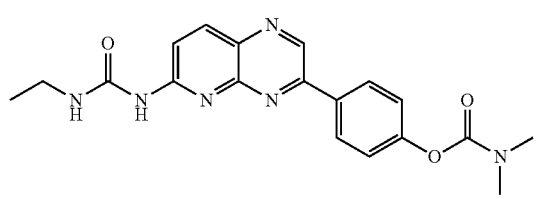

4-[6-(3-ethylurea)pyrido[2,3-b]pyrazin-3-yl]phenyl
diemethylcarbamate

Compound 20

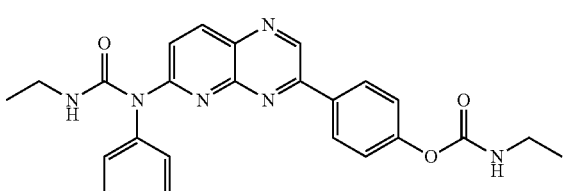

4-[6-(3-ethy-1-phenylurea)pyrido[2,3-b]pyrazin-3-yl]phenyl
ethylcarbamate

Compound 21

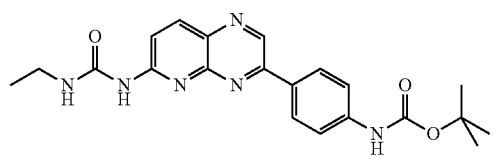

tert-butyl{4-[6-(3-ethylurea)pyrido[2,3-b]pyrazin-3-yl]phenyl}-
carbamate

Compound 22

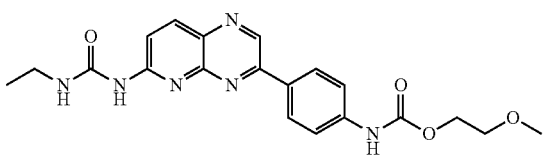

2-methoxyethyl 4-[6-(3-ethylurea)pyrido[2,3-b]pyrazin-3-yl]phenyl}-
carbamate

-continued

Compound 23

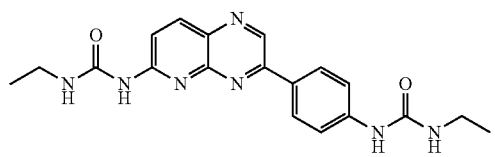

1-ethyl-3-{3-[4-(3-ethylurea)phenyl]pyrido[2,3-b]pyrazin-6-yl}urea

Compound 24

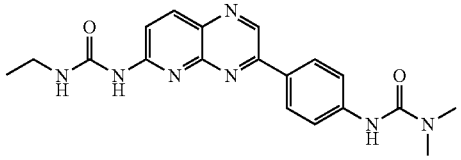

1-{3-[4-(3,3-dimethylurea)phenyl]pyrido[2,3-b]pyrazin-6-yl}-3-ethylurea

Compound 25

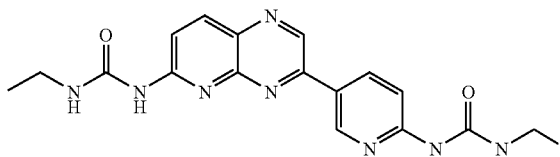

1-ethyl-3-{3-[6-(3-ethylurea)pyridin-3-yl]pyrido[2,3-b]pyrazin-6-yl}urea

Compound 26

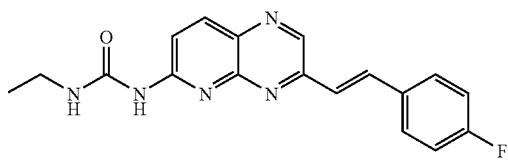

1-ethyl-3-{3-[2-(4-fluorophenyl)ethyl]pyrido[2,3-b]pyrazin-6-yl}urea

Compound 27

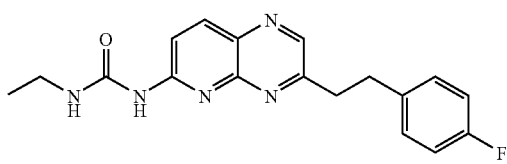

1-ethyl-3-{3-[(E)-2-(4-fluorophenyl)vinyl]pyrido[2,3-b]pyrazin-6-yl}-urea

Compound 28

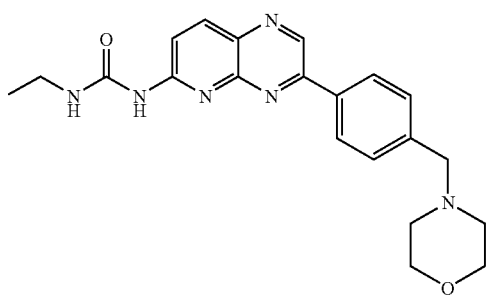

1-ethyl-3-[3-(4-morpholin-4-ylmethylphenyl)pyrido[2,3-b]pyrazin-6-yl]urea

Compound 29

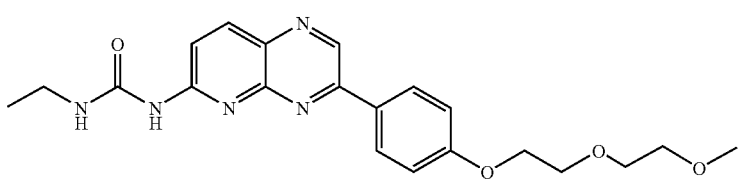

1-ethyl-3-(3-{4-[2-(2-methoxyethoxy)ethoxy]phenyl}pyrido[2,3-b]pyrazin-6-yl)urea Compound 30

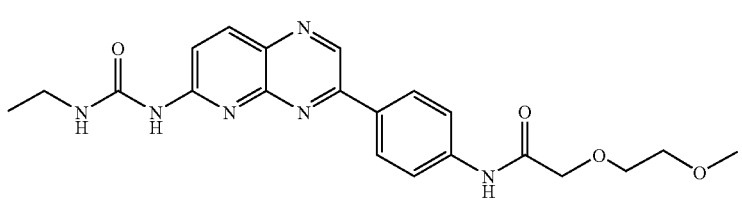

N-{4-[6-(3-ethylurea)pyrido[2,3-b]pyrazin-3-yl]phenyl}-2-(2-methoxyethoxy)acetamide Compound 31

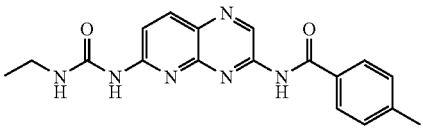

N-[6-(3-ethylurea)pyrido[2,3-b]pyrazin-3-yl]-4-methylbenzamide

Compound 32

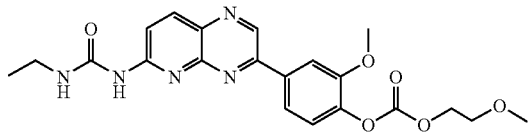

4-[6-(3-ethylurea)pyrido[2,3-b]pyrazin-3-yl]-2-methoxyphenyl 2-methoxyethyl carbonate Compound 33

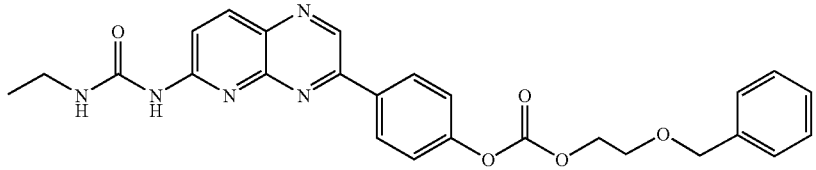

2-benzyloxyethyl 4-[6-(3-ethylurea)pyrido[2,3-b]pyrazin-3-yl]phenyl carbonate

Compound 34

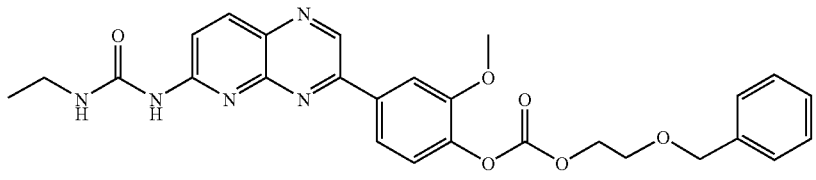

2-benzyloxyethyl 4-[6-(3-ethylurea)pyrido[2,3-b]pyrazin-3-yl]-2-methoxyphenyl carbonate Compound 35

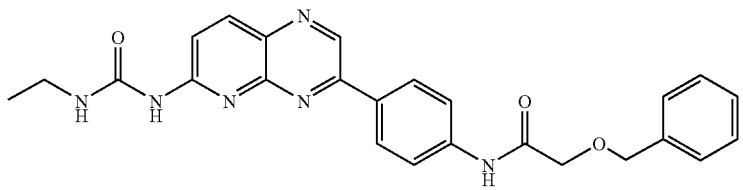

2-benzyloxy-N-{4-[6-(3-ethylurea)pyrido[2,3-b]pyrazin-3-yl]phenyl-acetamide

Compound 36

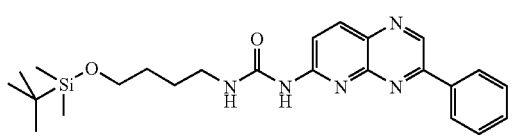

1-[4-(tert-butyldimethylsilanyloxy)butyl]-3-
(3-phenylpyrido[2,3-b]-pyrazin-6-yl)urea Compound 37

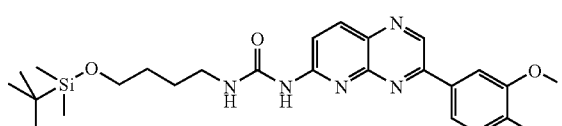

1-[4-(tert-butyldimethylsilanyloxy)butyl]-3-[3-(4-hydroxy-3-
methoxyphenyl)pyrido[2,3-b]pyrazin-6-yl]urea Compound 38

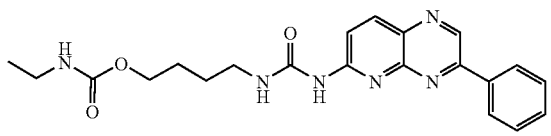

4-[3-(3-phenylpyrido[2,3-b]pyrazin-6-yl)urea]butyl
ethylcarbamate

Compound 39

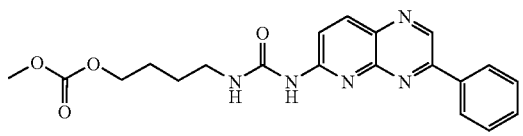

methyl 4-[3-(3-phenylpyrido[2,3-b]pyrazin-6-yl)urea]butyl
carbonate

Compound 40

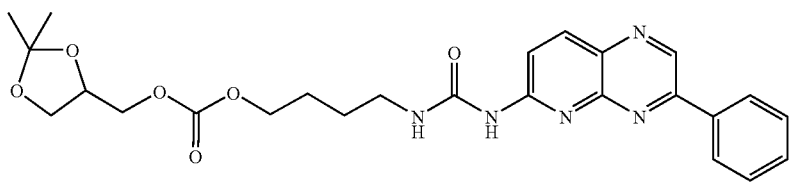

2,2-dimethyl[1,3]dioxolan-4-ylmethyl 4-[3-(3-phenylpyrido[2,3-
b]pyrazin-6-yl)urea]butyl carbonate Compound 41

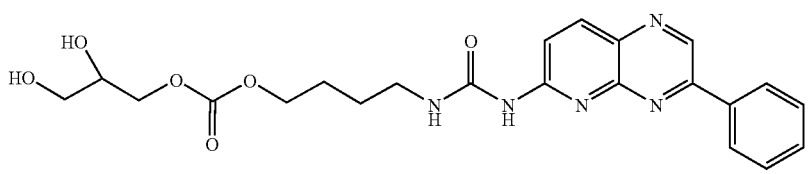

2,3-dihydroxypropyl 4-[3-(3-phenylpyrido[2,3-
b]pyrazin-6-yl)urea]-butyl carbonate -continued Compound 42

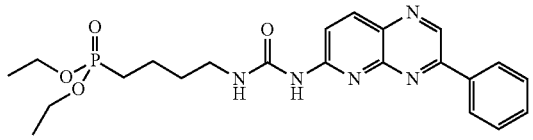

diethyl {4-[3-(3-phenylpyrido[2,3-b]pyrazin-6-yl)urea]butyl}-phosphate

Compound 43

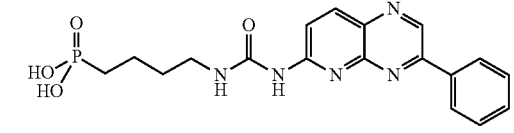

{4-[3-(3-phenylpyrido[2,3-b]pyrazin-6-yl)urea]butyl}phosphoric acid

Compound 44

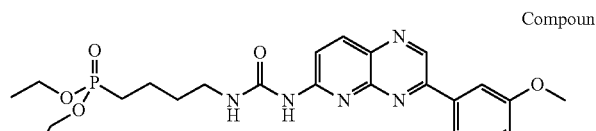

diethyl (4-{3-[3-(4-hydroxy-3-methoxyphenyl)pyrido[2,3-b]pyrazin-6-yl]urea}butyl)phosphate Compound 45

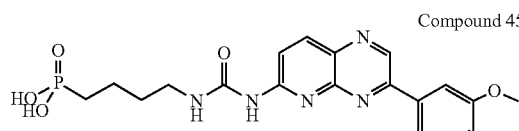

(4-{3-[3-(4-hydroxy-3-methoxyphenyl)pyrido[2,3-b]pyrazin-6-yl]urea}butyl)phosphoric acid Compound 46

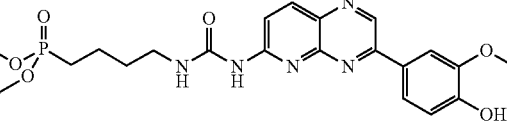

1-ethyl-3-[3-(3-trimethylsilanylphenyl)pyrido[2,3-b]pyrazin-6-yl]urea

Compound 47

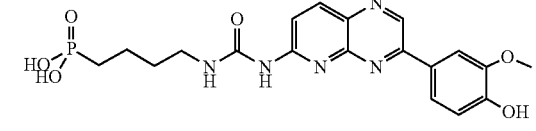

1-[3-(4-cyclohexylphenylamino)pyrido[2,3-b]pyrazin-6-yl]-3-ethylurea

Compound 48

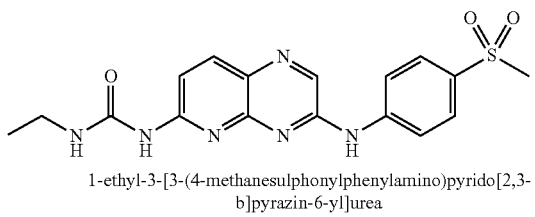

1-ethyl-3-[3-(4-methanesulphonylphenylamino)pyrido[2,3-b]pyrazin-6-yl]urea

Compound 49

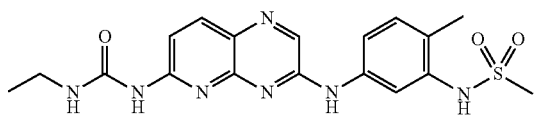

N-{5-[6-(3-ethylurea)pyrido[2,3-b]pyrazin-3-ylamino]-2-methyl-phenyl}methanesulphonamide Compound 50

3-[6-(3-ethylurea)pyrido[2,3-b]pyrazin-3-ylamino]-N-methyl-benzamide

Compound 51

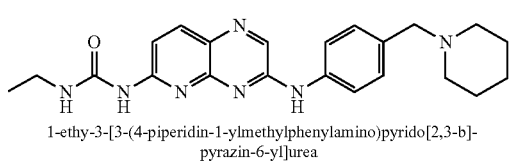

1-ethy-3-[3-(4-piperidin-1-ylmethylphenylamino)pyrido[2,3-b]-pyrazin-6-yl]urea

Compound 52

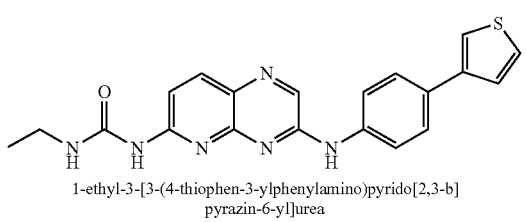

1-ethyl-3-[3-(4-thiophen-3-ylphenylamino)pyrido[2,3-b]pyrazin-6-yl]urea

Compound 53

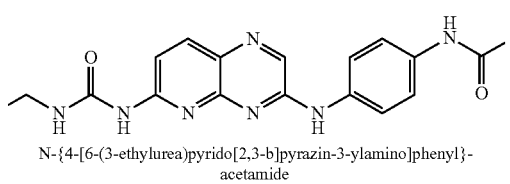

N-{4-[6-(3-ethylurea)pyrido[2,3-b]pyrazin-3-ylamino]phenyl}-acetamide

Compound 54

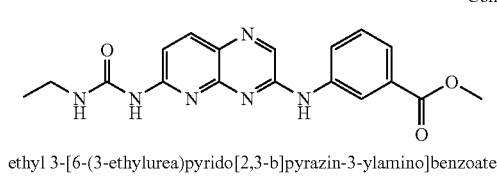

ethyl 3-[6-(3-ethylurea)pyrido[2,3-b]pyrazin-3-ylamino]benzoate

Compound 55

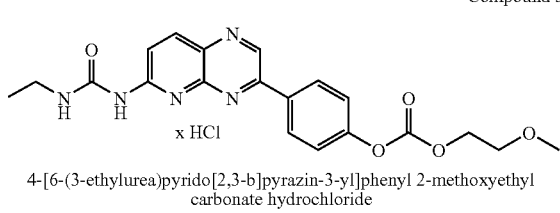

4-[6-(3-ethylurea)pyrido[2,3-b]pyrazin-3-yl]phenyl 2-methoxyethyl carbonate hydrochloride -continued Compound 56

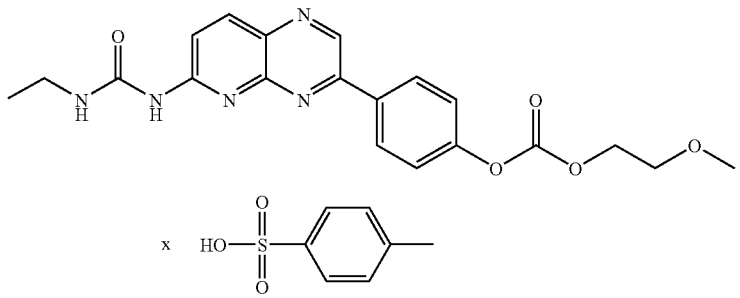

2-methoxyethyl 4-[6-(3-ethylurea)pyrido[2,3-b]pyrazin-3-yl]phenyl carbonate p-toluenesulphonate Compound 57

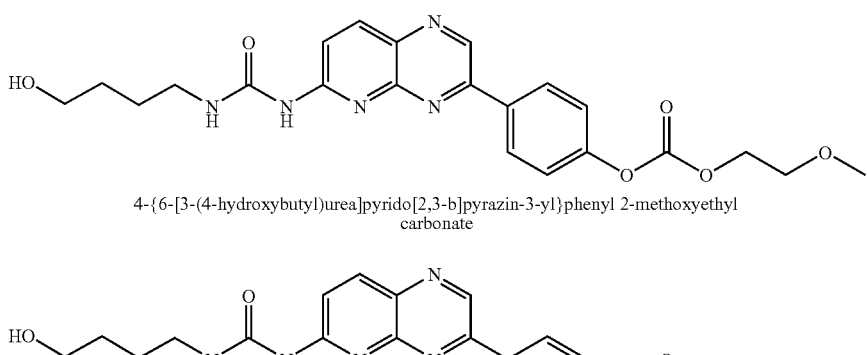

4-{6-[3-(4-hydroxybutyl)urea]pyrido[2,3-b]pyrazin-3-yl}phenyl 2-methoxyethyl carbonate Compound 58

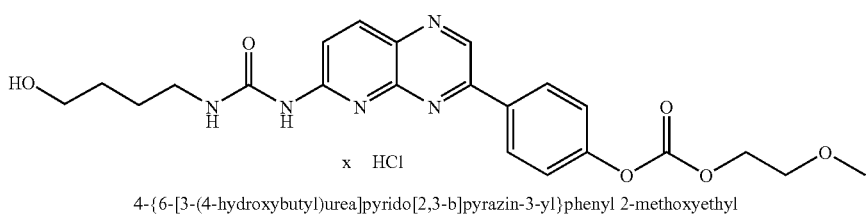

4-{6-[3-(4-hydroxybutyl)urea]pyrido[2,3-b]pyrazin-3-yl}phenyl 2-methoxyethyl carbonate hydrochloride Compound 59

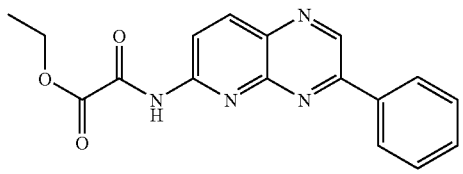

N-(3-phenylpyrido[2,3-b]pyrazin-6-yl)oxalic monoamide ethyl ester

Compound 60

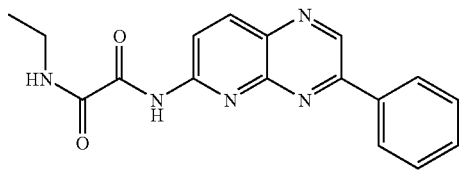

N-ethyl-N'-(3-phenylpyrido[2,3-b]pyrazin-6-yl)oxalamide

Compound 61

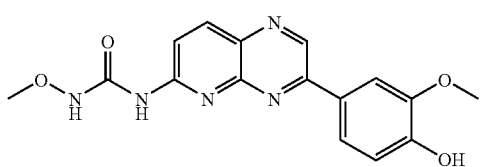

Compound 62

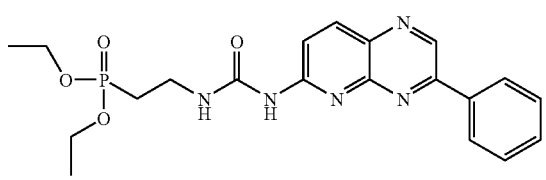

diethyl {2-[3-(3-phenylpyrido[2,3-b]pyrazin-6-yl)urea]ethyl}-phosphate

Compound 63

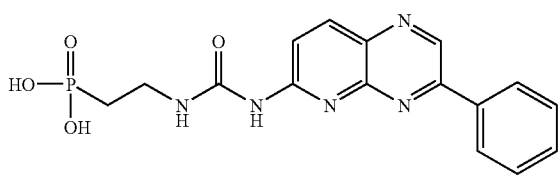

{2-[3-(3-phenylpyrido[2,3-b]pyrazin-6-yl)urea]ethyl}phosphoric acid

Compound 64

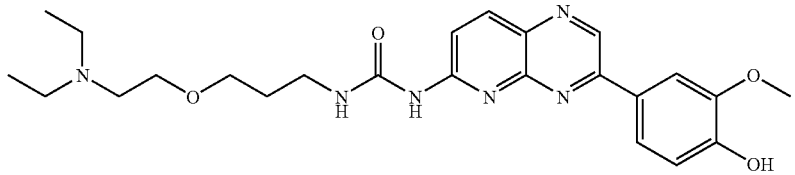

1-[3-(2-diethylaminoethoxy)propyl]-3-[3-(4-hydroxy-3-methoxy-phenyl)pyrido[2,3-b]pyrazin-6-yl]urea Compound 65

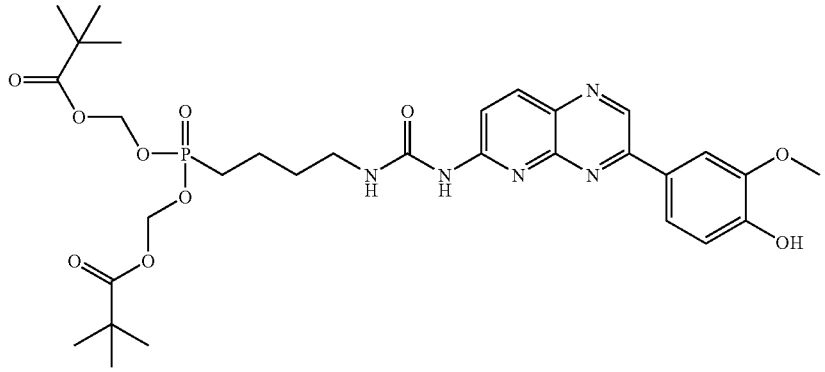

(2,2-dimethylpropionyloxymethoxy)-(4-{3-[3-(4-hydroxy-3-methoxy-phenyl)pyrido[2,3-b]pyrazin-6-yl]urea}butyl)phosphinoyloxymethyl 2,2-dimethyl-propanoate Compound 66

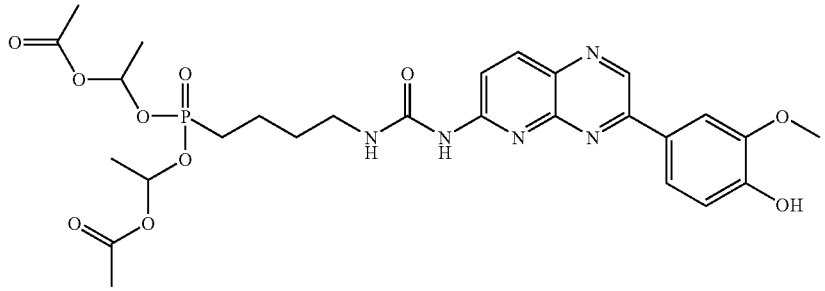

1-[(1-acetoxyethoxy)-(4-{3-[3-(4-hydroxy-3-methoxy-phenyl)-pyrido[2,3-b]pyrazin-6-yl]urea}butyl)phosphinoyloxy]ethyl acetate Compound 67

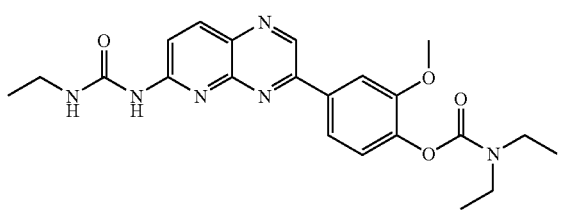

4-[6-(3-ethylurea)pyrido[2,3-b]pyrazin-3-yl]2-methoxyphenyl diethyl-carbamate

Compound 68

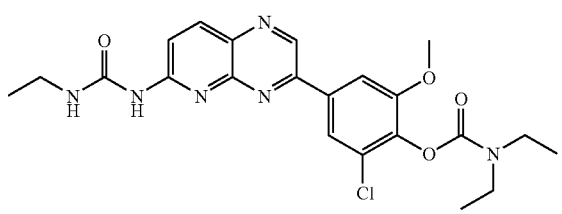

2-chloro-4-[6-(3-ethylurea)pyrido[2,3-b]pyrazin-3-yl]-6-methoxy-phenyl diethylcarbamate Compound 69

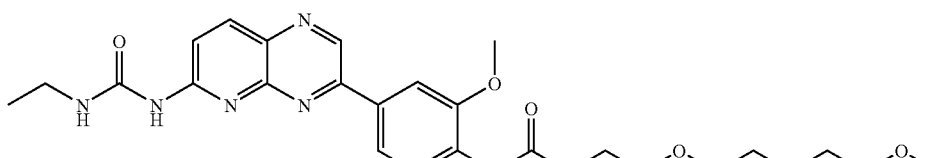

4-[6-(3-ethylurea)pyrido[2,3-b]pyrazin-3-yl]-2-methoxyphenyl 2-[2-(2-methoxyethoxy)ethoxy]ethyl carbonate -continued Compound 70

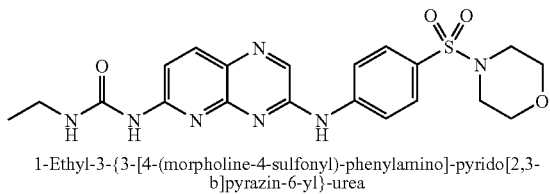

1-Ethyl-3-{3-[4-(morpholine-4-sulfonyl)-phenylamino]-pyrido[2,3-b]pyrazin-6-yl}-urea Compound 71

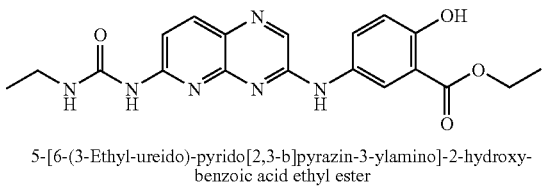

5-[6-(3-Ethyl-ureido)-pyrido[2,3-b]pyrazin-3-ylamino]-2-hydroxy-benzoic acid ethyl ester Compound 72

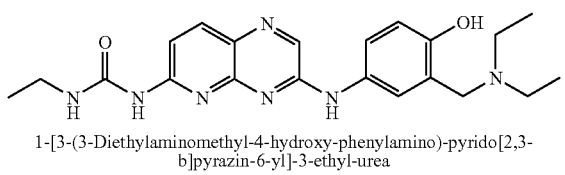

1-[3-(3-Diethylaminomethyl-4-hydroxy-phenylamino)-pyrido[2,3-b]pyrazin-6-yl]-3-ethyl-urea Compound 73

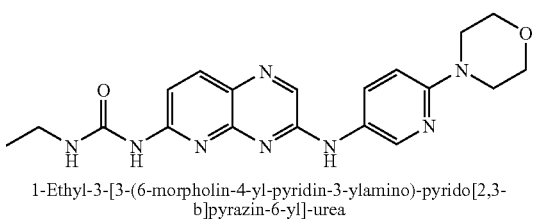

1-Ethyl-3-[3-(6-morpholin-4-yl-pyridin-3-ylamino)-pyrido[2,3-b]pyrazin-6-yl]-urea Compound 74

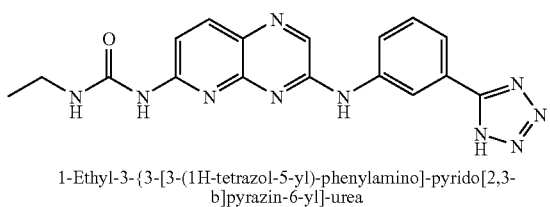

1-Ethyl-3-{3-[3-(1H-tetrazol-5-yl)-phenylamino]-pyrido[2,3-b]pyrazin-6-yl}-urea

Compound 75

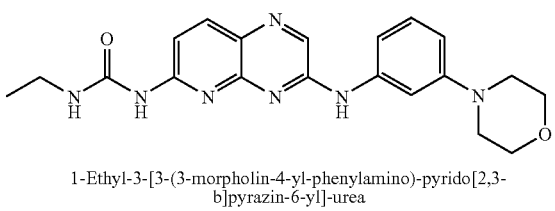

1-Ethyl-3-[3-(3-morpholin-4-yl-phenylamino)-pyrido[2,3-b]pyrazin-6-yl]-urea

Compound 76

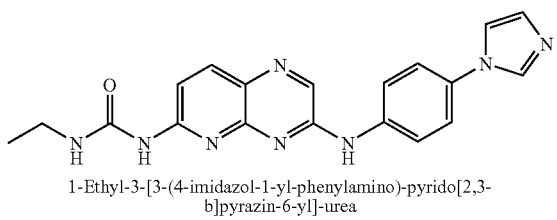

1-Ethyl-3-[3-(4-imidazol-1-yl-phenylamino)-pyrido[2,3-b]pyrazin-6-yl]-urea

Compound 77

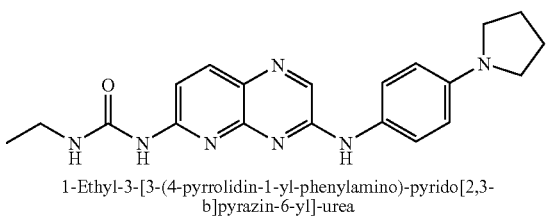

1-Ethyl-3-[3-(4-pyrrolidin-1-yl-phenylamino)-pyrido[2,3-b]pyrazin-6-yl]-urea

Compound 78

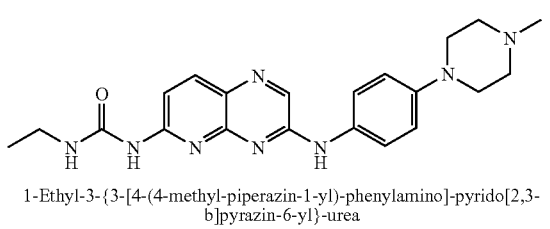

1-Ethyl-3-{3-[4-(4-methyl-piperazin-1-yl)-phenylamino]-pyrido[2,3-b]pyrazin-6-yl}-urea Compound 79

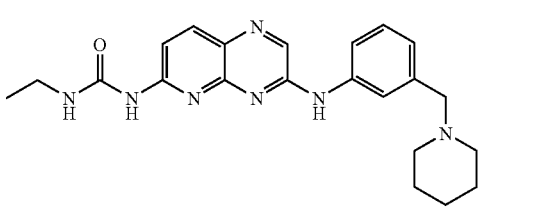

1-Ethyl-3-[3-(3-piperidin-1-ylmethyl-phenylamino)-pyrido[2,3-b]pyrazin-6-yl]-urea Compound 80

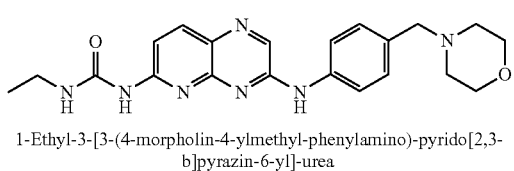

1-Ethyl-3-[3-(4-morpholin-4-ylmethyl-phenylamino)-pyrido[2,3-b]pyrazin-6-yl]-urea Compound 81

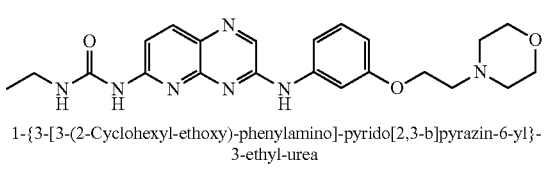

1-{3-[3-(2-Cyclohexyl-ethoxy)-phenylamino]-pyrido[2,3-b]pyrazin-6-yl}-3-ethyl-urea

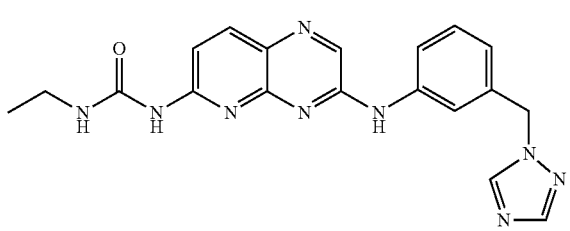

1-Ethyl-3-[3-(3-[1,2,4]triazol-1-ylmethyl-phenylamino)-pyrido[2,3-b]pyrazin-6-yl]-urea Compound 82

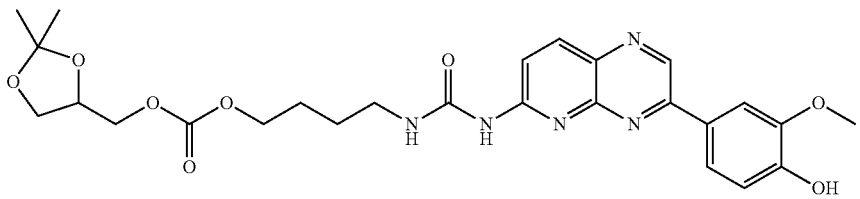

Carbonic acid 2,2-dimethyl-[1,3]dioxolan-4-ylmethyl ester 4-{3-[3-(4-hydroxy-3-methoxy-phenyl)-pyrido[2,3-b]pyrazin-6-yl]-ureido}-butyl ester Compound 83

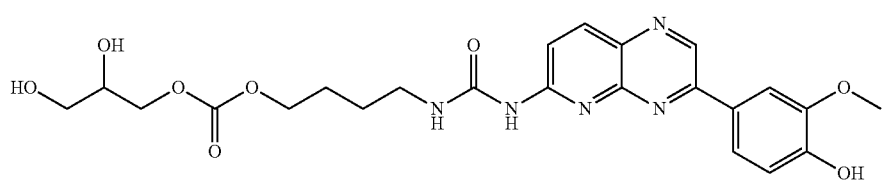

Carbonic acid 2,3-dihydroxy-propylester 4-{3-[3-(4-hydroxy-3-methoxy-phenyl)-pyrido[2,3-b]pyrazin-6-yl]-ureido}-butyl ester Compound 84

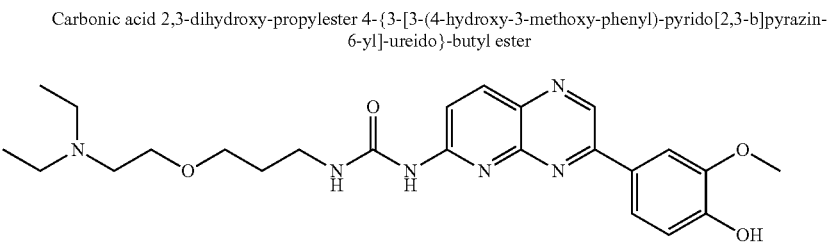

1-[3-(2-Diethylamino-ethoxy)-propyl]-3-[3-(4-hydroxy-3-methoxy-phenyl)-pyrido[2,3-b]pyrazin-6-yl]-urea Compound 85

In order to avoid ambiguities: when chemical structure and chemical name of the explicit compounds shown above erroneously do not match one another, the chemical structure shall unambiguously define the particular explicit compound.

The generic compounds of the general formulae (I) and (II) shown above, the preferred embodiments and the pyridopyrazine compounds 1 to 85 mentioned explicitly are referred to collectively hereinafter as "inventive compounds".

The expressions and terms specified to illustrate the inventive compounds are in principle each defined, unless stated otherwise in the description or in the claims, as follows:

In the context of this invention, the expression "alkyl" encompasses acyclic saturated or unsaturated hydrocarbon radicals which may be branched or straight-chain and have 1 to 8 carbon atoms, i.e. $C_{1-8}$-alkanyls, $C_{2-8}$-alkenyls and $C_{2-8}$-alkynyls. Alkenyls have at least one C—C double bond and alkynyls at least one C—C triple bond. Alkynyls may additionally also have at least one C—C double bond. Preferred alkyl radicals are methyl, ethyl, n-propyl, 2-propyl, n-butyl, sec-butyl, tert-butyl, n-pentyl, isopentyl, neo-pentyl, n-hexyl, 2-hexyl, n-heptyl, n-octyl, n-nonyl, n-decyl, n-undecyl, n-dodecyl, ethylenyl (vinyl), ethynyl, propenyl (—$CH_2CH=CH_2$; —$CH=CH—CH_3$, —$C(=CH_2)$—$CH_3$), propynyl (—$CH_2$—C≡CH, —C≡C—$CH_3$), butenyl, butynyl, pentenyl, pentynyl, hexenyl, hexynyl, heptenyl, heptynyl, octenyl, octadienyl and octynyl.

In the context of this invention, the expression "($C_9$-$C_{30}$) alkyl" describes acyclic saturated or unsaturated hydrocarbon radicals which may be branched or straight-chain and have 9 to 30 carbon atoms, i.e. $C_{9-30}$-alkanyls, $C_{9-30}$-alkenyls and $C_{9-30}$-alkynyls. $C_{9-30}$-Alkenyls have at least one C—C double bond and $C_{9-30}$-alkynyls at least one C—C triple bond. $C_{9-30}$-Alkynyls may additionally also have at least one C—C double bond. Preferred ($C_9$-$C_{30}$)alkyl radicals are tetradecyl, hexadecyl, octadecyl, eicosanyl, cis-13-docosenyl (erucyl), trans-13-docosenyl (brassidyl), cis-15-tetracosenyl (nervonyl) and trans-15-tetracosenyl.

For the purposes of this invention, the expression "cycloalkyl" means cyclic non-aromatic hydrocarbons having 1 to 3 rings with 3 to 20, preferably 3 to 12 carbon atoms, which may be saturated or unsaturated, more preferably ($C_3$-$C_8$)cycloalkyl. The cycloalkyl radical may also be part of a bi- or polycyclic system, where, for example, the cycloalkyl radical is fused to an aryl, heteroaryl or heterocyclyl radical as defined herein by any possible and desired ring member(s).

The bonding to the compounds of the general formulae (I), (II) can be effected via any possible ring member of the cycloalkyl radical. Preferred cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl.

The expression "heterocyclyl" represents a 3- to 14-membered, preferably 3-, 4-, 5-, 6-, 7- or 8-membered, cyclic organic radical which contains at least 1 heteroatom, optionally 2, 3, 4 or 5 heteroatoms, especially nitrogen, oxygen and/or sulphur, the heteroatoms being the same or different and the cyclic radical being saturated or unsaturated but not aromatic. The heterocyclyl radical may also be part of a bi- or polycyclic system, where, for example, the heterocyclyl radical is fused to an aryl, heteroaryl or cycloalkyl radical as defined herein by any possible and desired ring member(s). The bonding to the compounds of the general formulae (I), (II) can be effected via any possible ring member of the heterocyclyl radical. Preferred heterocyclyl radicals are tetrahydrofuryl, pyrrolidinyl, imidazolidinyl, thiazolidinyl, tetrahydropyranyl, piperidinyl, piperazinyl, morpholinyl, thiapyrrolidinyl, oxapiperazinyl, oxapiperidinyl and oxadiazolyl.

In the context of this invention, the expression "aryl" means aromatic hydrocarbons having 3 to 14 carbon atoms, preferably 5 to 14 carbon atoms, more preferably 6 to 14 carbon atoms. The aryl radical may also be part of a bi- or polycyclic system, where, for example, the aryl radical is fused to a heterocyclyl, heteroaryl or cycloalkyl radical as defined herein by any possible and desired ring member(s), for example to tetrahydrofuran, tetrahydrothiophene, pyrrolidine, imidazolidine, thiazolidine, tetrahydropyran, dihydropyran, piperidine, furan, thiophene, imidazole, thiazole, oxazole, isoxazole. The bonding to the compounds of the general formulae (I), (II) can be effected via any possible ring member of the aryl radical. Preferred aryl radicals are phenyl, biphenyl, naphthyl and anthracenyl, but likewise indanyl, indenyl or 1,2,3,4-tetrahydronaphthyl.

The expression "heteroaryl" represents a 5-, 6- or 7-membered cyclic aromatic radical which contains at least 1 heteroatom, if appropriate also 2, 3, 4 or 5 heteroatoms, especially nitrogen, oxygen and/or sulphur, the heteroatoms being the same or different. The number of nitrogen atoms is preferably 0 to 3, that of oxygen and sulphur atoms preferably 0 or 1. The heteroaryl radical may also be part of a bi- or polycyclic system, where, for example, the heteroaryl radical is fused to a heterocyclyl, aryl or cycloalkyl radical as defined herein by any possible and desired ring member(s). The bonding to the compounds of the general formulae (I), (II) can be effected via any possible ring member of the heteroaryl radical. Preferred heteroaryl radicals are pyrrolyl, furyl, thienyl, thiazolyl, isothiazolyl, oxazolyl, oxadiazolyl, isoxazolyl, pyrazolyl, imidazolyl, triazole, tetrazole, pyridinyl, pyrimidinyl, pyridazinyl, pyrazinyl, triazinyl, phthalazinyl, indolyl, indazolyl, indolizinyl, quinolinyl, isoquinolinyl, quinoxalinyl, quinazolinyl, pteridinyl, carbazolyl, phenazinyl, phenoxazinyl, phenothiazinyl, and acridinyl.

For the purposes of the present invention, the expressions "alkyl-cycloalkyl", "cycloalkylalkyl", "alkyl-heterocyclyl", "heterocyclylalkyl", "alkyl-aryl", "arylalkyl", "alkylheteroaryl" and "heteroarylalkyl" mean that alkyl, cycloalkyl, heterocycl, aryl and heteroaryl are each as defined above, and the cycloalkyl, heterocyclyl, aryl and heteroaryl radical is bonded to the compounds of the general formulae (I), (II) via an alkyl radical, preferably $C_1$-$C_8$-alkyl radical, more preferably $C_1$-$C_4$-alkyl radical.

In connection with "alkyl", "cycloalkyl", "heterocyclyl", "aryl", "heteroaryl", "alkylcycloalkyl", "alkyl-heterocyclyl", "alkyl-aryl" and "alkyl-heteroaryl", the term "substituted" in the context of this invention, unless defined explicitly above in the description or the claims, is understood to mean the substitution of one or more hydrogen radicals by F, Cl, Br, I, CN, $CF_3$, $NH_2$, NH-Alkyl, NH-aryl, $N(alkyl)_2$, $NO_2$, SH, S-alkyl, OH, $OCF_3$, $O(-alkyl-O)_p$-alkyl, O-aryl, $OSO_3H$, $OP(O)(OH)_2$, $OP(O)(OAlkyl)_2$, $OP(O)(OAryl)_2$, CHO, C(O)OH, C(O)OR36, $C(O)NH_2$, C(O)NHR36, C(O)NR36R37, $SO_3H$, $SO_2$alkyl, $SO_2$aryl, $P(O)(OH)_2$, $P(O)(Oalkyl)_2$, $P(O)(Oaryl)_2$, alkyl, cycloalkyl, heterocyclyl, aryl, heteroaryl or alkylaryl, where p may assume the value of 0, 1, 2, 3, 4 or 5, and where the R36 and R37 radicals may each independently be alkyl, cycloalkyl, heterocyclyl, aryl, heteroaryl, alkyl-cycloalkyl, alkyl-heterocyclyl, alkyl-aryl or alkyl-heteroaryl, and R36 and R37 may together form a heterocyclyl ring. The substituents may be the same or different and the substitution may occur in any desired and possible position of the alkyl, cycloalkyl, heterocyclyl, aryl and heteroaryl radical.

In the context of this invention, the expression "halogen" encompasses the halogen atoms fluorine, chlorine, bromine and iodine.

Polysubstituted radicals are understood to mean those which are polysubstituted, for example di- or trisubstituted, either at different atoms or at the same atom, for example trisubstituted on the same carbon atom as in the case of $CF_3$, —$CH_2CF_3$ or at different positions as in the case of —CH(OH)—CH=CH—$CHCl_2$. The polysubstitution can be effected with the same substituent or different substituents.

When the inventive compounds have at least one centre of asymmetry, they may be present in the form of their racemates, in the form of the pure enantiomers and/or diastereomers, or in the form of mixtures of these enantiomers and/or diastereomers, and either in substance or as pharmaceutically acceptable salts of these compounds. The mixtures may be present in any desired mixing ratio of the stereoisomers.

For example, the inventive compounds which have one or more centres of chirality and which occur as racemates can be separated by methods known per se into their optical isomers, i.e. enantiomers or diastereomers. The separation can be effected by column separation on chiral phases or by recrystallization from an optically active solvent or using an optically active acid or base or by derivatization with an optically active reagent, for example an optically active alcohol, and subsequent detachment of the radical.

The inventive compounds may be present in the form of their double bond isomers as "pure" E or Z isomers, or in the form of mixtures of these double bond isomers. Where possible, the inventive compounds may be present in the form of the tautomers.

The inventive compounds may, if they have a sufficiently basic group, for example a primary, secondary or tertiary amine, be converted to their physiologically tolerated salts with inorganic and organic acids. The pharmaceutically acceptable salts of the inventive compounds are preferably formed with hydrochloric acid, hydrobromic acid, sulphuric acid, phosphoric acid, methanesulphonic acid, p-toluenesulphonic acid, carbonic acid, formic acid, acetic acid, trifluoroacetic acid, sulphoacetic acid, oxalic acid, malonic acid, maleic acid, succinic acid, tartaric acid, pyruvic acid, malic acid, embonic acid, mandelic acid, fumaric acid, lactic acid, citric acid, glutamic acid or aspartic acid. The salts formed include hydrochlorides, hydrobromides, sulphates, hydrogensulphates, phosphates, methanesulphonates, tosylates, carbonates, hydrogencarbonates, formates, acetates, triflates, sulphoacetates, oxalates, malonates, maleates, succinates, tartrates, malates, embonates, mandelates, fumarates, lactates, citrates, glutamates and aspartates. The stoichiometry of the salts of the inventive compounds formed may be whole or fractional multiples of one.

The inventive compounds may, if they have a sufficiently acidic group, for example the carboxyl group or the phosphoric acid group, be converted to their physiologically tolerated salts with inorganic and organic bases. Examples of useful inorganic bases include sodium hydroxide, potassium hydroxide, calcium hydroxide; examples of useful organic bases include ethanolamine, diethanolamine, triethanolamine, cyclohexylamine, dibenzylethylenediamine and lysine. The stoichiometry of the salts of the inventive compounds formed may be whole or fractional multiples of one.

Preference is likewise given to solvates and especially hydrates of the inventive compounds, which can be obtained, for example, by crystallization from a solvent or from aqueous solution. It is possible for one, two, three or as many as possible solvate or water molecules to bond with the inventive compounds to form solvates and hydrates.

It is known that chemical substances form solids which are present in various states of order, which are referred to as polymorphic forms or modifications. The physical properties of the different modifications of a polymorphic substance can differ greatly.

The inventive compounds may be present in various polymorphic forms; certain modifications may be metastable.

It is likewise possible for the inventive compounds to occur in the form of any prodrugs, for example esters, carbonates, carbamates, ureas, amides or phosphates, in which the actually biologically active form is only released by metabolism.

It is known that chemical substances are converted to metabolites in the body, which may in some cases likewise cause the desired biological effect—under some circumstances even in more marked form.

Corresponding prodrugs and metabolites of the inventive compounds should be considered to be part of the invention.

It has now been found in a surprising and advantageous manner that the inventive compounds can also act, i.e. have a modulating or inhibiting effect, on two or more signal transduction pathways or enzymes of such pathways. It has been found that the inventive compounds act, i.e. modulate or inhibit, with high selectivity.

Such a simultaneous, for example dual, modulation or inhibition of two or more signal transduction pathways, for example ras-Raf-Mek-Erk signal pathway, PI3K-Akt signal pathway and/or SAPK signal pathway, more specifically Erk1/Erk2 and/or PI3K and/or Jnk and/or p38, is advantageous over the only single modulation or inhibition of one signal transduction pathway, since synergistic therapeutic effects can be brought about, for example enhanced apoptosis and more rapid and efficient tumour regression.

The surprising advantageous effects of the inventive compounds enable multiple therapeutic approaches to be pursued in the physiological and/or pathophysiological states or conditions which are sensitive to the treatment or modulation of, or are mediated by, two or more signal transduction pathways.

It has also been found in a surprising and advantageous manner that the inventive compounds can also act, i.e. have modulating or inhibiting action, with high selectivity on the ras-Raf-Mek-Erk signal transduction pathway or enzymes thereof, and that the multiple mechanisms of action and therapeutic approaches detailed above can also find use with this signal pathway or enzymes.

It has also been found in a surprising and advantageous manner that the inventive compounds can also act, i.e. have modulating or inhibiting action, with high selectivity on the PI3K-Akt signal transduction pathway or enzymes thereof, and that the multiple mechanisms of action and therapeutic approaches detailed above can also find use with this signal pathway or enzymes.

It has also been found in a surprising and advantageous manner that the inventive compounds can also act, i.e. have modulating or inhibiting action, with high selectivity on the SAPK signal transduction pathway or enzymes thereof, and that the multiple mechanisms of action and therapeutic approaches detailed above can also find use with this signal pathway or enzymes.

It has additionally been found in a surprising and advantageous manner that the inventive compounds can also act, i.e. have a modulating or inhibiting action, with high selectivity on enzymes such as ATM, ATR, mTOR, DNA-PK and/or hSMG-1, and that the multiple mechanisms of action and therapeutic approaches detailed above can also find use with these enzymes.

According to the invention, the term "modulation" is understood to mean the following: "activation, partial activation, inhibition, partial inhibition". It is within the technical knowledge of the average person skilled in the art to measure and to determine such an activation, partial activation, inhibition or partial inhibition by means of the customary measurement and determination methods. For example, a partial activation can be measured and determined in relation to a full activation; and likewise a partial inhibition in relation to a full inhibition.

According to the invention, the term "inhibition" is understood to mean the following: "partial or full inhibition". It is within the technical knowledge of the average person skilled in the art to measure and to determine such a partial or full inhibition by means of the customary measurement and determination methods. For example, partial inhibition can be measured and determined in relation to full inhibition.

The terms "modulation" and "inhibition" relate, in connection with "enzymes" and/or "kinases" in the context of this invention, both to the inactive form (enzymatically inactive) and/or active form (enzymatically active) of the particular enzyme and/or kinase. This means in the context of this invention that an inventive compound can display its modulating action on the inactive form, active form or both forms of the enzyme and/or kinase.

In a further aspect, the object of the invention was surprisingly achieved by the provision of a medicament comprising at least one inventive compound.

In a further aspect, the object of the invention was surprisingly achieved by the provision of a medicament comprising at least one inventive compound in combination with at least one further active pharmaceutical ingredient and/or pharmaceutically acceptable carriers and/or excipients.

In a further aspect, the object of the invention is surprisingly achieved by the provision of a process for producing a medicament, characterized in that one or more inventive compounds are processed, i.e. brought into a therapeutically usable form, with pharmaceutically acceptable carriers and/or excipients to give pharmaceutical formulations.

In a further aspect, the object of the invention is surprisingly achieved by the provision of the inventive compounds which can be used as active ingredients in medicaments for modulating misdirected cellular signal transduction processes, especially for influencing the function of active and inactive receptor tyrosine kinases, and also cytoplasmic tyrosine, serine/threonine and lipid kinases, such as c-Raf, B-Raf, Mek, MAPKs, PDGFRbeta, Flt-3, IGF1R, PI3K, PKB/Akt1, c-Kit, c-Abl, FGFR1 and KDR.

In a further aspect, the object of the invention is surprisingly achieved by providing the inventive compounds which can be used to produce a medicament for the treatment or prophylaxis of physiological and/or pathophysiological states in mammals, the treatment or prophylaxis being brought about by modulation of the signal transduction pathway(s) selected from the group consisting of: "ras-Raf-Mek-Erk signal transduction pathway, PI3K-Akt signal transduction pathway and/or SAPK signal transduction pathway".

In a further aspect, the object of the invention is surprisingly achieved by the provision of the inventive compounds which can be used to produce a medicament for the treatment or prophylaxis of physiological and/or pathophysiological states mediated by enzymes selected from the group consisting of: "ATM, ATR, mTOR, DNA-PK, hSMG-1" in mammals.

In a further aspect, the object of the invention is surprisingly achieved by the provision of the inventive compounds which can be used to produce a medicament for the treatment or prophylaxis of physiological and/or pathophysiological states in mammals, the treatment or prophylaxis being brought about by modification of one or more enzymes selected from the group consisting of: "ATM, ATR, mTOR, DNA-PK, hSMG-1".

In a preferred embodiment, the inventive compounds are provided for use for the production of a medicament for the treatment and/or prophylaxis of physiological and/or pathophysiological states mediated by the ras-Raf-Mek-Erk signal transduction pathway and/or the PI3K-Akt signal transduction pathway in mammals, and/or for the production of a medicament for the treatment or prophylaxis of physiological and/or pathophysiological states in mammals, the treatment or prophylaxis being brought about by modulation of the ras-Raf-Mek-Erk signal transduction pathway and of the PI3K-Akt signal transduction pathway.

In a further aspect, the object of the invention is surprisingly achieved by the provision of the inventive compounds which can be used to produce a medicament for the treatment or prophylaxis of physiological and/or pathophysiological states mediated by the ras-Raf-Mek-Erk signal transduction pathway in mammals.

In a further aspect, the object of the invention is surprisingly achieved by the provision of the inventive compounds which can be used to produce a medicament for the treatment or prophylaxis of physiological and/or pathophysiological states mediated by the PI3K-Akt signal transduction pathway in mammals.

In a further aspect, the object of the invention is surprisingly achieved by the provision of the inventive compounds which can be used to produce a medicament for the treatment or prophylaxis of physiological and/or pathophysiological states in mammals, the treatment or prophylaxis being brought about by modulation of the PI3K-Akt signal transduction pathway.

In a preferred embodiment, the inventive compounds are provided for use for the production of a medicament for the treatment and/or prophylaxis of physiological and/or pathophysiological states mediated by the SAPK signal transduction pathway and/or the PI3K-Akt signal transduction pathway in mammals, and/or for the production of a medicament for the treatment or prophylaxis of physiological and/or pathophysiological states in mammals, the treatment or prophylaxis being brought about by modulation of the SAPK signal transduction pathway and of the PI3K-Akt signal transduction pathway.

In a further aspect, the object of the invention is surprisingly achieved by the provision of the inventive compounds which can be used to produce a medicament for the treatment or prophylaxis of physiological and/or pathophysiological states mediated by the SAPK signal transduction pathway in mammals.

In a further aspect, the object of the invention is surprisingly achieved by the provision of the inventive compounds which can be used to produce a medicament for the treatment or prophylaxis of physiological and/or pathophysiological states in mammals, the treatment or prophylaxis being brought about by modulation of the SAPK signal transduction pathway.

In a preferred embodiment, the inventive compounds are provided for the uses detailed above, the modulation of the ras-Raf-Mek-Erk signal transduction pathway being brought about by modulation of one or more enzymes selected from the group consisting of: "tyrosine kinase, serine/threonine kinase, receptor tyrosine kinase, cytoplasmic tyrosine kinase, cytoplasmic serine/threonine kinase" and preferably selected from the group consisting of "Erk, Erk1, Erk2".

In a further preferred embodiment, the inventive compounds are provided for the use as detailed above, the modulation of the PI3K-Akt signal transduction pathway being brought about by modulation of one or more enzymes selected from the group consisting of "lipid kinases" and preferably selected from the group consisting of: "PI3K, PI3Kalpha, PI3Kbeta, PI3Kgamma, PI3Kdelta, PI3K-C2alpha, PI3K-C2beta, PI3K-Vps34p".

In a further preferred embodiment, the inventive compounds are provided for the use as detailed above, the modulation of the SAPK signal transduction pathway being brought about by modulation of one or more enzymes selected from the group consisting of: "tyrosine kinase, serine/threonine kinase, receptor tyrosine kinase, cytoplasmatic tyrosine kinase, cytoplasmatic serine/threonine kinase" and preferably selected from the group consisting of: "Jnk, Jnk1, Jnk2, Jnk3, p38, p38alpha, p38beta, p38gamma, p38delta".

In a further aspect, the object of the invention is surprisingly achieved by the provision of the inventive compounds according to the aspects, preferred embodiments and uses detailed above, which can be used to produce a medicament for the treatment or prophylaxis of physiological and/or pathophysiological states in mammals, the treatment or prophylaxis being brought about by modulation of two or more enzymes.

In a more preferred embodiment, the inventive compounds are provided for the uses detailed above, at least one enzyme in the treatment or prophylaxis brought about by modulation of two or more enzymes being selected from the group consisting of: "Erk, Erk1, Erk2" and at least one enzyme being selected from the group consisting of: "PI3K, PI3Kalpha, PI3Kbeta, PI3Kgamma, PI3Kdelta, PI3K-C2alpha, PI3K-C2beta, PI3K-Vps34p".

In a more preferred embodiment, the inventive compounds are provided for the uses detailed above, at least one enzyme in the treatment or prophylaxis brought about by modulation of two or more enzymes being selected from the group consisting of: "Jnk, Jnk1, Jnk2, Jnk3, p38, p38alpha, p38beta, p38gamma, p38delta" and at least one enzyme being selected from the group consisting of: "PI3K, PI3Kalpha, PI3Kbeta, PI3Kgamma, PI3Kdelta, PI3K-C2alpha, PI3K-C2beta, PI3K-Vps34p".

In a more preferred embodiment, the inventive compounds are provided for the uses detailed above, at least one enzyme in the treatment or prophylaxis brought about by modulation of two or more enzymes being selected from the group consisting of: "Erk, Erk1, Erk2" and at least one enzyme being selected from the group consisting of: "ATM, ATR, mTOR, DNA-PK, hSMG-1".

In a more preferred embodiment, the inventive compounds are provided for the uses detailed above, at least one enzyme in the treatment or prophylaxis brought about by modulation of two or more enzymes being selected from the group consisting of: "Jnk, Jnk1, Jnk2, Jnk3, p38, p38alpha, p38beta, p38gamma, p38delta" and at least one enzyme being selected from the group consisting of: "ATM, ATR, mTOR, DNA-PK, hSMG-1".

In a more preferred embodiment, the inventive compounds are provided for the uses detailed above, at least one enzyme in the treatment or prophylaxis brought about by modulation of two or more enzymes being selected from the group consisting of: "PI3K, PI3Kalpha, PI3Kbeta, PI3Kgamma, PI3Kdelta, PI3K-C2alpha, PI3K-C2beta, PI3K-Vps34p" and at least one enzyme being selected from the group consisting of: "ATM, ATR, mTOR, DNA-PK, hSMG-1".

In another preferred embodiment, the inventive compounds are provided for the uses detailed above, the modulation being an inhibition.

In the context of this invention, the inventive compounds may be administered to all known mammals, especially to the human, for treatment and/or prophylaxis.

In another preferred embodiment, the inventive compounds are provided for the use as detailed above, the mammal being selected from the group consisting of: "humans, useful animals, livestock, domestic pets, beef cattle, cows, sheep, pigs, goats, horses, ponies, donkeys, hinnies, mules, hares, rabbits, cats, dogs, guinea pigs, hamsters, rats, mice" and preferably being a human.

In the context of this invention, the inventive compounds may be used for the treatment and/or prophylaxis of all known physiological and/or pathophysiological states.

In a preferred embodiment, the inventive compounds are provided for the uses detailed above, the physiological and/or pathophysiological states being selected from the group consisting of: "malignant tumours, benign tumours, inflammatory disorders, inflammations, pain, rheumatic disorders, arthritic disorders, HIV infections, neurological or neurodegenerative disorders, rheumatism, arthritis, AIDS, ARC (AIDS related complex), Kaposi's sarcoma, tumours emanating from the brain and/or nervous system and/or meninges, dementia, Alzheimer's, hyperproliferative disorders, psoriasis, endometriosis, scar formation, benign prostate hyperplasia (BPH), disorders of the immune system, autoimmune disorders, immune deficiency disorders, colon tumour, stomach tumour, intestine tumour, lung tumour, pancreas tumour, ovarial tumour, prostate tumour, leukaemia, melanoma, liver tumour, kidney tumour, head tumour, throat tumour, glioma, breast tumour, uterine cancer, endometrial cancer, cervical cancer, brain tumour, adenocanthoma, bladder cancer, colorectal tumour, oesophageal cancer, gynaecological tumour, ovarian tumour, thyroid cancer, lymphoma, chronic leukaemia, acute leukaemia, restenosis, diabetes, diabetic nephropathy, fibrotic disorders, cystic fibrosis, malignant nephrosclerosis, thrombotic microangiopathy syndrome, organ transplant rejection, glomerulopathies, disorders of the metabolism, solid tumours, rheumatic arthritis, diabetic retinopathy, asthma, allergies, allergic disorders, chronic obstructive pulmonary disorders, inflammatory bowel disorder, fibrosis, atherosclerosis, cardiac disorders, cardiovascular disorders, disorders of the heart muscle, vascular disorders, angiogenetic disorders, kidney disorders, rhinitis, Grave's disease, focal ischaemia, heart failure, ischaemia, cardiac hypertrophy, kidney failure, cardiac myocyte dysfunction, high blood pressure, vascular constriction, stroke, anaphylactic shock, blood platelet agglutination, skeletal muscular atrophy, obesity, excess weight, glucose homeostasis, congestive heart failure, angina, heart attack, myocardial infarction, hyperglycaemia, hypoglycaemia, hypertension".

In a further aspect of the present invention, the object of the invention is surprisingly achieved by the provision of the inventive compounds according to the aspects, preferred embodiments and uses detailed above for use for the production of a medicament for the treatment or prophylaxis of physiological and/or pathophysiological states in mammals, the medicament comprising at least one further pharmacologically active substance.

In a further aspect of the present invention, the object of the invention is surprisingly achieved by the provision of the inventive compounds according to the aspects, preferred embodiments and uses detailed above for use for the production of a medicament for the treatment or prophylaxis of physiological and/or pathophysiological states in mammals, the medicament being administered before and/or during and/or after the treatment with at least one further pharmacologically active substance.

In a further aspect of the present invention, the object of the invention is surprisingly achieved by the provision of the inventive compounds according to the aspects, preferred embodiments and uses detailed above for use for the production of a medicament for the treatment or prophylaxis of physiological and/or pathophysiological states in mammals, the medicament being administered before and/or during and/or after the treatment with radiation therapy and/or surgery.

In the context of this invention, the inventive compounds may be administered with all known pharmacologically active substances in a combination therapy as detailed.

In a preferred embodiment, the inventive compounds are provided for the uses detailed above, the further pharmacologically active substance being selected from the group consisting of: "DNA topoisomerase I and/or II inhibitors, DNA intercalators, alkylating agents, microtubuli destabilizers, hormone and/or growth factor receptor agonists and/or antagonists, antibodies against growth factors and their receptors, kinase inhibitors, antimetabolites".

In a preferred embodiment, the inventive compounds are provided for the above uses, the further pharmacologically active substance being selected from the group consisting of: "asparaginase, bleomycin, carboplatin, carmustine, chlorambucil, cisplatin, colaspase, cyclophosphamide, cytarabine, dacarbazine, dactinomycin, daunorubicin, doxorubicin (adriamycin), epirubicin, etoposide, 5-fluorouracil, hexamethylmelamine, hydroxyurea, ifosfamide, irinotecan, leucovorin, lomustine mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, vindesine, aminoglutethimide, L-asparaginase, azathioprine, 5-azacytidine cladribine, busulfan, diethylstilbestrol, 2',2'-difluorodeoxycytidine, docetaxel, erythrohydroxynonyladenine, ethynylestradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, oxaliplatin, pentostatin, N-phosphonoacetyl-L-aspartate (PALA), plicamycin, semustine, teniposide, testosterone propionate, thiotepa, trimethylmelamine, uridine, vinorelbine, epothilone, gemcitabine, taxotere, BCNU, CCNU, DTIC, 5-fluorouarcil, herceptin, avastin, erbitux, sorafenib, gleevec, iressa, tarceva, rapamycin, actinomycin D".

The oral administration can be effected, for example, in solid form as a tablet, capsule, gel capsule, coated tablet, granule or powder, but also in the form of a drinkable solution. For oral administration, the novel, inventive compounds as defined above can be combined with known and commonly used, physiologically acceptable carriers and excipients, for example gum arabic, talc, starch, sugar, for example mannitol, methylcelulose, lactose, gelatin, surfactants, magnesium stearate, cyclodextrins, aqueous or nonaqueous carriers, diluents, dispersants, emulsifiers, lubricants, preservatives and flavourings (e.g. essential oils). The inventive compounds may also be dispersed in a microparticulate, for example nanoparticulate, composition.

The nonoral administration can be effected, for example, by intravenous, subcutaneous or intramuscular injection of sterile aqueous or oily solutions, suspensions or emulsions, by means of implants or by means of ointments, creams or suppositories. If appropriate, administration can also be effected in sustained-release form. Implants may comprise inert materials, for example biodegradable polymers or synthetic silicones, for example silicon rubber. Intravaginal administration can be effected, for example, by means of vaginal rings. Intrauterine administration can be effected, for example, by means of diaphragms or other suitable intrauterine devices. Additionally envisaged is transdermal administration, especially by means of a formulation suitable therefor and/or suitable means, for example plasters.

The inventive medicaments may be administered in a suitable administration form to the skin, epicutaneously as a solution, suspension, emulsion, foam, ointment, paste or plaster; via the oral and lingual mucosa, buccally, lingually or sublingually as a tablet, pastille, coated tablet, linctus or gargle; via the gastric and intestinal mucosa, enterally as a tablet, coated tablet, capsule, solution, suspension or emulsion; via the rectal mucosa, rectally as a suppository, rectal capsule or ointment; via the nasal mucosa, nasally as drops, an ointment or spray; via the bronchial and alveolar epithelium, pulmonarily or by inhalation as an aerosol or inhalate; via the conjunctiva, conjunctivally as eye drops, eye ointment, eye tablets, lamellae or eyewash; via the mucosa of the genital organs, intravaginally as vaginal suppositories, ointments and douche, intrauterinally as a uterus pessary; via the urinary tract, intraurethrally as an irrigation, ointment or bougie; into an artery, intraarterially as an injection; into a vein, intravenously as an injection or infusion; into the skin, intracutaneously as an injection or implant; under the skin, subcutaneously as an injection or implant; into the muscle, intramuscularly as an injection or implant; into the abdominal cavity, intraperitoneally as an injection or infusion.

With regard to practical therapeutic requirements, the medicament action of the inventive compounds can be prolonged by means of suitable measures. This aim can be achieved by a chemical and/or pharmaceutical route. Examples of the achievement of a prolonged action are the use of implants and liposomes, the formation of sparingly soluble salts and complexes, or the use of crystal suspensions.

As already explained above, the novel inventive compounds can also be combined with further pharmaceutically active ingredients. In the context of a combination therapy, the individual active constituents can be administered simultaneously or separately, either by the same route (for example orally) or by separate routes (for example orally and as an injection). The may be present or be administered in the same amount or different amounts in a unit dose. It is also possible to employ a certain dosage regime when this appears appropriate. In this way, it is also possible to combine a plurality of the novel inventive compounds with one another.

The dosage may vary within a wide range depending on the type of indication, the severity of the disorder, the type of administration, and the age, gender, body weight and the sensitivity of the subject to be treated. It is within the abilities of a person skilled in the art to determine a "pharmacologically active amount" of the combined pharmaceutical composition. The administration can be effected in a single dose or a plurality of separate doses.

A suitable unit dose is, for example, 0.001 mg to 100 mg of the active ingredient, i.e. of at least one inventive compound and optionally of a further active pharmaceutical ingredient, per kg of body weight of a patient.

In a further aspect of the present invention, the present invention accordingly also encompasses pharmaceutical compositions comprising a pharmacologically active amount of at least one inventive compound, preferably compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84 and/or compound 85, and also optionally pharmaceutically tolerated carriers and/or excipients.

Preferred and particularly preferred inventive compositions are those which comprise at least one of the aforementioned preferred inventive compounds. In pharmaceutical compositions according to the present invention, not only at least one inventive compound as defined above but also at least one further pharmaceutically active ingredient as already described in detail above may be present.

In the inventive pharmaceutical compositions, at least one of the novel inventive compounds as defined above is present in a pharmacologically active amount, preferably in a unit dose, for example the aforementioned unit dose, and preferably in an administration form which enables oral administration.

With regard to the pharmaceutical compositions comprising the inventive compounds, and with regard to the use of the inventive compounds as a medicament, reference is made to the statements already made in connection with the use of the novel inventive compounds themselves with regard to possible uses and administration means.

In a further aspect of the present invention, the object of the invention is surprisingly achieved by the provision of a kit comprising a pharmacologically active amount of at least one preferred inventive compound as detailed above and a pharmacologically active amount of at least one further pharmacologically active ingredient as defined above.

General Synthesis Methods for the Inventive Compounds

The processes for preparing inventive substituted pyrido[2,3-b]pyrazines are illustrated below.

The inventive compounds are obtainable according to the following schemes (schemes 1-9) and corresponding processes known to those skilled in the art:

The definition of the R1 to R36 radicals shown in the following schemes corresponds to the substituents defined above in connection with the general formulae (I) and (II), for example Z radicals, R radicals, X radicals, T radicals, etc. The individual assignment can be accomplished in a simple manner by the person skilled in the art on the basis of his or her average technical knowledge.

Scheme 1

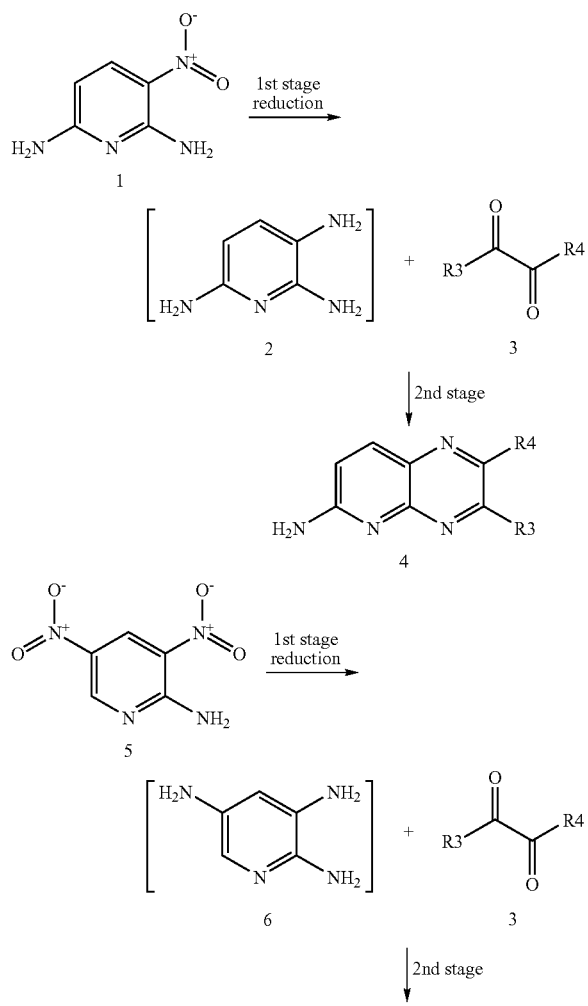

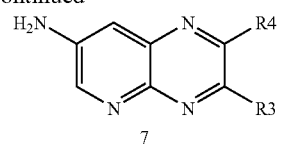

Precursors for selected examples of the inventive pyrido[2,3-b]pyrazines in which the substituents R2 and R4 are to be substituted by hydrogen are, for example, obtainable by the process in scheme 2 or a corresponding process known to those skilled in the art.

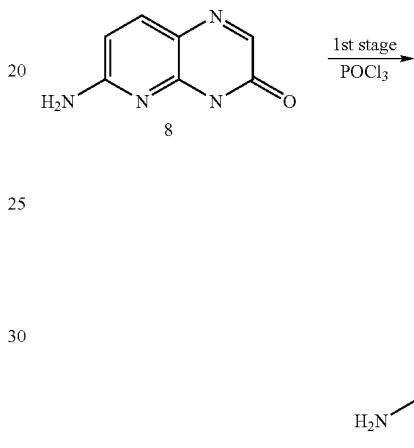

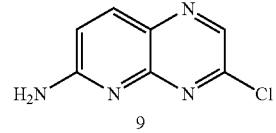

Precursors for selected examples of the inventive pyrido[2,3-b]pyrazines in which the substituents R3 and/or R4 are to be the OR31, SR32, NR33R34 radicals are, for example, obtainable by the process in scheme 3 or a corresponding process known to those skilled in the art.

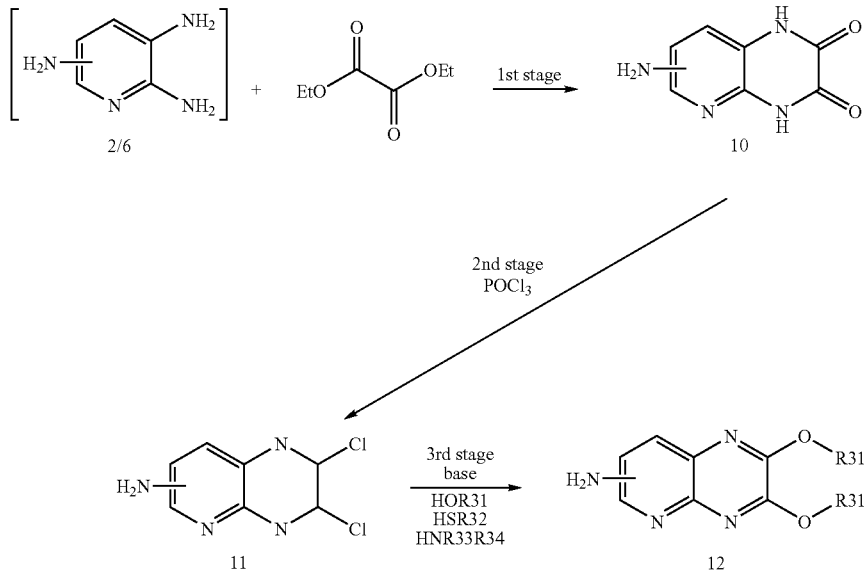

-continued

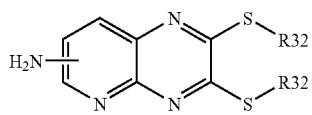

13

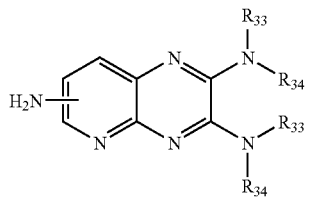

14

For the precursor 11 shown above, the intermediate 22 from scheme 6 or else the intermediates 20, 21, 21a and 21 b from scheme 5 may be used.

Precursors for selected examples of the inventive pyrido[2,3-b]pyrazines in which the substituent R9 is not to be H are, for example, obtainable by the process in scheme 4 or a corresponding process known to those skilled in the art.

Scheme 4

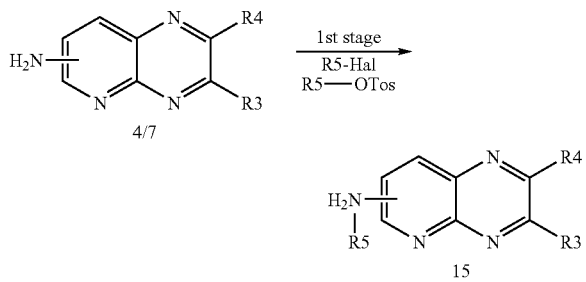

The precursors 4, 7, 9 and 15 from schemes 1-4 can be converted to the inventive substituted pyrido[2,3-b]pyrazines, for example, by the process in scheme 5 or a corresponding process known to those skilled in the art.

Schema 5

1st stage

-continued

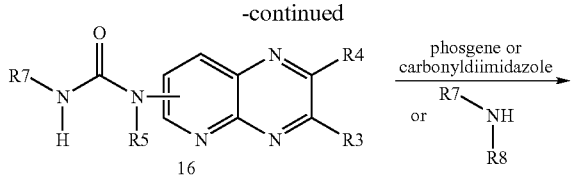

Scheme 5

1st stage

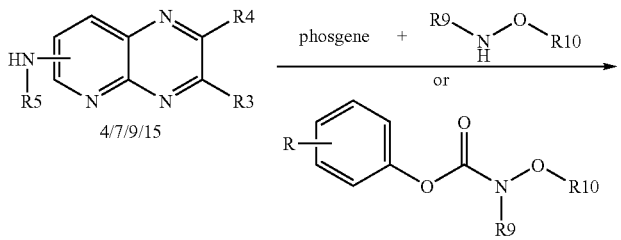

-continued
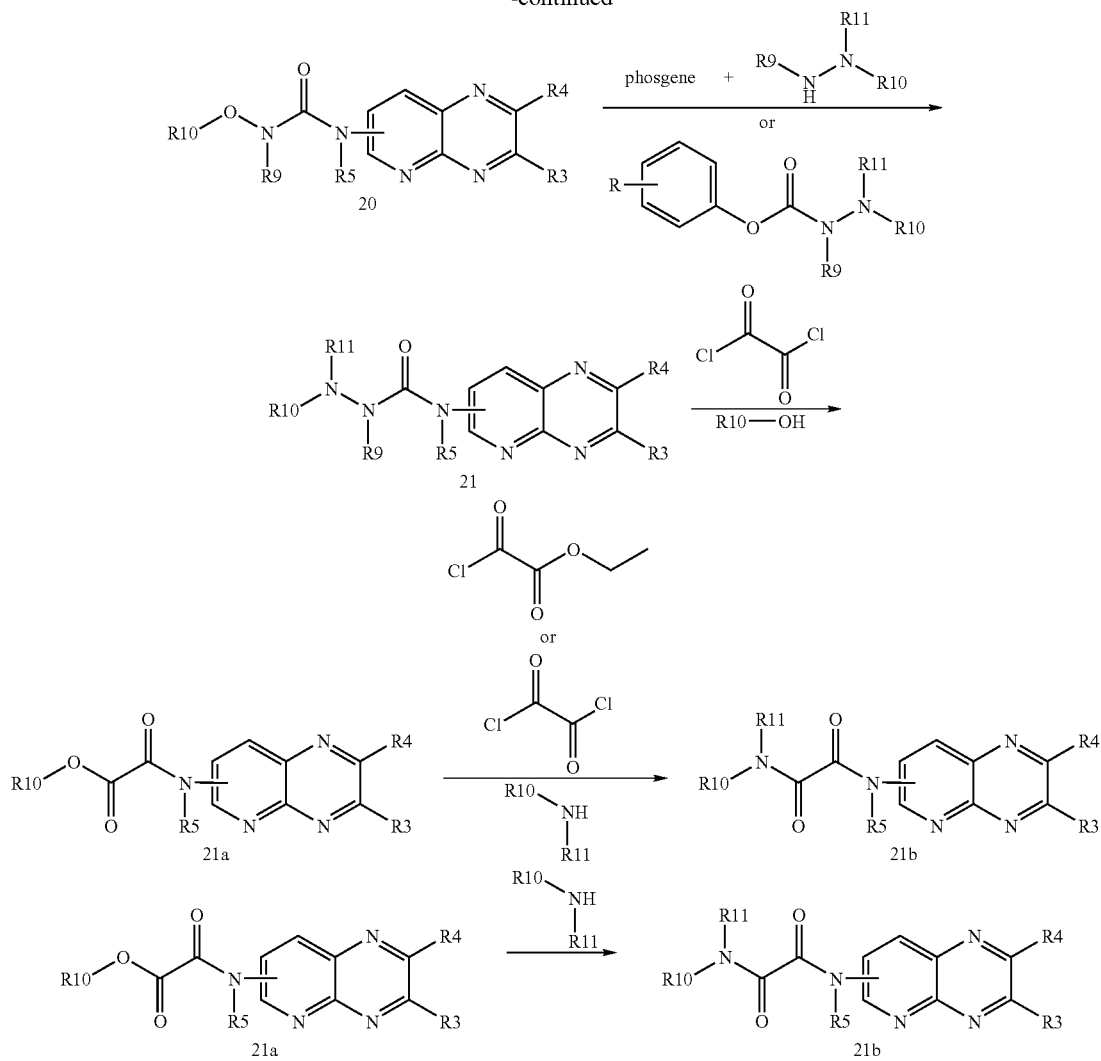
Selected examples of the inventive pyrido[2,3-b]pyrazines in which the substituents R3 and/or R4 may be selected substituted aryl, heteroaryl, alkyl, alkenyl or alkynyl radicals are, for example, obtainable by the process in scheme 6 or corresponding processes known to those skilled in the art.
Scheme 6
1st stage
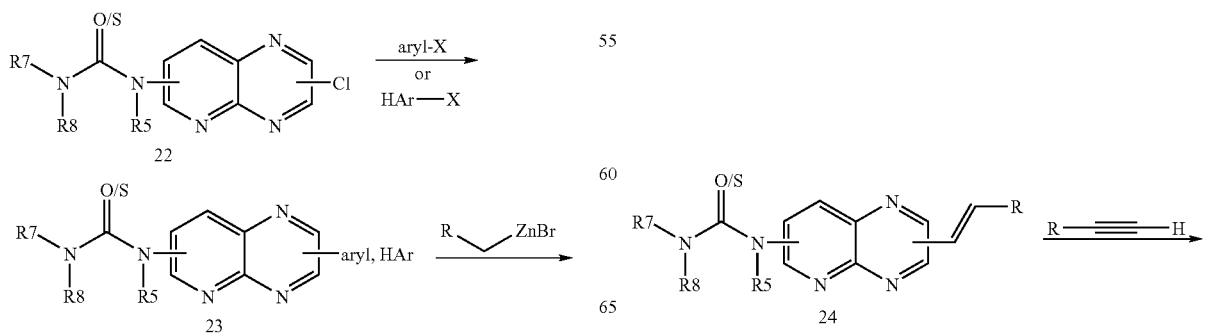
-continued
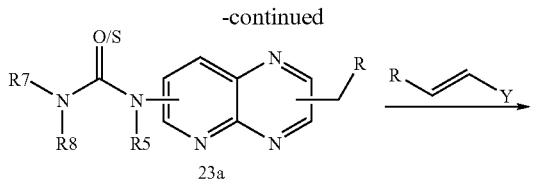

-continued

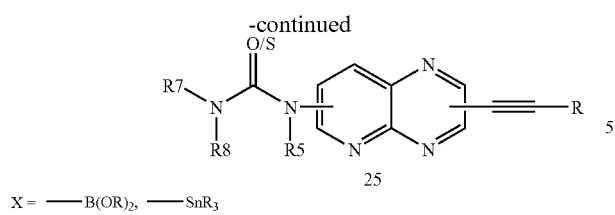

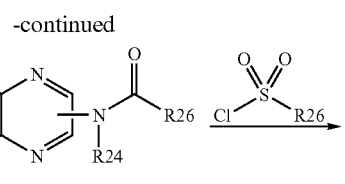

X = —B(OR)$_2$, —SnR$_3$
Y = H, —B(OR)$_2$, —SnR$_3$
R = alkyl, aryl, HAr, etc.

Selected examples of the inventive pyrido[2,3-b]pyrazines in which the substituents R3 and/or R4 are —N—C(O)—, —N—SO$_2$—, —N—C(O)—O— and —N—C(O)—N— are, for example, obtainable by the process in scheme 7 or corresponding processes known to those skilled in the art.

Scheme 7

1st state

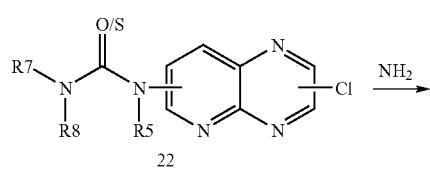

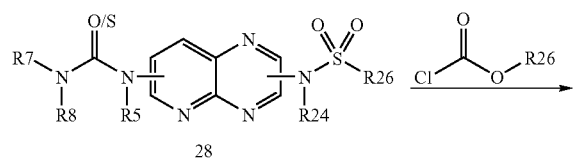

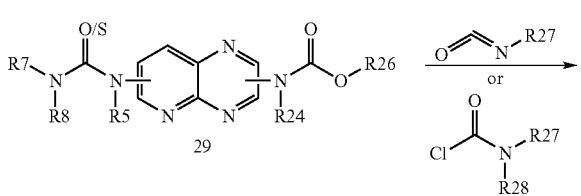

2nd stage

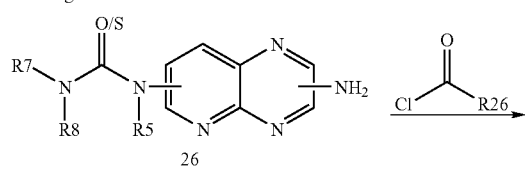

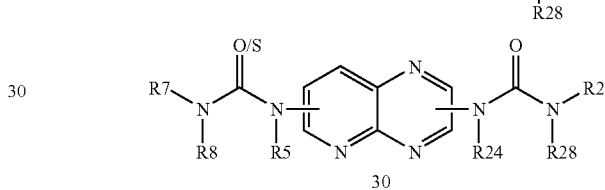

Selected examples of the inventive pyrido[2,3-b]pyrazines in which the substituents R3 and/or R4 may be selected urea-, carbamate- or carbonate-substituted radicals are, for example, obtainable by the process in scheme 8 or corresponding processes known to those skilled in the art.

Scheme 8

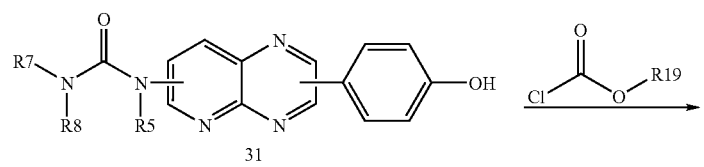

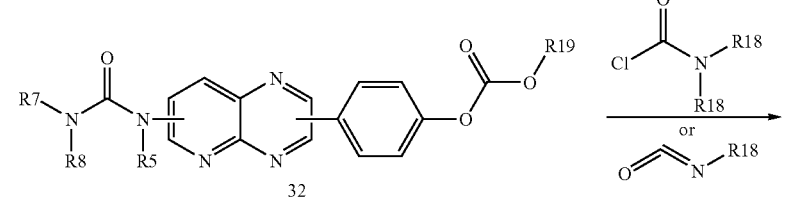

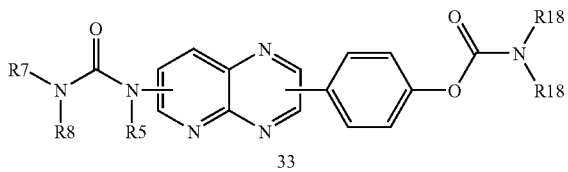

-continued

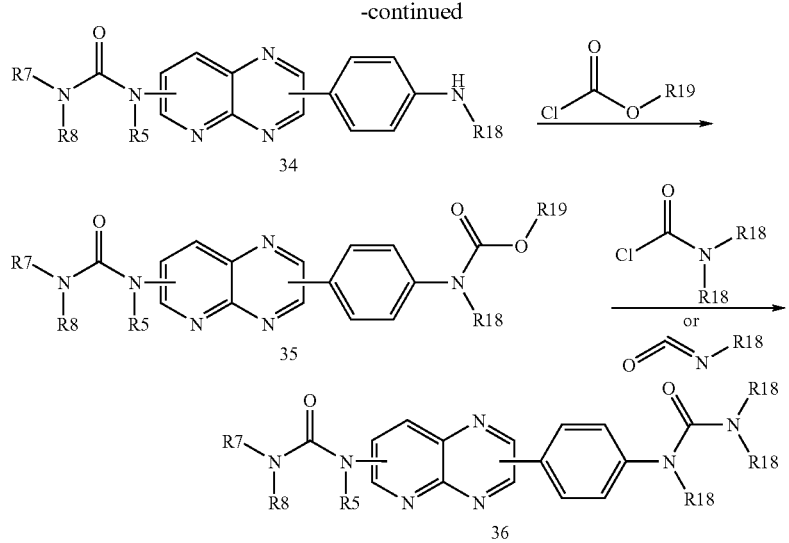

Selected examples of the inventive pyrido[2,3-b]pyrazines in which the substituents R3 and/or R4 may be selected O-, S-, N-substituted radicals are, for example, obtainable by the process in scheme 9 or corresponding processes known to those skilled in the art.

Scheme 9

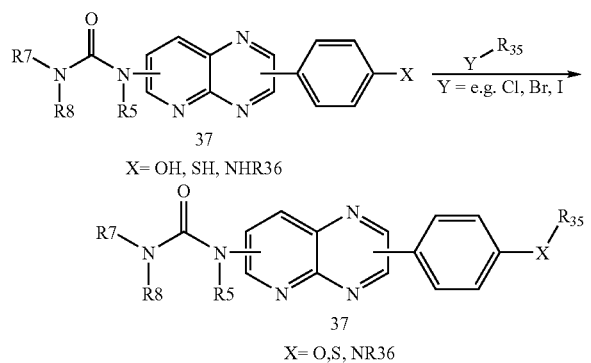

The starting compounds and intermediates are either commercially available or can be prepared by procedures known per se or known to those skilled in the art. The reactants 4, 7, 9-15, 22, 26, 31, 34 and 37 are valuable intermediates for the preparation of the inventive pyridopyrazines.

For the preparation of the starting compounds, intermediates and the inventive pyridopyrazines, reference is made inter alia to the patents WO 2004/104002 and WO 2004/104003, and also, for example, to the following primary literature whose contents are hereby incorporated into the disclosure of the present application:

1) Houben-Weyl, Methoden der Organischen Chemie, volume 4/1a, pp 343-350
2) Houben-Weyl, Methoden der Organischen Chemie, 4th ed., volume E 7b (part 2), p. 579; Degussa GB 1184848 (1970); S. Seko, et al. EP 735025 (1996)
3) D. Catarzi, et al.; J. Med. Chem. 1996, 1330-1336; J. K. Seydel, et al.; J. Med. Chem. 1994, 3016-3022
4) Houben-Weyl, Methods of Organic Chemistry, Volume E 9c, pp. 231-235
5) Houben-Weyl/Science of Synthesis, Volume 16, p. 1269
6) C. L. Leese, H. N. Rydon J. Chem. Soc. 1955, 303-309; T. S. Osdene, G. M. Timmis J. Chem. Soc. 1955, 2033-2035
7) W. He, et al. Bioorg. Med. Chem. Lett. 2003, 13, 3097-3100
8) M. S. A. El-Gaby, et al. Indian J. Chem. Sect. B 2001, 40, 195-200; M. R. Myers, et al. Bioorg. Med. Chem. Lett. 2003, 13, 3091-3096; A. R. Renslo, et al. J. Amer. Chem. Soc. 1999, 121, 7459-7460; C. O. Okafor, et al. J. Heterocyclic Chem. 1983, 20, 199-203; C. R. Hopkins, et al. Tet. Lett. 2004, 45, 8631-8633
9) J. Yin, et al. Org. Lett. 2002, 4, 3481-3484; O. A. El-Sayed, et al. Arch. Pharm. 2002, 335, 403-410; C. Temple, et al. J. Med. Chem. 1992, 35, 988-993
10) A. M. Thompson, et al. J. Med. Chem. 2000, 43, 4200-4211; N. A. Dales, et al. Org. Lett. 2001, 2313-2316; G. Dannhardt, et al. Arch. Pharm. 2000, 267-274; G. S. Poindexter, et al. Bioorg. Med. Chem. 2004, 12, 507-521; J.-M. Receveur, et al. Bioorg. Med. Chem. Lett. 2004, 14, 5075-5080
11) G. Heinisch, et al. Arch. Pharm. 1997, 207-210; K. Matsuno, et al. J. Med. Chem. 2002, 45, 4513-4523; A. M. Papini, et al. J. Med. Chem. 2004, 47, 5224-5229
12) J. Mindl, et al. Collect. Czech. Chem. Commun. 1983, 48, 900-905; S. Sasaki, et al. J. Med. Chem. 2003, 46, 113-124; B.-B. Zeng, et al. Bioorg. Med. Chem. Lett. 2004, 14, 5565-5568
13) Q. Wang, et al. Synthetic Commun. 2004, 34, 255-264; W. Mederski, et al. Bioorg. Med. Chem. Lett. 2003, 13, 13715-3718; R. J. Brown, et al. Tetrahedron 2004, 60, 4361-4375
14) L. Mao, et al. Synthesis 2004, 15, 2535-2539; M. Darabantu, et al. Tetrahedron 2005, 61, 2897-2905; E. Ford, et al. Tet. Lett. 2000, 41, 3197-3198; T. Shiota, et al. J. Org. Chem. 1999, 64, 453-457; E. C. Taylor, et al. Synthetic Commun. 1987, 17, 1865-1868; G. A. Molander, et al. J. Org. Chem. 2002, 67, 8424-8429; G. Hughes, et al. Org. & Biomolecular Chem. 2004, 2, 3363-3367
15) R. P. Tangaltapally, et al. J. Med. Chem. 2004, 47, 5276-5283; R. H. Bradburry, et al. J. Med. Chem. 1997, 40, 996-1004
16) X. He, et al. Bioorg. Med. Chem. 2004, 12, 4003-4008; A. Gopatsamy, et al. Bioorg. Med. Chem. Lett. 2005, 15, 1591-1594; J.-F. Cheng, et al. *Bioorg. Med. Chem. Lett.* 2004, 14, 2411-2416; E. R. Parmee, et al. *Bioorg. Med. Chem. Lett.* 2004, 14, 43-46

17) G. Yang, et al. *Synthetic Commun.* 2006, 36, 5611-5619; H. B. Woo, et al. *Bioorg. Med. Chem. Lett.* 2005, 15, 3782-3786.

18) J. F. Miravet, et al. *Org. Lett.* 2005, 7, 4791-4794; A. L. Castelhano, et al. *Bioorg. Med. Chem. Lett.* 2005, 15, 1501-1504.

19) Y. Lu, et al. *Bioorg. Med. Chem. Lett.* 2006, 16, 915-919; J. W. Szewczyk, et al. *Bioorg. Med. Chem. Lett.* 2006, 16, 3055-3060.

General Methods for the Preparation of the Inventive Compounds:

Scheme 1: 1st Stage 2,6-Diamino-3-nitropyridine or 2-amino-3,5-dinitropyridine are dissolved in a suitable inert solvent, for example methanol, ethanol, dimethylformamide or dioxane. After adding a catalyst, for example Raney nickel, palladium on carbon or platinum(IV) dioxide, the reaction mixture is placed under a hydrogen atmosphere, and a pressure between 1 and 5 bar is established. The reaction mixture is allowed to react for several hours, for example 1-16 hours, within a temperature range between 20° C. and 60° C. Once the reaction has ended, the insoluble residues are filtered off, for which the filter medium may consist of silica gel, Celite or commercial glass fibre filters, and they are washed with the appropriate solvent. The crude product, present in solution, is used for the next reaction without further purification.

2nd Stage

The 1,2-dione derivative is initially charged in a suitable inert solvent, for example methanol, ethanol, dioxane, toluene or dimethylformamide. 2,3,6-Triaminopyridine or 2,3,5-triaminopyridine, directly after the reduction, as a solution of the crude products in one of the abovementioned solvents, are added to the initially charged 1,2-dione, optionally with addition of an acid, for example acetic acid or a base, for example potassium hydroxide. The reaction mixture is allowed to react within a temperature range of 20° C. to 80° C. for a certain time, for example 20 minutes to 40 hours. Once the reaction has ended, any precipitated solid is filtered off, for which the filter medium may consist, for example, of commercial filter paper, and washed with the appropriate solvent, and the remaining solid is dried under reduced pressure, or the reaction mixture is freed of solvent under reduced pressure. When dimethylformamide is used, the reaction mixture is stirred into a large amount of water and the precipitated solid is filtered off, or the aqueous phase is extracted with a suitable organic solvent, for example dichloromethane or ethyl acetate, and the organic phases are concentrated under reduced pressure. The remaining crude product is purified by recrystallization from a suitable solvent, for example dioxane, or by column or flash chromatography on silica gel or alumina. The eluent used is, for example, a mixture of methanol and dichloromethane.

Scheme 2: 1st Stage

The pyridopyrazinone derivative 8 is initially charged in a suitable inert solvent, for example dimethylformamide, dioxane or toluene, or without solvent. A chlorinating agent, for example phosphoryl chloride or thionyl chloride, is added at room temperature and the reaction mixture is allowed to react within a temperature range of from 20° C. to 100° C. for a certain time, for example 1 hour to 24 hours. Once the reaction has ended, the reaction mixture is poured onto water and neutralized with a suitable aqueous base, for example sodium hydroxide solution. Any precipitated solid is filtered off, for which the filter medium may consist, for example, of commercial filter paper, and washed with the appropriate solvent, and the remaining residue is dried under reduced pressure, or the aqueous phase is extracted with a suitable organic solvent, for example dichloromethane or ethyl acetate, and the organic phases are concentrated under reduced pressure. The remaining crude product is purified by recrystallization from a suitable solvent, for example dioxane or toluene, or by column or flash chromatography on silica gel or alumina. The eluent used is, for example, a mixture of methanol and dichloromethane.

Scheme 3: 1st Stage 2,3,6-Triaminopyridine or 2,3,5-triaminopyridine are, directly after the reduction, as a solution of the crude products, initially charged in one of the abovementioned solvents. After an oxalic acid derivative has been added, for example diethyl oxalate or oxalyl chloride, the reaction mixture, optionally with addition of an acid, for example hydrochloric acid, sulphuric acid or glacial acetic acid, is allowed to react within a temperature range of 20° C. to 150° C. for a certain time, for example 10 minutes to 24 hours. After the reaction has ended, any precipitated solid is filtered off, for which the filter medium may consist, for example, of commercial filter paper, and washed with the appropriate solvent, and the remaining solid is dried under reduced pressure, or the reaction mixture is freed from the solvent under reduced pressure. Alternatively, the reaction mixture can be stirred into a large amount of water and the precipitated solid can be filtered off, or the aqueous phase, after neutralization with a suitable aqueous base, for example sodium hydroxide solution, can be extracted with a suitable organic solvent, for example dichloromethane or ethyl acetate, and the organic phase concentrated under reduced pressure. The remaining crude product is purified by recrystallization from a suitable solvent, for example dioxane or toluene, or by column or flash chromatography on silica gel or alumina. The eluent used is, for example, a mixture of methanol and dichloromethane.

2nd Stage

The dione derivative 10 is initially charged in a suitable inert solvent, for example dimethylformamide, dioxane or toluene, or without solvent. A chlorinating agent, for example phosphoryl chloride or thionyl chloride, is added at room temperature and the reaction mixture is allowed to react within a temperature range of from 20° C. to 100° C. for a certain time, for example 1 hour to 24 hours. Once the reaction has ended, the reaction mixture is poured onto water and neutralized with a suitable aqueous base, for example sodium hydroxide solution. Any precipitated solid is filtered off, for which the filter medium may consist, for example, of commercial filter paper, and washed with the appropriate solvent, and the remaining residue is dried under reduced pressure, or the aqueous phase is extracted with a suitable organic solvent, for example dichloromethane or ethyl acetate, and the organic phases are concentrated under reduced pressure. The remaining crude product is purified by recrystallization from a suitable solvent, for example dioxane or toluene, or by column or flash chromatography on silica gel or alumina. The eluent used is, for example, a mixture of methanol and dichloromethane.

3rd Stage

The intermediate 11 can be reacted with an appropriate alcohol, thiol or amine and optionally with a suitable base, preferably sodium hydride, pyridine, triethylamine, potassium carbonate or sodium methoxide in methanol, in a suitable inert solvent, for example dimethylformamide, dimethyl sulphoxide, methanol, toluene, or in a base as the solvent, for example pyridine or triethylamine, or without solvent. The reaction mixture is allowed to react for a certain time, for example 30 minutes to 2 days, in a temperature range between 20° C. and 140° C. Alternatively, the intermediate 11 can be reacted with an appropriate amine and a suitable catalyst, for example tris(dibenzylideneacetone)dipalladium(0) or tetrakis(triphenylphosphine)palladium(0), and a suitable ligand, for example 2-(dicyclohexylphosphanyl)biphenyl, and a suitable base, for example sodium tert-butoxide, in a suitable solvent, for example toluene or dimethylformamide. The reaction mixture is allowed to react for a certain time, for example 2 hours to 30 hours, in a temperature range between 60° C. and 120° C. After the reaction has ended, any precipitated solid is filtered off, for which the filter medium may consist, for example, of commercial filter paper, and washed with the appropriate solvent, and the remaining solid is dried under reduced pressure, or the reaction mixture is freed from the solvent under reduced pressure. Alternatively, the reaction mixture can be stirred into a large amount of water and the precipitated solid can be filtered off, or the aqueous phase, after neutralization with a suitable aqueous acid, for example hydrochloric acid, can be extracted with a suitable organic solvent, for example dichloromethane or ethyl acetate, and the organic phase concentrated under reduced pressure. The remaining crude product is purified by recrystallization from a suitable solvent, for example dioxane, ethyl acetate or toluene, or by column or flash chromatography on silica gel or alumina. The eluent used is, for example, a mixture of methanol and dichloromethane.

Scheme 4: 1st Stage

The intermediates 4 and 7 can be reacted with an appropriate, suitable chloride, bromide or tosylate and optionally with a suitable base, for example sodium hydride, pyridine, triethylamine, potassium carbonate or sodium methoxide in methanol, in a suitable inert solvent, for example dimethylformamide, dimethyl sulphoxide, methanol, or in a base as a solvent, for example pyridine or triethylamine, or without solvent. The reaction mixture is allowed to react for a certain time, for example 1 hour to 24 hours, in a temperature range between 20° C. and 150° C. Alternatively, the intermediates 4 and 7 can be reacted with an appropriate aryl bromide or iodide and a suitable catalyst, for example palladium acetate or $Pd_2(dba)_3$, and a suitable ligand, for example BINAP, and suitable base, for example potassium carbonate or sodium tert-butoxide, in a suitable solvent, for example toluene or dioxane. The reaction mixture is allowed to react for a certain time, for example 10 hours to 30 hours, in a temperature range between 60° C. and 120° C. Once the reaction has ended, any precipitated solid is filtered off, for which the filter medium may consist, for example, of commercial filter paper, and washed with the appropriate solvent, and the remaining solid is dried under reduced pressure, or any catalyst residues are filtered off and washed with the appropriate solvent, and the solvent is dried under reduced pressure, or the reaction mixture is freed of the solvent under reduced pressure. Alternatively, the reaction mixture can be stirred into a large amount of water and the precipitated solid can be filtered off, or the aqueous phase, after neutralization with a suitable aqueous acid, for example hydrochloric acid, can be extracted with a suitable organic solvent, for example dichloromethane or ethyl acetate, and the organic phase concentrated under reduced pressure. The remaining crude product is purified by recrystallization from a suitable solvent, for example ethanol or toluene, or by column or flash chromatography on silica gel or alumina. The eluent used is, for example, a mixture of methanol and dichloromethane.

Scheme 5: 1st Stage

After the basic process, the products formed by the basic process can be converted in conversion reactions to inventive conversion products in a procedure known to the person skilled in the art.

For instance, when the product is to be a derivative of compound 16 according to scheme 5, the reaction product 4, 7, 9 or 15 can be reacted with an appropriate isocyanate and optionally a suitable base, preferably sodium hydride, potassium hexamethyldisilazide, pyridine, triethylamine or potassium carbonate, in a suitable inert solvent, for example dimethylformamide, dimethyl sulphoxide, acetonitrile, dichloromethane, 1,2-dichlorethane or dioxane, or in a base as the solvent, for example pyridine or triethylamine, or without solvent. The reaction mixture is allowed to react for several hours, for example 1-24 hours, within a temperature range between 0 and 80° C. Once the reaction has ended, any precipitated solid is filtered off, for which the filter medium may consist, for example, of commercial filter paper, and washed with the appropriate solvent, and the remaining solid is dried under reduced pressure, or the reaction mixture is freed of the solvent under reduced pressure. Alternatively, the reaction mixture can be stirred into a large amount of water and the precipitated solid can be filtered off, or the aqueous phase, after neutralization with a suitable aqueous acid, for example hydrochloric acid, can be extracted with a suitable organic solvent, for example dichloromethane or ethyl acetate, and the organic phase concentrated under reduced pressure. The remaining crude product is purified by recrystallization from a suitable solvent, for example ethanol or ethyl acetate, or by column or flash chromatography on silica gel or alumina. The eluent used is, for example, a mixture of methanol and dichloromethane.

Or, alternatively, when the product is to be a derivative of compound 17 according to scheme 5, the reaction product 4, 7, 9 or 15 may be reacted with phosgene or carbonyldiimidazole and an appropriate amine in a suitable inert solvent, for example dimethylformamide, tetrahydrofuran, toluene, dichloromethane or acetonitrile. If appropriate, a suitable base, preferably pyridine, sodium hydrogencarbonate, triethylamine, N-methylmorpholine or sodium acetate, is used. The reaction mixture is allowed to react for a certain time, for example 15 minutes to 24 hours, in a temperature range between 0 and 60° C. Alternatively, the reaction product 4, 7, 9 or 15 can be reacted with an appropriate amine-phenylcarbamate reagent and optionally with a suitable base, preferably pyridine, sodium carbonate, triethylamine or sodium hydride, in a suitable inert solvent, for example tetrahydrofuran, dioxane, dichloromethane, dimethylformamide or acetonitrile, or in a base as a solvent, for example pyridine or triethylamine, or without solvent. The reaction mixture is allowed to react for a certain time, for example 1 hour to 18 hours, within a temperature range between 0° C. and 120° C. Once the reaction has ended, any precipitated solid is filtered off, for which the filter medium may consist, for example, of commercial filter paper, and washed with the appropriate solvent, and the remaining solid is dried under reduced pressure, or the reaction mixture is freed of the solvent under reduced pressure. Alternatively, the reaction mixture can be stirred into a large amount of water and the precipitated solid can be filtered off, or the aqueous phase, after neutralization with a suitable aqueous acid, for example hydrochloric acid, can be extracted with a suitable organic solvent, for example dichloromethane or ethyl acetate, and the organic phase concentrated under reduced pressure.

The remaining crude product is purified by recrystallization from a suitable solvent, for example ethanol or ethyl acetate, or by column or flash chromatography on silica gel or alumina. The eluent used is, for example, a mixture of methanol and dichloromethane.

For instance, when the product is to be a derivative of compound 18 according to scheme 5, the reaction product 4, 7, 9 or 15 can be reacted with an appropriate isothiocyanate and appropriately a suitable base, preferably sodium hydride, triethylamine, potassium carbonate or pyridine, in a suitable inert solvent, for example dimethylformamide, tetrahydrofuran, acetone or toluene, or in a base as a solvent, for example, pyridine or triethylamine, or without solvent. The reaction mixture is allowed to react for a certain time, for example 30 minutes to 90 hours, within a temperature range between 0 and 115° C. Once the reaction has ended, any precipitated solid is filtered off, for which the filter medium may consist, for example, of commercial filter paper, and washed with the appropriate solvent, and the remaining solid is dried under reduced pressure, or the reaction mixture is freed of the solvent under reduced pressure. Alternatively, the reaction mixture can be stirred into a large amount of water and the precipitated solid can be filtered off, or the aqueous phase, after neutralization with a suitable aqueous acid, for example hydrochloric acid, can be extracted with a suitable organic solvent, for example dichloromethane or ethyl acetate, and the organic phase concentrated under reduced pressure. The remaining crude product is purified by recrystallization from a suitable solvent, for example ethanol or ethyl acetate, or by column or flash chromatography on silica gel or alumina. The eluent used is, for example, a mixture of methanol and dichloromethane.

Or, alternatively, when the product is to be a derivative of the compound 19 according to scheme 5, the reaction product 4, 7, 9 or 15 can be reacted with thiophosgene or thiocarbonyldiimidazole and an appropriate amine in a suitable inert solvent, for example dimethylformamide, tetrahydrofuran, toluene, dichloromethane, ethanol or acetonitrile. Optionally, a suitable base, preferably pyridine, sodium hydrogencarbonate, potassium carbonate, triethylamine or imidazole is used. The reaction mixture is allowed to react for several hours, for example 1 to 24 hours, in a temperature range between −10 and 80° C. Once the reaction has ended, any precipitated solid is filtered off, for which the filter medium may consist, for example, of commercial filter paper, and washed with the appropriate solvent, and the remaining solid is dried under reduced pressure, or the reaction mixture is freed of the solvent under reduced pressure. Alternatively, the reaction mixture can be stirred into a large amount of water and the precipitated solid can be filtered off, or the aqueous phase, after neutralization with a suitable aqueous acid, for example hydrochloric acid, can be extracted with a suitable organic solvent, for example dichloromethane or ethyl acetate, and the organic phase concentrated under reduced pressure. The remaining crude product is purified by recrystallization from a suitable solvent, for example ethanol or ethyl acetate, or by column or flash chromatography on silica gel or alumina. The eluent used is, for example, a mixture of methanol and dichloromethane.

For instance, when the product is to be a derivative of compound 20 according to scheme 5, the reaction product 4, 7, 9 or 15 can be reacted with phosgene or carbonyldiimidazole and an appropriate hydroxylamine in a suitable inert solvent, for example dimethylformamide, tetrahydrofuran, dioxane, dichloromethane or toluene. Optionally, a suitable base, preferably pyridine, sodium carbonate, triethylamine or sodium acetate, is used. The reaction mixture is allowed to react for a certain time, for example 1 hour to 24 hours, within a temperature range between 0 and 100° C. Alternatively, the reaction product 4, 7, 9 or 15 can be reacted with an appropriate hydroxylamine-phenylcarbamate reagent and optionally with a suitable base, preferably pyridine, sodium carbonate, triethylamine or sodium acetate, in a suitable inert solvent, for example tetrahydrofuran, dioxane, dichloromethane, dimethylformamide or toluene, or in a base as a solvent, for example pyridine or triethylamine, or without solvent. The reaction mixture is allowed to react for a certain time, for example 1 hour to 18 hours, within a temperature range between room temperature and 100° C. Once the reaction has ended, any precipitated solid is filtered off, for which the filter medium may consist, for example, of commercial filter paper, and washed with the appropriate solvent, and the remaining solid is dried under reduced pressure, or the reaction mixture is freed of the solvent under reduced pressure. Alternatively, the reaction mixture can be stirred into a large amount of water and the precipitated solid can be filtered off, or the aqueous phase, after neutralization with a suitable aqueous acid, for example hydrochloric acid, can be extracted with a suitable organic solvent, for example dichloromethane or ethyl acetate, and the organic phase concentrated under reduced pressure. The remaining crude product is purified by recrystallization from a suitable solvent, for example ethanol or ethyl acetate, or by column or flash chromatography on silica gel or alumina. The eluent used is, for example, a mixture of methanol and dichloromethane.

For instance, when the product is to be a derivative of compound 21 according to scheme 5, the reaction product 4, 7, 9 or 15 can be reacted with phosgene or carbonyldiimidazole and an appropriate hydrazine in a suitable inert solvent, for example dioxane, chloroform, toluene or ethanol. Optionally, a suitable base, preferably pyridine, sodium carbonate, diisopropylethylamine or sodium acetate, is used. The reaction mixture is allowed to react for a certain time, for example 1 hour to 24 hours, within a temperature range between 0 and 100° C. Alternatively, the reaction product 4, 7, 9 or 15 can be reacted with an appropriate hydrazine-phenyl-carbamate reagent and optionally with a suitable base, preferably pyridine, sodium carbonate, triethylamine or sodium acetate, in a suitable inert solvent, for example tetrahydrofuran, dioxane, dichloromethane, dimethylformamide or toluene, or in a base as a solvent, for example pyridine or triethylamine, or without solvent. The reaction mixture is allowed to react for a certain time, for example 1 hour to 15 hours, within a temperature range between 0° C. and 100° C. Once the reaction has ended, any precipitated solid is filtered off, for which the filter medium may consist, for example, of commercial filter paper, and washed with the appropriate solvent, and the remaining solid is dried under reduced pressure, or the reaction mixture is freed of the solvent under reduced pressure. Alternatively, the reaction mixture can be stirred into a large amount of water and the precipitated solid can be filtered off, or the aqueous phase, after neutralization with a suitable aqueous acid, for example hydrochloric acid, can be extracted with a suitable organic solvent, for example dichloromethane or ethyl acetate, and the organic phase concentrated under reduced pressure. The remaining crude product is purified by recrystallization from a suitable solvent, for example ethanol or ethyl acetate, or by column or flash chromatography on silica gel or alumina. The eluent used is, for example, a mixture of methanol and dichloromethane.

Or, alternatively, when the product is to be a derivative of the compound 21a according to scheme 5, the reaction product 4, 7, 9 or 15 can be reacted with oxalyl chloride and an appropriate alcohol, optionally with a suitable base, preferably pyridine, sodium hydroxide, triethylamine, in a suitable inert solvent, for example tetrahydrofuran, toluene, dichloromethane, ethanol, or in a base as a solvent, for example pyridine or triethylamine. The reaction mixture is allowed to react for a certain time, for example 15 minutes to 24 hours, with in a temperature range between −10 and 60° C. Once the reaction has ended, any precipitated solid is filtered off, for which the filter medium may consist, for example, of commercial filter paper, and washed with the appropriate solvent, and the remaining solid is dried under reduced pressure, or the reaction mixture is freed of the solvent under reduced pressure. Alternatively, the reaction mixture can be stirred into a large amount of water and the precipitated solid can be filtered off, or the aqueous phase, after neutralization with a suitable aqueous acid, for example hydrochloric acid, can be extracted with a suitable organic solvent, for example dichloromethane or ethyl acetate, and the organic phase concentrated under reduced pressure.

The remaining crude product is purified by recrystallization from a suitable solvent, for example ethanol or ethyl acetate, or by column or flash chromatography on silica gel or alumina. The eluent used is, for example, a mixture of methanol and dichloromethane.

Or, alternatively, when the product is to be a derivative of the compound 21 b according to scheme 5, the reaction product 4, 7, 9 or 15 can be reacted with oxalyl chloride or ethyloxalyl chloride and an appropriate amine, optionally with a suitable base, preferably pyridine, sodium hydroxide, triethylamine, in a suitable inert solvent, for example tetrahydrofuran, toluene, dichloromethane, ethanol, or in a base as a solvent, for example pyridine or triethylamine. The reaction mixture is allowed to react for a certain time, for example 15 minutes to 24 hours, with in a temperature range between −10 and 60° C. Alternatively, the intermediate 21a can be reacted with an appropriate amine, optionally with a suitable base, preferably pyridine, sodium hydride or triethylamine, in a suitable inert solvent, for example tetrahydrofuran, toluene, dichloromethane, ethanol, or in a base as a solvent, for example pyridine or triethylamine. The reaction mixture is allowed to react for a certain time, for example 1 hour to 50 hours, within a temperature range between 10 and 120° C. Once the reaction has ended, any precipitated solid is filtered off, for which the filter medium may consist, for example, of commercial filter paper, and washed with the appropriate solvent, and the remaining solid is dried under reduced pressure, or the reaction mixture is freed of the solvent under reduced pressure. Alternatively, the reaction mixture can be stirred into a large amount of water and the precipitated solid can be filtered off, or the aqueous phase, after neutralization with a suitable aqueous acid, for example hydrochloric acid, can be extracted with a suitable organic solvent, for example dichloromethane or ethyl acetate, and the organic phase concentrated under reduced pressure. The remaining crude product is purified by recrystallization from a suitable solvent, for example ethanol or ethyl acetate, or by column or flash chromatography on silica gel or alumina. The eluent used is, for example, a mixture of methanol and dichloromethane.

Scheme 6: 1st Stage

After the basic process, the products formed by the basic process can be converted to inventive conversion products in conversion reactions in a procedure known to those skilled in the art.

For instance, when the product is to be a derivative of compound 23 according to scheme 6, the reaction product 22 can be reacted with appropriate aryl/heteroarylboronic acid derivatives or aryl/heteroarylorganotin compounds and a suitable catalyst, for example Pd(PPh$_3$)$_4$, [1,1'-bis(diphenylphosphino)ferrocene]dichloropalladium(II) or Pd$_2$(dba)$_3$, and a suitable base, for example sodium carbonate, caesium carbonate or triethylamine, in a suitable solvent, for example dimethylformamide, dimethylformamide/water, toluene, acetonitrile, dimethoxyethane or dioxane. The reaction mixture is allowed to react for a certain time, for example 6 hours to several days, within a temperature range between 60° C. and 120° C. Once the reaction has ended, any precipitated solid is filtered off, for which the filter medium may consist, for example, of commercial filter paper, and washed with the appropriate solvent, and the remaining solid is dried under reduced pressure, or any catalyst residues present are filtered off and washed with the appropriate solvent, and the solvent is removed under reduced pressure, or the reaction mixture is freed from the solvent under reduced pressure. Alternatively, the reaction mixture can be stirred into a large amount of water and the precipitated solid filtered off, or the aqueous phase, after neutralization with a suitable aqueous acid, for example hydrochloric acid, can be extracted with a suitable organic solvent, for example dichloromethane or ethyl acetate, and the organic phase concentrated under reduced pressure. The remaining crude product is purified by recrystallization from a suitable solvent, for example ethanol or ethyl acetate, or by column or flash chromatography on silica gel or alumina. The eluent used is, for example, a mixture of methanol and dichloromethane.

For instance, when the product is to be a derivative of the compound 23a according to scheme 6, the reaction product 22 can be reacted with appropriate alkylzinc halides and a suitable catalyst, for example Pd(PPh$_3$)$_4$, [1,1'-bis(diphenylphosphino)ferrocene]dichloropalladium(II) or PdCl$_2$(PPh$_3$)$_2$ in a suitable solvent, for example dimethylformamide, tetrahydrofuran, toluene, dimethoxyethane or dioxane. The reaction mixture is allowed to react for a certain time, for example 30 minutes to 48 hours, within a temperature range between room temperature and 120° C. Once the reaction has ended, any precipitated solid is filtered off, for which the filter medium may consist, for example, of commercial filter paper, and washed with the appropriate solvent, and the remaining solid is dried under reduced pressure, or any catalyst residues present are filtered off and washed with the appropriate solvent, and the solvent is removed under reduced pressure, or the reaction mixture is freed from the solvent under reduced pressure. Alternatively, the reaction mixture can be stirred into a large amount of water and the precipitated solid filtered off, or the aqueous phase, can be extracted with a suitable organic solvent, for example dichloromethane or ethyl acetate, and the organic phase concentrated under reduced pressure. The remaining crude product is purified by recrystallization from a suitable solvent, for example ethanol or ethyl acetate, or by column or flash chromatography on silica gel or alumina. The eluent used is, for example, a mixture of methanol and dichloromethane.

For instance, when the product is to be a derivative of the compound 24 according to scheme 6, the reaction product 22 can be reacted with appropriate vinylboronic acid derivatives, vinylorganotin compounds or alkene derivatives and a suitable catalyst, for example Pd(PPh$_3$)$_4$, [1,1'-bis(diphenylphosphino)ferrocene]dichloropalladium(II) or Pd(OAc)$_2$, and a suitable ligand, for example triphenylphosphine or tri-o-tolylphosphine, and a suitable base, for example potassium carbonate, sodium carbonate, triethylamine or sodium acetate, in a suitable solvent, for example toluene, dimethylformamide, dimethylformamide/water, acetonitrile, dimethoxyethane or dimethylacetamide.

The reaction mixture is allowed to react for a certain time, for example 3 hours to 24 hours, within a temperature range between 60° C. and 140° C. Once the reaction has ended, any precipitated solid is filtered off, for which the filter medium may consist, for example, of commercial filter paper, and washed with the appropriate solvent, and the remaining solid is dried under reduced pressure, or any catalyst residues present are filtered off and washed with the appropriate solvent, and the solvent is removed under reduced pressure, or the reaction mixture is freed from the solvent under reduced pressure. Alternatively, the reaction mixture can be stirred into a large amount of water and the precipitated solid filtered off, or the aqueous phase, after neutralization with a suitable aqueous acid, for example hydrochloric acid, can be extracted with a suitable organic solvent, for example dichloromethane or ethyl acetate, and the organic phase concentrated under reduced pressure. The remaining crude product is purified by recrystallization from a suitable solvent, for example ethanol or toluene, or by column or flash chromatography on silica gel or alumina. The eluent used is, for example, a mixture of methanol and dichloromethane.

For instance, when the product is to be a derivative of compound 25 according to scheme 6, the reaction product 22 can be reacted with appropriate alkyne derivatives and a suitable catalyst, for example $Pd(PPh_3)_4$, $PdCl_2(PPh_3)_2$ or $Pd_2(dba)_3$, and a suitable additive, for example copper(I) iodide, and a suitable base, for example potassium carbonate, triethylamine or potassium acetate, in a suitable solvent, for example dimethylformamide, tetrahydrofuran, tetrahydrofuran/water, toluene or dimethylacetamide.

The reaction mixture is allowed to react for a certain time, for example 1 hour to several days, within a temperature range between room temperature and 120° C. Once the reaction has ended, any precipitated solid is filtered off, for which the filter medium may consist, for example, of commercial filter paper, and washed with the appropriate solvent, and the remaining solid is dried under reduced pressure, or any catalyst residues present are filtered off and washed with the appropriate solvent, and the solvent is removed under reduced pressure, or the reaction mixture is freed from the solvent under reduced pressure. Alternatively, the reaction mixture can be stirred into a large amount of water and the precipitated solid filtered off, or the aqueous phase, after neutralization with a suitable aqueous acid, for example hydrochloric acid, can be extracted with a suitable organic solvent, for example dichloromethane or ethyl acetate, and the organic phase concentrated under reduced pressure. The remaining crude product is purified by recrystallization from a suitable solvent, for example ethanol or toluene, or by column or flash chromatography on silica gel or alumina. The eluent used is, for example, a mixture of methanol and dichloromethane.

Scheme 7: 1st Stage

After the basic process, the products formed by the basic process can be converted to inventive conversion products in conversion reactions in a procedure known to those skilled in the art.

The intermediate 22 can be reacted with an appropriate amine and optionally with a suitable base, preferably sodium hydride, pyridine, triethylamine, potassium carbonate or sodium methoxide in methanol, in a suitable inert solvent, for example dimethylformamide, dimethyl sulphoxide, methanol, toluene, or in a base as a solvent, for example pyridine or triethylamine, or without solvent. The reaction mixture is allowed to react for a certain time, for example 1 hour to several days, within a temperature range between 20° C. and 140° C. Alternatively, the intermediate 22 can be reacted with an appropriate amine and a suitable catalyst, for example palladium acetate or $Pd_2(dba)_3$, and a suitable ligand, for example BINAP, and a suitable base, for example potassium carbonate or sodium tert-butoxide, in a suitable solvent, for example toluene or dioxane.

The reaction mixture is allowed to react for a certain time, for example 10 hours to 30 hours, in a temperature range between 60° C. and 120° C. Once the reaction has ended, any precipitated solid is filtered off, for which the filter medium may consist, for example, of commercial filter paper, and washed with the appropriate solvent, and the remaining solid is dried under reduced pressure, or any catalyst residues present are filtered off and washed with the appropriate solvent, and the solvent is removed under reduced pressure, or the reaction mixture is freed from the solvent under reduced pressure. Alternatively, the reaction mixture can be stirred into a large amount of water and the precipitated solid filtered off, or the aqueous phase, after neutralization with a suitable aqueous acid, for example hydrochloric acid, can be extracted with a suitable organic solvent, for example dichloromethane or ethyl acetate, and the organic phase concentrated under reduced pressure. The remaining crude product is purified by recrystallization from a suitable solvent, for example dioxane, ethyl acetate or toluene, or by column or flash chromatography on silica gel or alumina. The eluent used is, for example, a mixture of methanol and dichloromethane.

2nd Stage

For instance, when the product is to be a derivative of compound 27 according to scheme 7, the reaction product 26 can be reacted with an appropriate carbonyl chloride and optionally a suitable base, preferably sodium hydride, potassium hydroxide, pyridine, triethylamine or potassium carbonate, and optionally a catalyst, for example dimethylaminopyridine, in a suitable inert solvent, for example tetrahydrofuran, toluene, acetonitrile, dichloromethane, acetone or dioxane, or in a base as a solvent, for example pyridine or triethylamine, or without solvent. The reaction mixture can be reacted for a certain time, for example 30 minutes to 24 hours, within a temperature range between 0 and 110° C. Once the reaction has ended, any precipitated solid is filtered off, for which the filter medium may consist, for example, of commercial filter paper, and washed with the appropriate solvent, and the remaining solid is dried under reduced pressure, or the reaction mixture is freed from the solvent under reduced pressure. Alternatively, the reaction mixture can be stirred into a large amount of water and the precipitated solid filtered off, or the aqueous phase, after neutralization with a suitable aqueous acid, for example hydrochloric acid, can be extracted with a suitable organic solvent, for example dichloromethane or ethyl acetate, and the organic phase concentrated under reduced pressure. The remaining crude product is purified by recrystallization from a suitable solvent, for example ethanol or ethyl acetate, or by column or flash chromatography on silica gel or alumina. The eluent used is, for example, a mixture of methanol and dichloromethane.

For instance, when the product is to be a derivative of the compound 28 according to scheme 7, the reaction product 26 can be reacted with an appropriate sulphonyl chloride and optionally a suitable base, preferably sodium hydride, potassium hydroxide, pyridine, triethylamine or potassium carbonate, and optionally a catalyst, for example dimethylaminopyridine, in a suitable inert solvent, for example tetrahydrofuran, toluene, acetonitrile, dichloromethane, acetone, dimethylformamide or dioxane, or in a base as a solvent, for example pyridine or triethylamine, or without solvent. The reaction mixture is allowed to react for a certain time, for example 30 minutes to 16 hours, within a temperature range between 0 and 120° C. Once the reaction has ended, any precipitated solid is filtered off, for which the filter medium may consist, for example, of commercial filter paper, and washed with the appropriate solvent, and the remaining solid is dried under reduced pressure, or the reaction mixture is freed from the solvent under reduced pressure. Alternatively, the reaction mixture can be stirred into a large amount of water and the precipitated solid filtered off, or the aqueous phase, after neutralization with a suitable aqueous acid, for example hydrochloric acid, can be extracted with a suitable organic solvent, for example dichloromethane or ethyl acetate, and the organic phase concentrated under reduced pressure. The remaining crude product is purified by recrystallization from a suitable solvent, for example ethanol or ethyl acetate, or by column or flash chromatography on silica gel or alumina. The eluent used is, for example, a mixture of methanol and dichloromethane.

For instance, when the product is to be a derivative of the compound 29 according to scheme 7, the reaction product 26 can be reacted with an appropriate chlorocarbonic ester and optionally a suitable base, preferably sodium hydride, sodium hydroxide, pyridine, triethylamine or potassium carbonate, and optionally a catalyst, for example dimethylaminopyridine, in a suitable inert solvent, for example dioxane, tetrahydrofuran, dichloromethane, acetone, dimethylformamide or dichloroethane, or in a base as a solvent, for example pyridine or triethylamine, or without solvent. The reaction mixture is allowed to react for a certain time, for example 1 hour to 24 hours, within a temperature range between −10° C. and 100° C. Once the reaction has ended, any precipitated solid is filtered off, for which the filter medium may consist, for example, of commercial filter paper, and washed with the appropriate solvent, and the remaining solid is dried under reduced pressure, or the reaction mixture is freed from the solvent under reduced pressure. Alternatively, the reaction mixture can be stirred into a large amount of water and the precipitated solid filtered off, or the aqueous phase, after neutralization with a suitable aqueous acid, for example hydrochloric acid, can be extracted with a suitable organic solvent, for example dichloromethane or ethyl acetate, and the organic phase concentrated under reduced pressure. The remaining crude product is purified by recrystallization from a suitable solvent, for example ethanol or ethyl acetate, or by column or flash chromatography on silica gel or alumina. The eluent used is, for example, a mixture of methanol and dichloromethane.

For instance, when the product is to be a derivative of the compound 30 according to scheme 7, the reaction product 26 can be reacted with an appropriate isocyanate or carbamoyl chloride and optionally a suitable base, preferably sodium hydride, pyridine, triethylamine, piperidine or potassium carbonate, and optionally a catalyst, for example dimethylaminopyridine, in a suitable inert solvent, for example dioxane, tetrahydrofuran, dimethylformamide, toluene or acetonitrile, or in a base as a solvent, for example pyridine or triethylamine, or without solvent. The reaction mixture is allowed to react for a certain time, for example 2 hours to 40 hours, within a temperature range between room temperature and 100° C. Once the reaction has ended, any precipitated solid is filtered off, for which the filter medium may consist, for example, of commercial filter paper, and washed with the appropriate solvent, and the remaining solid is dried under reduced pressure, or the reaction mixture is freed from the solvent under reduced pressure. Alternatively, the reaction mixture can be stirred into a large amount of water and the precipitated solid filtered off, or the aqueous phase, after neutralization with a suitable aqueous acid, for example hydrochloric acid, can be extracted with a suitable organic solvent, for example dichloromethane or ethyl acetate, and the organic phase concentrated under reduced pressure. The remaining crude product is purified by recrystallization from a suitable solvent, for example ethanol or ethyl acetate, or by column or flash chromatography on silica gel or alumina. The eluent used is, for example, a mixture of methanol and dichloromethane.

Schema 8: 1 st Stage

After the basic processes, the products formed by the basic process can be converted to inventive conversion products in conversion reactions in a procedure known to those skilled in the art.

For instance, when the product is to be a derivative of the compound 32 or 35 according to scheme 8, the reaction product 31 or 34 can be reacted with an appropriate chlorocarbonic ester and optionally a suitable base, preferably sodium hydride, sodium hydroxide, pyridine, triethylamine or potassium carbonate, and optionally a catalyst, for example dimethylaminopyridine, in a suitable inert solvent, for example dioxane, tetrahydrofuran, dichloromethane, acetone, dimethylformamide or dichloroethane, or in a base as a solvent, for example pyridine or triethylamine, or without solvent. The reaction mixture is allowed to react for a certain time, for example 1 hour to 24 hours, within a temperature range between −10° C. and 100° C. Once the reaction has ended, any precipitated solid is filtered off, for which the filter medium may consist, for example, of commercial filter paper, and washed with the appropriate solvent, and the remaining solid is dried under reduced pressure, or the reaction mixture is freed from the solvent under reduced pressure. Alternatively, the reaction mixture can be stirred into a large amount of water and the precipitated solid filtered off, or the aqueous phase, after neutralization with a suitable aqueous acid, for example hydrochloric acid, can be extracted with a suitable organic solvent, for example dichloromethane or ethyl acetate, and the organic phase concentrated under reduced pressure. The remaining crude product is purified by recrystallization from a suitable solvent, for example ethanol or ethyl acetate, or by column or flash chromatography on silica gel or alumina. The eluent used is, for example, a mixture of methanol and dichloromethane.

For instance, when the product is to be a derivative of the compound 33 order 36 according to scheme 8, the reaction product 31 or 34 can be reacted with an appropriate isocyanate or carbamoyl chloride and optionally a suitable base, preferably sodium hydride, pyridine, triethylamine, piperidine or potassium carbonate, and optionally a catalyst, for example dimethylaminopyridine, in a suitable inert solvent, for example dioxane, tetrahydrofuran, dimethylformamide, toluene or acetonitrile, or in a base as a solvent, for example pyridine or triethylamine, or without solvent. The reaction mixture is allowed to react for a certain time, for example 2 hours to 40 hours, within a temperature range between room temperature and 100° C. Once the reaction has ended, any precipitated solid is filtered off, for which the filter medium may consist, for example, of commercial filter paper, and washed with the appropriate solvent, and the remaining solid is dried under reduced pressure, or the reaction mixture is freed from the solvent under reduced pressure. Alternatively, the reaction mixture can be stirred into a large amount of water and the precipitated solid filtered off, or the aqueous phase, after neutralization with a suitable aqueous acid, for example hydrochloric acid, can be extracted with a suitable organic solvent, for example dichloromethane or ethyl acetate, and the organic phase concentrated under reduced pressure. The remaining crude product is purified by recrystallization from a suitable solvent, for example ethanol or ethyl acetate, or by column or flash chromatography on silica gel or alumina. The eluent used is, for example, a mixture of methanol and dichloromethane.

Scheme 9: 1st Stage

After the basic processes, the products formed by the basic process can be converted to inventive conversion products in conversion reactions in a procedure known to those skilled in the art.

For instance, when the product is to be a derivative of the compound 38 according to scheme 9, the reaction product 37 can be reacted, for example, with an appropriate chloride, bromide or iodide and optionally with a suitable base, preferably sodium hydride, pyridine, triethylamine, potassium carbonate or sodium methoxide in methanol, in a suitable inert solvent, for example dimethylformamide, dimethyl sulphoxide, methanol, dioxane, tetrahydrofuran, toluene, or in a base as a solvent, for example pyridine or triethylamine, or without solvent. The reaction mixture is allowed to react for a certain time, for example 30 minutes to 2 days, in a temperature range between 0° C. and 140° C. Alternatively, an amino-substituted intermediate 37 can be reacted, for example, with an appropriate chloride, bromide or iodide and a suitable catalyst, for example tris(dibenzylideneacetone)dipalladium (0) or tetrakis(triphenylphosphine)palladium(0), and a suitable ligand, for example 2-(dicyclohexylphosphanyl)biphenyl, and a suitable base, for example sodium tertbutoxide, in a suitable solvent, for example toluene or dimethylformamide. The reaction mixture is allowed to react for a certain time, for example 2 hours to 30 hours, within a temperature range between 60° C. and 120° C. Once the reaction has ended, any precipitated solid is filtered off, for which the filter medium may consist, for example, of commercial filter paper, and washed with the appropriate solvent, and the remaining solid is dried under reduced pressure, or the reaction mixture is freed from the solvent under reduced pressure. Alternatively, the reaction mixture can be stirred into a large amount of water and the precipitated solid filtered off, or the aqueous phase, after neutralization with a suitable aqueous acid, for example hydrochloric acid, can be extracted with a suitable organic solvent, for example dichloromethane or ethyl acetate, and the organic phase concentrated under reduced pressure. The remaining crude product is purified by recrystallization from a suitable solvent, for example dioxane, ethyl acetate or toluene, or by column or flash chromatography on silica gel or alumina. The eluent used is, for example, a mixture of methanol and dichloromethane.

Under some of the reaction conditions specified, OH, SH and $NH_2$ groups may possibly enter into undesired side reactions. It is therefore preferred to provide them with protecting groups or, in the case of $NH_2$, to replace it with $NO_2$, and then to eliminate the protecting group or to reduce the $NO_2$ group. For instance, in a modification of the above-described processes, at least one OH group in the starting compounds can be replaced, for example, by a benzyloxy group, and/or at least one SH group can be replaced, for example, by an S-benzyl group and/or at least one $NH_2$ group can be replaced, for example, by an NH-benzyl group or by an $NO_2$ group. Subsequently, at least one—preferably all—benzyloxy group(s) or NH-benzyl group(s) can be eliminated, for example, with hydrogen and palladium on carbon, and/or at least one—preferably all—S-benzyl group(s) can be eliminated, for example, with sodium in ammonia, and/or at least one—preferably all—$NO_2$ group(s) can be reduced, for example, with hydrogen and Raney nickel to $NH_2$.

Under some of the reaction conditions mentioned, OH, $NH_2$ and COOH groups may possibly enter into undesired side reactions. It is therefore preferred to convert starting compounds and intermediates which contain at least one OH group and/or at least one $NH_2$ group and/or at least one COOH group to corresponding carboxylic ester and carboxamide derivatives. In a modification of the above-described processes, starting compounds and intermediates which have at least one OH group and/or which have at least one $NH_2$ group can be converted to carboxylic ester or carboxamide derivatives by reaction with an activated carboxylic acid group, for example a carbonyl chloride group. In a modification of the above-described processes, starting compounds and intermediates which contain at least one COOH can be converted to carboxylic ester or carboxamide derivatives by reaction with an activating agent, for example thionyl chloride or carbonyldiimidazole, and subsequent reaction with a suitable alcohol or amine. Subsequently, at least one—preferably all—carboxylic ester or carboxamide group(s) in the starting compounds and intermediates can be detached, for example, with dilute aqueous acids or bases, in order to release one—preferably all—OH group(s) and/or $NH_2$ group(s) and/or COOH group(s).

The inventive compounds and especially compounds 1 to 85 were named with the AutoNom 2000 software (ISIS™/Draw 2.5; MDL).

The invention will be illustrated in detail with reference to the examples which follow, but without being restricted to these examples.

EXAMPLES

I) Preparation of Inventive Compounds

The general synthesis methods which are based on the synthesis schemes 1-9 were used to synthesize the following inventive compounds. In addition, their NMR spectroscopy data and mass spectrometry data and melting points are included.

The precursors used for the preparation of the inventive compounds can—unless stated otherwise—be synthesized by processes known to those skilled in the art.

The chemicals and solvents used were obtained commercially from the conventional suppliers (Acros, Aldrich, Fluka, Lancaster, Maybridge, Merck, Sigma, TCI, etc.) or synthesized.

Example 1

1-Ethyl-3-(3-phenylethynylpyrido[2,3-b]pyrazin-6-yl)urea (compound 1)

Preparation of 1-(3-chloropyrido[2,3-b]pyrazin-6-yl)-3-ethylurea (reaction according to scheme 5)

100 mg of 3-chloropyrido[2,3-b]pyrazin-6-ylamine (0.55 mmol) were initially charged in 5 ml of pyridine and 44 µl of ethyl isocyanate (0.55 mmol) were added at room temperature. The mixture was left to stir at 75° C. for 3 h and then another 132 µl in total of ethyl isocyanate (1.65 mmol) were added to the reaction mixture is small portions over 18 h. The solvent was then removed under reduced pressure. The resulting solid was purified by means of column chromatography on silica gel (dichloromethane/methanol eluent). This gave a bright yellow solid.

Preparation of 1-ethyl-3-(3-phenylethynylpyrido[2,3-b]pyrazin-6-yl)urea (reaction according to scheme 6)

98.1 mg of 1-(3-chloropyrido[2,3-b]pyrazin-6-yl)-3-ethylurea (0.39 mmol), 10.1 mg copper(I) iodide (0.05 mmol) and 193 µl of triethylamine (1.38 mmol) were initially charged in 2 ml of anhydrous dimethylformamide under nitrogen as a protective gas. Subsequently, 29.1 mg of dichlorobis(triphenylphosphine)palladium(II) (0.04 mmol) and 54 µl of phenylacetylene (0.49 mmol) were added, and the mixture was stirred at room temperature for 16 h. For workup, the mixture was diluted with dichloromethane and added to dilute hydrochloric acid. The precipitated solid was filtered off with suction, and the organic phase was washed with dilute hydrochloric acid and distilled water. After phase separation, the organic solvent was removed under reduced pressure. The further purification was effected by column chromatography on silica gel (dichloromethane/methanol eluent). This gave a yellow solid.

Melting point: 236-238° C. (decomp.)
ESI-MS: found m/z=318.0 (M+H$^+$); calc. 317 amu
$^1$H NMR (d$_6$-DMSO): δ=1.20 (t, 3H), 3.35-3.45 (m, 2H), 7.51-7.59 (m, 3H), 7.68 (d, 1H), 7.75 (d, 2H), 8.37 (d, 1H), 9.01 (s, 1H), 9.14 (s, 1H), 10.23 (s, 1H) ppm.

The following examples were synthesized in accordance with Example 1 and the general synthesis methods:

Example 2

1-Ethyl-3-(3-thiophen-3-ylethynylpyrido[2,3-b]pyrazin-6-yl)urea (compound 2)

m.p.: 239-242° C. (decomp.)
ESI-MS: found m/z=324.2 (M+H$^+$); calc. 323 amu
$^1$H NMR (d$_6$-DMSO): δ=1.20 (t, 3H), 3.25-3.35 (m, 2H), 7.43 (d, 1H), 7.66 (d, 1H), 7.76 (dd, 1H), 8.21 (d, 1H), 8.36 (d, 1H), 8.97 (s, 1H), 9.14 (s, 1H), 10.23 (s, 1H) ppm.

Example 3

1-(3-Cyclopropylethynylpyrido[2,3-b]pyrazin-6-yl)-3-ethylurea (compound 3)

m.p.: 227-228° C. (decomp.)
ESI-MS: found m/z=282.3 (M+H$^+$); calc. 281 amu
$^1$H NMR (d$_6$-DMSO): δ=1.00-1.10 (m, 2H), 1.19 (t, 3H), 1.69-1.79 (m, 1H), 3.25-3.35 (m, 2H), 7.63 (d, 1H), 8.32 (d, 1H), 8.77 (s, 1H), 9.11 (s, 1H), 10.18 (s, 1H) ppm.

Example 4

1-[3-(3-Dimethylaminoprop-1-ynyl)pyrido[2,3-b]pyrazin-6-yl]-3-ethylurea (compound 4)

ESI-MS: found m/z=299.2 (M+H$^+$); calc. 298 amu
$^1$H NMR (d$_6$-DMSO): δ=1.19 (t, 3H), 2.33 (s, 6H), 3.27-3.35 (m, 2H), 3.67 (s, 2H), 7.67 (d, 1H), 8.34 (d, 1H), 8.85 (s, 1H), 9.05 (s, 1H), 10.19 (s, 1H) ppm.

Example 5

1-[3-((E)-2-Cyclohexylvinyl)pyrido[2,3-b]pyrazin-6-yl]-3-ethylurea (compound 5)

Preparation of 1-[3-((E)-2-cyclohexylvinyl)pyrido[2,3-b]pyrazin-6-yl]-3-ethylurea (reaction according to scheme 6)

99.6 mg of 1-(3-chloropyrido[2,3-b]pyrazin-6-yl)-3-ethylurea (0.40 mmol), 73.6 mg of cyclohexylvinylboronic acid (0.48 mmol), 84.4 mg of sodium carbonate (0.80 mmol) and 33.4 mg of [1,1'-bis(diphenylphosphino)ferrocene]dichloropalladium(II) (0.04 mmol) were initially charged in 6 ml of dimethylformamide/water (1:1) under nitrogen. The mixture was then heated to 90° C. for 6.5 h. Distilled water was then added to the reaction mixture and the resulting precipitate was filtered off with suction. The further purification was effected by column chromatography on silica gel (ethyl acetate/heptane eluent mixture). A light brown solid was obtained.

m.p.: 202-204° C. (decomp.)
ESI-MS: found m/z=326.0 (M+H$^+$); calc. 325 amu
$^1$H NMR (d$_6$-DMSO): δ=1.10-1.40 (m, 8H), 1.65-1.90 (m, 5H), 2.28-2.38 (m, 1H), 3.25-3.35 (m, 2H), 6.69 (d, 1H), 7.15 (dd, 1H), 7.58 (d, 1H), 8.28 (d, 1H), 8.98 (s, 1H), 9.15 (s, 1H), 10.05 (s, 1H) ppm.

The following examples were synthesized according to Example 5 and the general synthesis methods:

Example 6

1-Ethyl-3-[3-((E)-3-methoxypropenyl)pyrido[2,3-b]pyrazin-6-yl]urea (compound 6)

ESI-MS: found m/z=288.3 (M+H$^+$); calc. 287 amu
$^1$H NMR (d$_6$-DMSO): δ=1.20 (t, 3H), 3.25-3.35 (m, 2H), 3.39 (s, 3H), 4.25 (d, 2H), 6.92 (d, 1H), 7.15-7.25 (m, 1H), 7.62 (d, 1H), 8.30 (d, 1H), 9.02 (s, 1H), 9.15 (s, 1H), 10.10 (s, 1H) ppm.

Example 7

1-Ethyl-3-{3-[(E)-2-(4-fluorophenyl)vinyl]pyrido[2,3-b]pyrazin-6-yl}urea (Compound 27)

m.p.: 217-219° C.
ESI-MS: found m/z=338.2 (M+H$^+$); calc. 337 amu
$^1$H NMR (d$_6$-DMSO): δ=1.20 (t, 3H), 3.25-3.38 (m, 2H), 7.10 (t, 2H), 7.32 (dd, 2H), 7.54 (d, 1H), 7.61 (d, 1H), 7.87 (t, 2H), 8.02 (d, 1H), 8.31 (d, 1H), 9.09 (s, 1H), 9.17 (bs, 1H), 10.09 (s, 1H) ppm.

Example 8

4-[6-(3-Ethylurea)pyrido[2,3-b]pyrazin-3-yl]phenyl methyl carbonate (compound 9)

Preparation of 1-ethyl-3-[3-(4-hydroxyphenyl)pyrido[2,3-b]pyrazin-6-yl]urea (reaction according to scheme 5)

0.50 g of 4-(6-aminopyrido[2,3-b]pyrazin-3-yl)phenol (2.10 mmol) were initially charged in 5.0 ml of pyridine. 183 µl of ethyl isocyanate (2.31 mmol) were added dropwise at room temperature and the mixture was heated to 70-80° C. for 2 h. Thereafter, another 183 µl of ethyl isocyanate were added and the mixture was heated to 70-80° C. for a further 2 h. Once the reaction had ended, the reaction mixture was added to ice-water and neutralized with 1N hydrochloric acid. The precipitated product was filtered off with suction and dried. The product which had been filtered was partly dissolved in ethanol and admixed with 52 mg of potassium hydroxide (0.93 mmol), dissolved in water. The mixture was heated to 40° C. for approx. 1 h. Thereafter, the reaction solution was neutralized with 1N hydrochloric acid and the solvent was removed under reduced pressure. The resulting solid was purified by column chromatography on silica gel (dichloromethane/methanol eluent). This gave a yellow solid.

Preparation of 4-[6-(3-ethylurea)pyrido[2,3-b]pyrazin-3-yl]phenyl methyl carbonate (reaction according to scheme 8)

100 mg of 1-ethyl-3-[3-(4-hydroxyphenyl)pyrido[2,3-b]pyrazin-6-yl]urea (0.32 mmol), 30 µl of methyl chloroformate (0.39 mmol) and 45 µl of triethylamine (0.32 mmol) were initially charged in 10 ml of anhydrous dioxane and heated to 100° C. for 1 h. After cooling, the precipitated solid was filtered off with suction and dried. Recrystallization from ethanol afforded a pale yellow solid.

m.p.: 243-245° C.

ESI-MS: found m/z=368.2 (M+H$^+$); calc. 367 amu $^1$H NMR (d$_6$-DMSO): δ=1.20 (t, 3H), 3.30-3.39 (m, 2H), 3.90 (s, 3H), 7.49 (d, 2H), 7.70 (d, 1H), 8.38 (d, 1H), 8.42 (d, 2H), 9.03 (s, 1H), 9.47 (s, 1H), 10.09 (s, 1H) ppm, The following examples were synthesized according to Example 8 and the general synthesis methods:

Example 9

4-[6-(3-Ethylurea)pyrido[2,3-b]pyrazin-3-yl]phenyl (2-methoxyethyl)carbonate (compound 10)

m.p.: 230-232° C.

ESI-MS: found m/z=412.2 (M+H$^+$); calc. 411 amu $^1$H NMR (d$_6$-DMSO): δ=1.20 (t, 3H), 3.30-3.39 (m, 5H), 3.68 (t, 2H), 4.40 (t, 2H), 7.50 (d, 2H), 7.70 (d, 1H), 8.38 (d, 1H), 8.41 (d, 2H), 9.10 (s, 1H), 9.50 (s, 1H), 10.15 (s, 1H) ppm.

Example 10

4-[6-(3-Ethylurea)pyrido[2,3-b]pyrazin-3-yl]phenyl phenyl carbonate (compound 11)

ESI-MS: found m/z=430.2 (M+H$^+$); calc. 429 amu $^1$H NMR (d$_6$-DMSO): δ=1.21 (t, 3H), 3.30-3.33 (m, 2H), 7.33-7.38 (m, 1H), 7.43 (d, 2H), 7.51 (t, 2H), 7.65 (d, 2H), 8.39 (d, 1H), 8.45 (d, 2H), 9.11 (s, 1H), 9.50 (s, 1H), 10.19 (s, 1H) ppm.

Example 11

4-[6-(3-Ethylurea)pyrido[2,3-b]pyrazin-3-yl]phenyl diethylcarbamate (compound 12)

ESI-MS: found m/z=409.4 (M+H$^+$); calc. 408 amu $^1$H NMR (d$_6$-DMSO): δ=1.15 (t, 3H), 1.20 (t, 3H), 1.24 (t, 3H), 3.30-3.39 (m, 4H), 3.45 (q, 2H), 7.37 (d, 2H), 7.69 (d, 1H), 8.34-8.39 (m, 3H), 9.11 (s, 1H), 9.48 (s, 1H), 10.15 (s, 1H) ppm.

Example 12

3-[6-(3-Ethylurea)pyrido[2,3-b]pyrazin-3-yl]phenyl 2-methoxyethyl carbonate (compound 16)

ESI-MS: found m/z=412.2 (M+H$^+$); calc. 411 amu $^1$H NMR (d$_6$-DMSO): δ=1.20 (t, 3H), 3.33-3.38 (m, 5H), 3.63-3.66 (m, 2H), 4.37-4.39 (m, 2H), 7.48 (d, 2H), 7.68 (t, 1H), 7.72 (d, 1H), 8.22 (d, 1H), 8.29 (d, 1H), 8.39 (d, 1H), 9.06 (s, 1H), 9.48 (s, 1H), 10.14 (s, 1H) ppm.

Example 13

4-[6-(3-Ethylurea)pyrido[2,3-b]pyrazin-3-yl]phenyl isobutyl carbonate (compound 17)

ESI-MS: found m/z=410.3 (M+H$^+$); calc. 409 amu $^1$H NMR (d$_6$-DMSO): δ=0.97 (d, 6H), 1.20 (t, 3H), 2.02 (sep, 1H), 3.25-3.38 (m, 2H), 4.06 (d, 2H), 7.50 (d, 2H), 7.70 (d, 1H), 8.38 (d, 1H), 8.41 (d, 2H), 9.10 (s, 1H), 9.47 (s, 1H), 10.14 (s, 1H) ppm.

Example 14

But-2-ynyl 4-[6-(3-ethylurea)pyrido[2,3-b]pyrazin-3-yl]phenyl carbonate (compound 18)

ESI-MS: found m/z=406.1 (M+H$^+$); calc. 405 amu $^1$H NMR (d$_6$-DMSO): δ=1.20 (t, 3H), 1.89 (t, 3H), 3.25-3.38 (m, 2H), 4.90 (q, 2H), 7.50 (d, 2H), 7.70 (d, 1H), 8.38 (d, 1H), 8.41 (d, 2H), 9.09 (s, 1H), 9.47 (s, 1H), 10.14 (s, 1H) ppm.

Example 15

4-[6-(3-Ethylurea)pyrido[2,3-b]pyrazin-3-yl]phenyl dimethylcarbamate (compound 19)

Example 15 was prepared using sodium hydride as the base and dimethylformamide as the solvent.

m.p.: >230° C. (decomp.)

ESI-MS: found m/z=381.2 (M+H$^+$); calc. 380 amu $^1$H NMR (d$_6$-DMSO): δ=1.20 (t, 3H), 2.95 (s, 3H), 3.09 (s, 3H), 3.25-3.38 (m, 2H), 7.37 (d, 2H), 7.68 (d, 1H), 8.35-8.38 (m, 3H), 9.11 (s, 1H), 9.46 (s, 1H), 10.12 (s, 1H) ppm.

Example 16

4-[6-(3-Ethylurea)pyrido[2,3-b]pyrazin-3-yl]-2-methoxyphenyl 2-methoxyethyl carbonate (compound 32)

ESI-MS: found m/z=442.3 (M+H$^+$); calc. 441 amu $^1$H NMR (d$_6$-DMSO): δ=1.20 (t, 3H), 3.25-3.38 (m, 5H), 3.62 (dd, 2H), 3.97 (s, 3H), 4.35 (dd, 2H), 7.45 (d, 1H), 7.74 (d, 1H), 7.97 (d, 1H), 8.06 (s, 1H), 8.39 (d, 1H), 8.99 (bs, 1H), 9.52 (s, 1H), 10.15 (s, 1H) ppm.

Example 17

2-Benzyloxyethyl 4-[6-(3-ethylurea)pyrido[2,3-b]pyrazin-3-yl]phenyl carbonate (compound 33)

ESI-MS: found m/z=488.2 (M+H$^+$); calc. 487 amu $^1$H NMR (d$_6$-DMSO): δ=1.20 (t, 3H), 3.28-3.38 (m, 2H), 3.75 (t, 2H), 4.43 (t, 2H), 4.57 (s, 2H), 7.31 (t, 1H), 7.36-7.40 (m, 4H), 7.48 (d, 2H), 7.70 (d, 1H), 8.38 (d, 1H), 8.41 (d, 2H), 9.09 (bs, 1H), 9.47 (s, 1H), 10.13 (s, 1H) ppm.

Example 18

2-Benzyloxyethyl 4-[6-(3-ethylurea)pyrido[2,3-b]pyrazin-3-yl]-2-methoxyphenyl carbonate (compound 34)

m.p.: 172-174° C.
ESI-MS: found m/z=518.3 (M+H$^+$); calc. 517 amu
$^1$H NMR (d$_6$-DMSO): δ=1.20 (t, 3H), 3.28-3.38 (m, 2H), 3.74 (dd, 2H), 3.96 (s, 3H), 4.41 (dd, 2H), 4.56 (s, 2H), 7.31 (t, 1H), 7.35-7.40 (m, 3H), 7.44 (d, 2H), 7.74 (d, 1H), 7.97 (d, 1H), 8.06 (s, 1H), 8.39 (d, 1H), 8.99 (bs, 1H), 9.51 (s, 1H), 10.14 (s, 1H) ppm.

Example 19

4-[6-(3-Ethylurea)pyrido[2,3-b]pyrazin-3-yl]-2-methoxyphenyl diethylcarbamate (compound 67)

m.p.: 220-222° C.
ESI-MS: found m/z=439.3 (M+H$^+$); calc. 438 amu
$^1$H NMR (d$_6$-DMSO): δ=1.13 (t, 3H), 1.20 (t, 3H), 1.24 (t, 3H), 3.28-3.36 (m, 4H), 3.44 (q, 2H), 3.94 (s, 3H), 7.31 (d, 1H), 7.73 (d, 1H), 7.94 (d, 1H), 8.01 (s, 1H), 8.37 (d, 1H), 8.97 (bs, 1H), 9.50 (s, 1H), 10.11 (s, 1H) ppm.

Example 20

2-Chloro-4-[6-(3-ethylurea)pyrido[2,3-b]pyrazin-3-yl]-6-methoxyphenyl diethylcarbamate (compound 68)

m.p.: 237-239° C.
ESI-MS: found m/z=473.4 (M+H$^+$); calc. 472 amu
$^1$H NMR (d$_6$-DMSO): δ=1.14 (t, 3H), 1.19 (t, 3H), 1.27 (t, 3H), 3.25-3.38 (m, 4H), 3.46 (q, 2H), 3.97 (s, 3H), 7.76 (d, 1H), 8.00 (s, 1H), 8.09 (s, 1H), 8.39 (d, 1H), 8.94 (bs, 1H), 9.55 (s, 1H), 10.13 (s, 1H) ppm.

Example 21

4-[6-(3-Ethylurea)pyrido[2,3-b]pyrazin-3-yl]-2-methoxyphenyl 2-[2-(2-methoxyethoxy)ethoxy]ethyl carbonate (compound 69)

m.p.: 166-167° C.
ESI-MS: found m/z=530.2 (M+H$^+$); calc. 529 amu
$^1$H NMR (d$_6$-DMSO): δ=1.20 (t, 3H), 3.25 (s, 3H), 3.28-3.35 (m, 2H), 3.45 (t, 2H), 3.53-3.60 (m, 6H), 3.71 (t, 2H), 3.98 (s, 3H), 4.35 (t, 2H), 7.45 (d, 1H), 7.74 (d, 1H), 7.96 (d, 1H), 8.06 (s, 1H), 8.39 (d, 1H), 8.96 (bs, 1H), 9.51 (s, 1H), 10.12 (s, 1H) ppm.

Example 22

4-[6-(3-Ethylurea)pyrido[2,3-b]pyrazin-3-yl]phenyl (E)-3-phenylacrylate (compound 13)

Preparation of 4-[6-(3-ethylurea)pyrido[2,3-b]pyrazin-3-yl]phenyl (E)-3-phenylacrylate 38.9 mg of 1-ethyl-3-[3-(4-hydroxyphenyl)pyrido[2,3-b]pyrazin-6-yl]urea (0.13 mmol) were initially charged in 3.0 ml of dried pyridine. 17.5 mg of dimethylaminopyridine (0.14 mmol) and 22.9 mg of trans-cinnamyl chloride (0.13 mmol) were added at room temperature and the reaction mixture was stirred at room temperature. After 3 h, another 22.9 mg of trans-cinnamyl chloride (0.13 mmol) were added and the mixture was stirred at room temperature for a further 3 h. For workup, the reaction mixture was poured onto ice-water and neutralized with 1N hydrochloric acid. The precipitated solid was filtered off with suction and dried under reduced pressure. Without further purification, the product obtained was a yellow solid.

m.p.: 236-238° C.
ESI-MS: found m/z=440.3 (M+H$^+$); calc. 439 amu
$^1$H NMR (d$_6$-DMSO): δ=1.20 (t, 3H), 3.25-3.40 (m, 2H), 6.95 (d, 1H), 7.46-7.51 (m, 5H), 7.70 (d, 1H), 7.83-7.87 (m, 2H), 7.94 (d, 1H), 8.38 (d, 1H), 8.43 (d, 2H), 9.12 (s, 1H), 9.49 (s, 1H), 10.19 (s, 1H) ppm.

Example 23

4-[6-(3-Ethylurea)pyrido[2,3-b]pyrazin-3-yl]phenyl nonadecanoate (compound 14)

Preparation of 4-[6-(3-ethylurea)pyrido[2,3-b]pyrazin-3-yl]phenyl nonadecanoate 50.0 mg of 1-ethyl-3-[3-(4-hydroxyphenyl)pyrido[2,3-b]pyrazin-6-yl]urea (0.16 mmol) were initially charged in 5.0 ml of dried pyridine. 19.7 mg of dimethylaminopyridine (0.16 mmol) and 51.2 mg of nonadecanoyl chloride (0.16 mmol) were added at room temperature and the reaction mixture was stirred at room temperature for 4 h. For workup, the reaction mixture was added to approx. 200 ml of distilled water. The precipitated solid was filtered off with suction and washed with water. Column chromatography purification of the crude product on silica gel (dichloromethane/methanol eluent) afforded a white solid.

m.p.: 147.2° C.
$^1$H NMR (d$_6$-DMSO): δ=0.90 (t, 3H), 1.20-1.50 (m, 33H), 1.75-1.85 (m, 2H), 2.60-2.68 (m, 2H), 3.50-3.60 (m, 2H), 7.26-7.36 (m, 3H), 8.25-8.31 (m, 3H), 8.71 (s, 1H), 9.22 (s, 1H), 9.75 (s, 1H) ppm.

Example 24

1-(3-Benzylpyrido[2,3-b]pyrazin-6-yl]-3-ethylurea (compound 15)

Preparation of 1-(3-benzylpyrido[2,3-b]pyrazin-6-yl]-3-ethylurea (Reaction According to Scheme 6)

2.4 ml of a 0.5 M solution of benzylzinc bromide (1.20 mmol) in THF and 24.7 mg of tetrakis(triphenylphosphine)palladium(0) (0.02 mmol) were initially charged in 1 ml of dioxane under nitrogen. Subsequently, 102.4 mg of 1-(3-chloropyrido[2,3-b]pyrazin-6-yl)-3-ethylurea (0.41 mmol) and 1 ml of dioxane were added in portions. The mixture was then heated to 100° C. After 7 h, the reaction mixture was allowed to cool and then saturated ammonium chloride solution was added. The aqueous phase was extracted repeatedly with dichloromethane and the collected organic phases were washed with saturated sodium chloride solution, dried over sodium sulphate and freed from the solvent under reduced pressure. Column chromatography purification on silica gel (dichloromethane/methanol eluent) afforded a yellow solid.

ESI-MS: found m/z=308.3 (M+H$^+$); calc. 307 amu
$^1$H NMR (d$_6$-DMSO): δ=1.19 (t, 3H), 3.25-3.35 (m, 2H), 4.35 (s, 2H), 7.25 (t, 1H), 7.30-7.39 (m, 4H), 7.64 (d, 1H), 8.32 (d, 1H), 8.77 (s, 1H), 9.05 (s, 1H), 10.08 (s, 1H) ppm.

Example 25

1-Methoxy-3-(3-phenylpyrido[2,3-b]pyrazin-6-yl)urea (compound 7)

Preparation of 3-phenylpyrido[2,3-b]pyrazin-6-ylamine (reaction according to scheme 6)

1.00 g of 3-chloropyrido[2,3-b]pyrazin-6-ylamine (5.54 mmol), 743 mg of phenylboronic acid (6.09 mmol), 640 mg of tetrakis(triphenylphosphine)palladium(0) (0.55 mmol) and 1.76 g of sodium carbonate (16.6 mmol) were initially charged in 100 ml of dimethylformamide/water (1:1) under nitrogen as a protective gas and stirred at 80° C. for 2 h. Once the reaction had ended, the mixture was filtered off with suction and the filtrate was poured onto 800 ml of distilled water. The aqueous phase was extracted repeatedly with ethyl acetate. The organic phase was freed of solvents under reduced pressure. The resulting solid was purified by means of column chromatography on silica gel (dichloromethane/methanol eluent). This gave a yellow solid.

Preparation of 1-methoxy-3-(3-phenylpyrido[2,3-b]pyrazin-6-yl)urea (reaction according to scheme 5)

100 mg of 3-phenylpyrido[2,3-b]pyrazin-6-ylamine (0.45 mmol) were dissolved in pyridine and admixed with 191 mg of p-nitrophenyl N-methycarbamate (0.90 mmol). The mixture was heated under reflux for 4 h. For workup, the pyridine was removed under reduced pressure, and the residue was partitioned in ethyl acetate and distilled water. The phases were separated and the aqueous phase was extracted twice with ethyl acetate. The combined organic phases were dried over $MgSO_4$ and the solvent was removed under reduced pressure. The residue was purified by column chromatography on silica gel (dichloromethane/methanol eluent). A light beige solid was isolated.

ESI-MS: found m/z=296.2 (M+H$^+$); calc. 295 amu
$^1$H NMR (d$_6$-DMSO): δ=3.75 (s, 3H), 7.58-7.65 (m, 3H), 8.03 (s, 1H), 8.36 (d, 2H), 8.45 (d, 1H), 9.52 (s, 1H), 10.16 (s, 1H), 11.01 (s, 1H) ppm.

The following examples were synthesized according to Example 25 and the general synthesis methods:

Example 26

1-Allyloxy-3-(3-phenylpyrido[2,3-b]pyrazin-6-yl)urea (compound 8)

ESI-MS: found m/z=322.2 (M+H$^+$); calc. 321 amu
$^1$H NMR (d$_6$-DMSO): δ=4.44 (d, 2H), 5.33 (d, 1H), 5.41 (d, 1H), 6.02-6.10 (m, 1H), 7.58-7.65 (m, 3H), 8.00 (s, 1H), 8.36 (d, 2H), 8.45 (d, 1H), 9.52 (s, 1H), 10.13 (s, 1H), 11.07 (s, 1H) ppm.

Example 27

1-[4-(tert-Butyldimethylsilanyloxy)butyl]-3-(3-phenylpyrido[2,3-b]pyrazin-6-yl)urea (compound 36)

ESI-MS: found m/z=452.6 (M+H$^+$); calc. 451 amu
$^1$H NMR (DMSO-d$_6$) δ=0.02 (s, 6H), 0.84 (s, 9H), 1.62-1.65 (m, 4H), 3.30-3.33 (m, 2H), 3.66-3.69 (m, 2H), 7.59-7.62 (m, 3H), 7.64 (d, 1H), 8.35 (d, 2H), 8.38 (d, 1H), 9.37 (s, 1H), 9.47 (s, 1H), 10.15 (s, 1H) ppm.

Example 28

1-[4-(tert-Butydimethylsilanyloxy)butyl]-3-[3-(4-hydroxy-3-methoxyphenyl)pyrido[2,3-b]pyrazin-6-yl]urea (compound 37)

ESI-MS: found m/z=498.5 (M+H$^+$); calc. 497 amu
$^1$H NMR (DMSO-d$_6$) δ=0.01 (s, 6H), 0.83 (s, 9H), 1.61-1.66 (m, 4H), 3.30-3.33 (m, 2H), 3.65-3.68 (m, 2H), 3.93 (s, 3H), 6.96 (d, 1H), 7.59 (d, 1H), 7.86 (dd, 1H), 7.92 (d, 1H), 8.32 (d, 1H), 9.29 (s, 1H), 9.42 (s, 1H), 9.73 (s, 1H), 10.08 (s, 1H) ppm.

Example 29

Diethyl{4-[3-(3-phenylpyrido[2,3-b]pyrazin-6-yl)urea]butyl}phosphonate (compound 42)

ESI-MS: found m/z=458.2 (M+H$^+$); calc. 457 amu
$^1$H NMR (DMSO-d$_6$) δ=1.16 (t, 6H), 1.59-1.69 (m, 4H), 1.77-1.84 (m, 2H), 3.33-3.36 (m, 2H), 3.90-3.99 (m, 4H), 7.58-7.63 (m, 3H), 7.68 (d, 1H), 8.36 (d, 2H), 8.38 (d, 1H), 9.22 (s, 1H), 9.47 (s, 1H), 10.16 (s, 1H) ppm.

Example 30

Diethyl (4-{3-[3-(4-hydroxy-3-methoxyphenyl)pyrido[2,3-b]pyrazin-6-yl]urea}butyl)phosphonate (compound 44)

ESI-MS: found m/z=504.5 (M+H$^+$); calc. 503 amu
$^1$H NMR (DMSO-d$_6$) δ=1.15 (t, 6H), 1.58-1.69 (m, 4H), 1.76-1.82 (m, 2H), 3.30-3.33 (m, 2H), 3.89-3.97 (m, 7H), 6.97 (d, 1H), 7.63 (d, 1H), 7.86 (dd, 1H), 7.91 (d, 1H), 8.32 (d, 1H), 9.13 (s, 1H), 9.41 (s, 1H), 9.71 (s, 1H), 10.07 (s, 1H) ppm.

Example 31

1-Methoxy-3-[3-(4-hydroxy-3-methoxy-phenyl)-pyrido[2,3-b]pyrazin-6-yl]-urea (compound 61)

ESI-MS: found m/z=342.3 (M+H$^+$); calc. 341 amu
$^1$H-NMR (d$_6$-DMSO): δ=3.74 (s, 3H), 3.93 (s, 3H), 6.98 (d, 1H), 7.87 (dd, 11H), 7.91 (d, 1H), 8.02 (d, 1H), 8.39 (d, 1H), 9.46 (s, 1H), 9.74 (s, 1H), 10.03 (s, 1H), 10.84 (s, 1H) ppm.

Example 32

Diethyl{2-[3-(3-Phenyl-pyrido[2,3-b]pyrazin-6-yl)-urea]-ethyl}-phosphate (Compound 62)

ESI-MS: found m/z=430.1 (M+H$^+$); calc. 429 amu
$^1$H-NMR (d$_6$-DMSO): δ=1.21 (t, 6H), 2.08-2.14 (m, 2H), 3.48-3.55 (m, 2H), 3.98-4.08 (m, 4H), 7.58-7.63 (m, 3H), 7.72 (d, 1H), 8.35 (d, 2H), 8.39 (d, 1H), 9.14 (s, 1H), 9.47 (s, 1H), 10.22 (s, 1H) ppm.

Example 33

4-[3-(3-Phenylpyrido[2,3-b]pyrazin-6-yl)urea]butyl ethylcarbamate (compound 38)

Preparation of 1-(4-hydroxybutyl)-3-(3-phenylpyrido[2,3-b]pyrazin-6-yl)urea 360 mg (0.22 mmol) of 1-[4-(tert-butyldimethylsilanyloxy)butyl]-3-(3-phenylpyrido[2,3-b]pyrazin-6-yl)urea were dissolved in 20 ml of dichloromethane and admixed with 5 ml of a 2 molar isopropanolic HCl solution. After stirring at room temperature for 12 h, the reaction mixture was washed with water and dried (Na$_2$SO$_4$). Removal of the solvent under reduced pressure afforded a bright yellow solid.

ESI-MS: found m/z=338.3 (M+H$^+$); calc. 337 amu $^1$H NMR (DMSO-d$_6$) δ=1.58-1.64 (m, 4H), 3.30-3.34 (m, 2H), 3.48-3.53 (m, 2H), 4.48 (t, 1H), 7.57-7.63 (m, 3H), 7.66 (d, 1H), 8.35-8.38 (m, 2H), 9.30 (s, 1H), 9.46 (s, 1H), 10.13 (s, 1H) ppm.

Preparation of 4-[3-(3-phenylpyrido[2,3-b]pyrazin-6-yl)urea]butyl ethylcarbamate 30 mg (0.08 mmol) of 1-(4-hydroxybutyl)-3-(3-phenylpyrido[2,3-b]pyrazin-6-yl)urea were dissolved in 5 ml of pyridine, admixed with 7.6 μl (0.10 mmol) of ethyl isocyanate and stirred at 100° C. for 6 h. The reaction mixture was poured onto 200 ml of water and stirred for 15 min. The precipitated solid was filtered off and dried. This gave a white solid.

ESI-MS: found m/z=409.4 (M+H$^+$); calc. 408 amu $^1$H NMR (DMSO-d$_6$) δ=0.97 (t, 3H), 1.60-1.77 (m, 4H), 2.96-3.00 (m, 2H), 3.33-3.35 (m, 2H), 4.01-4.04 (m, 2H), 7.07 (t, 1H), 7.58-7.64 (m, 3H), 7.66 (d, 1H), 8.35 (d, 2H), 8.38 (d, 1H), 9.32 (s, 1H), 9.47 (s, 1H), 10.17 (s, 1H) ppm.

Example 34

Methyl 4-[3-(3-phenylpyrido[2,3-b]pyrazin-6-yl)urea]butyl carbonate (compound 39)

Preparation of methyl 4-[3-(3-phenylpyrido[2,3-b]pyrazin-6-yl)urea]butyl carbonate 30 mg (0.08 mmol) of 1-(4-hydroxybutyl)-3-(3-phenylpyrido[2,3-b]pyrazin-6-yl)urea were suspended in 2 ml of dichloromethane and admixed with 9.3 μl (0.12 mmol) of methyl chloroformate, 23 μl (0.16 mmol) of triethylamine and 1 mg (0.01 mmol) of dimethylaminopyridine. The solution was stirred at room temperature for 4 h. The reaction mixture was diluted with 50 ml of dichloromethane, washed with water and dried (Na$_2$SO$_4$). The solvent was removed under reduced pressure and the residue was purified by column chromatography on silica gel (dichloromethane/methanol eluent). A white solid was isolated.

ESI-MS: found m/z=396.3 (M+H$^+$); calc. 395 amu $^1$H NMR (DMSO-d$_6$) δ=1.61-1.66 (m, 2H), 1.76-1.78 (m, 2H), 3.34-3.36 (m, 2H), 3.67 (s, 1H), 4.17-4.19 (m, 2H), 7.59-7.63 (m, 3H), 7.66 (d, 1H), 8.35 (d, 2H), 8.38 (d, 1H), 9.34 (s, 1H), 9.47 (s, 1H), 10.17 (s, 1H) ppm.

The following example was synthesized according to Example 34 and the general synthesis methods:

Example 35

2,2-Dimethyl[1,3]dioxolan-4-ylmethyl 4-[3-(3-phenylpyrido[2,3-b]pyrazin-6-yl)urea]butyl carbonate (Compound 40)

ESI-MS: found m/z=496.0 (M+H$^+$); calc. 495 amu $^1$H NMR (DMSO-d$_6$) δ=1.24 (s, 3H), 1.29 (s, 3H), 1.61-1.67 (m, 2H), 1.77-1.82 (m, 2H), 3.34-3.37 (m, 2H), 3.65 (dd, 1H), 3.98 (dd, 1H), 4.03 (dd, 1H), 4.15 (dd, 1H), 4.17-4.28 (m, 3H), 7.58-7.63 (m, 3H), 7.67 (d, 1H), 8.36 (d, 2H), 8.38 (d, 1H), 9.34 (s, 1H), 9.47 (s, 1H), 10.17 (s, 1H) ppm.

Example 36

2,3-Dihydroxypropyl 4-[3-(3-phenylpyrido[2,3-b]pyrazin-6-yl)urea]butyl carbonate (compound 41)

Preparation of 2,3-dihydroxypropyl 4-[3-(3-phenylpyrido[2,3-b]pyrazin-6-yl)urea]butyl carbonate 50 mg (0.10 mmol) of 2,2-dimethyl[1,3]dioxolan-4-ylmethyl 4-[3-(3-phenylpyrido[2,3-b]pyrazin-6-yl)urea]butyl carbonate were dissolved in 20 ml of dichloromethane, admixed with 17 μl (0.13 mmol) of boron trifluoride ethyl etherate and stirred at room temperature for 4 h. The solvent was removed under reduced pressure and the residue was purified by column chromatography on silica gel (dichloromethane/methanol eluent). A white solid was isolated.

ESI-MS: found m/z=456.4 (M+H$^+$); calc. 455 amu $^1$H NMR (DMSO-d$_6$) δ=1.62-1.67 (m, 2H), 1.76-1.82 (m, 2H), 3.28-3.52 (m, 4H), 3.62-3.66 (m, 1H), 3.96 (dd, 1H), 4.11 (dd, 1H), 4.16-4.20 (m, 2H), 4.66 (t, 1H), 4.96 (d, 1H), 7.58-7.65 (m, 3H), 7.67 (d, 1H), 8.35 (d, 2H), 8.38 (d, 1H), 9.31 (s, 1H), 9.47 (s, 1H), 10.17 (s, 1H) ppm.

Example 37

{4-[3-(3-Phenylpyrido[2,3-b]pyrazin-6-yl)urea]butyl}phosphonic acid (compound 43)

Preparation of {4-[3-(3-phenylpyrido[2,3-b]pyrazin-6-yl)urea]butyl}phosphonic acid 60 mg (0.13 mmol) of diethyl {4-[3-(3-phenylpyrido[2,3-b]pyrazin-6-yl)urea]butyl}phosphonate were dissolved in 5 ml each of dichloromethane and hexamethyldisilazide, and admixed with 100 mg (0.66 mmol) of bromotrimethylsilane. After stirring at room temperature for 6 h, the reaction mixture was concentrated under reduced pressure and the residue was stirred with water for 2 h. This gave a yellow solid.

ESI-MS: found m/z=402.3 (M+H$^+$); calc. 401 amu $^1$H NMR (DMSO-d$_6$) δ=1.51-1.68 (m, 6H), 3.33-3.36 (m, 2H), 7.58-7.63 (m, 3H), 7.73 (d, 1H), 8.33-8.37 (m, 3H), 9.06 (s, 1H), 9.44 (s, 1H), 10.12 (s, 1H) ppm.

The following example was synthesized according to Example 37 and the general synthesis methods:

Example 38

(4-{3-[3-(4-Hydroxy-3-methoxyphenyl)pyrido[2,3-b]pyrazin-6-yl]urea}butyl)phosphonic acid (compound 45)

ESI-MS: found m/z=448.3 (M+H$^+$); calc. 447 amu $^1$H NMR (DMSO-d$_6$) δ=1.48-1.67 (m, 6H), 3.24-3.28 (m, 2H), 3.92 (s, 3H), 6.98 (d, 1H), 7.70 (d, 1H), 7.85 (dd, 1H), 7.89 (d, 1H), 8.28 (d, 1H), 8.95 (s, 1H), 9.38 (s, 1H), 10.02 (s, 1H) ppm.

Example 39

{2-[3-(3-Phenyl-pyrido[2,3-b]pyrazin-6-yl)-urea]-ethyl}-phosphoric acid (compound 63)

ESI-MS: found m/z=374.2 (M+H$^+$); calc. 373 amu
$^1$H-NMR (d$_6$-DMSO): δ=1.86-1.93 (m, 2H), 3.45-3.52 (m, 2H), 7.57-7.63 (m, 3H), 7.76 (d, 1H), 8.35 (d, 2H), 8.37 (d, 1H), 8.96 (s, 1H), 9.45 (s, 1H), 10.17 (s, 1H) ppm.

Example 40

Ethyl N-(3-phenylpyrido[2,3-b]pyrazin-6-yl)oxalamidate (compound 59)

Preparation of ethyl N-(3-phenylpyrido[2,3-b]pyrazin-6-yl)oxalamidate (reaction according to scheme 5)

200 mg (0.90 mmol) of 3-phenylpyrido[2,3-b]pyrazin-6-ylamine were dissolved in 20 ml of pyridine and admixed with 0.11 ml (0.99 mmol) of ethyloxalyl chloride. After stirring at room temperature for 2 h, the solution was poured onto ice-water. The precipitated solid was filtered off and washed thoroughly with water. This gave a bright yellow solid.

ESI-MS: found m/z=323.2 (M+H$^+$); calc. 322 amu
$^1$H NMR (DMSO-d$_6$) δ=1.37 (t, 3H), 4.35-4.41 (m, 2H), 7.60-7.66 (m, 3H), 8.38 (d, 2H), 8.43 (bs, 1H), 8.61 (d, 1H), 9.63 (s, 1H), 11.67 (s, 1H) ppm.

Example 41

N-Ethyl-N'-(3-phenylpyrido[2,3-b]pyrazin-6-yl)oxalamide (compound 60)

Preparation of N-Ethyl-N'-(3-phenylpyrido[2,3-b]pyrazin-6-yl)oxalamide (reaction according to scheme 5)

23 mg (0.07 mmol) of ethyl N-(3-phenylpyrido[2,3-b]pyrazin-6-yl)oxalamidate were dissolved in 5ml of dry THF and admixed with 0-15 ml (0.38 mmol) of a 2.0 M ethylamine solution in THF.

After stirring at room temperature for 48 hours the reaction mixture was neutralized. The precipitated solid was filtered off and the filtrate was concentrated to dryness under reduced pressure. The resulting solid was purified by column chromatography on silica gel (dichloromethane/methanol elutent). This gave a bright yellow solid.

ESI-MS: found m/z=322.3 (M+H$^+$); calc. 321 amu
$^1$H NMR (DMSO-d$_6$) δ=1.13 (t, 3H), 3.27 (q, 2H), 7.60-7.66 (m, 3H), 8.39 (d, 2H), 8.54 (d, 1H), 8.65 (d, 1H), 9.24 (t, 1H), 9.64 (s, 1H), 10.31 (s, 1H) ppm.

Example 42

Ethyl 4-[6-(3-ethyl-1-phenylurea)pyrido[2,3-b]pyrazin-3-yl]phenylcarbamate (compound 20)

Preparation of ethyl 4-[6-(3-ethyl-1-phenylurea)pyrido[2,3-b]pyrazin-3-yl]phenylcarbamate (reaction according to scheme 5)

100 mg of 4-(6-phenylaminopyrido[2,3-b]pyrazin-3-yl)phenol hydrochloride (0.28 mmol) were initially charged in 3 ml of pyridine, and 65.3 mg of ethyl isocyanate (0.90 mmol) were added at room temperature. The mixture was left to stir at 80° C. for 5 h, then another 32.0 mg of ethyl isocyanate (0.45 mmol) were added and the mixture was left to stir at 80° C. for a further 4 h. The solvent was then removed under reduced pressure. The resulting solid was purified twice by means of column chromatography on silica gel (dichloromethane/methanol and n-heptane/acetone eluent). This gave a bright yellow solid.

m.p.: 147-151° C.
ESI-MS: found m/z=457.3 (M+H$^+$); calc. 456 amu
$^1$H NMR (CDCl$_3$): δ=1.28 (t, 3H), 1.40 (t, 3H), 3.39 (quint, 2H), 3.57 (quint, 2H), 5.09 (t, 1H), 6.80 (d, 1H), 7.37 (d, 2H), 7.40 (d, 2H), 7.50 (t, 1H), 7.57 (t, 2H), 8.10 (d, 1H), 8.30 (d, 2H), 9.25 (s, 1H), 10.76 (t, 1H) ppm.

For the preparation of 4-(6-phenylaminopyrido[2,3-b]pyrazin-3-yl)phenol hydrochloride, reference is made here to WO 99/17759.

Example 43 tert-Butyl {4-[6-(3-ethylurea)pyrido[2,3-b]pyrazin-3-yl]phenyl}carbamate (compound 21)

Preparation of tert-butyl {4-[6-(3-ethylurea)pyrido[2,3-b]pyrazin-3-yl]phenyl}carbamate (reaction according to scheme 6)

83 mg of 1-(3-chloropyrido[2,3-b]pyrazin-6-yl)-3-ethylurea (0.33 mmol), 120 mg of tert-butyl[4-(4,4,5,5-tetramethyl[1,3,2]dioxaborolan-2-yl)phenyl]carbamate (0.36 mmol), 106 mg of sodium carbonate (1.00 mmol) and 19 mg of tetrakis-(triphenylphosphine)-palladium (0.02 mmol) were initially charged in 7 ml of degassed dimethylformamide/water mixture. The mixture was heated to 100° C. for 4 h. The cooled mixture was admixed with water. The precipitated solid was filtered off and washed with water and dichloromethane. This gave a beige solid.

m.p.: 281-283° C.
ESI-MS: found m/z=409.4 (M+H$^+$); calc. 408 amu
$^1$H NMR (d$_6$-DMSO): δ=1.20 (t, 3H), 1.52 (s, 9H), 3.25-3.38 (m, 2H), 7.65 (d, 1H), 7.69 (d, 2H), 8.29 (d, 2H), 8.33 (d, 1H), 9.09 (bs, 1H), 9.41 (s, 1H), 9.72 (s, 1H), 10.09 (s, 1H) ppm.

The following examples were synthesized according to Example 43 and the general synthesis methods:

Example 44

2-Methoxyethyl {4-[6-(3-ethylurea)pyrido[2,3-b]pyrazin-3-yl]phenyl}carbamate (compound 22)

m.p.: 249-251° C.
ESI-MS: found m/z=411.3 (M+H$^+$); calc. 410 amu
$^1$H NMR (d$_6$-DMSO): δ=1.20 (t, 3H), 3.31 (s, 3H), 3.45-3.38 (m, 2H), 3.58-3.64 (m, 2H), 4.24-4.27 (m, 2H), 7.65 (d, 1H), 7.70 (d, 2H), 8.31 (d, 2H), 8.37 (d, 1H), 9.08 (bs, 1H), 9.41 (s, 1H), 10.09 (s, 1H), 10.11 (s, 1H) ppm.

Example 45

1-Ethyl-3-{3-[4-(3-ethylurea)phenyl]pyrido[2,3-b]pyrazin-6-yl}urea (compound 23)

m.p.: >350° C. (decomp.)
ESI-MS: found m/z=380.2 (M+H$^+$); calc. 379 amu
$^1$H NMR (d$_6$-DMSO): δ=1.08 (t, 3H), 1.20 (t, 3H), 3.14 (quint, 2H), 3.32-3.38 (m, 2H), 6.33 (t, 1H), 7.60-7.64 (m, 3H), 8.25 (d, 2H), 8.32 (d, 1H), 8.88 (s, 1H), 9.12 (bs, 1H), 9.39 (s, 1H), 10.06 (s, 1H) ppm.

Example 46

1-{3-[4-(3,3-Dimethylurea)phenyl]pyrido[2,3-b]pyrazin-6-yl}-3-ethylurea (Compound 24)

m.p.: >350° C.
ESI-MS: found m/z=380.3 (M+H$^+$); calc. 379 amu
$^1$H NMR (d$_6$-DMSO): δ=1.20 (t, 3H), 2.98 (s, 6H), 3.25-3.38 (m, 2H), 7.63 (d, 1H), 7.74 (d, 2H), 8.26 (d, 2H), 8.33 (d, 1H), 8.63 (s, 1H), 9.12 (bs, 1H), 9.41 (s, 1H), 10.07 (s, 1H) ppm.

Example 47

1-Ethyl-3-{3-[6-(3-ethylurea)pyridin-3-yl]pyrido[2,3-b]pyrazin-6-yl}urea (Compound 25)

ESI-MS: found m/z=381.2 (M+H$^+$); calc. 380 amu
$^1$H NMR (d$_6$-DMSO): δ=1.13 (t, 3H), 1.20 (t, 3H), 3.23 (quint, 2H), 3.25-3.38 (m, 2H), 7.63 (d, 1H), 7.67 (d, 1H), 8.25 (d, 1H), 8.00 (bs, 1H), 8.35 (d, 1H), 8.61 (d, 1H), 9.08 (bs, 1H), 9.17 (s, 1H), 9.44 (s, 1H), 9.55 (s, 1H), 10.12 (s, 1H) ppm.

Example 48

1-Ethyl-3-[3-(4-morpholin-4-ylmethylphenyl)pyrido[2,3-b]pyrazin-6-yl]urea (Compound 28)

ESI-MS: found m/z=393.4 (M+H$^+$); calc. 392 amu
$^1$H NMR (d$_6$-DMSO): δ=1.20 (t, 3H), 2.41 (bs, 4H), 3.33-3.38 (m, 2H), 3.58 (s, 2H), 3.61 (t, 4H), 7.55 (d, 2H), 7.69 (t, 1H), 8.30 (d, 2H), 8.37 (d, 1H), 9.10 (bs, 1H), 9.44 (s, 1H), 10.13 (s, 1H) ppm.

Example 49

N-{4-[6-(3-Ethylurea)pyrido[2,3-b]pyrazin-3-yl]phenyl}-2-(2-methoxyethoxy)acetamide (compound 30)

m.p.: 212-215° C.
ESI-MS: found m/z=425.2 (M+H$^+$); calc. 424 amu
$^1$H NMR (d$_6$-DMSO): δ=1.20 (t, 3H), 3.32 (s, 3H), 3.34-3.38 (m, 2H), 3.56 (dd, 2H), 3.71 (dd, 2H), 4.15 (s, 2H), 7.66 (d, 1H), 7.89 (d, 2H), 8.33-8.36 (m, 3H), 9.11 (bs, 1H), 9.43 (s, 1H), 9.97 (s, 1H), 10.11 (s, 1H) ppm.

Example 50

2-Benzyloxy-N-{4-[6-(3-ethylurea)pyrido[2,3-b]pyrazin-3-yl]phenyl}acetamide (compound 35)

m.p.: 254-256° C.
ESI-MS: found m/z=457.3 (M+H$^+$); calc. 456 amu
$^1$H NMR (d$_6$-DMSO): δ=1.20 (t, 3H), 3.28-3.38 (m, 2H), 4.16 (s, 2H), 4.66 (s, 2H), 7.31 (t, 1H), 7.33 (t, 1H), 7.40 (t, 2H), 7.44 (d, 1H), 7.66 (d, 1H), 7.91 (d, 2H), 8.33-8.36 (m, 3H), 9.11 (bs, 1H), 9.44 (s, 1H), 10.10 (s, 1H), 10.14 (s, 1H) ppm.

Example 51

1-Ethyl-3-[3-(3-trimethylsilanylphenyl)pyrido[2,3-b]pyrazin-6-yl]urea (compound 46)

m.p.: 224-228° C.
ESI-MS: found m/z=366.4 (M+H$^+$); calc. 365 amu
$^1$H NMR (d$_6$-DMSO): δ=0.35 (s, 9H), 1.21 (t, 3H), 3.28-3.38 (m, 2H), 7.60 (t, 1H), 7.73 (t, 2H), 8.32 (d, 1H), 8.37 (d, 1H), 8.46 (s, 1H), 9.04 (bs, 1H), 9.48 (s, 1H), 10.12 (s, 1H) ppm.

In Example 51, dioxane/water was used as the solvent instead of dimethylformamide/water. Commercially unavailable boronic acid derivatives were prepared by the following method or processes known to those skilled in the art:

Preparation of 2-methoxyethyl[4-(4,4,5,5-tetramethyl[1,3,2]dioxaborolan-2-yl)phenyl]carbamate 107 mg of 4-(4,4,5,5-tetramethyl[1,3,2]dioxaborolan-2-yl)phenylamine (0.48 mmol) were dissolved in tetrahydrofuran. 96 mg of 2-methoxyethyl chloroformate (0.68 mmol) and 79 mg of N-methylmorpholine (0.78 mmol) were added at room temperature. The mixture was left to stir at room temperature for 1 day, precipitated solid was filtered off and the solvent was removed under reduced pressure. This gave a yellowish oil which was used without further purification in the next reaction.

The following boronic acid derivatives were prepared by the above method or processes known to those skilled in the art:
1-ethyl-3-[4-(4,4,5,5-tetramethyl-[1,3,2]dioxaborolan-2-yl)phenyl]urea
1,1-dimethyl-3-[4-(4,4,5,5-tetramethyl-[1,3,2]dioxaborolan-2-yl)phenyl]urea
1-ethyl-3-[5-(4,4,5,5-tetramethyl-[1,3,2]dioxaborolan-2-yl)pyridin-2-yl]urea
2-(2-methoxyethoxy)-N-[4-(4,4,5,5-tetramethyl-[1,3,2]dioxaborolan-2-yl)phenyl]acetamide
2-benzyloxy-N-[4-(4,4,5,5-tetramethyl-[1,3,2]dioxaborolan-2-yl)phenyl]acetamide

Example 52

1-Ethyl-3-{3-[2-(4-fluorophenyl)ethyl]pyrido[2,3-b]pyrazin-6-yl}urea (compound 26)

Preparation of 1-ethyl-3-{3-[2-(4-fluorophenyl)ethyl]pyrido[2,3-b]pyrazin-6-yl}urea 108 mg of 1-ethyl-3-{3-[2-(4-fluorophenyl)vinyl]pyrido[2,3-b]pyrazin-6-yl}urea (0.32 mmol) (Example 27) were dissolved in hot ethanol. 112 mg of ammonium formate (1.78 mmol) and 110 mg of palladium (10%) on carbon were added, and the reaction mixture was heated under reflux for 7.5 h. The catalyst was filtered off from the cooled reaction mixture, and the mother liquor was freed from the solvent. The crude product was purified by column chromatography on silica gel (dichloromethane/methanol eluent). This gave a yellow solid.
m.p.: 207-209° C.
ESI-MS: found m/z=340.2 (M+H$^+$); calc. 339 amu $^1$H NMR (d$_6$-DMSO): δ=1.20 (t, 3H), 3.12 (t, 2H), 3.25-3.38 (m, 4H), 7.10 (t, 2H), 7.32 (dd, 2H), 7.63 (d, 1H), 8.31 (d, 1H), 8.71 (s, 1H), 9.09 (bs, 1H), 10.06 (s, 1H) ppm.

Example 53

1-Ethyl-3-(3-{4-[2-(2-methoxyethoxy)ethoxy]phenyl}pyrido[2,3-b]pyrazin-6-yl)urea (compound 29)

Preparation of 1-ethyl-3-(3-{4-[2-(2-methoxyethoxy)ethoxy]phenyl}pyrido[2,3-b]pyrazin-6-yl)urea (reaction according to scheme 9)

29 mg of sodium hydride (0.71 mmol) (60% suspension in mineral oil) were initially charged in 4 ml of dried dimethylformamide. At 0° C., 70 mg of 1-ethyl-3-[3-(4-hydroxyphenyl)pyrido[2,3-b]pyrazin-6-yl]urea (0.23 mmol) were added dissolved in 2.5 ml of dimethylformamide. The mixture was stirred at room temperature for 1 h. Subsequently, 68 mg of 1-bromo-2-(2-ethoxymethoxy)ethane (0.34 mmol) were added at 0° C. and the reaction mixture was stirred at room temperature for 17 h. Thereafter, another 22 mg of 1-bromo-2-(2-ethoxymethoxy)ethane (0.12 mmol) were added and the reaction mixture was stirred at 80° C. for 2 h. Water was added to the cooled reaction mixture and the aqueous phase was extracted with dichloromethane. After the organic phase had been dried over sodium sulphate, the solvent was removed and the crude product was purified by column chromatography on silica gel (dichloromethane/methanol) eluent. This gave a yellow solid.

ESI-MS: found m/z=412.3 (M+H$^+$); calc. 411 amu $^1$H NMR (d$_6$-DMSO): δ=1.20 (t, 3H), 3.26 (s, 3H), 3.29-3.38 (m, 2H), 3.48 (dd, 2H), 3.62 (dd, 2H), 3.80 (dd, 2H), 4.22 (dd, 2H), 7.17 (d, 2H), 7.64 (t, 1H), 8.31-8.35 (m, 3H), 9.14 (bs, 1H), 9.42 (s, 1H), 10.09 (s, 1H) ppm.

Example 54

N-[6-(3-Ethylurea)pyrido[2,3-b]pyrazin-3-yl]-4-methylbenzamide (compound 31)

Preparation of N-[6-(3-ethylurea)pyrido[2,3-b]pyrazin-3-yl]-4-methylbenzamide (reaction according to scheme 7)

100 mg of 1-(3-aminopyrido[2,3-b]pyrazin-6-yl)-3-ethylurea (0.43 mmol) were initially charged in 5 ml of dried pyridine, and 57 μl of p-tolyl chloride (0.43 mmol) were added dropwise. The mixture was stirred at 60° C. for 2 h. Thereafter, another 29 μl of p-tolyl chloride (0.22 mmol) were added dropwise and the reaction mixture was stirred at 60° C. for a further 2 h. The cooled reaction mixture was added to ice-water and neutralized with 1N HCl, and the solid was filtered off with suction. The crude product was purified by column chromatography on silica gel (dichloromethane/methanol eluent). This gave a yellowish solid.

ESI-MS: found m/z=351.1 (M+H$^+$); calc. 350 amu $^1$H NMR (d$_6$-DMSO): δ=1.18 (t, 3H), 2.42 (s, 3H), 3.31 (quint, 2H), 7.37 (d, 2H), 7.55 (d, 1H), 8.04 (d, 2H), 8.31 (d, 1H), 9.10 (bs, 1H), 9.56 (s, 1H), 9.96 (s, 1H), 11.39 (bs, 1H) ppm.

Example 55

1-[3-(4-Cyclohexylphenylamino)pyrido[2,3-b]pyrazin-6-yl]-3-ethylurea (compound 47)

Preparation of 1-[3-(4-cyclohexylphenylamino)pyrido[2,3-b]pyrazin-6-yl]-3-ethylurea (reaction according to scheme 3)

83 mg of 1-(3-chloropyrido[2,3-b]pyrazin-6-yl)-3-ethylurea (0.33 mmol), 99 mg of 4-cyclohexylaniline (0.55 mmol), 30 mg of sodium tert-butoxide (0.30 mmol), 29 mg of tris(dibenzylideneacetone)dipalladium(0) (0.03 mmol) and 68 mg of 2-(dicyclohexylphosphanyl)biphenyl (0.19 mmol) were initially charged in 1.5 ml of dried toluene. The reaction mixture was heated to 100° C. under nitrogen in a microwave (100 watt) for 30 minutes. The solvent was removed under reduced pressure and the crude product was purified by column chromatography on silica gel (dichloromethane/methanol eluent). This gave a yellow solid.

m.p.: 246-248° C.

ESI-MS: found m/z=391.3 (M+H$^+$); calc. 390 amu $^1$H NMR (d$_6$-DMSO): δ=1.18 (t, 3H), 1.22-1.26 (m, 1H), 1.33-1.44 (m, 4H), 1.71 (d, 1H), 1.80 (d, 4H), 2.45-2.51 (m, 1H), 3.25-3.30 (m, 2H), 7.22 (d, 2H), 7.40 (d, 1H), 7.89 (d, 2H), 8.08 (d, 1H), 8.37 (s, 1H), 8.73 (bs, 1H), 9.87 (s, 1H), 10.06 (s, 1H) ppm.

The following examples were synthesized according to Example 55 and the general synthesis methods:

Example 56

1-Ethyl-3-[3-(4-methanesulphonylphenylamino)pyrido[2,3-b]pyrazin-6-yl]urea (Compound 48)

m.p.: 275-280° C.

ESI-MS: found m/z=387.3 (M+H$^+$); calc. 386 amu $^1$H NMR (d$_6$-DMSO): δ=1.20 (t, 3H), 3.19 (s, 3H), 3.25-3.38 (m, 2H), 7.54 (d, 1H), 7.92 (d, 2H), 8.16 (d, 1H), 8.24 (d, 2H), 8.49 (s, 1H), 8.62 (bs, 1H), 9.93 (s, 1H), 10.56 (s, 1H) ppm.

Example 57

N-{5-[6-(3-Ethylurea)pyrido[2,3-b]pyrazin-3-ylamino]-2-methylphenyl}methanesulphonamide (Compound 49)

m.p.: 247-250° C.

ESI-MS: found m/z=416.2 (M+H$^+$); calc. 415 amu $^1$H NMR (d$_6$-DMSO): δ=1.17 (t, 3H), 2.28 (s, 3H), 3.03 (s, 3H), 3.25-3.38 (m, 2H), 7.23 (d, 1H), 7.33 (d, 1H), 7.75 (d, 1H), 8.06-8.09 (m, 2H), 8.37 (s, 1H), 8.92 (bs, 1H), 9.09 (s, 1H), 9.77 (s, 1H), 10.09 (s, 1H) ppm.

Example 58

3-[6-(3-Ethylurea)pyrido[2,3-b]pyrazin-3-ylamino]-N-methylbenzamide (compound 50)

m.p.: 228-234° C.

ESI-MS: found m/z=366.4 (M+H$^+$); calc. 365 amu $^1$H NMR (d$_6$-DMSO): δ=1.19 (t, 3H), 2.80 (d, 3H), 3.25-3.38 (m, 2H), 7.39-7.48 (m, 3H), 8.09-8.11 (m, 2H), 8.41 (s, 2H), 8.46 (s, 1H), 8.83 (bs, 1H), 9.86 (s, 1H), 10.22 (s, 1H) ppm.

Example 59

1-Ethyl-3-[3-(4-piperidin-1-ylmethylphenylamino)pyrido[2,3-b]pyrazin-6-yl]urea (compound 51)

m.p.: 221-224° C.
ESI-MS: found m/z=406.4 (M+H$^+$); calc. 405 amu
$^1$H NMR (d$_6$-DMSO): δ=1.19 (t, 3H), 1.39 (bs, 2H), 1.49 (quint, 4H), 2.32 (bs, 4H), 3.25-3.35 (m, 2H), 3.39 (s, 2H), 7.27 (d, 2H), 7.39 (d, 1H), 7.92 (d, 2H), 8.08 (d, 1H), 8.38 (s, 1H), 8.78 (bs, 1H), 9.82 (s, 1H), 10.05 (s, 1H) ppm.

Example 60

1-Ethyl-3-[3-(4-thiophen-3-ylphenylamino)pyrido[2,3-b]pyrazin-6-yl]urea (compound 52)

m.p.: 264-267° C.
ESI-MS: found m/z=391.4 (M+H$^+$); calc. 390 amu
$^1$H NMR (d$_6$-DMSO): δ=1.21 (t, 3H), 3.25-3.35 (m, 2H), 7.47 (d, 1H), 7.58 (d, 1H), 7.65 (dd, 1H), 7.74 (d, 2H), 7.82 (d, 1H), 8.05 (d, 2H), 8.11 (d, 1H), 8.42 (s, 1H), 8.62 (bs, 1H), 9.86 (s, 1H), 10.18 (s, 1H) ppm.

Example 61

N-{4-[6-(3-Ethylurea)pyrido[2,3-b]pyrazin-3-ylamino]phenyl}acetamide (compound 53)

ESI-MS: found m/z=366.2 (M+H$^+$); calc. 365 amu
$^1$H NMR (d$_6$-DMSO): δ=1.20 (t, 3H), 2.03 (s, 3H), 3.25-3.35 (m, 2H), 7.27 (d, 1H), 7.34 (d, 2H), 7.57 (d, 2H), 7.90 (d, 1H), 8.07 (d, 1H), 8.94 (bs, 1H), 9.79 (s, 1H), 9.89 (s, 1H), 10.03 (s, 1H) ppm.

Example 62

Ethyl 3-[6-(3-ethylurea)pyrido[2,3-b]pyrazin-3-ylamino]benzoate (compound 54)

m.p.: 252-255° C.
ESI-MS: found m/z=381.3 (M+H$^+$); calc. 380 amu
$^1$H NMR (d$_6$-DMSO): δ=1.19 (t, 3H), 1.35 (t, 3H), 3.25-3.35 (m, 2H), 4.35 (q, 2H), 7.40 (d, 1H), 7.52 (t, 1H), 7.64 (d, 1H), 8.12 (d, 1H), 8.29 (d, 1H), 8.41 (s, 1H), 8.62 (s, 1H), 8.90 (bs, 1H), 9.86 (s, 1H), 10.31 (s, 1H) ppm.

Example 63

4-[6-(3-Ethylurea)pyrido[2,3-b]pyrazin-3-yl]phenyl 2-methoxyethyl carbonate hydrochloride (compound 55)

Preparation of 4-[6-(3-ethylurea)pyrido[2,3-b]pyrazin-3-yl]phenyl 2-methoxyethyl carbonate hydrochloride 21 mg of 4-[6-(3-ethylurea)pyrido[2,3-b]pyrazin-3-yl]phenyl 2-methoxyethyl carbonate (0.05 mmol) (Example 10) were dissolved in 2.5 ml of dichloromethane/methanol (2:1). 0.02 ml of 5-6N HCl solution in 2-propanol was added and the mixture was stirred at room temperature for 1 day. The solvent was then removed. This gave a yellow solid.
m.p.: 190-193° C.
$^1$H NMR (d$_6$-DMSO): δ=1.20 (t, 3H), 3.31-3.35 (m, 5H), 3.63-3.66 (m, 2H), 4.37 (dd, 2H), 7.50 (d, 2H), 7.70 (d, 1H), 8.38 (d, 1H), 8.41 (d, 2H), 9.09 (bs, 1H), 9.47 (s, 1H), 10.14 (s, 1H) ppm.

Example 64

4-[6-(3-Ethylurea)pyrido[2,3-b]pyrazin-3-yl]phenyl 2-methoxyethyl carbonate p-toluenesulphonate (compound 56)

Preparation of 4-[6-(3-ethylurea)pyrido[2,3-b]pyrazin-3-yl]phenyl 2-methoxyethyl carbonate p-toluenesulphonate 48 mg of 4-[6-(3-ethylurea)pyrido[2,3-b]pyrazin-3-yl]phenyl 2-methoxyethyl carbonate (0.12 mmol) were initially charged in 4 ml of dichloromethane and 0.7 ml of methanol. 23 mg of p-toluenesulphonic acid monohydrate (0.12 mmol) were added at room temperature dissolved in 2 ml of dichloromethane and 0.5 ml of methanol. The reaction mixture was stirred at 0° C. for 1 h and at room temperature for 1 day. The solvent was removed and the residue recrystallized from dichloromethane/n-heptane. The precipitated product was filtered off with suction and washed with n-heptane. This gave a yellow solid.
m.p.: 145-147° C.
$^1$H NMR (d$_6$-DMSO): δ=1.20 (t, 3H), 2.29 (s, 3H), 3.30-3.36 (m, 5H), 3.64 (dd, 2H), 4.38 (dd, 2H), 7.11 (d, 2H), 7.47 (d, 2H), 7.50 (d, 2H), 7.70 (d, 1H), 8.38 (d, 1H), 8.41 (d, 2H), 9.09 (bs, 1H), 9.47 (s, 1H), 10.14 (s, 1H) ppm.

Example 65

4-{6-[3-(4-Hydroxybutyl)urea]pyrido[2,3-b]pyrazin-3-yl}phenyl 2-methoxyethyl carbonate hydrochloride (compound 58)

Preparation of 4-{6-[3-(4-hydroxybutyl)urea]pyrido[2,3-b]pyrazin-3-yl}phenyl 2-methoxyethyl carbonate hydrochloride 117 mg of 4-{6-[3-(4-(tert-butyldimethylsilanyloxy)butyl)urea]pyrido[2,3-b]pyrazin-3-yl}phenyl 2-methoxyethyl carbonate (0.21 mmol) were dissolved in 40 ml of predried dichloromethane. 0.5 ml of 5-6N HCl solution in 2-propanol was added and the reaction mixture was stirred at room temperature for 15 minutes. The organic phase was washed with water, dried over sodium sulphate and concentrated. This gave a yellow solid.
m.p.: 165-168° C.
ESI-MS: found m/z=456.2 (M+H$^+$); calc. 455 amu
$^1$H NMR (d$_6$-DMSO): δ=1.61 (quint, 4H), 2.29 (s, 3H), 3.30-3.36 (m, 2H), 3.49 (t, 2H), 3.64 (dd, 2H), 4.38 (dd, 2H), 7.49 (d, 2H), 7.66 (d, 1H), 8.38 (d, 1H), 8.43 (d, 2H), 9.33 (bs, 1H), 9.48 (s, 1H), 10.17 (s, 1H) ppm.

For the preparation of 4-{6-[3-(4-(tert-butyldimethylsilanyloxy)butyl)urea]pyrido[2,3-b]pyrazin-3-yl}phenyl 2-methoxyethyl carbonate, reference is made here to schemes 5, 6 and 8, the general synthesis methods and the processes known to those skilled in the art.

Example 66

1-[(1-acetoxyethoxy)-(4-{3-[3-(4-hydroxy-3-methoxyphenyl)-pyrido[2,3-b]pyrazin-6-yl]urea}butyl)phosphinoyloxy]ethyl acetate (compound 65)

Preparation of 1-[(1-acetoxyethoxy)-(4-{3-[3-(4-hydroxy-3-methoxyphenyl)-pyrido[2,3-b]pyrazin-6-yl]urea}butyl)phosphinoyloxy]acetate 94 mg 4-{3-[3-(4-Hydroxy-3-methoxy-phenyl)-pyrido[2,3-b]pyrazin-6-yl]-urea}-butyl)phosphoric acid (0.20 mmol) were dissolved in 15 ml DMF, 360 μL Pivalic acid chloromethylester (2.40 mmol) and 30 μL Triethylamine (0.21 mmol) were added and stirred for 10 h at 60° C. The reaction mixture was poured onto 50 mL water and extracted three times with Ethylacetate. The combined organic phases were dried over MgSO4 and the solvent removed in vacuo. The concentrate was afterwards purified by column chromatography (solvent dichloromethane/Methanol). This gave a beige solid.

ESI-MS: found m/z=676.4 (M+H$^+$); calc. 675 amu
$^1$H-NMR (d$_6$-DMSO): δ=1.12 (s, 18H), 1.57-1.68 (m, 4H), 1.90-1.97 (m, 2H), 3.28-3.31 (m, 3.93 (s, 3H), 5.54-5.59 (m, 4H), 6.97 (d, 1H), 7.64 (d, 1H), 7.86 (dd, 1H), 7.91 (d, 1H), 8.32 (d, 1H), 9.08 (s, 1H), 9.41 (s, 1H), 9.70 (s, 1H), 10.06 (s, 1H) ppm.

II) Biological Effects of the Inventive Compounds

II.1) Cell-Free Kinase Assays (by Means of ALPHA Technology)

The inhibitory effect of the inventive compounds was tested on various human serine/threonine kinases, tyrosine kinases and lipid kinases in enzymatic assays. Recombinant human kinases, for example Erk2, PI3Kalpha, -beta, -gamma, -delta, p38alpha, p38gamma, Jnk1, Jnk2 and others were used, in some cases as full-length kinases, in some cases as truncated fragments—but at least consisting of the functional kinase domains. The commercial kinase proteins (Proqinase, Upstate) were used as recombinant fusion proteins with GST (glutathione S-transferase) tag or His tag. Depending on the substrate type, the different kinase reactions were quantified by means of suitable ALPHA™ beads (PerkinElmer).

Testing

The substrate testing on the Erk assay is described in detail below. Selected test results of the Erk2, PI3Kalpha assays are cited below. To determine the IC$_{50}$ value, the potential inhibitor substances were investigated at 10 half-logarithmically graduated concentrations of 3.16 nM-100 μM.

a) Erk2-ALPHA: The test substance, 0.625 ng of Erk2 (#14-173, Upstate), 10 μM ATP and 15 nM biotinylated MBP (myelin basic protein) substrate were incubated on a 384-well Optiplate (Perkin Elmer) in a volume of 15 μl for 1 h in 25 mM Tris, 10 mM MgCl$_2$, 0.1% Tween-20, 100 μM NaVO$_4$, 2 mM DTT at pH 7.5. The kinase reaction was then stopped by adding 10 μl of the ALPHA bead mix (10 μg/ml, #6760617/PerkinElmer), pre-incubated with anti-phospho MBP antibody (320 μM, #05-429/Upstate), in 25 mM Tris, 200 mM NaCl, 100 mM EDTA and 0.3% BSA, and left to stand overnight.

b) PI3K-ALPHAs (e.g. PI3Kalpha): The test substance, 1 ng of PI3Kalpha (#14-602, Upstate), 100 μM ATP and 20 μM PIP$_2$ substrate (#P4508, Echelon) on a 384-well Optiplate (Perkin Elmer) for 1 h in 50 mM Hepes, 50 mM NaCl, 5 mM MgCl$_2$, 0.05% Chaps, 5 mM DTT at pH 7.4. Subsequently, the kinase reaction was stopped by adding the ALPHA bead mix (10 μg/ml, #6760603/PerkinElmer), preincubated with 1 nM GST:Grp1 fusion protein (Upstate) and 15 nM biotinylated PIP3 (#C-39B6/Echelon) in 50 mM Hepes, 50 mM NaCl, 50 mM EDTA and 0.1% BSA, and left to stand overnight.

The fluorescence was detected the next morning in a Fusion™ alpha instrument (Perkin Elmer).

Evaluation

The calculation of % inhibition values per substance concentration was done by means of the following formula from the raw data determined in the Fusion™ alpha:

$$\% kinase\,inhibition_{(sample)} = 100 - \left(100 \times \frac{mean_{(sample)} - mean_{(0\% \, control)}}{mean_{(100\% \, control)} - mean_{(0\% \, control)}}\right)$$

The controls were each determined 8 times, the substance samples each twice. 0% control contained neither any ATP nor any substrate; the 100% control contained no test substance. The IC$_{50}$ values were determined with GraphPad-Prism.

The inventive compounds exhibited effective inhibition of Erk, PI3K, p38alpha and Jnk1+Jnk2 with IC$_{50}$ values up to 88nM (see Table 1).

TABLE 1

MAPK and PI3Kalpha kinase assay test results (IC50 [μM] at 10 μM or 100 μM* ATP)

| Compound | Erk2 | PI3Kalpha | p38alpha | Jnk1 + Jnk2 |
|---|---|---|---|---|
| 3 | 5.8 | 16.8 | Not tested | not tested |
| 6 | 2.4 | 21.3 | Not tested | not tested |
| 7 | 0.407 | 27.9 | >100 | 11.4 |
| 8 | 4.1 | 27.2 | >100 | 19.4 |
| 9 | 0.117 | 7.8 | >100 | >100 |
| 10 | 0.088 | 2.6 | >100 | 2.9 |
| 11 | 0.27 | >31.6 | >100 | >100 |
| 12 | 2.8 | 3.4 | 8.8 | 0.637 |
| 13 | 0.64 | >31.6 | >100 | >100 |
| 16 | 0.513 | 3.3 | >100 | 5.6 |
| 17 | 0.167 | 11.8 | >100 | >100 |
| 19 | 3.9 | 2.3 | >100 | 10.1 |
| 21 | >100 | 1.2 | >100 | >31.6 |
| 22 | >100 | 1.2 | >100 | >31.6 |
| 23 | 1.9 | 1.3 | >100 | 5.7 |
| 25 | 3.4 | 4.4 | >100 | 24.2 |
| 28 | 0.364 | 1.8 | >100 | 5 |
| 29 | 0.396 | 2.3 | >100 | 24.2 |
| 30 | >31.6 | 0.749 | >100 | 13.8 |
| 32 | 0.824 | 1.3 | >100 | 4.2 |
| 44 | 2.8 | 10.7 | >100 | 8.4 |
| 45 | 0.243 | 12.5 | >100 | 0.974 |
| 48 | >100 | 1.1 | >100 | >31.6 |
| 49 | 9.6 | 1.9 | 4 | >31.6 |
| 50 | 4.7 | 0.683 | 18.1 | >31.6 |
| 51 | 19.1 | 7.5 | >100 | >31.6 |
| 53 | 16.5 | 0.677 | >100 | 20.4 |
| 55 | 0.812 | 3.6 | >100 | 2.9 |
| 56 | 0.272 | 1.3 | >100 | 3.1 |
| 58 | 0.763 | 4.3 | >31.6 | 2.5 |
| 61 | 0.3 | 1.5 | >100 | 2.1 |

II.2) Cellular Assay: Testing for Anti-Proliferative Action (XTT Assay)

The principle of this test is based on the intracellular reduction of the tetrazolium dye XTT (sodium 3'-[1-(phenylaminocarbonyl)-3,4-tetrazolium]bis(4-methoxy-6-nitro)benzenesulphonic acid, Sigma) to a formazan dye by mitochondrial dehydrogenases.

The dye is formed only by metabolically active cells; its photometrically measurable intensity is a quantitative indicator for the presence of living cells. The reduction in the dye formation as a result of incubation of the cells with substances serves as a parameter for the anti-proliferative action.

Testing

The tumour cell lines (ATCC) were seeded in 96-well microtitre plates in a defined cell count (5000 cells/well for BxPC3 and Hct116; 10 000 cells/well for MDA MB468), and then incubated overnight in an incubator at 37° C., 5% $CO_2$ and 95% air humidity. The test substances were made up as stock solutions (10 mM) in DMSO. To determine the $EC_{50}$ values, the potential inhibitor substances were added to the cells in quaterlogarithmically graded dilutions, so as to result in final concentrations of 0.28 µM-50 µM. The cell plates were then incubated for 45 h in an incubator at 37° C., 5% $CO_2$ and 95% air humidity.

For the detection reaction, the XTT substrate was admixed with PMS (N-methyldibenzopyrazine methylsulphate, Sigma) and added to the cells, so as to result in a final concentration of 325 µg of XTT/ml and 2.5 µg PMS/ml. The mixture was then incubated for 3 h at 37° C., 95% air humidity. Subsequently the formazan salt formed by cellular dehydrogenases was quantified at an absorption of 490 nm.

Evaluation

The evaluation of the % inhibition values was done by means of the following formula from the values for the optical densities measured in each case at 490 nm:

$$\% \text{ inhibition of cell } proliferation_{(sample)} = 100 - \left(100 \times \frac{mean_{(sample)} - mean_{(0\% \text{ control})}}{mean_{(100\% \text{ control})} - mean_{(0\% \text{ control})}}\right)$$

The controls were determined 8 times each, the substance samples twice each. 0% control contained no cells; the 100% control contained no test substance. The $EC_{50}$ values were determined with GraphPadPrism.

The inventive compounds exhibited effective inhibition of cell proliferation in some cases with $EC_{50}$ values up to 2.2 µM (see Table 2).

TABLE 2

XTT assay test results (EC50 [µM])

| Compound | BxPC3 | MDA-MB468 | Hct116 |
|---|---|---|---|
| 9 | 20 | 15 | 10 |
| 10 | 9 | 7 | 5 |
| 16 | >25 | 11 | 11 |
| 17 | >25 | >25 | 3.4 |
| 23 | >50 | >25 | 16 |
| 32 | 5.9 | 4.5 | 2.2 |
| 49 | not tested | 16 | approx. 20 |
| 56 | >20 | 15.5 | 9.4 |
| 61 | not tested | 7.1 | 6 |

II.3) Cellular Assay: Testing on Substrate Inhibition (Western Blotting)

This method enables a statement of whether the kinase modulator investigated achieves the desired effect in a cellular context too, i.e., in this case, a substrate protein downstream of the target kinase is examined for its phosphorylation status. To this end, the cells incubated with substance are lysed and the overall protein is separated on a reducing polyacrylamide gel. Subsequently, the proteins are transferred by means of Western blotting to a PVDF membrane and the substrate bands sought are made visible with specific antibodies and a suitable detection method. The substrate proteins downstream of the target kinases are detected simultaneously with an anti-phospho antibody which is specific in each case and simultaneously a total antibody which recognizes the substrate total protein. The duplex technology of the ODYSSEY imager (LiCOR) enables this simultaneous measurement. The intensity of the total substrate bands is employed to normalize and quantify the phosphorylation inhibition or activation.

Testing

Suitable tumour cell lines (e.g. BxPC3, Hct116 or MDA MB468) were seeded into 6-well microtitre plates in a defined cell count (e.g. 350 000 cells/well for BxPC3 and Hct116) in the particular standard complete media and then incubated overnight in an incubator at 37° C., 5% $CO_2$ and 95% air humidity. The cells were then incubated further for a further 24 h under reduced-serum conditions, i.e. in the particular medium except at only 0.25% serum. The test substances were made up as stock solutions (10 mM) in DMSO and incubated with the cells at final concentrations of 5, 15.8 and 50 µM for 5 h. This was followed by cell lysis in 25 mM Tris, 150 mM NaCl, 10 mM sodium pyrophosphate, 2 mM EGTA, 25 mM beta-glycerophosphate, 25 mM NaF, 10% glycerol, 0.75% NP-40, 100 µM $NaVO_4$ buffer. After protein quantification by means of BCA (bicinchonic acid protein assay kit, Sigma) assay, amounts of protein of about 20 µg per track were separated on a Lammli polyacrylamide gel and then transferred onto a PVDF membrane (Millipore) by means of semi-dry Western blotting at 0.8 mA/cm$^2$ for 1 h. This was followed by prehybridization of the membrane for 1 hour in I-block reagent (Applied Biosystems) and overnight incubation with the specific antibodies. To determine the Erk and PI3K inhibition, the next substrates Rsk1 downstream were detected with the total antibody (Rsk #sc-231g C-21, Santa Cruz) and the phospho antibody (Phospho-p90RSK (S380) #9341, NEB Cell Signalling) and Akt with the total antibody (Akt1 #sc-20, Santa Cruz) and the phospho antibody (Phospho-Akt (Ser 473) #9271, NEB Cell Signaling). After the membrane had been washed, the secondary antibodies were incubated with anti-rabbit IR Dye 800 (#611-732-127, Rockland) for the phospho antibody and anti-goat Alexa Fluor 680 (#A-21081, Molecular samples) for the total protein antibody. After incubation for 30 min at room temperature in the dark, the hybridization of the detection antibody was detected on the membrane by scanning in an ODYSSEY imager (LiCOR).

Evaluation

At concentrations of 5-50 µM, the inventive compounds exhibited dual inhibition of Erk (MAPK1/2) and of PI3K (Table 3), which is indicated by inhibition of the band intensity of the two corresponding phospho-substrate proteins Rsk1 and Akt.

TABLE 3

Inhibition of cellular substrate phosphorylation (at 50 µM)

| Compound | Erk →pRsk | PI3K →pAkt |
|---|---|---|
| 9 | 90% | 50% |
| 10 | 100% | 100% |
| 23 | 0% | 70% |
| 32 | 100% | 90% |
| 49 | 0% | 90% |

Abbreviations

Akt from: murine Akt8 retrovirus or protein kinase B (PKB)
Ask1 apoptosis signal-regulating kinase
ATR ataxia-telangiectasia and Rad3-related ATM ataxia-telangiectasia mutated
Bag1 Bcl-2 associated athanogene-1
Bcl-2 B-cell leukaemia/lymhoma-2 gene
DNA-PK DNA-dependent protein kinase
Erk extracellular signal-regulated kinase
Flt-3 fms like tyrosine kinase 3
GSK-3 glycogen synthase kinase-3
hSMG-1 human orthologue of product of seven nematode gene-1
JAK-3 Janus kinase 3
JNK c-jun N-terminal kinase
MAPK mitogen activated protein kinase
Mek MAP or Erk kinase
mTOR mammalian target of rapamycin
PDGFR platelet derived growth factor receptor
PI3K phosphoinositol 3-kinase
PIKK phosphoinositol 3-kinase related kinase
$PIP_2$ phosphatidylinositol biphosphate
$PIP_3$ phosphatidylinositol triphosphate
PtdIns phosphatidylinositol
Raf rapid accelerated fibrosarcoma
Ras rat sarcoma
RTK receptor tyrosine kinase
SAPK stress-activated protein kinase
Ser serine
Syk spleen tyrosine kinase
Thr threonine
Tyr tyrosine
VEGFR vascular endothelial growth factor receptor

The invention claimed is:
1. A pyrido[2,3-b]pyrazine of formulae (I) selected from the group consisting of:

Compound 1

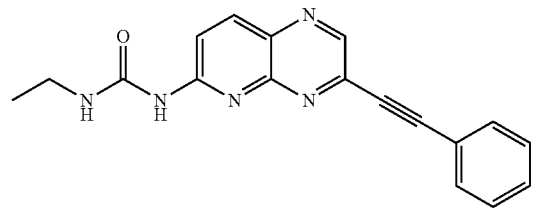

1-ethyl-3-(3-phenylethynylpyrido[2,3-b]pyrazin-6-yl)urea

Compound 2

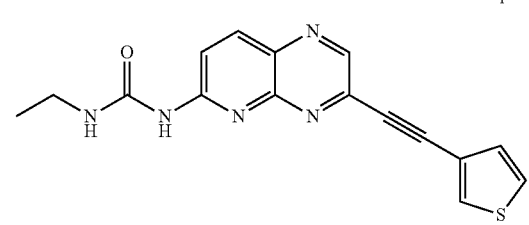

1-ethyl-3-(3-thiophen-3-ylethynylpyrido[2,3-b]pyrazin-6-yl)urea

Compound 3

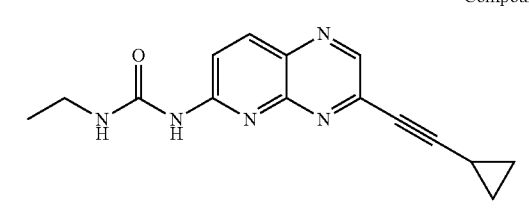

1-(3-cyclopropylethynylpyrido[2,3-b]pyrazin-6-yl)-3-ethylurea

Compound 5

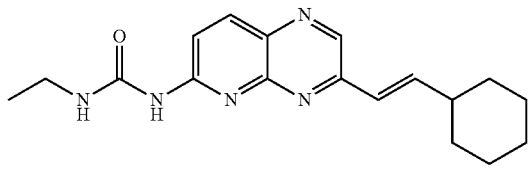

1-[3-((E)-2-cyclohexylvinyl)pyrido[2,3-b]pyrazin-6-yl]-3-ethylurea

Compound 9

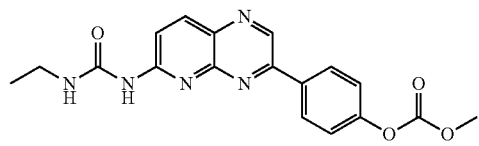

4-[6-(3-ethylurea)pyrido[2,3-b]pyrazin-3-yl]phenyl methyl carbonate

Compound 10

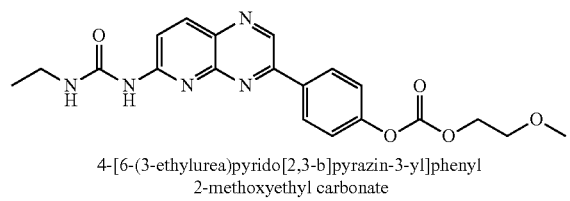

4-[6-(3-ethylurea)pyrido[2,3-b]pyrazin-3-yl]phenyl 2-methoxyethyl carbonate

Compound 11

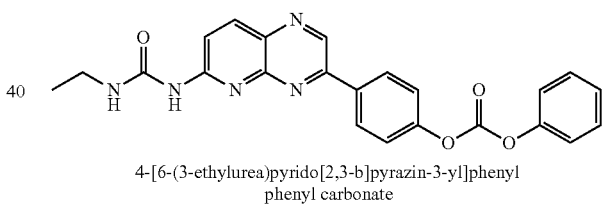

4-[6-(3-ethylurea)pyrido[2,3-b]pyrazin-3-yl]phenyl phenyl carbonate

Compound 12

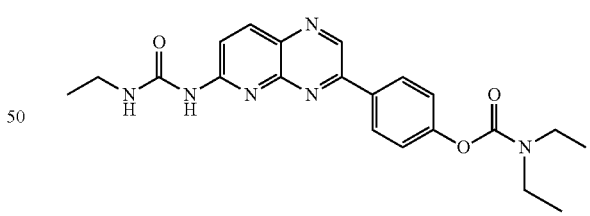

4-[6-(3-ethylurea)pyrido[2,3-b]pyrazin-3-yl]phenyl diethylcarbamate

Compound 13

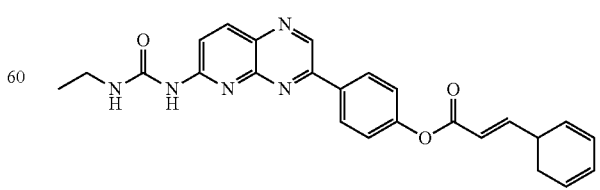

4-[6-(3-ethylurea)pyrido[2,3-b]pyrazin-3-yl]phenyl -3-phen

Compound 14

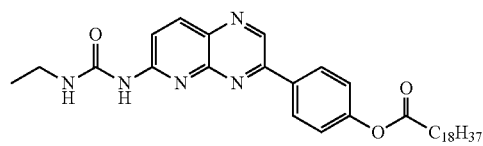

4-[6-(3-ethylurea)pyrido[2,3-b]pyrazin-3-yl]phenyl nonadecanoate

Compound 15

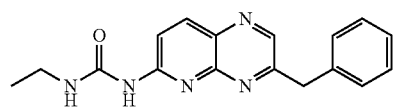

1-(3-benzylpyrido[2,3-b]pyrazin-6-yl)-3-ethylurea

Compound 16

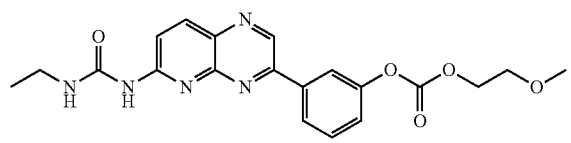

3-[6-(3-ethylurea)pyrido[2,3-b]pyrazin-3-yl]phenyl 2-methoxyethyl carbonate

Compound 17

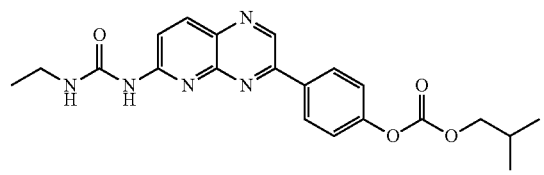

4-[6-(3-ethylurea)pyrido[2,3-b]pyrazin-3-yl]phenyl isobutyl carbonate

Compound 18

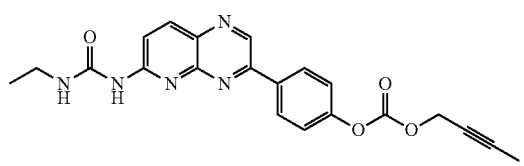

but-2-ynyl 4-[6-(3-ethylurea)pyrido[2,3-b]pyrazin-3-yl]phenyl carbonate

Compound 19

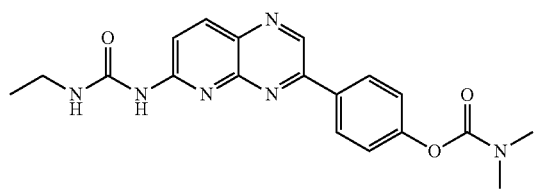

4-[6-(3-ethylurea)pyrido[2,3-b]pyrazin-3-yl]phenyl diemethylcarbamate

Compound 19

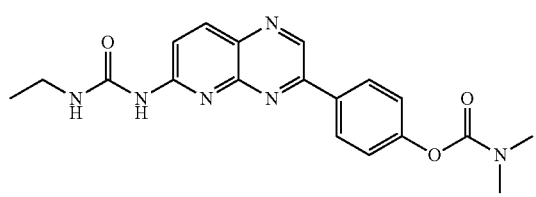

4-[6-(3-ethylurea)pyrido[2,3-b]pyrazin-3-yl]phenyl diemethylcarbamate

Compound 21

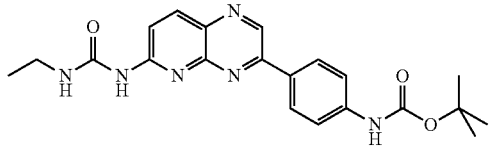

tert-butyl{4-[6-(3-ethylurea)pyrido[2,3-b]pyrazin-3-yl]phenyl}-carbamate

Compound 22

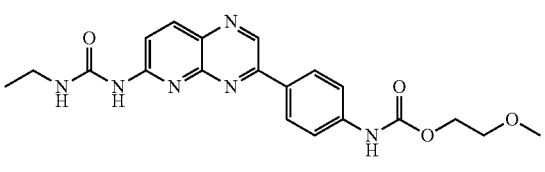

2-methoxyethyl 4-[6-(3-ethylurea)pyrido[2,3-b]pyrazin-3-yl]phenyl}-carbamate

Compound 23

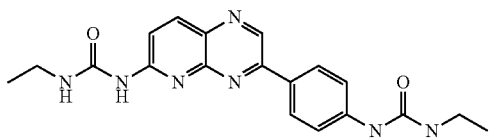

1-ethyl-3-{3-[4-(3-ethylurea)phenyl]pyrido[2,3-b]pyrazin-6-yl}urea

Compound 24

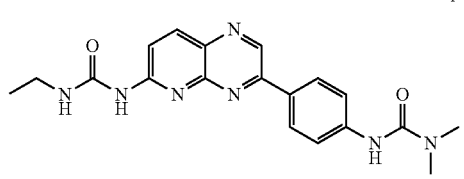

1-{3-[4-(3,3-dimethylurea)phenyl]pyrido[2,3-b]pyrazin-6-yl}-3-ethylurea

Compound 25

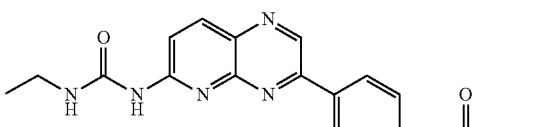

1-ethyl-3-{3-[6-(3-ethylurea)pyridin-3-yl]pyrido[2,3-b]pyrazin-6-yl}urea

Compound 26

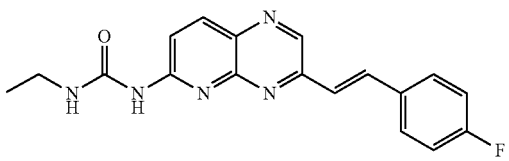

1-ethyl-3-{3-[2-(4-fluorophenyl)ethyl]pyrido[2,3-b]pyrazin-6-yl}urea

Compound 27

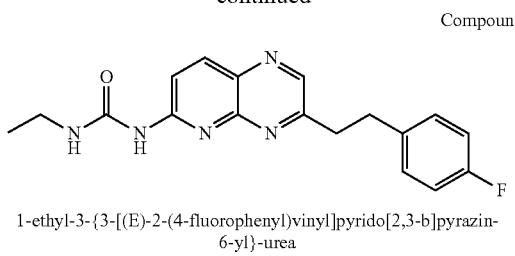

1-ethyl-3-{3-[(E)-2-(4-fluorophenyl)vinyl]pyrido[2,3-b]pyrazin-6-yl}-urea

Compound 28

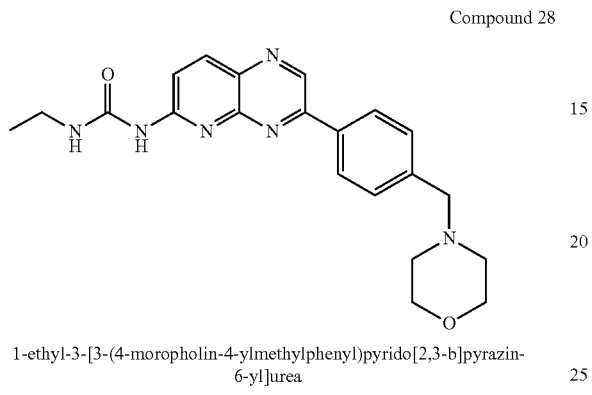

1-ethyl-3-[3-(4-moropholin-4-ylmethylphenyl)pyrido[2,3-b]pyrazin-6-yl]urea

Compound 29

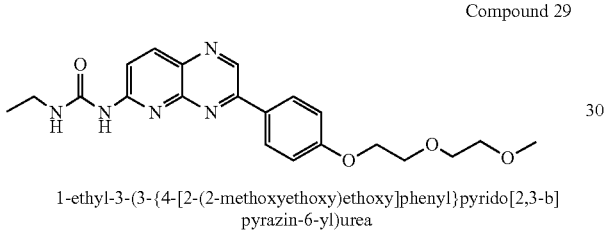

1-ethyl-3-(3-{4-[2-(2-methoxyethoxy)ethoxy]phenyl}pyrido[2,3-b]pyrazin-6-yl)urea Compound 30

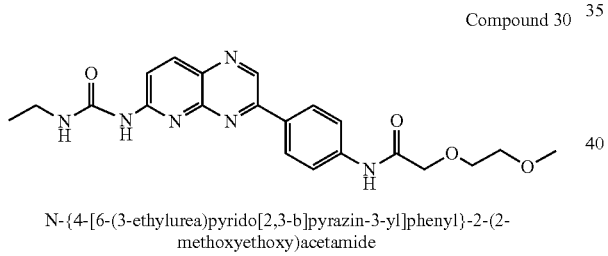

N-{4-[6-(3-ethylurea)pyrido[2,3-b]pyrazin-3-yl]phenyl}-2-(2-methoxyethoxy)acetamide Compound 31

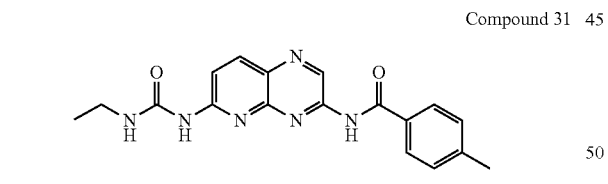

N-[6-(3-ethylurea)pyrido[2,3-b]pyrazin-3-yl]-4-methylbenzamide

Compound 32

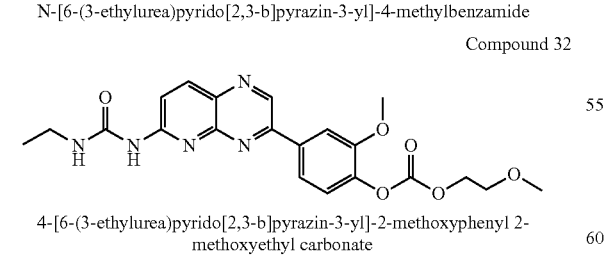

4-[6-(3-ethylurea)pyrido[2,3-b]pyrazin-3-yl]-2-methoxyphenyl 2-methoxyethyl carbonate Compound 33

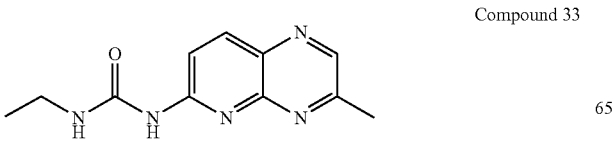

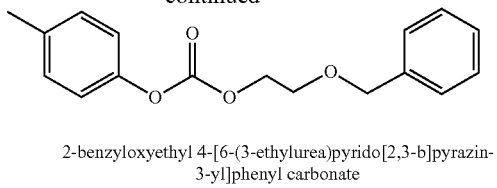

2-benzyloxyethyl 4-[6-(3-ethylurea)pyrido[2,3-b]pyrazin-3-yl]phenyl carbonate

Compound 34

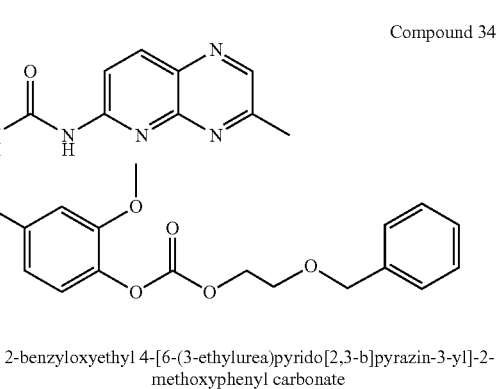

2-benzyloxyethyl 4-[6-(3-ethylurea)pyrido[2,3-b]pyrazin-3-yl]-2-methoxyphenyl carbonate Compound 35

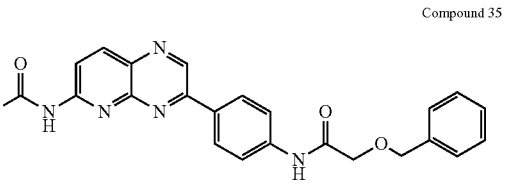

2-benzyloxy-N-{4-[6-(3-ethylurea)pyrido[2,3-b]pyrazin-3-yl]phenyl-acetamide

Compound 46

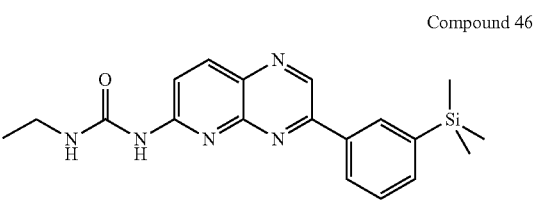

1-ethyl-3-[3-(3-trimethylsilanylphenyl)pyrido[2,3-b]pyrazin-6-yl]urea

Compound 47

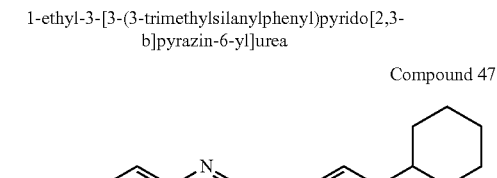

1-[3-(4-cyclohexylphenylamino)pyrido[2,3-b]pyrazin-6-yl]-3-ethylurea

Compound 48

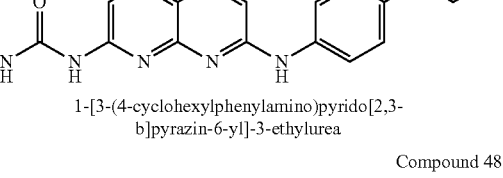

1-ethyl-3-[3-(4-methanesulphonylphenylamino)pyrido[2,3-b]pyrazin-6-yl]urea

Compound 49

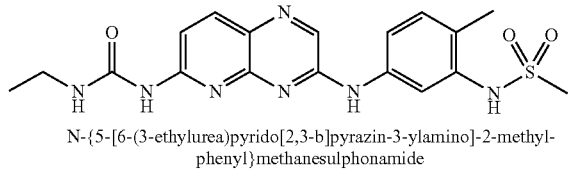

N-{5-[6-(3-ethylurea)pyrido[2,3-b]pyrazin-3-ylamino]-2-methyl-phenyl}methanesulphonamide Compound 50

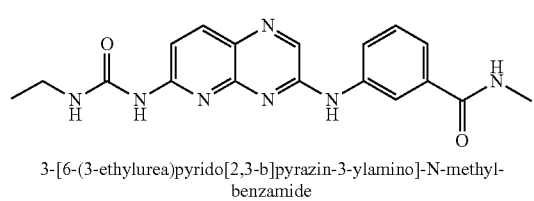

3-[6-(3-ethylurea)pyrido[2,3-b]pyrazin-3-ylamino]-N-methyl-benzamide

Compound 51

1-ethy-3-[3-(4-piperidin-1-ylmethylphenylamino)pyrido[2,3-b]-pyrazin-6-yl]urea

Compound 52

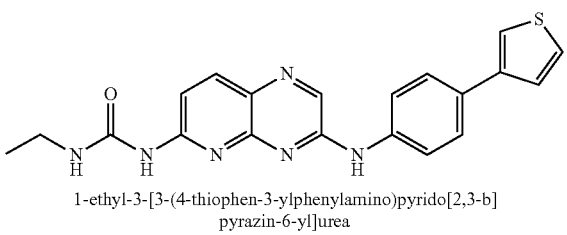

1-ethyl-3-[3-(4-thiophen-3-ylphenylamino)pyrido[2,3-b]pyrazin-6-yl]urea

Compound 53

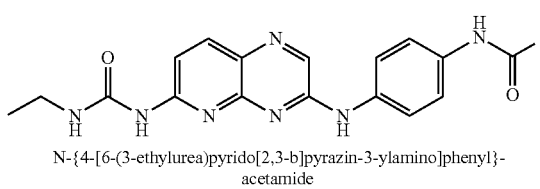

N-{4-[6-(3-ethylurea)pyrido[2,3-b]pyrazin-3-ylamino]phenyl}-acetamide

Compound 54

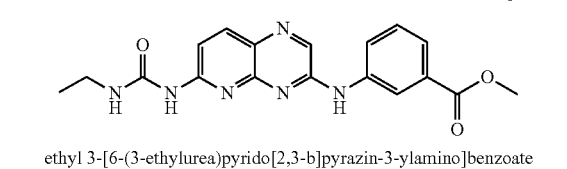

ethyl 3-[6-(3-ethylurea)pyrido[2,3-b]pyrazin-3-ylamino]benzoate

Compound 55

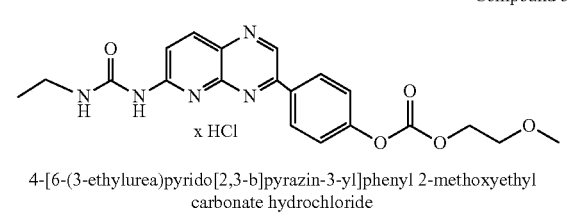

4-[6-(3-ethylurea)pyrido[2,3-b]pyrazin-3-yl]phenyl 2-methoxyethyl carbonate hydrochloride Compound 56

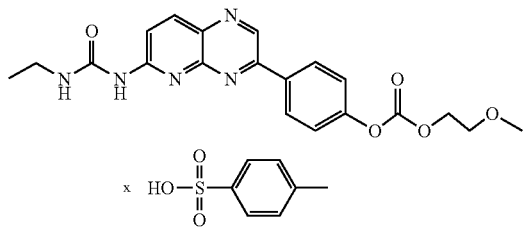

2-methoxyethyl 4-[6-(3-ethylurea)pyrido[2,3-b]pyrazin-3-yl]phenyl carbonate p-toluenesulphonate Compound 67

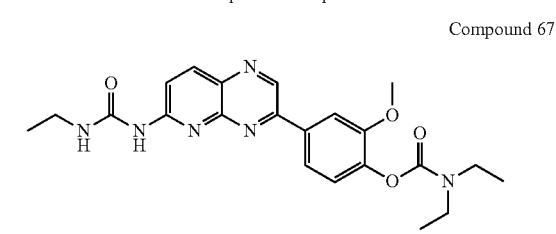

4-[6-(3-ethylurea)pyrido[2,3-b]pyrazin-3-yl]2-methoxyphenyl diethyl-carbamate

Compound 68

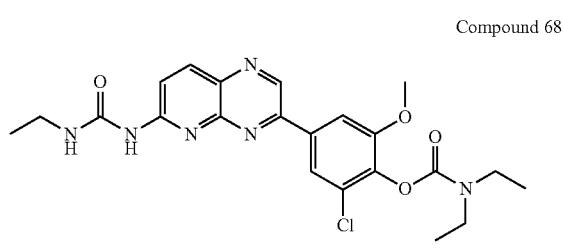

2-chloro-4-[6-(3-ethylurea)pyrido[2,3-b]pyrazin-3-yl]-6-methoxy-phenyl diethylcarbamate Compound 69

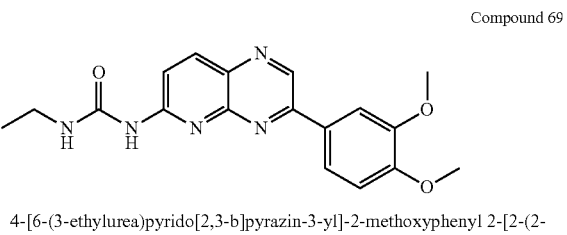

4-[6-(3-ethylurea)pyrido[2,3-b]pyrazin-3-yl]-2-methoxyphenyl 2-[2-(2-methoxyethoxy)ethoxy]ethyl carbonate Compound 70

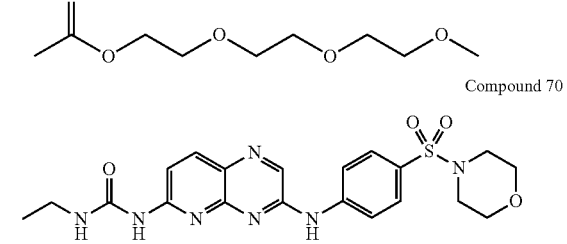

1-Ethyl-3-{3-[4-(morpholine-4-sulfonyl)-phenylamino]-pyrido[2,3-b]pyrazin-6-yl}-urea Compound 71

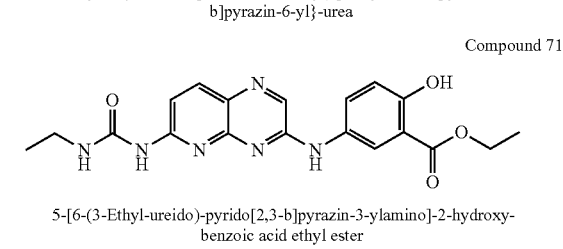

5-[6-(3-Ethyl-ureido)-pyrido[2,3-b]pyrazin-3-ylamino]-2-hydroxy-benzoic acid ethyl ester Compound 72

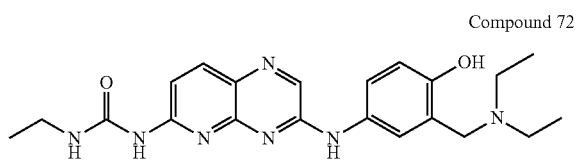

1-[3-(3-Diethylaminomethyl-4-hydroxy-phenylamino)-pyrido[2,3-b]pyrazin-6-yl]-3-ethyl-urea Compound 73

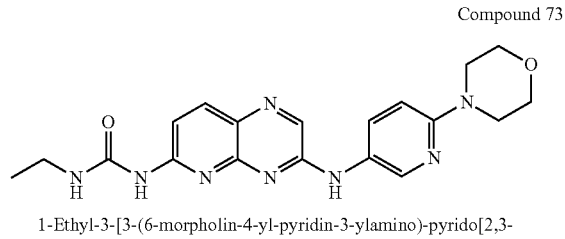

1-Ethyl-3-[3-(6-morpholin-4-yl-pyridin-3-ylamino)-pyrido[2,3-b]pyrazin-6-yl]-urea Compound 74

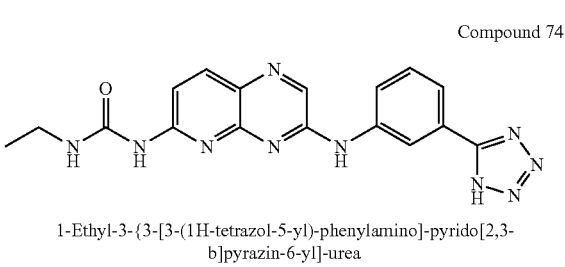

1-Ethyl-3-{3-[3-(1H-tetrazol-5-yl)-phenylamino]-pyrido[2,3-b]pyrazin-6-yl}-urea

Compound 75

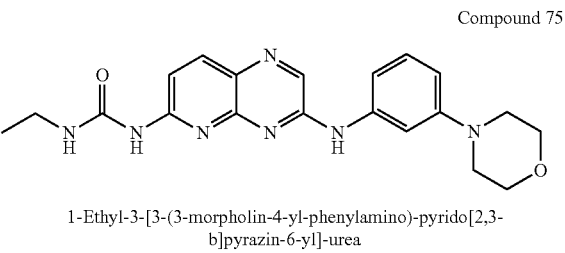

1-Ethyl-3-[3-(3-morpholin-4-yl-phenylamino)-pyrido[2,3-b]pyrazin-6-yl]-urea

Compound 76

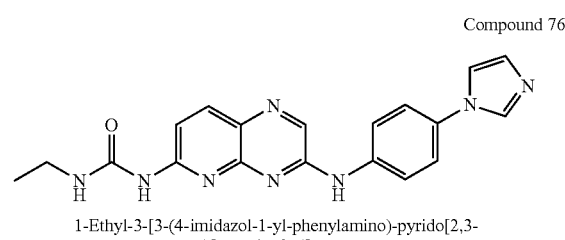

1-Ethyl-3-[3-(4-imidazol-1-yl-phenylamino)-pyrido[2,3-b]pyrazin-6-yl]-urea

Compound 77

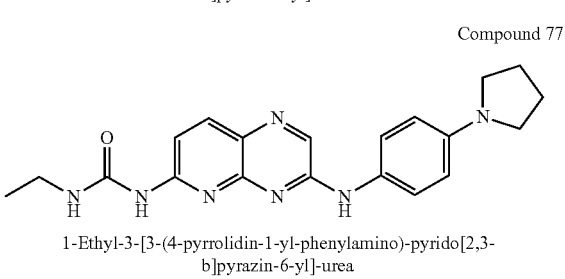

1-Ethyl-3-[3-(4-pyrrolidin-1-yl-phenylamino)-pyrido[2,3-b]pyrazin-6-yl]-urea

Compound 78

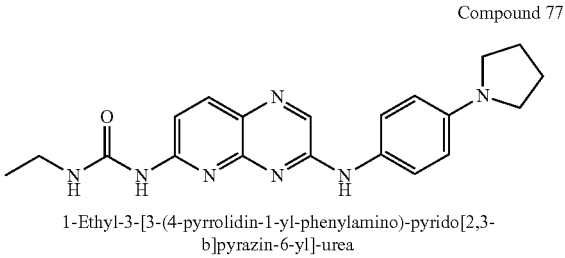

1-Ethyl-3-{3-[4-(4-methyl-piperazin-1-yl)-phenylamino]-pyrido[2,3-b]pyrazin-6-yl}-urea Compound 79

1-Ethyl-3-[3-(3-piperidin-1-ylmethyl-phenylamino)-pyrido[2,3-b]pyrazin-6-yl]-urea Compound 80

1-Ethyl-3-[3-(4-morpholin-4-ylmethyl-phenylamino)-pyrido[2,3-b]pyrazin-6-yl]-urea Compound 81

1-{3-[3-(2-Cyclohexyl-ethoxy)-phenylamino]-pyrido[2,3-b]pyrazin-6-yl}-3-ethyl-urea and Compound 82

1-Ethyl-3-[3-(3-[1,2,4]triazol-1-ylmethyl-phenylamino)-pyrido[2,3-b]pyrazin-6-yl]-urea

2. A process for producing a medicament, comprising processing one or more pyrido[2,3-b]pyrazines according to claim 1 with pharmaceutically acceptable carriers and/or excipients to give pharmaceutical formulations in a therapeutically usable form.

3. A composition which comprises a pharmacologically active amount of at least one pyrido[2,3-b]pyrazine compound according to claim 1 and a pharmaceutically acceptable carrier and/or excipient.

4. The composition according to claim 3, wherein the pyrido[2,3-b]pyrazine is present in a unit dose of 0.001 mg to 100 mg per kg of body weight of a patient.

5. 4-[6-(3-ethylurea)pyrido[2,3-b]pyrazin-3-yl]phenyl 2-methoxyethyl carbonate

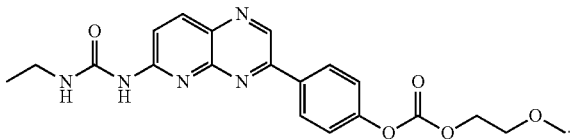

6. A process for producing a medicament, comprising processing 4-[6-(3-ethylurea)pyrido[2,3-b]pyrazin-3-yl]phenyl 2-methoxyethyl carbonate according to claim 5 with pharmaceutically acceptable carriers and/or excipients to give pharmaceutical formulations in a therapeutically usable form.

7. A composition which comprises a pharmacologically active amount of 4-[6-(3-ethylurea)pyrido[2,3-b]pyrazin-3-yl]phenyl 2-methoxyethyl carbonate according to claim 5 and a pharmaceutically acceptable carrier and/or excipient.

8. The composition according to claim 7, wherein the 4-[6-(3-ethylurea)pyrido[2,3-b]pyrazin-3-yl]phenyl 2-methoxyethyl carbonate is present in a unit dose of 0.001 mg to 100 mg per kg of body weight of a patient.

* * * * *